United States Patent
Felts et al.

(10) Patent No.: US 7,985,188 B2
(45) Date of Patent: Jul. 26, 2011

(54) VESSEL, COATING, INSPECTION AND PROCESSING APPARATUS

(75) Inventors: John T. Felts, Alameda, CA (US);
Thomas E. Fisk, Green Valley, AZ (US);
Robert S. Abrams, Albany, NY (US);
John Ferguson, Auburn, AL (US);
Johnathan R. Freedman, Auburn, AL (US); Robert J. Pangborn, Harbor Springs, MI (US); Peter J. Sagona, Pottstown, PA (US)

(73) Assignee: CV Holdings LLC, Amsterdam, NY (US)

( * ) Notice: Subject to any disclaimer, the term of this patent is extended or adjusted under 35 U.S.C. 154(b) by 0 days.

(21) Appl. No.: 12/779,007

(22) Filed: May 12, 2010

(65) Prior Publication Data
US 2010/0298738 A1    Nov. 25, 2010

Related U.S. Application Data

(60) Provisional application No. 61/177,984, filed on May 13, 2009, provisional application No. 61/222,727, filed on Jul. 2, 2009, provisional application No. 61/213,904, filed on Jul. 24, 2009, provisional application No. 61/234,505, filed on Aug. 17, 2009, provisional application No. 61/261,321, filed on Nov. 14, 2009, provisional application No. 61/263,289, filed on Nov. 20, 2009, provisional application No. 61/285,813, filed on Dec. 11, 2009, provisional application No. 61/298,159, filed on Jan. 25, 2010, provisional application No. 61/299,888, filed on Jan. 29, 2010, provisional application No. 61/318,197, filed on Mar. 26, 2010, provisional application No. 61/333,625, filed on May 11, 2010.

(51) Int. Cl.
| | |
|---|---|
| *A61B 5/00* | (2006.01) |
| *B65D 81/00* | (2006.01) |
| *C08F 2/46* | (2006.01) |
| *C08J 7/18* | (2006.01) |
| *H05H 1/00* | (2006.01) |
| *H05H 1/24* | (2006.01) |
| *C23C 14/14* | (2006.01) |
| *C23C 14/16* | (2006.01) |
| *B05D 3/14* | (2006.01) |
| *H01L 21/469* | (2006.01) |

(52) U.S. Cl. ........ 600/573; 427/488; 427/489; 427/527; 427/563; 427/579; 438/788; 438/789; 438/792; 438/793

(58) Field of Classification Search .................. 600/573, 600/576–584; 427/2.28, 488, 489, 527, 563, 427/579; 438/788, 789, 792, 793; 604/181, 604/187, 199, 232–235, 416
See application file for complete search history.

(56) References Cited

U.S. PATENT DOCUMENTS
3,442,686 A    5/1969    Jones
(Continued)

FOREIGN PATENT DOCUMENTS
AT    414209 B    10/2006
(Continued)

OTHER PUBLICATIONS
European Patent Office, Communication with extended European search report, in Application No. EP10162756.0, dated Nov. 17, 2010.
(Continued)

*Primary Examiner* — Jeffrey G Hoekstra
*Assistant Examiner* — Devin Henson
(74) *Attorney, Agent, or Firm* — McAndrews, Held & Malloy, Ltd.

(57) ABSTRACT

Methods for processing a vessel, for example to provide a gas barrier or lubricity, are disclosed. First and second PECVD or other vessel processing stations or devices and a vessel holder comprising a vessel port are provided. An opening of the vessel can be seated on the vessel port. The interior surface of the seated vessel can be processed via the vessel port by the first and second processing stations or devices. Vessel barrier, lubricity and hydrophobic coatings and coated vessels, for example syringes and medical sample collection tubes are disclosed. A vessel processing system and vessel inspection apparatus and methods are also disclosed.

77 Claims, 36 Drawing Sheets

U.S. PATENT DOCUMENTS

| | | |
|---|---|---|
| 3,590,634 A | 7/1971 | Pasternak |
| 3,957,653 A | 5/1976 | Blecher |
| 4,111,326 A | 9/1978 | Percarpio |
| 4,136,794 A | 1/1979 | Percarpio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWhorter |
| 4,452,679 A | 6/1984 | Dunn |
| 4,478,873 A | 10/1984 | Masso |
| 4,486,378 A | 12/1984 | Hirata |
| 4,522,510 A | 6/1985 | Rosencwaig |
| 4,552,791 A | 11/1985 | Hahn |
| 4,648,107 A | 3/1987 | Latter |
| 4,652,429 A | 3/1987 | Konrad |
| 4,664,279 A | 5/1987 | Obrist |
| 4,667,620 A | 5/1987 | White |
| 4,697,717 A | 10/1987 | Grippi |
| 4,703,187 A | 10/1987 | Hofling |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,809,876 A | 3/1989 | Tomaswick |
| 4,824,444 A | 4/1989 | Nomura |
| 4,844,986 A | 7/1989 | Karakelle |
| 4,846,101 A | 7/1989 | Montgomery |
| 4,869,203 A | 9/1989 | Pinkhasov |
| 4,872,758 A | 10/1989 | Miyazaki |
| 4,880,675 A | 11/1989 | Mehta |
| 4,883,686 A | 11/1989 | Doehler |
| 4,894,256 A | 1/1990 | Gartner |
| 4,948,628 A | 8/1990 | Montgomery |
| 4,991,104 A | 2/1991 | Miller |
| 4,999,014 A | 3/1991 | Gold |
| 5,028,566 A | 7/1991 | Lagendijk |
| 5,030,475 A | 7/1991 | Ackermann |
| 5,041,303 A | 8/1991 | Wertheimer |
| 5,042,951 A | 8/1991 | Gold |
| 5,084,356 A | 1/1992 | Deak |
| 5,085,904 A | 2/1992 | Deak |
| 5,113,790 A | 5/1992 | Geisler |
| 5,120,966 A | 6/1992 | Kondo |
| 5,131,752 A | 7/1992 | Yu |
| 5,154,943 A | 10/1992 | Etzkorn |
| 5,204,141 A | 4/1993 | Roberts |
| 5,224,441 A | 7/1993 | Felts |
| 5,232,111 A | 8/1993 | Burns |
| 5,260,095 A | 11/1993 | Affinito |
| 5,271,274 A | 12/1993 | Khuri-Yakub |
| 5,272,417 A | 12/1993 | Ohmi |
| 5,275,299 A | 1/1994 | Konrad |
| 5,294,011 A | 3/1994 | Konrad |
| 5,294,464 A | 3/1994 | Geisler |
| 5,298,587 A | 3/1994 | Hu |
| 5,308,649 A | 5/1994 | Babacz |
| 5,314,561 A | 5/1994 | Komiya |
| 5,320,875 A | 6/1994 | Hu |
| 5,330,578 A | 7/1994 | Sakama |
| 5,333,049 A | 7/1994 | Ledger |
| 5,361,921 A | 11/1994 | Burns |
| 5,364,665 A | 11/1994 | Felts |
| 5,364,666 A | 11/1994 | Williams |
| 5,374,314 A | 12/1994 | Babacz |
| 5,378,510 A | 1/1995 | Thomas |
| 5,395,644 A | 3/1995 | Affinito |
| 5,396,080 A | 3/1995 | Hannotiau |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,449,432 A | 9/1995 | Hanawa |
| 5,452,082 A | 9/1995 | Sanger |
| 5,468,520 A | 11/1995 | Williams |
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Plester |
| 5,569,810 A | 10/1996 | Tsuji |
| 5,571,366 A | 11/1996 | Ishii |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,665,280 A | 9/1997 | Tropsha |
| 5,667,840 A | 9/1997 | Tingey |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas et al. |
| 5,716,683 A | 2/1998 | Harvey |
| 5,718,967 A | 2/1998 | Hu |
| 5,725,909 A | 3/1998 | Shaw |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,763,033 A | 6/1998 | Tropsha |
| 5,766,362 A | 6/1998 | Montgomery |
| 5,779,074 A | 7/1998 | Burns |
| 5,779,849 A | 7/1998 | Blalock |
| 5,788,670 A | 8/1998 | Reinhard |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,820,603 A | 10/1998 | Tucker |
| 5,824,198 A | 10/1998 | Williams |
| 5,833,752 A | 11/1998 | Martin |
| 5,837,888 A | 11/1998 | Mayer |
| 5,853,833 A | 12/1998 | Sudo |
| 5,871,700 A | 2/1999 | Konrad |
| 5,877,895 A | 3/1999 | Shaw |
| 5,897,508 A | 4/1999 | Konrad |
| 5,900,284 A | 5/1999 | Hu |
| 5,900,285 A | 5/1999 | Walther |
| 5,914,189 A | 6/1999 | Hasz |

| | | |
|---|---|---|
| 5,919,328 A | 7/1999 | Tropsha |
| 5,919,420 A | 7/1999 | Niermann |
| 5,952,069 A | 9/1999 | Tropsha |
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |
| 5,972,436 A | 10/1999 | Walther |
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,032,813 A | 3/2000 | Niermann |
| 6,035,717 A | 3/2000 | Carodiskey |
| 6,054,188 A | 4/2000 | Tropsha |
| 6,068,884 A | 5/2000 | Rose |
| 6,081,330 A | 6/2000 | Nelson |
| 6,083,313 A | 7/2000 | Venkatraman et al. |
| 6,110,544 A | 8/2000 | Yang |
| 6,112,695 A | 9/2000 | Felts |
| 6,116,081 A | 9/2000 | Ghandhi |
| 6,117,243 A | 9/2000 | Walther |
| 6,118,844 A | 9/2000 | Fischer |
| 6,125,687 A | 10/2000 | McClelland |
| 6,126,640 A | 10/2000 | Tucker |
| 6,136,275 A | 10/2000 | Niermann |
| 6,139,802 A | 10/2000 | Niermann |
| 6,149,982 A | 11/2000 | Plester |
| 6,156,399 A | 12/2000 | Spallek |
| 6,161,712 A | 12/2000 | Savitz |
| 6,165,138 A | 12/2000 | Miller |
| 6,165,542 A | 12/2000 | Jaworowski |
| 6,165,566 A | 12/2000 | Tropsha |
| 6,175,612 B1 | 1/2001 | Sato |
| 6,177,142 B1 | 1/2001 | Felts |
| 6,180,185 B1 | 1/2001 | Felts |
| 6,180,191 B1 | 1/2001 | Felts |
| 6,188,079 B1 | 2/2001 | Juvinall |
| 6,190,992 B1 | 2/2001 | Sandhu |
| 6,200,658 B1 | 3/2001 | Walther |
| 6,200,675 B1 | 3/2001 | Neerinck |
| 6,204,922 B1 | 3/2001 | Chalmers |
| 6,210,791 B1 | 4/2001 | Skoog |
| 6,214,422 B1 | 4/2001 | Yializis |
| 6,223,683 B1 | 5/2001 | Plester |
| 6,236,459 B1 | 5/2001 | Negahdaripour |
| 6,248,397 B1 | 6/2001 | Ye |
| 6,254,983 B1 | 7/2001 | Namiki |
| 6,261,643 B1 | 7/2001 | Hasz |
| 6,263,249 B1 | 7/2001 | Stewart |
| 6,271,047 B1 | 8/2001 | Ushio |
| 6,276,296 B1 | 8/2001 | Plester |
| 6,277,331 B1 | 8/2001 | Konrad |
| 6,279,505 B1 | 8/2001 | Plester |
| 6,308,556 B1 | 10/2001 | Sagi et al. |
| 6,346,596 B1 | 2/2002 | Mallen |
| 6,348,967 B1 | 2/2002 | Nelson |
| 6,350,415 B1 | 2/2002 | Niermann |
| 6,354,452 B1 | 3/2002 | DeSalvo |
| 6,365,013 B1 | 4/2002 | Beele |
| 6,375,022 B1 | 4/2002 | Zurcher |
| 6,376,028 B1 | 4/2002 | Laurent |
| 6,379,757 B1 | 4/2002 | Iacovangelo |
| 6,382,441 B1 | 5/2002 | Carano |
| 6,399,944 B1 | 6/2002 | Vasilyev |
| 6,410,926 B1 | 6/2002 | Munro |
| 6,413,645 B1 | 7/2002 | Graff |
| 6,432,494 B1 | 8/2002 | Yang |
| 6,470,650 B1 | 10/2002 | Lohwasser |
| 6,475,622 B2 | 11/2002 | Namiki |
| 6,486,081 B1 | 11/2002 | Ishikawa |
| 6,500,500 B1 | 12/2002 | Okamura |
| 6,503,579 B1 | 1/2003 | Murakami |
| 6,539,890 B1 | 4/2003 | Felts |
| 6,551,267 B1 | 4/2003 | Cohen |
| 6,565,791 B1 | 5/2003 | Laurent |
| 6,584,828 B2 | 7/2003 | Sagi |
| 6,597,193 B2 | 7/2003 | Lagowski |
| 6,599,594 B1 | 7/2003 | Walther |
| 6,602,206 B1 | 8/2003 | Niermann |
| 6,623,861 B2 | 9/2003 | Martin |
| 6,638,876 B2 | 10/2003 | Levy |
| 6,651,835 B2 | 11/2003 | Iskra |
| 6,658,919 B2 | 12/2003 | Chatard |
| 6,662,957 B2 | 12/2003 | Zurcher |
| 6,670,200 B2 | 12/2003 | Ushio |
| 6,680,621 B2 | 1/2004 | Savtchouk |
| 6,683,308 B2 | 1/2004 | Itagaki |
| 6,684,683 B2 | 2/2004 | Potyrailo |
| 6,702,898 B2 | 3/2004 | Hosoi |
| 6,706,412 B2 | 3/2004 | Yializis |
| 6,746,430 B2 | 6/2004 | Willis, Jr. |
| 6,749,078 B2 | 6/2004 | Iskra |
| 6,753,972 B1 | 6/2004 | Hirose |
| 6,757,056 B1 | 6/2004 | Meeks |
| 6,764,714 B2 | 7/2004 | Wei |
| 6,766,682 B2 | 7/2004 | Engle |
| 6,774,018 B2 | 8/2004 | Mikhael |
| 6,796,780 B1 | 9/2004 | Chatard |
| 6,800,852 B2 | 10/2004 | Larson |
| 6,808,753 B2 | 10/2004 | Rule |
| 6,810,106 B2 | 10/2004 | Sato |
| 6,815,014 B2 | 11/2004 | Gabelnick |
| 6,818,310 B2 | 11/2004 | Namiki |
| 6,837,954 B2 | 1/2005 | Carano |
| 6,844,075 B1 | 1/2005 | Saak |
| 6,858,259 B2 | 2/2005 | Affinito |
| 6,863,731 B2 | 3/2005 | Elsayed-Ali |
| 6,872,428 B2 | 3/2005 | Yang |
| 6,885,727 B2 | 4/2005 | Tamura |
| 6,887,578 B2 | 5/2005 | Gleason |
| 6,891,158 B2 | 5/2005 | Larson |
| 6,892,567 B1 | 5/2005 | Morrow |
| 6,905,769 B2 | 6/2005 | Komada |
| 6,910,597 B2 | 6/2005 | Iskra |
| 6,919,107 B2 | 7/2005 | Schwarzenbach |
| 6,919,114 B1 | 7/2005 | Darras |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,039,158 B1 | 5/2006 | Janik |
| 7,052,736 B2 | 5/2006 | Wei |
| 7,052,920 B2 | 5/2006 | Ushio |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jaccoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,188,734 B2 | 3/2007 | Konrad |
| 7,189,290 B2 | 3/2007 | Hama |
| 7,193,724 B2 | 3/2007 | Isei |
| 7,206,074 B2 | 4/2007 | Fujimoto |
| 7,244,381 B2 | 7/2007 | Chatard |
| 7,253,892 B2 | 8/2007 | Semersky |
| 7,286,242 B2 | 10/2007 | Kim |
| 7,300,684 B2 | 11/2007 | Boardman |
| 7,306,852 B2 | 12/2007 | Komada |
| 7,332,227 B2 | 2/2008 | Hardman |
| 7,339,682 B2 | 3/2008 | Aiyer |
| 7,348,192 B2 | 3/2008 | Mikami |
| 7,362,425 B2 | 4/2008 | Meeks |
| 7,390,573 B2 | 6/2008 | Korevaar |
| 7,399,500 B2 | 7/2008 | Bicker |
| 7,405,008 B2 | 7/2008 | Domine |
| 7,409,313 B2 | 8/2008 | Ringermacher |

| | | |
|---|---|---|
| 7,411,685 B2 | 8/2008 | Takashima |
| RE40,531 E | 10/2008 | Graff |
| 7,431,989 B2 | 10/2008 | Sakhrani |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,552,620 B2 | 6/2009 | DeRoos |
| 7,553,529 B2 | 6/2009 | Sakhrani |
| 7,555,934 B2 | 7/2009 | DeRoos |
| 7,582,868 B2 | 9/2009 | Jiang |
| 7,595,097 B2 | 9/2009 | Iacovangelo |
| 7,624,622 B1 | 12/2009 | Mayer |
| 7,648,481 B2 | 1/2010 | Geiger |
| 7,754,302 B2 | 7/2010 | Yamasaki |
| 2001/0000279 A1 | 4/2001 | Daniels |
| 2001/0021356 A1 | 9/2001 | Konrad |
| 2001/0038894 A1 | 11/2001 | Komada |
| 2001/0042510 A1 | 11/2001 | Plester |
| 2001/0043997 A1 | 11/2001 | Uddin |
| 2002/0006487 A1 | 1/2002 | O'Connor |
| 2002/0125900 A1 | 9/2002 | Savtchouk |
| 2002/0130674 A1 | 9/2002 | Lagowski |
| 2002/0141477 A1 | 10/2002 | Akahori |
| 2002/0155218 A1 | 10/2002 | Meyer |
| 2002/0176947 A1 | 11/2002 | Darras |
| 2002/0190207 A1 | 12/2002 | Levy |
| 2003/0215652 A1 | 11/2003 | O'Connor |
| 2003/0219547 A1 | 11/2003 | Arnold |
| 2003/0232150 A1 | 12/2003 | Arnold |
| 2004/0125913 A1 | 7/2004 | Larson |
| 2004/0135081 A1 | 7/2004 | Larson |
| 2004/0149225 A1 | 8/2004 | Weikart |
| 2004/0177676 A1 | 9/2004 | Moore |
| 2004/0195960 A1 | 10/2004 | Czeremuszkin |
| 2004/0217081 A1 | 11/2004 | Konrad |
| 2004/0247948 A1 | 12/2004 | Behle |
| 2004/0267194 A1 | 12/2004 | Sano |
| 2005/0000962 A1 | 1/2005 | Crawford |
| 2005/0019503 A1 | 1/2005 | Komada |
| 2005/0037165 A1 | 2/2005 | Ahern |
| 2005/0057754 A1 | 3/2005 | Smith |
| 2005/0073323 A1 | 4/2005 | Kohno |
| 2005/0161149 A1 | 7/2005 | Yokota |
| 2005/0169803 A1 | 8/2005 | Betz |
| 2005/0196629 A1 | 9/2005 | Bariatinsky |
| 2005/0206907 A1 | 9/2005 | Fujimoto |
| 2005/0223988 A1 | 10/2005 | Behle |
| 2005/0227002 A1 | 10/2005 | Lizenberg |
| 2005/0227022 A1 | 10/2005 | Domine |
| 2005/0229850 A1 | 10/2005 | Behle |
| 2005/0233077 A1 | 10/2005 | Lizenberg |
| 2005/0233091 A1 | 10/2005 | Kumar |
| 2005/0284550 A1 | 12/2005 | Bicker |
| 2006/0046006 A1 | 3/2006 | Bastion |
| 2006/0051252 A1 | 3/2006 | Yuan |
| 2006/0051520 A1 | 3/2006 | Behle |
| 2006/0086320 A1 | 4/2006 | Lizenberg |
| 2006/0099340 A1 | 5/2006 | Behle |
| 2006/0121222 A1 | 6/2006 | Audrich |
| 2006/0121613 A1 | 6/2006 | Havens |
| 2006/0121623 A1 | 6/2006 | He |
| 2006/0135945 A1 | 6/2006 | Bankiewicz |
| 2006/0138326 A1 | 6/2006 | Jiang |
| 2006/0150909 A1 | 7/2006 | Behle |
| 2006/0178627 A1 | 8/2006 | Geiger |
| 2006/0192973 A1 | 8/2006 | Aiyer |
| 2006/0196419 A1 | 9/2006 | Tudhope |
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |
| 2007/0017870 A1 | 1/2007 | Belov |
| 2007/0048456 A1 | 3/2007 | Keshner |
| 2007/0102344 A1 | 5/2007 | Konrad |
| 2007/0148326 A1 | 6/2007 | Hastings |
| 2007/0187280 A1 | 8/2007 | Haines |
| 2007/0215009 A1 | 9/2007 | Shimazu |
| 2007/0215046 A1 | 9/2007 | Lupke |
| 2007/0218265 A1 | 9/2007 | Harris |
| 2007/0231655 A1 | 10/2007 | Ha |
| 2007/0232066 A1 | 10/2007 | Bicker |
| 2007/0243618 A1 | 10/2007 | Hatchett |
| 2007/0259184 A1 | 11/2007 | Martin |
| 2007/0281108 A1 | 12/2007 | Weikart |
| 2007/0287954 A1 | 12/2007 | Zhao |
| 2007/0298189 A1 | 12/2007 | Straemke |
| 2008/0011232 A1 | 1/2008 | Rius |
| 2008/0017113 A1 | 1/2008 | Goto |
| 2008/0023414 A1 | 1/2008 | Konrad |
| 2008/0027400 A1 | 1/2008 | Harding |
| 2008/0050567 A1 | 2/2008 | Kawashima |
| 2008/0050932 A1 | 2/2008 | Lakshmanan |
| 2008/0069970 A1 | 3/2008 | Wu |
| 2008/0071228 A1 | 3/2008 | Wu |
| 2008/0081184 A1 | 4/2008 | Kubo |
| 2008/0090039 A1 | 4/2008 | Klein |
| 2008/0110852 A1 | 5/2008 | Kuroda |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0187681 A1 | 8/2008 | Hofrichter |
| 2008/0223815 A1 | 9/2008 | Konrad |
| 2008/0292806 A1 | 11/2008 | Wei |
| 2008/0295772 A1 | 12/2008 | Park |
| 2008/0312607 A1 | 12/2008 | Delmotte |
| 2008/0314318 A1 | 12/2008 | Han |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0039240 A1 | 2/2009 | Van Nijnatten |
| 2009/0053491 A1 | 2/2009 | Laboda |
| 2009/0061237 A1 | 3/2009 | Gates |
| 2009/0104392 A1 | 4/2009 | Takada |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0155490 A1 | 6/2009 | Bicker |
| 2009/0162571 A1 | 6/2009 | Haines |
| 2009/0176031 A1 | 7/2009 | Armellin |
| 2009/0263668 A1 | 10/2009 | David |
| 2009/0280268 A1 | 11/2009 | Glukhoy |
| 2009/0297730 A1 | 12/2009 | Glukhoy |
| 2010/0075077 A1 | 3/2010 | Bicker |
| 2010/0186740 A1 | 7/2010 | Hilton |
| 2010/0193461 A1 | 8/2010 | Boutroy |
| 2010/0275847 A1 | 11/2010 | Yamasaki |

FOREIGN PATENT DOCUMENTS

| | | |
|---|---|---|
| AT | 504533 A1 | 6/2008 |
| AU | 2002354470 B2 | 5/2007 |
| CA | 2355681 | 7/2000 |
| CA | 2718253 | 9/2009 |
| CN | 1711310 A | 12/2005 |
| CN | 101147813 A | 3/2008 |
| CN | 201056331 Y | 5/2008 |
| DE | 1147836 | 4/1969 |
| DE | 1147838 | 4/1969 |
| DE | 3632748 A1 | 4/1988 |
| DE | 3908418 A1 | 9/1990 |
| DE | 4204082 A1 | 8/1993 |
| DE | 4316349 A1 | 11/1994 |
| DE | 4443359 | 5/1996 |
| DE | 19707645 A1 | 8/1998 |

| | | |
|---|---|---|
| DE | 19830794 A1 | 1/2000 |
| DE | 19912737 A1 | 6/2000 |
| DE | 10154404 C1 | 6/2003 |
| DE | 10201110 A1 | 10/2003 |
| DE | 102006061585 A1 | 2/2008 |
| EP | 0121340 A2 | 10/1984 |
| EP | 0535810 A1 | 4/1993 |
| EP | 0571116 A1 | 11/1993 |
| EP | 0580094 A1 | 1/1994 |
| EP | 0603717 A2 | 6/1994 |
| EP | 0645470 A1 | 3/1995 |
| EP | 0709485 B1 | 5/1996 |
| EP | 0719877 A1 | 7/1996 |
| EP | 0787824 A2 | 8/1997 |
| EP | 0787828 A2 | 8/1997 |
| EP | 0814114 A1 | 12/1997 |
| EP | 0833366 A2 | 4/1998 |
| EP | 0992610 A2 | 4/2000 |
| EP | 1365043 A1 | 11/2003 |
| EP | 1439241 A2 | 7/2004 |
| EP | 1510595 A1 | 3/2005 |
| EP | 1522403 A2 | 4/2005 |
| EP | 1653192 A1 | 5/2006 |
| EP | 1810758 A1 | 7/2007 |
| EP | 1881088 A1 | 1/2008 |
| GB | 2210826 A | 6/1989 |
| GB | 2246794 A | 2/1992 |
| GB | 2246795 A | 2/1992 |
| JP | 56027330 A | 3/1981 |
| JP | 58154602 A | 9/1983 |
| JP | 59087307 A | 5/1984 |
| JP | 59154029 | 9/1984 |
| JP | 63124521 A2 | 5/1988 |
| JP | 1023105 A | 1/1989 |
| JP | 1279745 | 11/1989 |
| JP | 2501490 | 5/1990 |
| JP | 3183759 A2 | 8/1991 |
| JP | 4000373 A | 1/1992 |
| JP | 4000374 A | 1/1992 |
| JP | 4000375 A | 1/1992 |
| JP | 4014440 A | 1/1992 |
| JP | 6010132 A | 1/1994 |
| JP | 6289401 | 10/1994 |
| JP | 7041579 A | 2/1995 |
| JP | 7126419 A | 5/1995 |
| JP | 8025244 A | 1/1996 |
| JP | 9005038 A | 1/1997 |
| JP | 10008254 A | 1/1998 |
| JP | 11-108833 A | 4/1999 |
| JP | 11106920 | 4/1999 |
| JP | 11344316 A | 12/1999 |
| JP | 2000109076 A | 4/2000 |
| JP | 2001033398 A | 2/2001 |
| JP | 2002371364 A | 12/2002 |
| JP | 2003171771 A | 6/2003 |
| JP | 2003-268550 A | 9/2003 |
| JP | 2003294431 A | 10/2003 |
| JP | 2004002928 A | 1/2004 |
| JP | 2004100036 A | 4/2004 |
| JP | 2004156444 A | 6/2004 |
| JP | 2004168359 A | 6/2004 |
| JP | 2004-253683 A | 9/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005200044 A | 7/2005 |
| JP | 2005-241524 A | 9/2005 |
| JP | 2005271997 A | 10/2005 |
| JP | 2006111967 A | 4/2006 |
| JP | 2006160268 A | 6/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2009-062620 A | 3/2009 |
| JP | 2009185330 A | 8/2009 |
| KR | 10-2006-0029694 | 4/2006 |
| KR | 10-0685594 B1 | 2/2007 |
| WO | WO9324243 A1 | 12/1993 |
| WO | WO9400247 A1 | 1/1994 |
| WO | WO9426497 A1 | 11/1994 |
| WO | WO9917334 A1 | 4/1999 |
| WO | WO0038566 A2 | 7/2000 |
| WO | WO0154816 A1 | 8/2001 |
| WO | WO0156706 A1 | 8/2001 |
| WO | WO0170403 A1 | 9/2001 |
| WO | WO0249925 A1 | 6/2002 |
| WO | WO02076709 A1 | 10/2002 |
| WO | WO03014415 A1 | 2/2003 |
| WO | WO03038143 | 5/2003 |
| WO | WO03040649 A1 | 5/2003 |
| WO | WO 2005/052555 A1 | 6/2005 |
| WO | WO2005051525 A1 | 6/2005 |
| WO | WO2005103605 A1 | 11/2005 |
| WO | WO2006027568 A1 | 3/2006 |
| WO | WO2006044254 A1 | 4/2006 |
| WO | WO2007028061 A2 | 3/2007 |
| WO | WO2007035741 A2 | 3/2007 |
| WO | WO2007036544 A1 | 4/2007 |
| WO | WO2007112328 A2 | 10/2007 |
| WO | WO2007133378 A1 | 11/2007 |
| WO | WO2007134347 A2 | 11/2007 |
| WO | WO2008014438 A2 | 1/2008 |
| WO | WO2008024566 A2 | 2/2008 |
| WO | WO2008040531 A1 | 4/2008 |
| WO | WO2008047541 A1 | 4/2008 |
| WO | WO2008067574 A1 | 6/2008 |
| WO | WO2008071458 A1 | 6/2008 |
| WO | WO2008093335 A2 | 8/2008 |
| WO | WO2009021257 A1 | 2/2009 |
| WO | WO2009030975 A1 | 3/2009 |
| WO | WO2009030976 A1 | 3/2009 |
| WO | WO2009031838 A1 | 3/2009 |
| WO | WO2009053947 A2 | 4/2009 |
| WO | WO2009112053 A1 | 9/2009 |
| WO | WO2009118361 A1 | 10/2009 |
| WO | WO2010095011 A1 | 8/2010 |

OTHER PUBLICATIONS

European Patent Office, Communication with extended European search report, in Application No. EP10162757.8, dated Nov. 10, 2010.
Patent Cooperation Treaty, Notification of Transmittal of the International Search Report and the Written Opinion of the International Searching Authority, in PCT/US2010/034568, dated Jan. 21, 2011.
Patent Cooperation Treaty, Notification of Transmittal of the International Search Report and the Written Opinion of the International Searching Authority, in PCT/US2010/034571, dated Jan. 26, 2011.
Patent Cooperation Treaty, Notification of Transmittal of the International Search Report and the Written Opinion of the International Searching Authority, in PCT/US2010/034576, dated Jan. 25, 2011.
Patent Cooperation Treaty, Notification of Transmittal of the International Search Report and the Written Opinion of the International Searching Authority, in PCT/US2010/034577, dated Jan. 21, 2011.
Patent Cooperation Treaty, Notification of Transmittal of the International Search Report and the Written Opinion of the International Searching Authority, in PCT/US2010/034582, dated Jan. 24, 2011.
European Patent Office, Communication with Extended Search Report, in Application No. EP 10162755.2, dated Nov. 9, 2010.
European Patent Office, Communication with Extended Search Report, in Application No. EP 10162760.2, dated Nov. 12, 2010.
PCT, Written Opinion of the International Searching Authority with International Search Report in Application No. PCT/US2010/034586, dated Mar. 15, 2011.
Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.
European Patent Office, Communication with extended Search Report, in Application No. EP 10162761.0, dated Feb. 10, 2011.
European Patent Office, Communication with partial Search Report, in Application No. EP 10162758.6, dated Aug. 19, 2010.
European Patent Office, Communication with extended Search Report, in Application No. EP 10162758.6, dated Dec. 21, 2010.

Yang, et al., Microstructure and tribological properties of SiOx/DLC films grown by PECVD, Surface and Coatings Technology, vol. 194, Apr. 20, 2005, pp. 128-135.

Allison, H.L., The Real Markets for Transparent Barrier Films, 37th Annual Technical Conference Proceedings, 1994, ISBN 1-878068-13-X, pp. 458.

Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.

Banks, B.A., et al., Fluoropolymer Filled SiO2 Coatings; Properties and Potential Applications, Society of Vacuum Coaters, 35th Annual Technical Conference Proceedings, 1992, ISBN 1-878068-11-3, pp. 89-93.

Baouchi, W., X-Ray Photoelectron Spectroscopy Study of Sodium Ion Migration through Thin Films of SiO2 Deposited on Sodalime Glass, 37th Annual Technical Conference Proceedings, 1994, ISBN 1-878068-13-X, pp. 419-422.

Boebel, F. et al., Simultaneous In Situ Measurement of Film Thickness and Temperature by Using Multiple Wavelengths Pyrometric Interferometry (MWPI), IEEE Transaction on Semiconductor Manufacturing, vol. 6, No. 2, May 1993, , pp. 112-118.

Bush, V. et al., The Evolution of Evacuated Blood Collection Tubes, BD Diagnostics—Preanalytical Systems Newsletter, vol. 19, No. 1, 2009.

Chahroudi, D., Deposition Technology for Glass Barriers, 33rd Annual Technical Conference Proceedings, 1990, ISBN 1-878068-09-1, pp. 212-220.

Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.

Chahroudi, D., Glassy Barriers from Electron Beam Web Coaters, 32nd Annual Technical Conference Proceedings, 1989, pp. 29-39.

Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.

Ebihara, K. et al., Application of the Dielectric Barrier Discharge to Detect Defects in a Teflon Coated Metal Surface, 2003 J. Phys. D: Appl. Phys. 36 2883-2886, doi: 10.1088/0022-3727/36/23/003, IOP Electronic Journals, http://www.iop.org/EJ/abstract/0022-3727/36/23/003, printed Jul. 14, 2009.

Egitto, F.D., et al., Plasma Modification of Polymer Surfaces, Society of Vacuum Coaters, 36th Annual Technical Conference Proceedings, 1993, ISBN 1-878068-12-1, pp. 10-21.

Erlat, A.G. et al., SIOx Gas Barrier Coatings on Polymer Substrates: Morphology and Gas Transport Considerations, ACS Publications, Journal of Physical Chemistry, published Jul. 2, 1999, http://pubs.acs.org/doi/abs/10.1021/jp990737e, printed Jul. 14, 2009.

Fayet, P., et al., Commercialism of Plasma Deposited Barrier Coatings for Liquid Food Packaging, 37th Annual Technical Conference Proceedings, 1995, ISBN 1-878068-13-X, pp. 15-16.

Felts, J., Hollow Cathode Based Multi-Component Depositions, Vacuum Technology & Coating, Mar. 2004, pp. 48-55.

Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.

Felts, J.T., Transparent Barrier Coatings Update: Flexible Substrates, Society of Vacuum Coaters, 36th Annual Technical Conference Proceedings, 1993, ISBN 1-878068-12-1, pp. 324-331.

Felts, J.T., Transparent Gas Barrier Technologies, 33rd Annual Technical Conference Proceedings, 1990, ISBN 1-878068-09-1, pp. 184-193.

Finson, E., et al., Transparent SiO2 Barrier Coatings: Conversion and Production Status, 37th Annual Technical Conference Proceedings, 1994, ISBN 1-878068-13-X, pp. 139-143.

Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.

Hora, R., et al., Plasma Polymerization: A New Technology for Functional Coatings on Plastics, 36th Annual Technical Conference Proceedings, 1993, ISBN 1-878068-12-1, pp. 51-55.

Izu, M., et al., High Performance Clear CoatTM Barrier Film, 36th Annual Technical Conference Proceedings, 1993, ISBN 1-878068-12-1, pp. 333-340.

Jost, S., Plasma Polymerized Organosilicon Thin Films on Reflective Coatings, 33rd Annual Technical Conference Proceedings, 1990, ISBN 1-878068-09-1, pp. 344-346.

Kaganowicz, G., et al., Plasma-Deposited Coatings—Properties and Applications, 23rd Annual Technical Conference Proceedings, 1980, pp. 24-30.

Kamineni, V. et al., Thickness Measurement of Thin Metal Films by Optical Metrology, College of Nanoscale Science and Engineering, University of Albany, Albany, NY.

Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.

Krug, T., et al., New Developments in Transparent Barrier Coatings, 36th Annual Technical Conference Proceedings, 1993, ISBN 1-878068-12-1, pp. 302-305.

Kuhr, M. et al., Multifunktionsbeschichtungen für innovative Applikationen von Kunststoff-Substraten, HiCotec Smart Coating Solutions.

Kulshreshtha, D.S., Specifications of a Spectroscopic Ellipsometer, Department of Physics & Astrophysics, University of Delhi, Delhi-110007, Jan. 16, 2009.

Krug, T.G., Transparent Barriers for Food Packaging, 33rd Annual Technical Conference Proceedings, 1990, ISBN 1-878068-09-1, pp. 163-169.

Lee, K. et al., The Ellipsometric Measurements of a Curved Surface, Japanese Journal of Applied Physics, vol. 44, No. 32, 2005, pp. L1015-L1018.

Lelait, L. et al., Microstructural Investigations of EBPVD Thermal Barrier Coatings, Journal De Physique IV, Colloque C9, supplément au Journal de Physique III, vol. 3, Dec. 1993, pp. 645-654.

Masso, J.D., Evaluation of Scratch Resistant and Antireflective Coatings for Plastic Lenses, 32nd Annual Technical Conference Proceedings, 1989, p. 237-240.

Misiano, C., et al., New Colourless Barrier Coatings (Oxygen & Water Vapor Transmission Rate) on Plastic Substrates, 35th Annual Technical Conference Proceedings, 1992, ISBN 1-878068-11-3, pp. 28-40.

Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.

Mount, E., Measuring Pinhole Resistance of Packaging, Corotec Corporation website, http://www.convertingmagazine.com, printed Jul. 13, 2009.

Murray, L. et al., The Impact of Foil Pinholes and Flex Cracks on the Moisture and Oxygen Barrier of Flexible Packaging.

Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.

Nelson, R.J., Scale-Up of Plasma Deposited SiOx Gas Diffusion Barrier Coatings, 35th Annual Technical Conference Proceedings, 1992, ISBN 1-878068-11-3, pp. 75-78.

Novotny, V. J., Ultrafast Ellipsometric Mapping of Thin Films, IBM Technical Disclosure Bulletin, vol. 37, No. 02A, Feb. 1994, pp. 187-188.

Rüger, M., Die Pulse Sind das Plus, PICVD-Beschichtungsverfahren.

Schultz, A. et al., Detection and Identification of Pinholes in Plasma-Polymerised Thin Film Barrier Coatings on Metal Foils, Surface & Coatings Technology 200, 2005, pp. 213-217.

Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.

Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.

Teyssedre, G. et al., Temperature Dependence of the Photoluminescence in Poly(Ethylene Terephthalate) Films, Polymer 42, 2001, pp. 8207-8216.

Tsung, L. et al., Development of Fast CCD Cameras for In-Situ Electron Microscopy, Microsc Microanal 14(Supp 2), 2008.

Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.

Yang, et al., Microstructure and tribological properties of SiOx/DLC films grown by PECVD, Surface and Coatings Technology, vol. 194, Issue 1, Apr. 20, 2005, pp. 128-135.

AN 451, Accurate Thin Film Measurements by High-Resoluiton Transmission Electron Microscopy (HRTEM), Evans Alalytical Group, Version 1.0, Jun. 12, 2008, pp. 1-2.

Benefits of TriboGlide, TriboGlide Silicone-Free Lubrication Systems, http://www.triboglide.com/benfits.htm, printed Aug. 31, 2009.

Coating Syringes, http://www.triboglide.com/syringes.htm, printed Aug. 31, 2009.

Coating/Production Process, http://www.triboglide.com/process.htm, printed Aug. 31, 2009.

Munich Exp, Materialica 2005: Fundierte Einblicke in den Werkstofsektor, Seite 1, von 4, ME095-6.

Schott Developing Syringe Production in United States, Apr. 14, 2009, http://www.schott.com/pharmaceutical_packaging, printed Aug. 31, 2009.

Sterile Prefillable Glass and Polymer Syringes, Schott forma vitrum, http://www.schott.com/pharmaceutical_packaging.

Transparent and recyclingfähig, neue verpackung, Dec. 2002, pp. 54-57.

European Patent Office, Communication with European Search Report, in Application No. 10162758.6, dated Aug. 19, 2010.

Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.

US 5,645,643, 07/1997, Thomas (withdrawn)

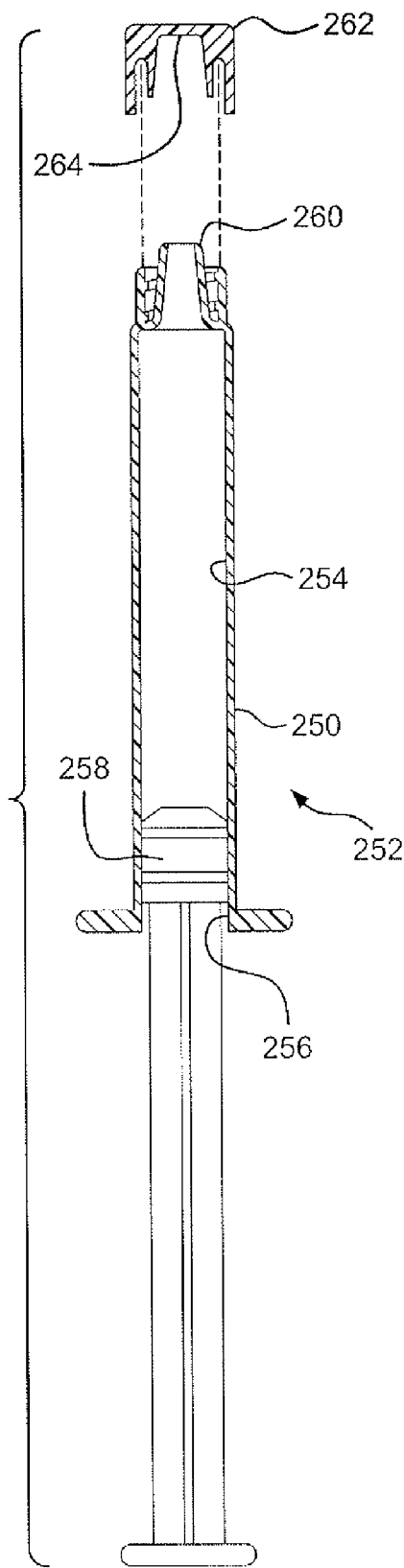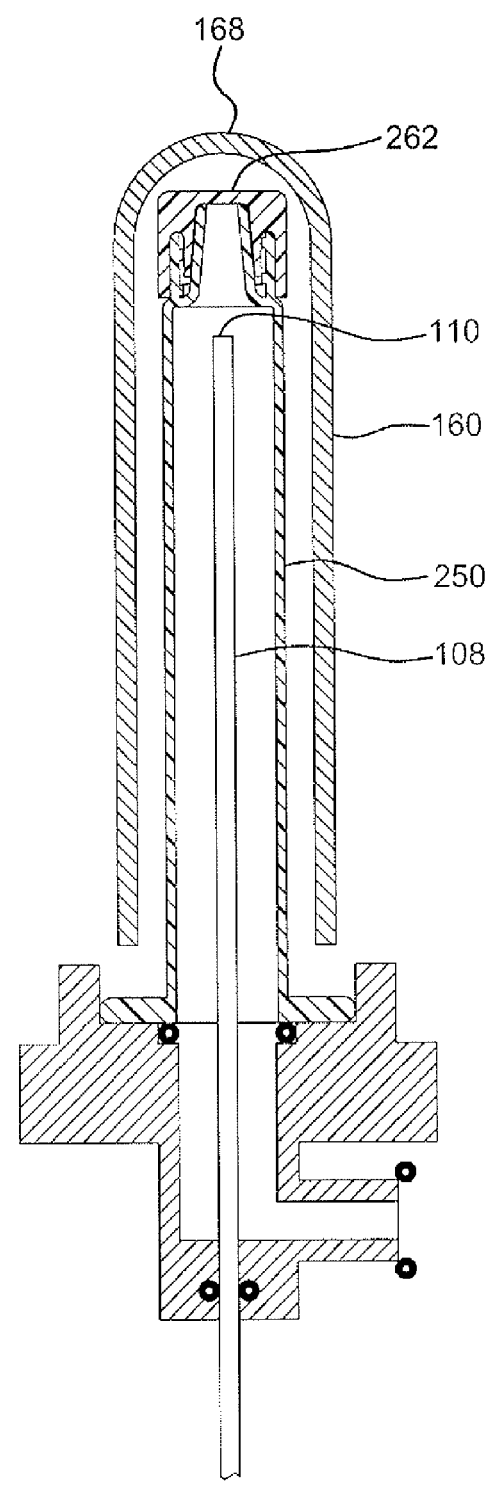
FIG. 20
FIG. 21

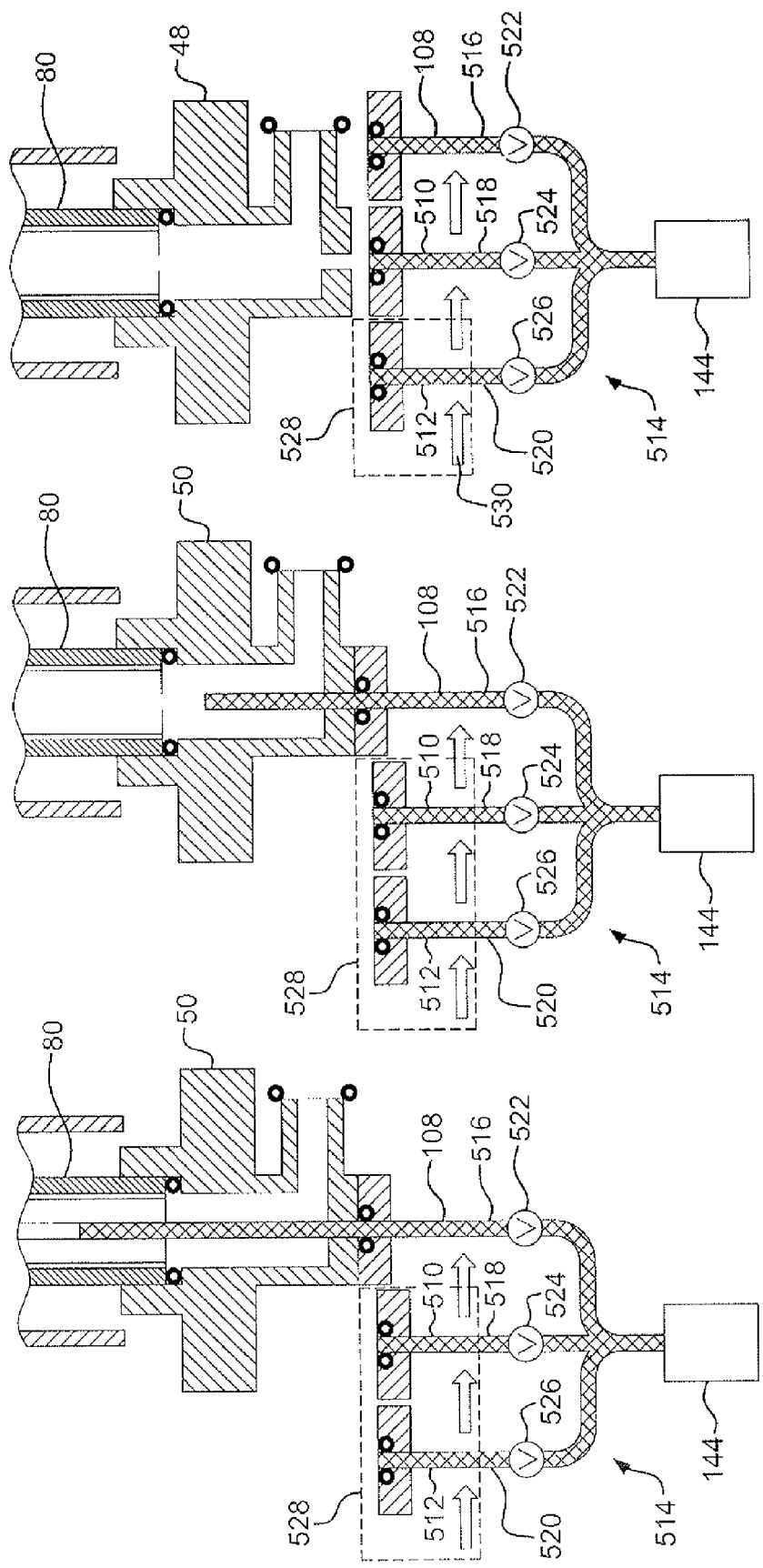

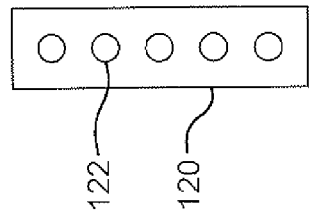
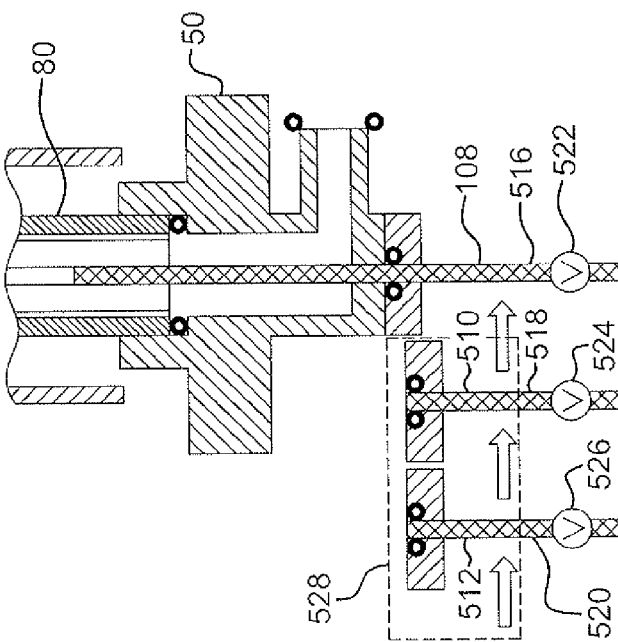
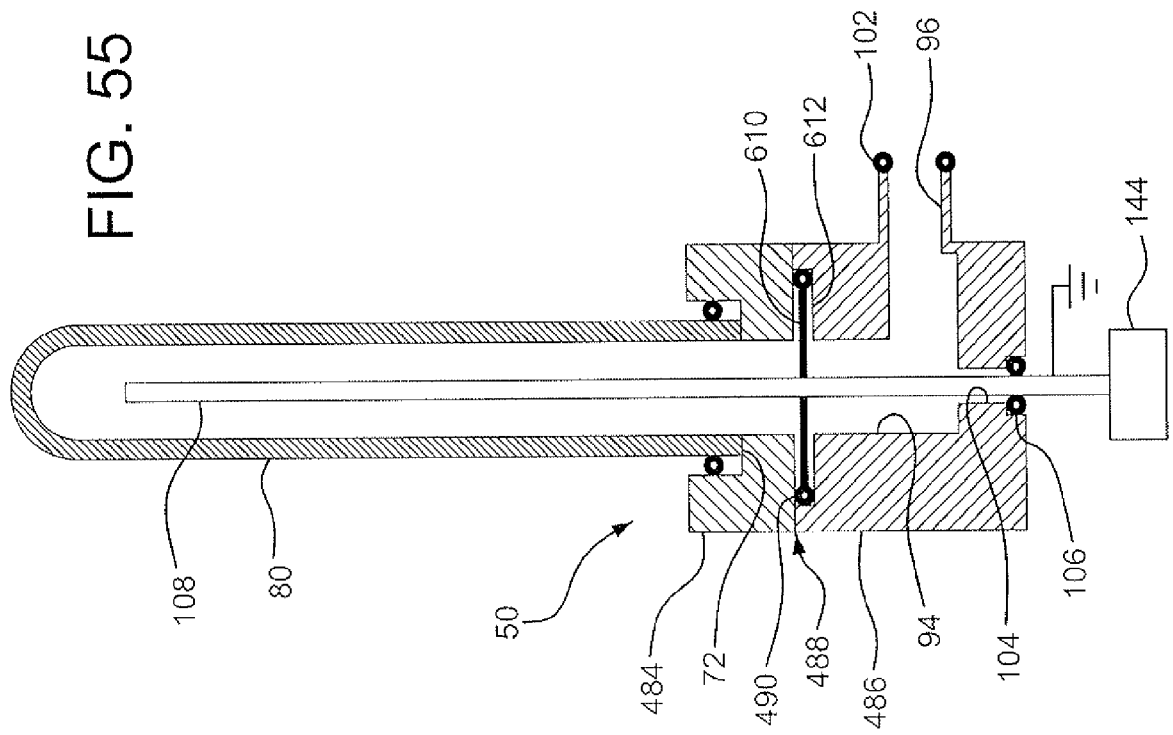

VESSEL, COATING, INSPECTION AND PROCESSING APPARATUS

This application claims the priority of U.S. Provisional Ser. No. 61/177,984 filed May 13, 2009; 61/222,727, filed Jul. 2, 2009; 61/213,904, filed Jul. 24, 2009; 61/234,505, filed Aug. 17, 2009; 61/261,321, filed Nov. 14, 2009; 61/263,289, filed Nov. 20, 2009; 61/285,813, filed Dec. 11, 2009; 61/298,159, filed Jan. 25, 2010; 61/299,888, filed Jan. 29, 2010; 61/318,197, filed Mar. 26, 2010, and 61/333,625, filed May 11, 2010. These applications are incorporated here by reference in their entirety.

Also incorporated by reference in their entirety are the following European patent applications: EP10162755.2 filed May 12, 2010; EP10162760.2 filed May 12, 2010; EP10162756.0 filed May 12, 2010; EP10162758.6 filed May 12, 2010; EP10162761.0 filed May 12, 2010; and EP10162757.8 filed May 12, 2010.

The present invention relates to the technical field of fabrication of coated vessels for storing biologically active compounds or blood. For example, the invention relates to a vessel processing system for coating of a vessel, vessel processing system for coating and inspection of a vessel, to a portable vessel holder for a vessel processing system, to a plasma enhanced chemical vapour deposition apparatus for coating an interior surface of a vessel, to a method for coating an interior surface of a vessel, to a method for coating an inspection of a vessel, to a method of processing a vessel, to the use of a vessel processing system, to a computer-readable medium and to a program element.

The present disclosure also relates to improved methods for processing vessels, for example multiple identical vessels used for venipuncture and other medical sample collection, pharmaceutical preparation storage and delivery, and other purposes. Such vessels are used in large numbers for these purposes, and must be relatively economical to manufacture and yet highly reliable in storage and use.

BACKGROUND OF THE INVENTION

Evacuated blood collection tubes are used for drawing blood from a patient for medical analysis. The tubes are sold evacuated. The patient's blood is communicated to the interior of a tube by inserting one end of a double-ended hypodermic needle into the patient's blood vessel and impaling the closure of the evacuated blood collection tube on the other end of the double-ended needle. The vacuum in the evacuated blood collection tube draws the blood (or more precisely, the blood pressure of the patient pushes the blood) through the needle into the evacuated blood collection tube, increasing the pressure within the tube and thus decreasing the pressure difference causing the blood to flow. The blood flow typically continues until the tube is removed from the needle or the pressure difference is too small to support flow.

Evacuated blood collection tubes should have a substantial shelf life to facilitate efficient and convenient distribution and storage of the tubes prior to use. For example, a one-year shelf life is desirable, and progressively longer shelf lives, such as 18 months, 24 months, or 36 months, are also desired in some instances. The tube desirably remains essentially fully evacuated, at least to the degree necessary to draw enough blood for analysis (a common standard is that the tube retains at least 90% of the original draw volume), for the full shelf life, with very few (optimally no) defective tubes being provided.

A defective tube is likely to cause the phlebotomist using the tube to fail to draw sufficient blood. The phlebotomist might then need to obtain and use one or more additional tubes to obtain an adequate blood sample.

Prefilled syringes are commonly prepared and sold so the syringe does not need to be filled before use. The syringe can be prefilled with saline solution, a dye for injection, or a pharmaceutically active preparation, for some examples.

Commonly, the prefilled syringe is capped at the distal end, as with a cap, and is closed at the proximal end by its drawn plunger. The prefilled syringe can be wrapped in a sterile package before use. To use the prefilled syringe, the packaging and cap are removed, optionally a hypodermic needle or another delivery conduit is attached to the distal end of the barrel, the delivery conduit or syringe is moved to a use position (such as by inserting the hypodermic needle into a patient's blood vessel or into apparatus to be rinsed with the contents of the syringe), and the plunger is advanced in the barrel to inject the contents of the barrel.

One important consideration in manufacturing pre-filled syringes is that the contents of the syringe desirably will have a substantial shelf life, during which it is important to isolate the material filling the syringe from the barrel wall containing it, to avoid leaching material from the barrel into the prefilled contents or vice versa.

Since many of these vessels are inexpensive and used in large quantities, for certain applications it will be useful to reliably obtain the necessary shelf life without increasing the manufacturing cost to a prohibitive level. It is also desirable for certain applications to move away from glass vessels, which can break and are expensive to manufacture, in favor of plastic vessels which are rarely broken in normal use (and if broken do not form sharp shards from remnants of the vessel, like a glass tube would). Glass vessels have been favored because glass is more gas tight and inert to pre-filled contents than untreated plastics. Also, due to its traditional use, glass is well accepted, as it is known to be relatively innocuous when contacted with medical samples or pharmaceutical preparations and the like.

A further consideration when regarding syringes is to ensure that the plunger can move at a constant speed and with a constant force when it is pressed into the barrel. For this purpose, a lubricity layer, either on one or on both of the barrel and the plunger, is desirable.

A non-exhaustive list of patents of possible relevance includes U.S. Pat. Nos. 6,068,884 and 4,844,986 and U.S. Published Applications 20060046006 and 20040267194.

SUMMARY OF THE INVENTION

An aspect of the present invention pertains to a syringe or syringe parts comprising: a barrel and a piston. The barrel has an inner surface and the piston has a side surface engaging the barrel inner surface. At least one of the inner surface and the side surface is a substrate coated with a lubricity layer configured to provide a lower piston sliding force or breakout force than the uncoated substrate.

The lubricity layer has one of the following atomic ratios, measured by X-ray photoelectron spectroscopy (XPS), $Si_wO_xC_y$ or $Si_wN_xC_y$, where w is 1, x in this formula is from about 0.5 to 2.4, and y is from about 0.6 to about 3.

The lubricity layer has a thickness by transmission electron microscopy (TEM) between 10 and 500 nm.

The lubricity layer is deposited by plasma enhanced chemical vapor deposition (PECVD) under conditions effective to form a coating. The lubricity layer is deposited from a precursor selected from a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

Another aspect of the invention is a syringe having a barrel and a plunger. The barrel has an inner surface and the plunger has a side surface engaging the barrel inner surface.

At least one of the inner surface and the side surface is a substrate treated by applying a lubricity layer having one of the following atomic ratios, measured by X-ray photoelectron spectroscopy (XPS), $Si_wO_xC_y$, or $Si_wN_xC_y$, where w is 1, x in this formula is from about 0.5 to 2.4, and y is from about 0.6 to about 3.

The lubricity layer is configured to provide a lower piston sliding force or breakout force than the uncoated substrate and is applied by the following process. A precursor is provided selected from a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors. The precursor is applied as a coating to a substrate. The coating is polymerized or crosslinked, or both, by plasma enhanced chemical vapor deposition (PECVD).

Other aspects of the invention will be apparent from this disclosure and the accompanying drawings.

BRIEF DESCRIPTION OF THE DRAWINGS

FIG. 20 is an exploded longitudinal sectional view of a syringe and cap adapted for use as a prefilled syringe.

FIG. 21 is a view generally similar to FIG. 2 showing a capped syringe barrel and vessel holder in a coating station according to an embodiment of the disclosure.

FIG. 42 also shows an alternative syringe barrel construction usable, for example, with the embodiments of FIGS. 2, 3, 6-10, 12-22, 26-28, 33-34, and 37-41.

FIG. 46 is a schematic sectional view of an array of gas delivery tubes and a mechanism for inserting and removing the gas delivery tubes from a vessel holder, showing a gas delivery tube in its fully advanced position.

FIG. 47 is a view similar to FIG. 46, showing a gas delivery tube in an intermediate position.

FIG. 48 is a view similar to FIG. 46, showing a gas delivery tube in a retracted position. The array of gas delivery tubes of FIGS. 46-48 are usable, for example, with the embodiments of FIGS. 1, 2, 3, 8, 9, 12-16, 18-19, 21-22, 26-28, 33-35, 37-45, 49, and 52-54. The mechanism of FIGS. 46-48 is usable, for example, with the gas delivery tube embodiments of FIGS. 2, 3, 8, 9, 12-16, 18-19, 21-22, 26-28, 33-35, 37-45, 49, and 52-54, as well as with the probes of the vessel inspection apparatus of FIGS. 6 and 7.

FIG. 55 is a diagrammatic view similar to FIG. 2 of an embodiment of the invention including a plasma screen.

FIG. 56 is a schematic sectional view of an array of gas delivery tubes, having independent gas supplies and a mechanism for inserting and removing the gas delivery tubes from a vessel holder.

FIG. 58 shows a linear rack, otherwise similar to FIG. 4.

Figure 1:
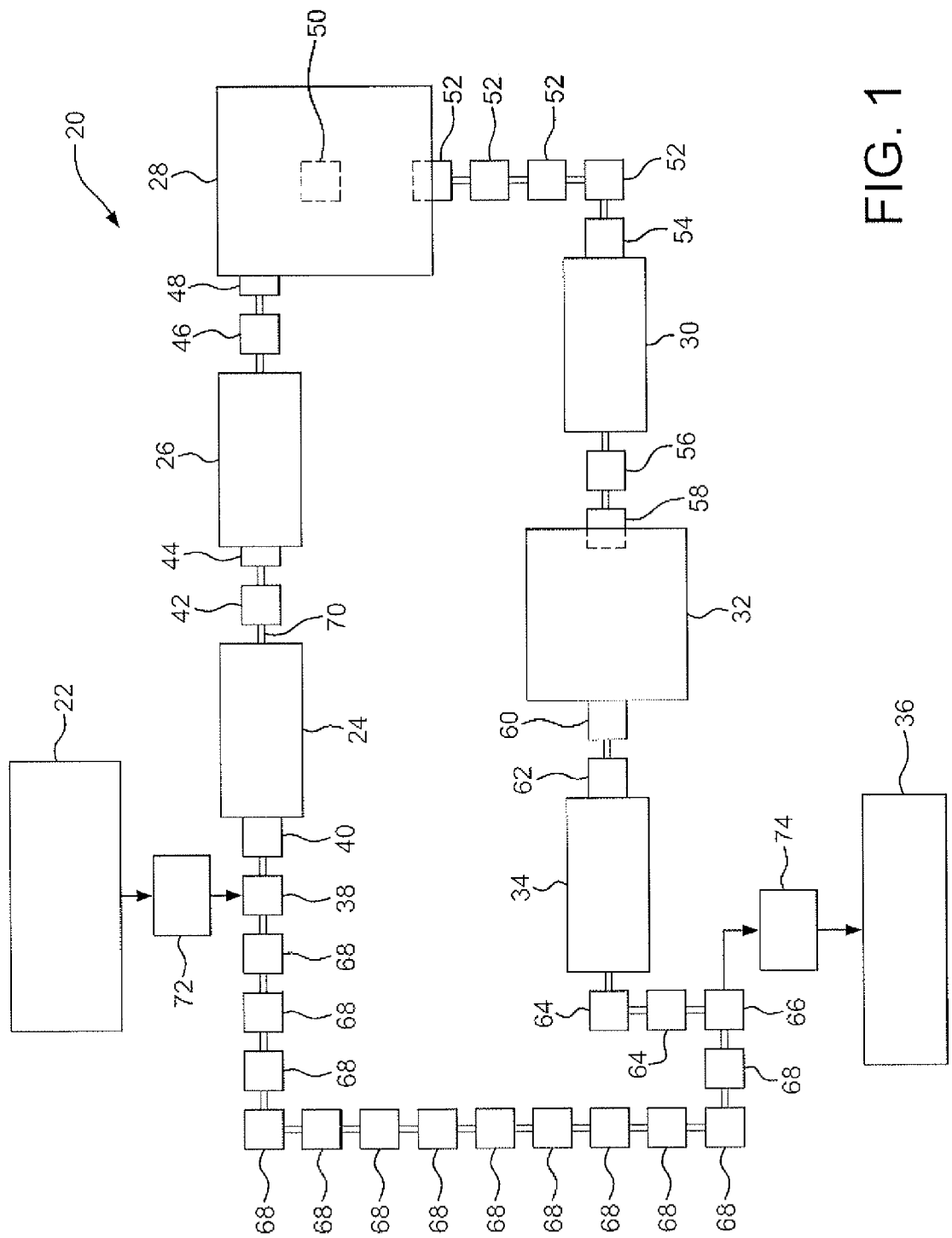
FIG. 1 is a schematic diagram showing a vessel processing system according to an embodiment of the disclosure.

The following reference characters are used in the drawing figures:

| | |
|---|---|
| 20 | Vessel processing system |
| 22 | Injection molding machine |
| 24 | Visual inspection station |
| 26 | Inspection station (pre-coating) |
| 28 | Coating station |
| 30 | Inspection station (post-coating) |
| 32 | Optical source transmission station (thickness) |
| 34 | Optical source transmission station (defects) |
| 36 | Output |
| 38 | Vessel holder |
| 40 | Vessel holder |
| 42 | Vessel holder |
| 44 | Vessel holder |
| 46 | Vessel holder |
| 48 | Vessel holder |
| 50 | Vessel holder |
| 52 | Vessel holder |
| 54 | Vessel holder |
| 56 | Vessel holder |
| 58 | Vessel holder |
| 60 | Vessel holder |
| 62 | Vessel holder |
| 64 | Vessel holder |
| 66 | Vessel holder |
| 68 | Vessel holder |
| 70 | Conveyor |
| 72 | Transfer mechanism (on) |
| 74 | Transfer mechanism (off) |
| 80 | Vessel |
| 82 | Opening |
| 84 | Closed end |
| 86 | Wall |
| 88 | Interior surface |
| 90 | Barrier layer |
| 92 | Vessel port |
| 94 | Vacuum duct |
| 96 | Vacuum port |
| 98 | Vacuum source |
| 100 | O-ring (of 92) |
| 102 | O-ring (of 96) |
| 104 | Gas inlet port |
| 106 | O-ring (of 100) |
| 108 | Probe (counter electrode) |
| 110 | Gas delivery port (of 108) |
| 112 | Vessel holder (FIG. 3) |
| 114 | Housing (of 50 or 112) |
| 116 | Collar |
| 118 | Exterior surface (of 80) |
| 120 | Vessel holder (array) |
| 122 | Vessel port (FIG. 4, 58) |
| 130 | Frame (FIG. 5) |
| 132 | Light source |
| 134 | Side channel |
| 136 | Shut-off valve |
| 138 | Probe port |
| 140 | Vacuum port |
| 142 | PECVD gas inlet port |
| 144 | PECVD gas source |
| 146 | Vacuum line (to 98) |
| 148 | Shut-off valve |
| 150 | Flexible line (of 134) |
| 152 | Pressure gauge |
| 154 | Interior of vessel 80 |
| 160 | Electrode |
| 162 | Power supply |
| 164 | Sidewall (of 160) |
| 166 | Sidewall (of 160) |
| 168 | Closed end (of 160) |
| 170 | Light source (FIG. 10) |
| 172 | Detector |

Figure 36:
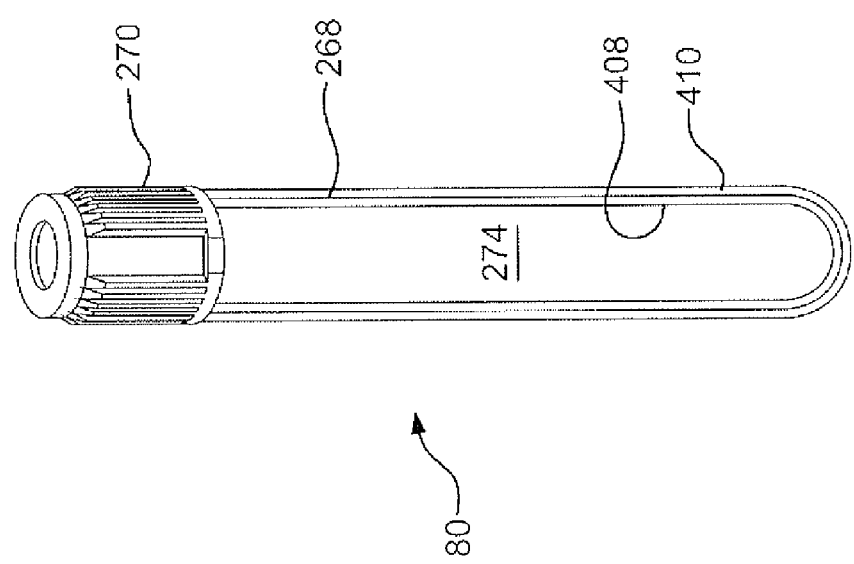
FIG. 36 is a perspective view of a double-walled blood collection tube assembly according to still another embodiment of the invention.

| | | |
|---|---|---|
| 174 | Pixel (of 172) | |
| 176 | Interior surface (of 172) | |
| 182 | Aperture (of 186) | |
| 184 | Wall (of 186) | |
| 186 | Integrating sphere | |
| 190 | Microwave power supply | |
| 192 | Waveguide | |
| 194 | Microwave cavity | |
| 196 | Gap | |
| 198 | Top end (of 194) | |
| 200 | Electrode | |
| 202 | Tube transport | |
| 204 | Suction cup | |
| 208 | Mold core | |
| 210 | Mold cavity | |
| 212 | Mold cavity liner | |
| 220 | Bearing surface (FIG. 2) | |
| 222 | Bearing surface (FIG. 2) | |
| 224 | Bearing surface (FIG. 2) | |
| 226 | Bearing surface (FIG. 2) | |
| 228 | Bearing surface (FIG. 2) | |
| 230 | Bearing surface (FIG. 2) | |
| 232 | Bearing surface (FIG. 2) | |
| 234 | Bearing surface (FIG. 2) | |
| 236 | Bearing surface (FIG. 2) | |
| 238 | Bearing surface (FIG. 2) | |
| 240 | Bearing surface (FIG. 2) | |
| 250 | Syringe barrel | |
| 252 | Syringe | |
| 254 | Interior surface (of 250) | |
| 256 | Back end (of 250) | |
| 258 | Plunger (of 252) | |
| 260 | Front end (of 250) | |
| 262 | Cap | |
| 264 | Interior surface (of 262) | |
| 266 | Fitting | |
| 268 | Vessel | |
| 270 | Closure | |
| 272 | Interior facing surface | |
| 274 | Lumen | |
| 276 | Wall-contacting surface | |
| 278 | Inner surface (of 280) | |
| 280 | Vessel wall | |
| 282 | Stopper | |
| 284 | Shield | |
| 286 | Lubricity layer | |
| 288 | Barrier layer | |
| 290 | Apparatus for coating, for example, 250 | |
| 292 | Inner surface (of 294) | |
| 294 | Restricted opening (of 250) | |
| 296 | Processing vessel | |
| 298 | Outer surface (of 250) | |
| 300 | Lumen (of 250) | |
| 302 | Larger opening (of 250) | |
| 304 | Processing vessel lumen | |
| 306 | Processing vessel opening | |
| 308 | Inner electrode | |
| 310 | Interior passage (of 308) | |
| 312 | Proximal end (of 308) | |
| 314 | Distal end (of 308) | |
| 316 | Distal opening (of 308) | |
| 318 | Plasma | |
| 320 | Vessel support | |
| 322 | Port (of 320) | |
| 324 | Processing vessel (conduit type) | |
| 326 | Vessel opening (of 324) | |
| 328 | Second opening (of 324) | |
| 330 | Vacuum port (receiving 328) | |
| 332 | First fitting (male Luer taper) | |
| 334 | Second fitting (female Luer taper) | |
| 336 | Locking collar (of 332) | |
| 338 | First abutment (of 332) | |
| 340 | Second abutment (of 332) | |
| 342 | O-ring | |
| 344 | Dog | |
| 346 | Wall | |
| 348 | Coating (on 346) | |
| 350 | Permeation path | |
| 352 | Vacuum | |
| 354 | Gas molecule | |
| 355 | Gas molecule | |
| 356 | Interface (between 346 and 348) | |
| 357 | Gas molecule | |
| 358 | PET vessel | |
| 359 | Gas molecule | |
| 360 | Seal | |
| 362 | Measurement cell | |
| 364 | Vacuum pump | |
| 366 | Arrows | |
| 368 | Conical passage | |
| 370 | Bore | |
| 372 | Bore | |
| 374 | Chamber | |
| 376 | Chamber | |
| 378 | Diaphragm | |
| 380 | Diaphragm | |
| 382 | Conductive surface | |
| 384 | Conductive surface | |
| 386 | Bypass | |
| 390 | Plot (glass tube) | |
| 392 | Plot (PET uncoated) | |
| 394 | Main plot (SiO$_2$ coated) | |
| 396 | Outliers (SiO$_2$ coated) | |
| 398 | Inner electrode and gas supply tube | |
| 400 | Distal opening | |
| 402 | Extension counter electrode | |
| 404 | Vent (FIG. 7) | |
| 406 | Valve | |
| 408 | Inner wall (FIG. 36) | |
| 410 | Outer wall (FIG. 36) | |
| 412 | Interior surface (FIG. 36) | |
| 414 | Plate electrode (FIG. 37) | |
| 416 | Plate electrode (FIG. 37) | |
| 418 | Vacuum conduit | |
| 420 | Vessel holder | |
| 422 | Vacuum chamber | |
| 424 | Vessel holder | |
| 426 | Counter electrode | |
| 428 | Vessel holder (FIG. 39) | |
| 430 | Electrode assembly | |
| 432 | Volume enclosed by 430 | |
| 434 | Pressure proportioning valve | |
| 436 | Vacuum chamber conduit | |
| 438 | Syringe barrel (FIG. 42) | |
| 440 | Flange (of 438) | |
| 442 | Back opening (of 438) | |
| 444 | Barrel wall (of 438) | |
| 450 | Vessel holder (FIG. 42) | |
| 452 | Annular lip | |
| 454 | Generally cylindrical sidewall (of 438) | |
| 456 | Generally cylindrical inner surface (of 450) | |
| 458 | Abutment | |
| 460 | Pocket | |
| 462 | O-ring | |
| 464 | Outside wall (of 460) | |
| 466 | Bottom wall (of 460) | |
| 468 | Top wall (of 460) | |
| 470 | Inner electrode (FIG. 44) | |
| 472 | Distal portion (of 470) | |
| 474 | Porous side wall (of 472) | |
| 476 | Internal passage (of 472) | |
| 478 | Proximal portion (of 470) | |
| 480 | Distal end (of 470) | |
| 482 | Vessel holder body | |
| 484 | Upper portion (of 482) | |
| 486 | Base portion (of 482) | |
| 488 | Joint (between 484 and 486) | |
| 490 | O-ring | |
| 492 | Annular pocket | |

| | |
|---|---|
| 494 | Radially extending abutment surface |
| 496 | Radially extending wall |
| 498 | Screw |
| 500 | Screw |
| 502 | Vessel port |
| 504 | Second O-ring |
| 506 | Inner diameter (of 490) |
| 508 | Vacuum duct (of 482) |
| 510 | Inner electrode |
| 512 | Inner electrode |
| 514 | Insertion and removal mechanism |
| 516 | Flexible hose |
| 518 | Flexible hose |
| 520 | Flexible hose |
| 522 | Valve |
| 524 | Valve |
| 526 | Valve |
| 528 | Electrode cleaning station |
| 530 | Inner electrode drive |
| 532 | Cleaning reactor |
| 534 | Vent valve |
| 536 | Second gripper |
| 538 | Conveyer |
| 539 | Solute retainer |
| 540 | Open end (of 532) |
| 542 | Interior space (of 532) |
| 544 | Syringe |
| 546 | Plunger |
| 548 | Body |
| 550 | Barrel |
| 552 | Interior surface (of 550) |
| 554 | Coating |
| 556 | Luer fitting |
| 558 | Luer taper |
| 560 | Internal passage (of 558) |
| 562 | Internal surface |
| 564 | Coupling |
| 566 | Male part (of 564) |
| 568 | Female part (of 564) |
| 570 | Barrier layer |
| 572 | Locking collar |
| 574 | Main vacuum valve |
| 576 | Vacuum line |
| 578 | Manual bypass valve |
| 580 | Bypass line |
| 582 | Vent valve |
| 584 | Main reactant gas valve |
| 586 | Main reactant feed line |
| 588 | Organosilicon liquid reservoir |
| 590 | Organosilicon feed line (capillary) |
| 592 | Organosilicon shut-off valve |
| 594 | Oxygen tank |
| 596 | Oxygen feed line |
| 598 | Mass flow controller |
| 600 | Oxygen shut-off valve |
| 602 | Syringe exterior barrier layer |
| 604 | Lumen |
| 606 | Barrel exterior surface |
| 610 | Plasma screen |
| 612 | Plasma screen cavity |
| 614 | Headspace |
| 616 | Pressure source |
| 618 | Pressure line |
| 620 | Capillary connection |
| 630 | Plots for uncoated COC |
| 632 | Plots for SiOx coated COC |
| 634 | Plots for glass |
| 5501 | First processing station |
| 5502 | Second processing station |
| 5503 | Third processing station |
| 5504 | Fourth processing station |
| 5505 | Processor |
| 5506 | User interface |
| 5507 | Bus |
| 5701 | PECVD apparatus |
| 5702 | First detector |
| 5703 | Second detector |
| 5704 | Detector |
| 5705 | Detector |
| 5706 | Detector |
| 5707 | Detector |
| 7001 | Conveyor exit branch |
| 7002 | Conveyor exit branch |
| 7003 | Conveyor exit branch |
| 7004 | Conveyor exit branch |

DETAILED DESCRIPTION OF THE PREFERRED EMBODIMENTS

The present invention will now be described more fully with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout.

DEFINITION SECTION

In the context of the present invention, the following definitions and abbreviations are used:

RF is radio frequency; sccm is standard cubic centimeters per minute.

The term "at least" in the context of the present invention means "equal or more" than the integer following the term. The word "comprising" does not exclude other elements or steps, and the indefinite article "a" or "an" does not exclude a plurality unless indicated otherwise.

"First" and "second" or similar references to, e.g., processing stations or processing devices refer to the minimum number of processing stations or devices that are present, but do not necessarily represent the order or total number of processing stations and devices. These terms do not limit the number of processing stations or the particular processing carried out at the respective stations.

For purposes of the present invention, an "organosilicon precursor" is a compound having at least one of the linkage:

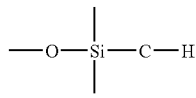

which is a tetravalent silicon atom connected to an oxygen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

In the context of the present invention, "essentially no oxygen" or (synonymously) "substantially no oxygen" is added to the gaseous reactant in some embodiments. This means that some residual atmospheric oxygen can be present in the reaction space, and residual oxygen fed in a previous step and not fully exhausted can be present in the reaction space, which are defined here as essentially no oxygen present. Essentially no oxygen is present in the gaseous reactant if the gaseous reactant comprises less than 1 vol % $O_2$, for example less than 0.5 vol % $O_2$, and optionally is $O_2$-free. If no oxygen is added to the gaseous reactant, or if no oxygen at all is present during PECVD, this is also within the scope of "essentially no oxygen."

A "vessel" in the context of the present invention can be any type of vessel with at least one opening and a wall defining an interior surface. The term "at least" in the context of the present invention means "equal or more" than the integer following the term. Thus, a vessel in the context of the present invention has one or more openings. One or two openings, like the openings of a sample tube (one opening) or a syringe barrel (two openings) are preferred. If the vessel has two openings, they can be of same or different size. If there is more than one opening, one opening can be used for the gas inlet for a PECVD coating method according to the present invention, while the other openings are either capped or open. A vessel according to the present invention can be a sample tube, e.g. for collecting or storing biological fluids like blood or urine, a syringe (or a part thereof, for example a syringe barrel) for storing or delivering a biologically active compound or composition, e.g. a medicament or pharmaceutical composition, a vial for storing biological materials or biologically active compounds or compositions, a pipe, e.g. a catheter for transporting biological materials or biologically active compounds or compositions, or a cuvette for holding fluids, e.g. for holding biological materials or biologically active compounds or compositions.

A vessel can be of any shape, a vessel having a substantially cylindrical wall adjacent to at least one of its open ends being preferred. Generally, the interior wall of the vessel is cylindrically shaped, like, e.g. in a sample tube or a syringe barrel. Sample tubes and syringes or their parts (for example syringe barrels) are contemplated.

A "hydrophobic layer" in the context of the present invention means that the coating lowers the wetting tension of a surface coated with the coating, compared to the corresponding uncoated surface. Hydrophobicity is thus a function of both the uncoated substrate and the coating. The same applies with appropriate alterations for other contexts wherein the term "hydrophobic" is used. The term "hydrophilic" means the opposite, i.e. that the wetting tension is increased compared to reference sample. The present hydrophobic layers are primarily defined by their hydrophobicity and the process conditions providing hydrophobicity, and optionally can have a composition according to the empirical composition or sum formula $Si_wO_xC_yH_z$, for example where w is 1, x is from about 0.5 to about 2.4, y is from about 0.6 to about 3, and z is from about 2 to about 9, optionally where w is 1, x is from about 0.5 to 1, y is from about 2 to about 3, and z is from 6 to about 9. These values of w, x, y, and z are applicable to the empirical composition $Si_wO_xC_yH_z$ throughout this specification. The values of w, x, y, and z used throughout this specification should be understood as ratios or an empirical formula (e.g. for a coating), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$.

"Wetting tension" is a specific measure for the hydrophobicity or hydrophilicity of a surface. An optional wetting tension measurement method in the context of the present invention is ASTM D 2578 or a modification of the method described in ASTM D 2578. This method uses standard wetting tension solutions (called dyne solutions) to determine the solution that comes nearest to wetting a plastic film surface for exactly two seconds. This is the film's wetting tension. The procedure utilized is varied herein from ASTM D 2578 in that the substrates are not flat plastic films, but are tubes made according to the Protocol for Forming PET Tube and (except for controls) coated according to the Protocol for Coating Tube Interior with Hydrophobic Layer (see Example 9).

A "lubricity layer" according to the present invention is a coating which has a lower frictional resistance than the uncoated surface. In other words, it reduces the frictional resistance of the coated surface in comparison to the a reference surface which is uncoated. The present lubricity layers are primarily defined by their lower frictional resistance than the uncoated surface and the process conditions providing lower frictional resistance than the uncoated surface, and optionally can have a composition according to the empirical composition $Si_wO_xC_yH_z$, as defined in this Definition Section. "Frictional resistance" can be static frictional resistance and/or kinetic frictional resistance. One of the optional embodiments of the present invention is a syringe part, e.g. a syringe barrel or plunger, coated with a lubricity layer. In this contemplated embodiment, the relevant static frictional resistance in the context of the present invention is the breakout force as defined herein, and the relevant kinetic frictional resistance in the context of the present invention is the plunger sliding force as defined herein. For example, the plunger sliding force as defined and determined herein is suitable to determine the presence or absence and the lubricity characteristics of a lubricity layer in the context of the present invention whenever the coating is applied to any syringe or syringe part, for example to the inner wall of a syringe barrel. The breakout force is of particular relevance for evaluation of the coating effect on a prefilled syringe, i.e. a syringe which is filled after coating and can be stored for some time, e.g. several months or even years, before the plunger is moved again (has to be "broken out").

The "plunger sliding force" in the context of the present invention is the force required to maintain movement of a plunger in a syringe barrel, e.g. during aspiration or dispense. It can advantageously be determined using the ISO 7886-1: 1993 test described herein and known in the art. A synonym for "plunger sliding force" often used in the art is "plunger force" or "pushing force".

The "breakout force" in the context of the present invention is the initial force required to move the plunger in a syringe, for example in a prefilled syringe.

Both "plunger sliding force" and "breakout force" and methods for their measurement are described in more detail in subsequent parts of this description.

"Slidably" means that the plunger is permitted to slide in a syringe barrel.

In the context of this invention, "substantially rigid" means that the assembled components (ports, duct, and housing, explained further below) can be moved as a unit by handling the housing, without significant displacement of any of the assembled components respecting the others. Specifically, none of the components are connected by hoses or the like that allow substantial relative movement among the parts in normal use. The provision of a substantially rigid relation of these parts allows the location of the vessel seated on the vessel holder to be nearly as well known and precise as the locations of these parts secured to the housing.

In the following, the apparatus for performing the present invention will be described first, followed by the coating methods, coatings and coated vessels, and the uses according to the present invention.

I. Vessel Processing System Having Multiple Processing Stations and Multiple Vessel Holders I. A vessel processing system is contemplated comprising a first processing station, a second processing station, a multiplicity of vessel holders, and a conveyor. The first processing station is configured for processing a vessel having an opening and a wall defining an interior surface. The second processing station is spaced from the first processing station and configured for processing a vessel having an opening and a wall defining an interior surface.

I. At least some, optionally all, of the vessel holders include a vessel port configured to receive and seat the opening of a vessel for processing the interior surface of a seated vessel via the vessel port at the first processing station. The conveyor is configured for transporting a series of the vessel holders and seated vessels from the first processing station to the second processing station for processing the interior surface of a seated vessel via the vessel port at the second processing station.

I. Referring first to FIG. 1, a vessel processing system generally indicated as 20 is shown. The vessel processing system can include processing stations which more broadly are contemplated to be processing devices. The vessel processing system 20 of the illustrated embodiment can include an injection molding machine 22 (which can be regarded as a processing station or device), additional processing stations or devices 24, 26, 28, 30, 32, and 34, and an output 36 (which can be regarded as a processing station or device). At a minimum, the system 20 has at least a first processing station, for example station 28, and a second processing station, for example 30, 32, or 34.

I. Any of the processing stations 22-36 in the illustrated embodiment can be a first processing station, any other processing station can be a second processing station, and so forth.

I. The embodiment illustrated in FIG. 1 can include eight processing stations or devices: 22, 24, 26, 28, 30, 32, 34, and 36. The exemplary vessel processing system 20 includes an injection molding machine 22, a post-molding inspection station 24, a pre-coating inspection station 26, a coating station 28, a post-coating inspection station 30, an optical source transmission station 32 to determine the thickness of the coating, an optical source transmission station 34 to examine the coating for defects, and an output station 36.

I. The system 20 can include a transfer mechanism 72 for moving vessels from the injection molding machine 22 to a vessel holder 38. The transfer mechanism 72 can be configured, for example, as a robotic arm that locates, moves to, grips, transfers, orients, seats, and releases the vessels 80 to remove them from the vessel forming machine 22 and install them on the vessel holders such as 38.

I. The system 20 also can include a transfer mechanism at a processing station 74 for removing the vessel from one or more vessel holders such as 66, following processing the interior surface of the seated vessel such as 80 (FIG. 1). The vessels 80 are thus movable from the vessel holder 66 to packaging, storage, or another appropriate area or process step, generally indicated as 36. The transfer mechanism 74 can be configured, for example, as a robotic arm that locates, moves to, grips, transfers, orients, places, and releases the vessels 80 to remove them from the vessel holders such as 38 and place them on other equipment at the station 36.

I. The processing stations or devices 32, 34, and 36 shown in FIG. 1 optionally carry out one or more appropriate steps downstream of the coating and inspection system 20, after the individual vessels 80 are removed from the vessel holders such as 64. Some non-limiting examples of functions of the stations or devices 32, 34, and 36 include:

placing the treated and inspected vessels 80 on a conveyor to further processing apparatus;
adding chemicals to the vessels;
capping the vessels;
placing the vessels in suitable processing racks;
packaging the vessels; and
sterilizing the packaged vessels.

I. The vessel processing system 20 as illustrated in FIG. 1 also can include a multiplicity of vessel holders (or "pucks," as they can in some embodiments resemble a hockey puck) respectively 38 through 68, and a conveyor generally indicated as an endless band 70 for transporting one or more of the vessel holders 38-68, and thus vessels such as 80, to or from the processing stations 22, 24, 26, 28, 30, 32, 34, and 36.

I. The processing station or device 22 can be a device for forming the vessels 80. One contemplated device 22 can be an injection molding machine. Another contemplated device 22 can be a blow molding machine. Vacuum molding machines, draw molding machines, cutting or milling machines, glass drawing machines for glass or other draw-formable materials, or other types of vessel forming machines are also contemplated. Optionally, the vessel forming station 22 can be omitted, as vessels can be obtained already formed.

II. Vessel Holders

II.A. The portable vessel holders 38-68 are provided for holding and conveying a vessel having an opening while the vessel is processed. The vessel holder includes a vessel port, a second port, a duct, and a conveyable housing.

II.A. The vessel port is configured to seat a vessel opening in a mutually communicating relation. The second port is configured to receive an outside gas supply or vent. The duct is configured for passing one or more gases between a vessel opening seated on the vessel port and the second port. The vessel port, second port, and duct are attached in substantially rigid relation to the conveyable housing. Optionally, the portable vessel holder weighs less than five pounds. An advantage of a lightweight vessel holder is that it can more readily be transported from one processing station to another.

II.A. In certain embodiments of the vessel holder the duct more specifically is a vacuum duct and the second port more specifically is a vacuum port. The vacuum duct is configured for withdrawing a gas via the vessel port from a vessel seated on the vessel port. The vacuum port is configured for communicating between the vacuum duct and an outside source of vacuum. The vessel port, vacuum duct, and vacuum port can be attached in substantially rigid relation to the conveyable housing.

II.A. The vessel holders of embodiments II.A. and II.A.1. are shown, for example, in FIG. 2. The vessel holder 50 has a vessel port 82 configured to receive and seat the opening of a vessel 80. The interior surface of a seated vessel 80 can be processed via the vessel port 82. The vessel holder 50 can include a duct, for example a vacuum duct 94, for withdrawing a gas from a vessel 80 seated on the vessel port 92. The vessel holder can include a second port, for example a vacuum port 96 communicating between the vacuum duct 94 and an outside source of vacuum, such as the vacuum pump 98. The vessel port 92 and vacuum port 96 can have sealing elements, for example O-ring butt seals, respectively 100 and 102, or side seals between an inner or outer cylindrical wall of the vessel port 82 and an inner or outer cylindrical wall of the vessel 80 to receive and form a seal with the vessel 80 or outside source of vacuum 98 while allowing communication through the port. Gaskets or other sealing arrangements can or also be used.

II.A. The vessel holder such as 50 can be made of any material, for example thermoplastic material and/or electrically nonconductive material. Or, the vessel holder such as 50 can be made partially, or even primarily, of electrically conductive material and faced with electrically nonconductive material, for example in the passages defined by the vessel port 92, vacuum duct 94, and vacuum port 96. Examples of suitable materials for the vessel holder 50 are: a polyacetal, for example Delrin® acetal material sold by E. I. du Pont De Nemours and Company, Wilmington Del.; polytetrafluoroethylene (PTFE), for example Teflon® PTFE sold by E. I. du Pont De Nemours and Company, Wilmington Del.; Ultra-High-Molecular-Weight Polyethylene (UHMWPE); High density Polyethylene (HDPE); or other materials known in the art or newly discovered.

Figure 2:
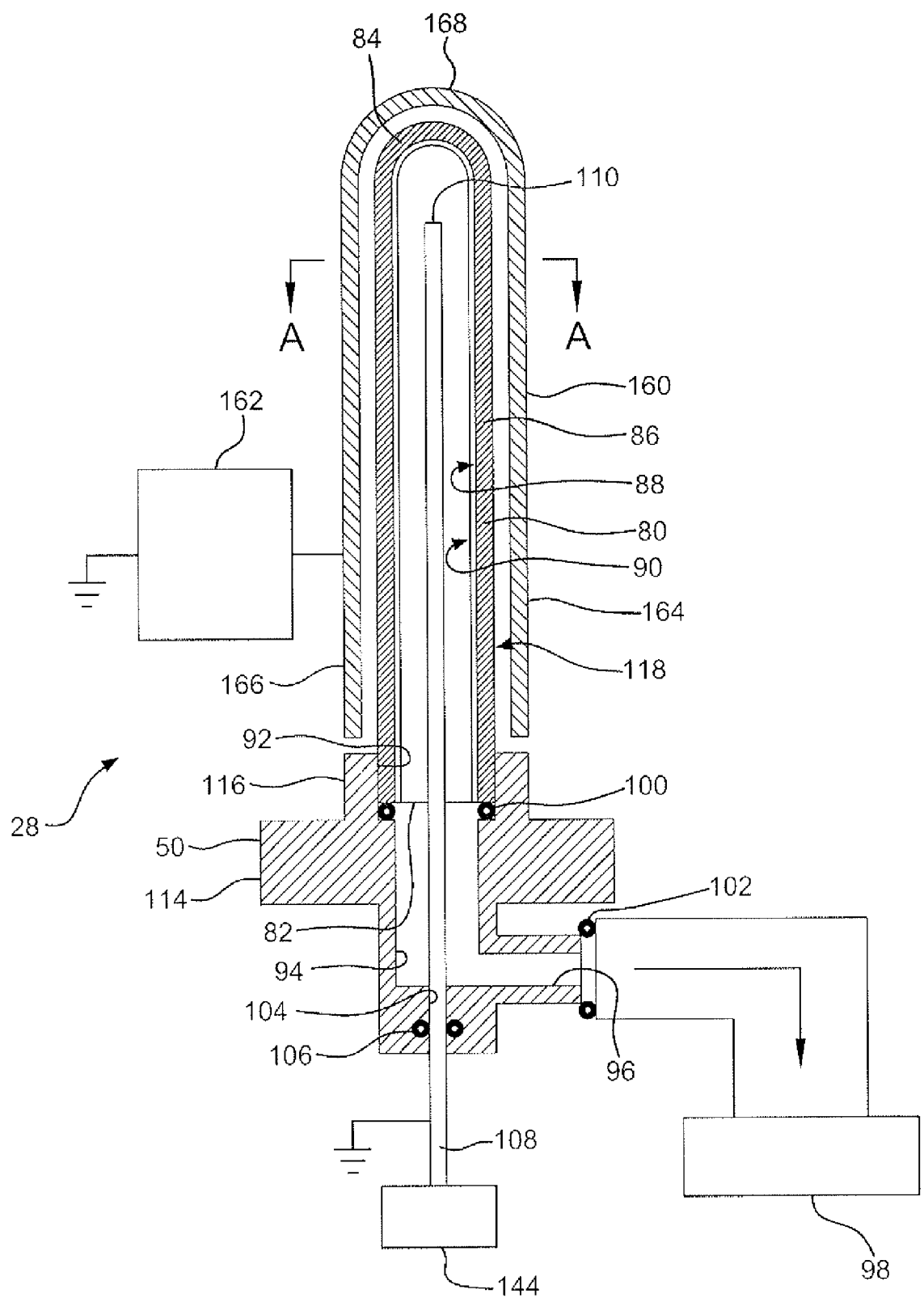
FIG. 2 is a schematic sectional view of a vessel holder in a coating station according to an embodiment of the disclosure.

II.A. FIG. 2 also illustrates that the vessel holder, for example 50, can have a collar 116 for centering the vessel 80 when it is approaching or seated on the port 92.

Array of Vessel Holders

II.A. Yet another approach to treat, inspect, and/or move parts through a production system can be to use an array of vessel holders. The array can be comprised of individual pucks or be a solid array into which the devices are loaded. An array can allow more than one device, optionally many devices, to be tested, conveyed or treated/coated simultaneously. The array can be one-dimensional, for example grouped together to form a linear rack, or two-dimensional, similar to a tub or tray.

Figure 4:
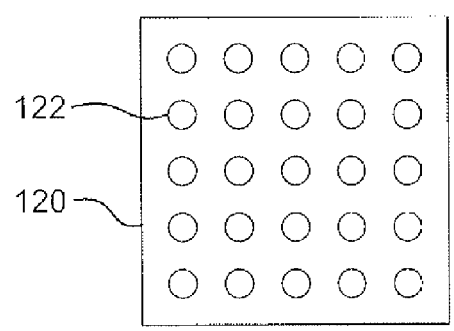
FIG. 4 is a diagrammatic plan view of an alternative embodiment of the vessel holder.
Figure 5:
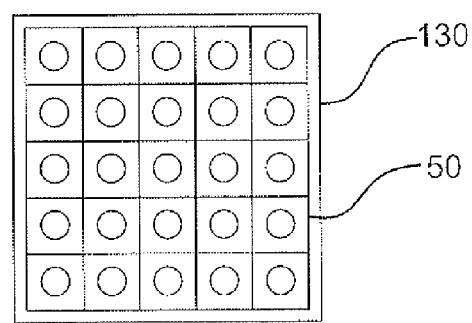
FIG. 5 is a diagrammatic plan view of another alternative embodiment of the vessel holder.

II.A. FIGS. 4, 5, and 58 show three array approaches. FIG. 4 shows a solid array 120 into (or onto) which the devices or vessels 80 are loaded. In this case, the devices or vessels 80 can move through the production process as a solid array, although they can be removed during the production process and transferred to individual vessel holders. A single vessel holder 120 has multiple vessel ports such as 122 for conveying an array of seated vessels such as 80, moving as a unit. In this embodiment, multiple individual vacuum ports such as 96 can be provided to receive an array of vacuum sources 98. Or, a single vacuum port connected to all the vessel ports such as 96 can be provided. Multiple gas inlet probes such as 108 can also be provided in an array. The arrays of gas inlet probes or vacuum sources can be mounted to move as a unit to process many vessels such as 80 simultaneously. Or, the multiple vessel ports such as 122 can be addressed one or more rows at a time, or individually, in a processing station. The number of devices in the array can be related to the number of devices that are molded in a single step or to other tests or steps that can allow for efficiency during the operation. In the case of treating/coating an array, the electrodes can either be coupled together (to form one large electrode), or can be individual electrodes each with its own power supply. All of the above approaches can still be applicable (from the standpoint of the electrode geometry, frequency etc.).

II.A. In FIG. 5, individual pucks or vessel holders (as discussed above) are brought together into an array, as by surrounding them with an external frame 130. This arrangement provides the advantages of the solid array of FIG. 4, when that is desired, and also allows the array to be disassembled for other processing steps in which the vessels 80 are addressed in different arrays or singly.

II.A. FIG. 58 shows a linear rack, otherwise similar to FIG. 4. If a linear rack is used, another option, in addition to those explained above, is to transport the rack in single file fashion through a processing station, processing the vessels serially.

II.B. Vessel Holder Including O-Ring Arrangement

Figure 42:
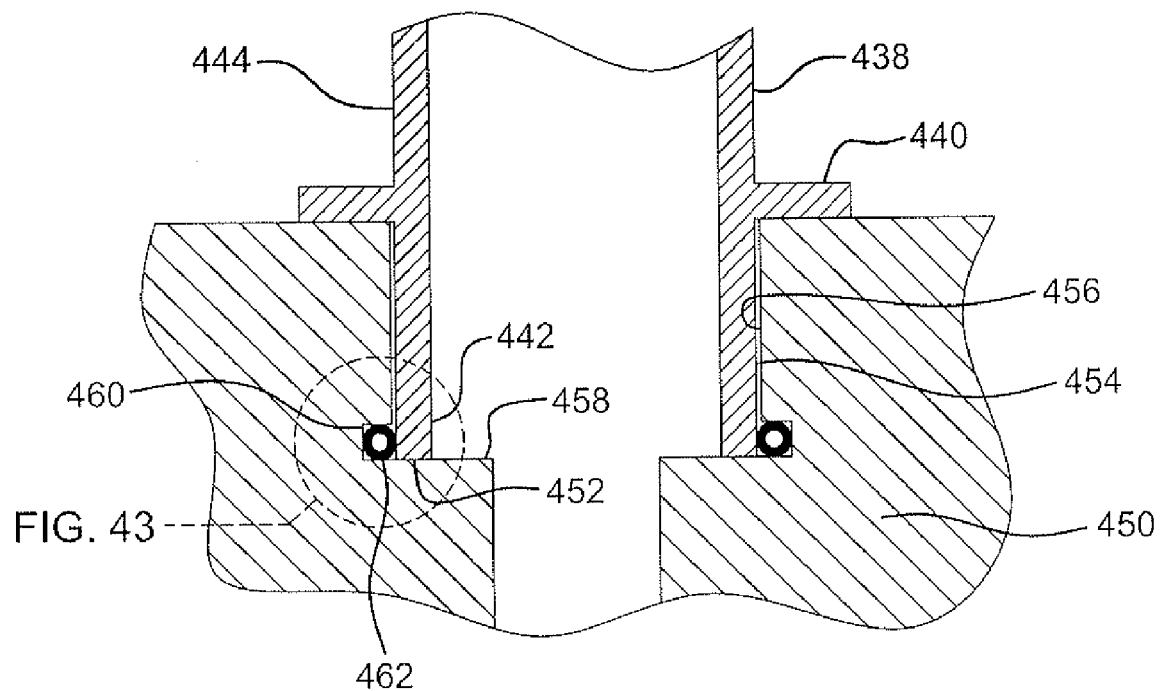
FIG. 42 is a fragmentary detail longitudinal section of an alternative sealing arrangement, usable for example, with the embodiments of FIGS. 1, 2, 3, 6-10, 12-16, 18, 19, 33, and 37-41 for seating a vessel on a vessel holder.
Figure 43:
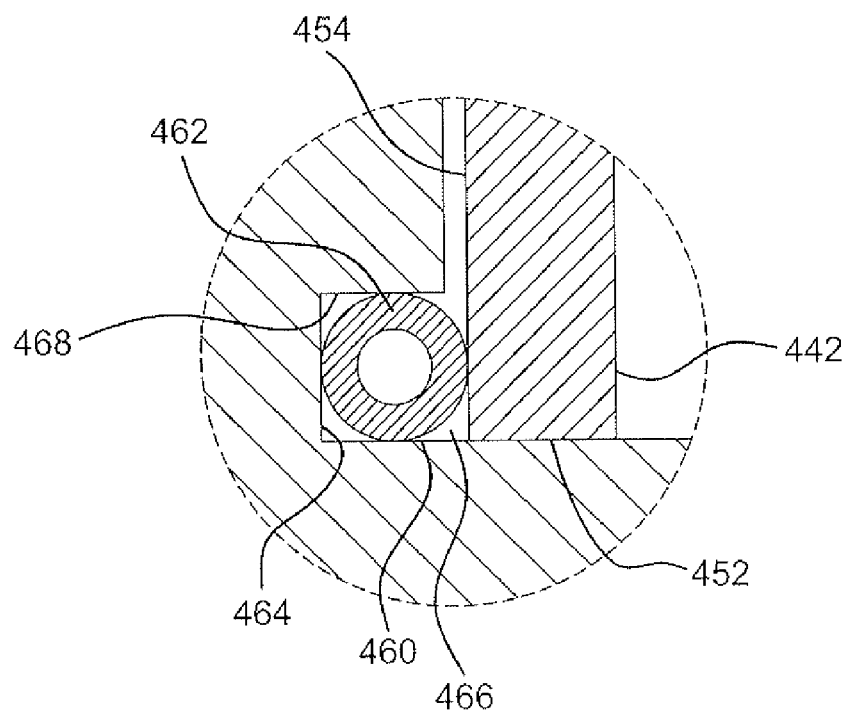
FIG. 43 is a further enlarged detail view of the sealing arrangement shown in FIG. 42.

II.B. FIGS. 42 and 43 are respectively a fragmentary detail longitudinal section and a detail view of a vessel holder 450 provided with an alternative sealing arrangement, usable for example, with the vessel holder embodiments of FIGS. 2, 3, 6, 7, 19, 12, 13, 16, 18, 19, 30, and 43 for seating a vessel on a vessel holder. Referring to FIG. 42, the vessel, for example a syringe barrel 438, seated on the vessel holder 450 has a back opening 442 defined by a generally annular (and commonly chamfered or rounded) lip 452, as well as a generally cylindrical sidewall 454. A medical fluid collection tube commonly has the same type of lip 452, but without a flange 440, and thus can be seated on the vessel holder 450 instead.

II.B. The vessel holder 450 in the embodiment as illustrated includes a generally cylindrical inner surface 456 that in the illustrated embodiment serves as a guide surface to receive the generally cylindrical sidewall 454 of the syringe barrel 438. The well is further defined by a generally annular abutment 458 against which the annular lip 452 abuts when the syringe barrel 438 is seated on the vessel holder 450. A generally annular pocket or groove 460 formed in the inner surface 456 is provided for retaining the sealing element, for example an O-ring 462. The radial depth of the pocket 460 is less than the radial cross-section of the sealing element, for example an O-ring 462 (as illustrated in FIG. 42), and the inner diameter of the O-ring 462 optionally is optionally slightly smaller than the outer diameter of the annular lip 452.

II.B. These relative dimensions cause the radial cross-section of the O-ring 462 to compress horizontally between at least the outside wall 464 of the pocket 460 and the generally cylindrical sidewall 454 of the syringe barrel 438, as shown in FIG. 42, when a vessel such as 438 is seated as shown in FIG. 42. This compression flattens the bearing surfaces of the O-ring 462, forming a seal between at least the outside wall 464 of the pocket 460 and the generally cylindrical sidewall 454 of the syringe barrel 438.

II.B. The pocket 460 optionally can be constructed, in relation to the dimensions of the O-ring 462, to form two more seals between the bottom and top walls 466 and 468 and the sidewall 454, by spacing the top and bottom walls 468 and 466 about as far apart as the corresponding radial cross-section diameter of the O-ring 462. When the O-ring 462 is squeezed between the outside wall 464 and the generally cylindrical sidewall 454 of the pocket 460, its resilience will cause it to expand upward and downward as shown in FIG. 43, thus also engaging the top and bottom walls 466 and 464 and flattening against them. The O-ring 462 optionally will thus be deformed both vertically and horizontally, tending to square its normally round cross-section. Additionally, the annular lip 452 seated on the abutment 458 will limit the flow of PECVD process reactants and other gases and materials introduced through or adjacent to the back opening 442.

II.B. As a result of this optional construction, only the gap at the lower right corner of the O-ring 462, as shown in FIG. 43, is outside the O-rings and thus exposed to process gases, plasma, etc. introduced to or generated in the interior of the vessel 438. This construction protects the O-ring 462 and the adjacent surfaces (as of the outside surface of the sidewall 438) from unwanted build-up of PECVD deposits and attack by the activated chemical species in the plasma. Additionally, the vessel 438 is more positively located by the hard surface of the abutment 458, as opposed to the resilient surface that would be presented by a butt seat of the annular lip 452 directly against the O-ring as illustrated in some of the other Figures. Further, the forces on the respective portions around the major circumference of the O-ring 462 are more evenly distributed, as the vessel 438 is constrained against any substantial rocking.

II.B. Or, the pocket 460 can be formed with its bottom wall 466 above the abutment 458 shown in FIG. 43. In another embodiment, more than one axially spaced pocket 460 can be provided to provide a double or higher-level seal and to further restrain the vessel 438 against rocking when seated against the abutment 458.

Figure 44:
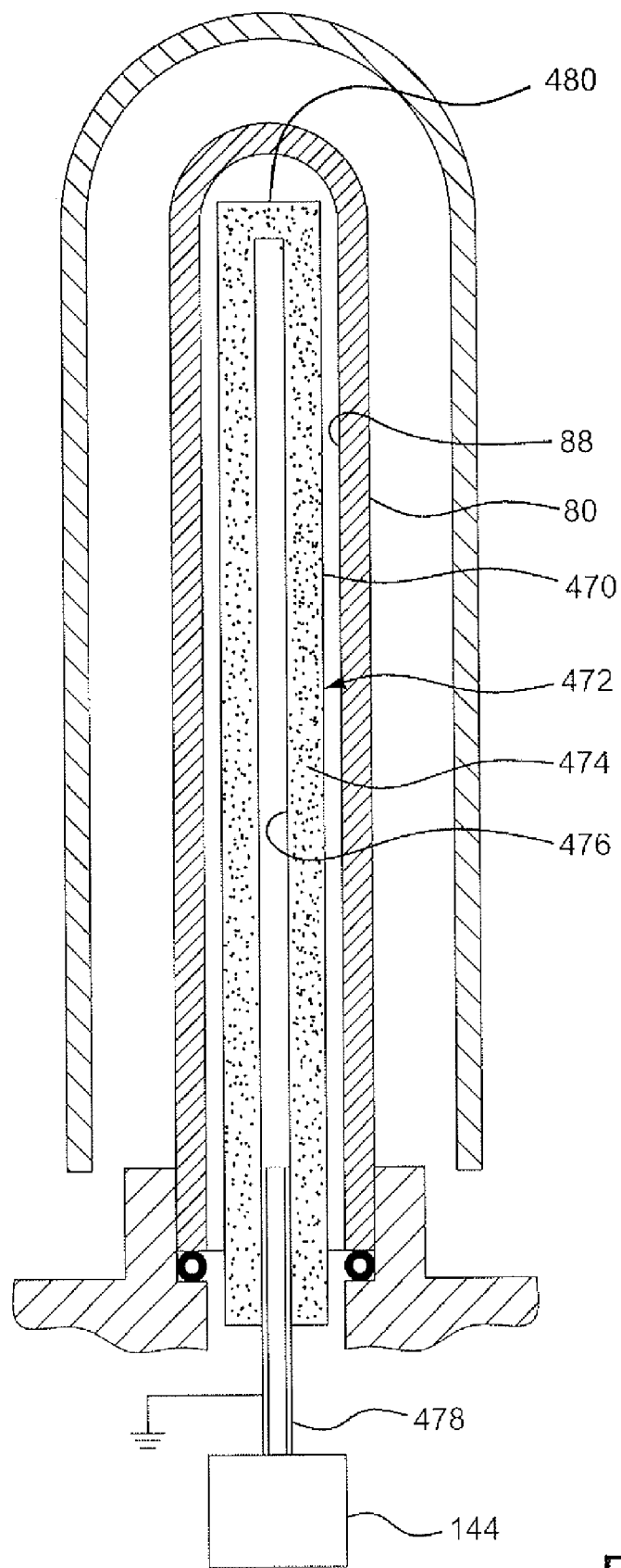
FIG. 44 is a view similar to FIG. 2 of an alternative gas delivery tube/inner electrode usable, for example with the embodiments of FIGS. 1, 2, 3, 8, 9, 12-16, 18-19, 21-22, 33, 37-43, 46-49, and 52-54.
Figure 45:
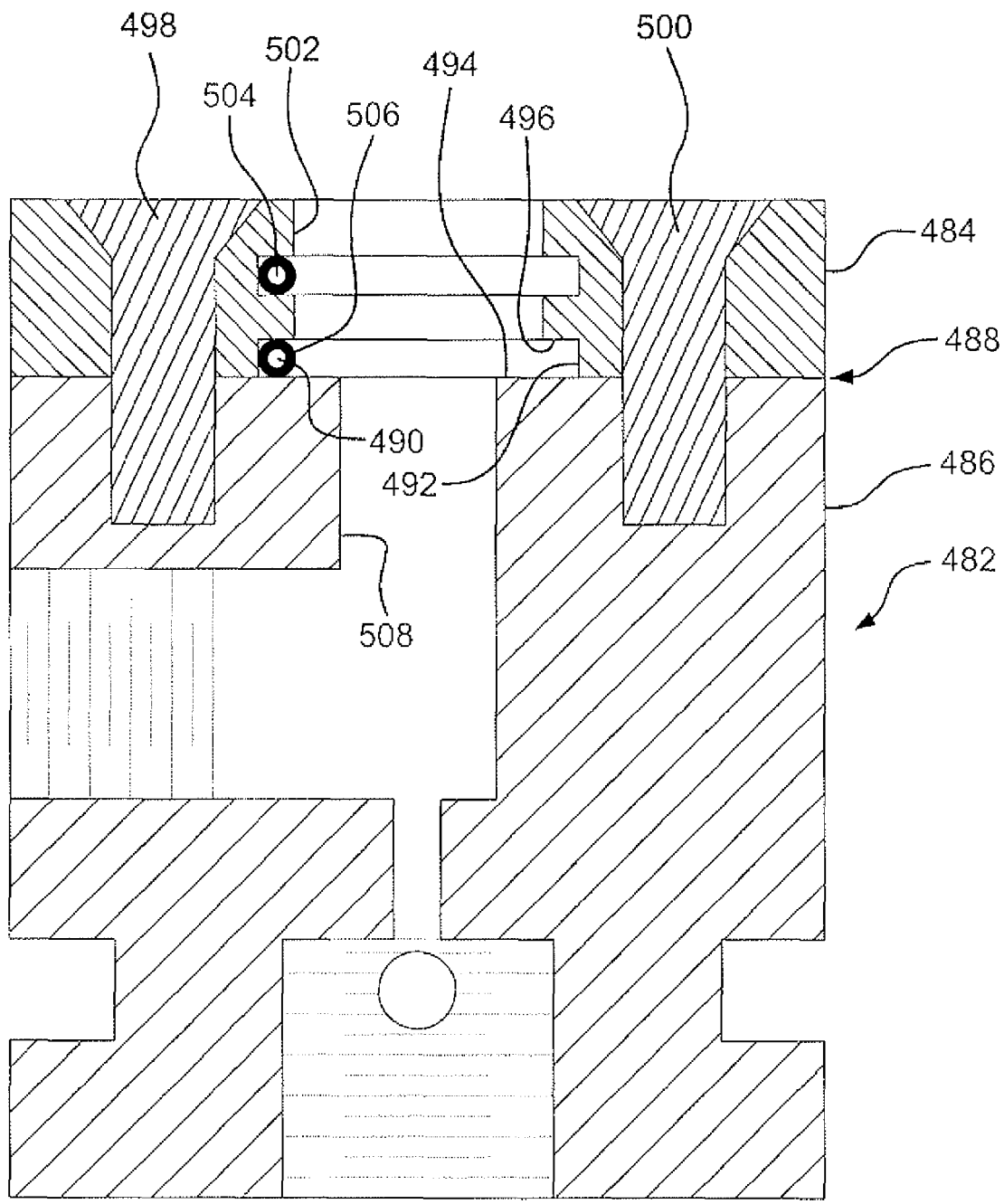
FIG. 45 is an alternative construction for a vessel holder usable, for example, with the embodiments of FIGS. 1, 2, 3, 6-10, 12-16, 18, 19, 21, 22, 26, 28, 33-35, and 37-44.

II.B. FIG. 45 is an alternative construction for a vessel holder 482 usable, for example, with the embodiments of FIGS. 1, 2, 3, 6-10, 12-16, 18, 19, 21, 22, 26, 28, 33-35, and 37-44. The vessel holder 482 comprises an upper portion 484 and a base 486 joined together at a joint 488. A sealing element, for example an O-ring 490 (the right side of which is cut away to allow the pocket retaining it to be described) is captured between the upper portion 484 and the base 486 at the joint 488. In the illustrated embodiment, the O-ring 490 is received in an annular pocket 492 to locate the O-ring when the upper portion 484 is joined to the base 486.

II.B. In this embodiment, the O-ring 490 is captured and bears against a radially extending abutment surface 494 and the radially extending wall 496 partially defining the pocket 492 when the upper portion 484 and the base 486 are joined, in this case by the screws 498 and 500. The O-ring 490 thus seats between the upper portion 484 and base 486. The O-ring 490 captured between the upper portion 484 and the base 486 also receives the vessel 80 (removed in this figure for clarity of illustration of other features) and forms a first O-ring seal of the vessel port 502 about the vessel 80 opening, analogous to the O-ring seal arrangement about the vessel back opening 442 in FIG. 42.

II.B. In this embodiment, though not a requirement, the vessel port 502 has both the first O-ring 490 seal and a second axially spaced O-ring 504 seal, each having an inner diameter such as 506 sized to receive the outer diameter (analogous to the sidewall 454 in FIG. 43) of a vessel such as 80 for sealing between the vessel port 502 and a vessel such as 80. The spacing between the O-rings 490 and 504 provides support for a vessel such as 80 at two axially spaced points, preventing the vessel such as 80 from being skewed with respect to the O-rings 490 and 504 or the vessel port 502. In this embodiment, though not a requirement, the radially extending abutment surface 494 is located proximal of the O-ring 490 and 506 seals and surrounding the vacuum duct 508.

Figure 10:
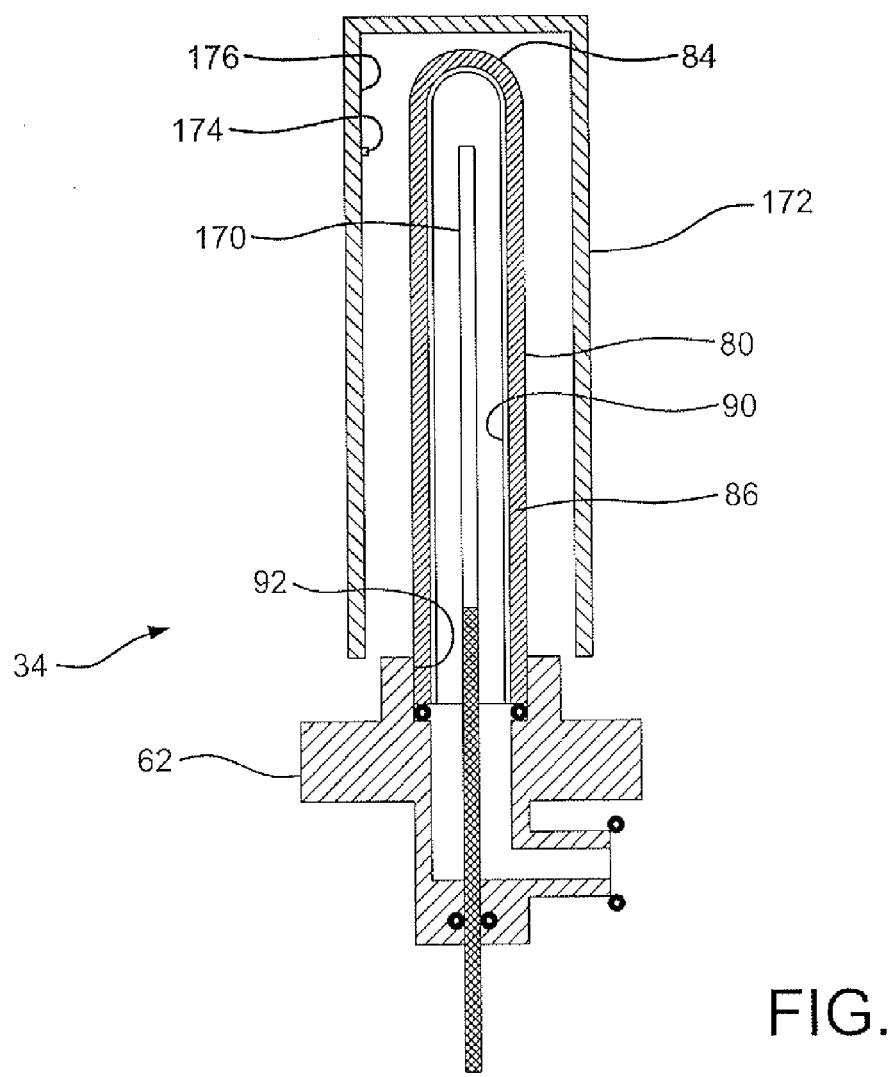
FIG. 10 is a view similar to FIG. 2 of a vessel holder in a coating station according to another embodiment of the disclosure, employing a CCD detector.

III. Methods for Transporting Vessels—Processing Vessels Seated on Vessel Holders III.A Transporting Vessel Holders to Processing Stations III.A. FIGS. 1, 2, and 10 show a method for processing a vessel 80. The method can be carried out as follows.

III.A. A vessel 80 can be provided having an opening 82 and a wall 86 defining an interior surface 88. As one embodiment, the vessel 80 can be formed in and then removed from a mold such as 22. Optionally within 60 seconds, or within 30 seconds, or within 25 seconds, or within 20 seconds, or within 15 seconds, or within 10 seconds, or within 5 seconds, or within 3 seconds, or within 1 second after removing the vessel from the mold, or as soon as the vessel 80 can be moved without distorting it during processing (assuming that it is made at an elevated temperature, from which it progressively cools), the vessel opening 82 can be seated on the vessel port 92. Quickly moving the vessel 80 from the mold 22 to the vessel port 92 reduces the dust or other impurities that can reach the surface 88 and occlude or prevent adhesion of the barrier or other type of coating 90. Also, the sooner a vacuum is drawn on the vessel 80 after it is made, the less chance any particulate impurities have of adhering to the interior surface 88.

III.A. A vessel holder such as 50 comprising a vessel port 92 can be provided. The opening 82 of the vessel 80 can be seated on the vessel port 92. Before, during, or after seating the opening 82 of the vessel 80 on the vessel port 92, the vessel holder such as 40 (for example in FIG. 6) can be transported into engagement with one or more of the bearing surfaces 220-240 to position the vessel holder 40 with respect to the processing device or station such as 24.

III.A. One, more than one, or all of the processing stations such as 24-34, as illustrated by the station 24 shown in FIG. 6, can include a bearing surface, such as one or more of the bearing surfaces 220, 222, 224, 226, 228, 230, 232, 234, 236, 238, or 240, for supporting one or more vessel holders such as 40 in a predetermined position while processing the interior surface 88 of the seated vessel 80 at the processing station or device such as 24. These bearing surfaces can be part of stationary or moving structure, for example tracks or guides that guide and position the vessel holder such as 40 while the vessel is being processed. For example, the downward-facing bearing surfaces 222 and 224 locate the vessel holder 40 and act as a reaction surface to prevent the vessel holder 40 from moving upward when the probe 108 is being inserted into the vessel holder 40. The reaction surface 236 locates the vessel holder and prevents the vessel holder 40 from moving to the left while a vacuum source 98 (per FIG. 2) is seated on the vacuum port 96. The bearing surfaces 220, 226, 228, 232, 238, and 240 similarly locate the vessel holder 40 and prevent horizontal movement during processing. The bearing surfaces 230 and 234 similarly locate the vessel holder such as 40 and prevent it from moving vertically out of position. Thus, a first bearing surface, a second bearing surface, a third bearing surface, or more can be provided at each of the processing stations such as 24-34.

III.A. The interior surface 88 of the seated vessel 80 can be then processed via the vessel port 92 at the first processing station, which can be, as one example, the barrier application or other type of coating station 28 shown in FIG. 2. The vessel holder 50 and seated vessel 80 are transported from the first processing station 28 to the second processing station, for example the processing station 32. The interior surface 88 of the seated vessel 80 can be processed via the vessel port 92 at the second processing station such as 32.

III.A. Any of the above methods can include the further step of removing the vessel 80 from the vessel holder such as 66 following processing the interior surface 88 of the seated vessel 80 at the second processing station or device.

III.A. Any of the above methods can include the further step, after the removing step, of providing a second vessel 80 having an opening 82 and a wall 86 defining an interior surface 88. The opening 82 of the second vessel such as 80 can be seated on the vessel port 92 of another vessel holder such as 38. The interior surface of the seated second vessel 80 can be processed via the vessel port 92 at the first processing station or device such as 24. The vessel holder such as 38 and seated second vessel 80 can be transported from the first processing station or device 24 to the second processing station or device such as 26. The seated second vessel 80 can be processed via the vessel port 92 by the second processing station or device 26.

III.B Transporting Processing Devices to Vessel Holders or Vice Versa.

III.B. Or, the processing stations can more broadly be processing devices, and either the vessel holders can be conveyed relative to the processing devices, the processing devices can be conveyed relative to the vessel holders, or some of each arrangement can be provided in a given system. In still another arrangement, the vessel holders can be conveyed to one or more stations, and more than one processing device can be deployed at or near at least one of the stations. Thus, there is not necessarily a one-to-one correspondence between the processing devices and processing stations.

III.B. A method including several parts is contemplated for processing a vessel. A first processing device such as the probe 108 (FIG. 2) and a second processing device such as a light source 170 (FIG. 10) are provided for processing vessels such as 80. A vessel 80 is provided having an opening 82 and a wall 86 defining an interior surface 88. A vessel holder 50 is provided comprising a vessel port 92. The opening 82 of the vessel 80 is seated on the vessel port 92.

III.B. The first processing device such as the probe 108 is moved into operative engagement with the vessel holder 50, or vice versa. The interior surface 88 of the seated vessel 80 is processed via the vessel port 92 using the first processing device or probe 108.

III.B. The second processing device such as 170 (FIG. 10) is then moved into operative engagement with the vessel holder 50, or vice versa. The interior surface 88 of the seated vessel 80 is processed via the vessel port 92 using the second processing device such as the light source 170.

III.B. Optionally, any number of additional processing steps can be provided. For example, a third processing device 34 can be provided for processing vessels 80. The third processing device 34 can be moved into operative engagement with the vessel holder 50, or vice versa. The interior surface of the seated vessel 80 can be processed via the vessel port 92 using the third processing device 34.

III.B. In another method for processing a vessel, the vessel 80 can be provided having an opening 82 and a wall 86 defining an interior surface 88. A vessel holder such as 50 comprising a vessel port 92 can be provided. The opening 82 of the vessel 80 can be seated on the vessel port 92. The interior surface 88 of the seated vessel 80 can be processed via the vessel port 92 at by the first processing device, which can be, as one example, the barrier or other type of coating device 28 shown in FIG. 2. The vessel holder 50 and seated vessel 80 are transported from the first processing device 28 to the second processing device, for example the processing device 34 shown in FIGS. 1 and 10. The interior surface 88 of the seated vessel 80 can be then processed via the vessel port 92 by the second processing device such as 34.

III.C Using Gripper for Transporting Tube to and from Coating Station

III.C. Yet another embodiment is a method of PECVD treatment of a first vessel, including several steps. A first vessel is provided having an open end, a closed end, and an interior surface. At least a first gripper is configured for selectively holding and releasing the closed end of the first vessel. The closed end of the first vessel is gripped with the first gripper and, using the first gripper, transported to the vicinity of a vessel holder configured for seating to the open end of the first vessel. The first gripper is then used to axially advance the first vessel and seat its open end on the vessel holder, establishing sealed communication between the vessel holder and the interior of the first vessel.

III.C. At least one gaseous reactant is introduced within the first vessel through the vessel holder. Plasma is formed within the first vessel under conditions effective to form a reaction product of the reactant on the interior surface of the first vessel.

III.C. The first vessel is then unseated from the vessel holder and, using the first gripper or another gripper, the first vessel is axially transported away from the vessel holder. The first vessel is then released from the gripper used to axially transport it away from the vessel holder.

III.C. Referring again to FIGS. 16 and 49, a series conveyor 538 can be used to support and transport multiple grippers such as 204 through the apparatus and process as described here. The grippers 204 are operatively connected to the series conveyor 538 and configured for successively transporting a series of at least two vessels 80 to the vicinity of the vessel holder 48 and carrying out the other steps of the cleaning method as described here.

IV. PECVD Apparatus for Making Vessels

IV.A. PECVD Apparatus Including Vessel Holder, Internal Electrode, Vessel as Reaction Chamber IV.A. Another embodiment is a PECVD apparatus including a vessel holder, an inner electrode, an outer electrode, and a power supply. A vessel seated on the vessel holder defines a plasma reaction chamber, which optionally can be a vacuum chamber. Optionally, a source of vacuum, a reactant gas source, a gas feed or a combination of two or more of these can be supplied. Optionally, a gas drain, not necessarily including a source of vacuum, is provided to transfer gas to or from the interior of a vessel seated on the port to define a closed chamber.

IV.A. The PECVD apparatus can be used for atmospheric-pressure PECVD, in which case the plasma reaction chamber does not need to function as a vacuum chamber.

IV.A. In the embodiment illustrated in FIG. 2, the vessel holder 50 comprises a gas inlet port 104 for conveying a gas into a vessel seated on the vessel port. The gas inlet port 104 has a sliding seal provided by at least one O-ring 106, or two O-rings in series, or three O-rings in series, which can seat against a cylindrical probe 108 when the probe 108 is inserted through the gas inlet port 104. The probe 108 can be a gas inlet conduit that extends to a gas delivery port at its distal end 110. The distal end 110 of the illustrated embodiment can be inserted deep into the vessel 80 for providing one or more PECVD reactants and other process gases.

IV.A. Optionally in the embodiment illustrated in FIG. 2, or more generally in any embodiment disclosed, such as the embodiments of FIG. 1-5, 8, 9, 12-16, 18, 19, 21, 22, 26-28, 33-35, 37-49, or 52-55, and as specifically disclosed in FIG. 55, a plasma screen 610 can be provided to confine the plasma formed within the vessel 80 generally to the volume above the plasma screen 610. The plasma screen 610 is a conductive, porous material, several examples of which are steel wool, porous sintered metal or ceramic material coated with conductive material, or a foraminous plate or disk made of metal (for example brass) or other conductive material. An example is a pair of metal disks having central holes sized to pass the gas inlet 108 and having 0.02-inch (0.5 mm) diameter holes spaced 0.04 inches (1 mm) apart, center-to-center, the holes providing 22% open area as a proportion of the surface area of the disk.

IV.A. The plasma screen 610, for example for embodiments in which the probe 108 also functions as an counter electrode, can make intimate electrical contact with the gas inlet 108 at or near the opening 82 of the tube, syringe barrel, or other vessel 80 being processed. Alternatively, the plasma screen 610 can be grounded, optionally having a common potential with the gas inlet 108. The plasma screen 610 reduces or eliminates the plasma in the vessel holder 50 and its internal passages and connections, for example the vacuum duct 94, the gas inlet port 104, the vicinity of the O-ring 106, the vacuum port 96, the O-ring 102, and other apparatus adjacent to the gas inlet 108. At the same time, the porosity of the plasma screen allows process gases, air, and the like to flow out of the vessel 80 into the vacuum port 96 and downstream apparatus.

Figure 3:
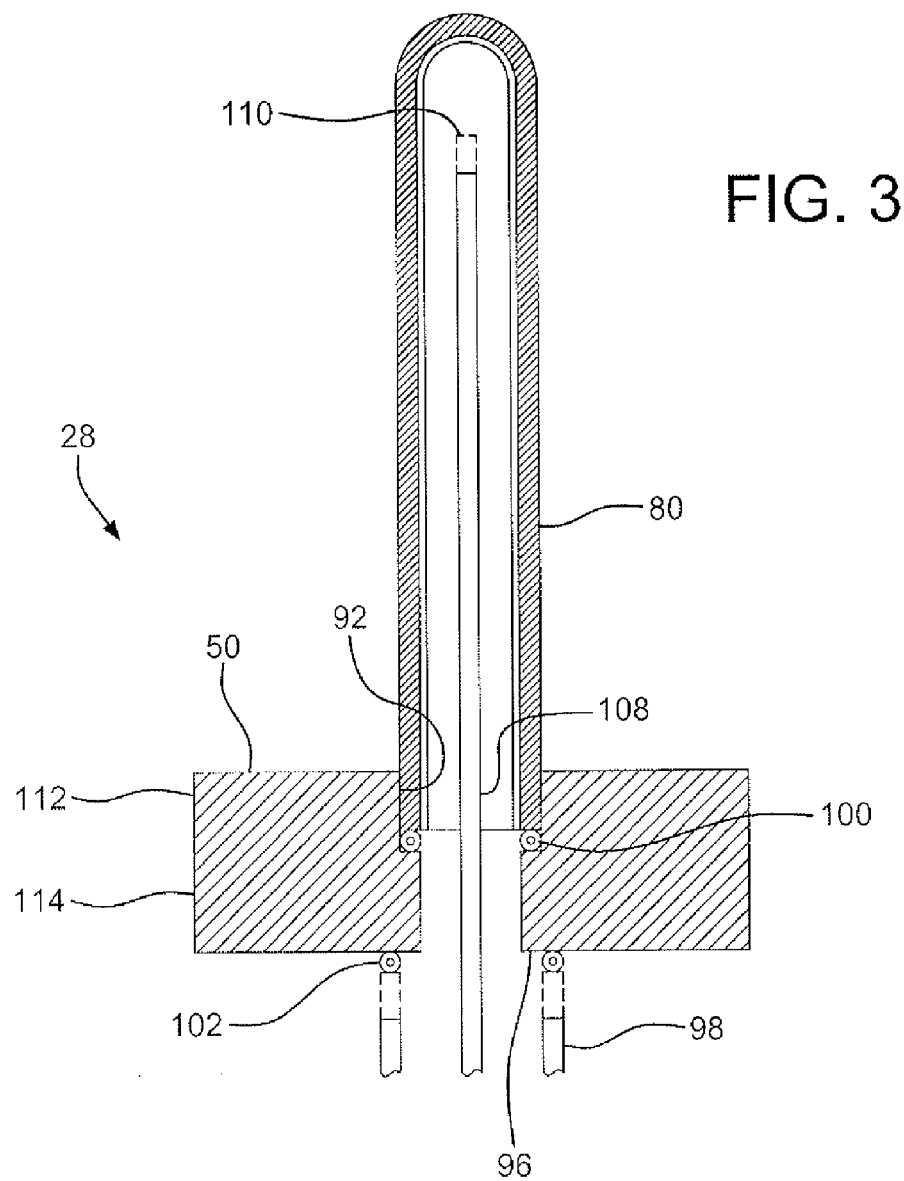
FIG. 3 is a view similar to FIG. 2 of an alternative embodiment of the disclosure.

IV.A. In the coating station 28 illustrated in FIG. 3, the vessel holder 112 comprises a composite gas inlet port and vacuum port 96 communicating with the vessel port 92, respectively for conveying a gas into a vessel 80 seated on the vessel port 92 (via the probe 108) and withdrawing a gas from a vessel seated on the vessel port 92 (via the vacuum source 98). In this embodiment, the gas inlet probe 108 and vacuum source 98 can be provided as a composite probe. The two probes can be advanced as a unit or separately, as desired. This arrangement eliminates the need for a third seal 106 and allows the use of butt seals throughout. A butt seal allows the application of an axial force, for example by drawing a vacuum within the vessel 80, to positively seat the vessel 80 and vacuum source 98 by deforming the O-rings, tending to close any gap left by the presence of any irregularities in the sealing surface on either side of the O-ring. In the embodiment of FIG. 3, the axial forces applied by the vessel 80 and vacuum source 98 on the vessel holder 112 are in opposition, tending to hold the vessel 80 and the vessel holder 112 together and maintain the respective butt seals.

Figure 13:
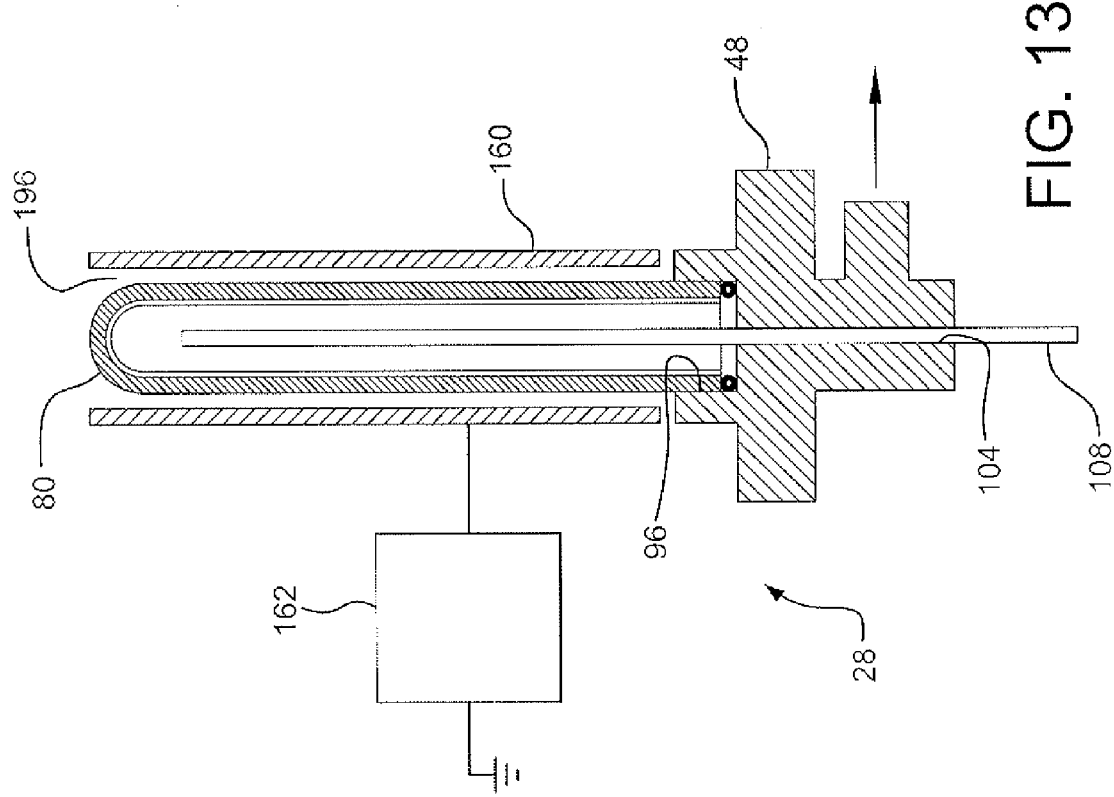
FIG. 13 is a view similar to FIG. 2 of a vessel holder in a coating station according to yet another embodiment of the disclosure, in which the vessel can be seated on the vessel holder at the process station.

IV.A. FIG. 13 is a view similar to FIG. 2 of a vessel holder 48 in a coating station according to yet another embodiment of the disclosure, in which the vessel 80 can be seated on the vessel holder 48 at the process station. This can be used to process a vessel 80 that does not travel with a vessel holder such as 48, or it can be used in a barrier or other type of coating station 28 that first seats the vessel 80 in a vessel holder such as 48 before the seated vessel 80 is conveyed to other apparatus by the system 20.

IV.A. FIG. 13 shows a cylindrical electrode 160 suited for frequencies from 50 Hz to 1 GHz, as an alternative to the U-shaped electrode of FIGS. 2 and 9. The vessel holder (or the electrode) can be moved into place prior to activation by either moving the electrode down or the vessel holder up. Or, the movement of the vessel holder and electrode in the vertical plane can be circumvented by creating an electrode 160 constructed like a clamshell (two half cylinders that can come together from opposite sides when the vessel holder is in position and ready for treatment/coating). IV.A. Optionally, at the coating station 28 the vacuum source 98 makes a seal with the puck or vessel holder 50 that can be maintained during movement of the vessel holder, if the process is a continuous process in which the tube is moved through the coating station such as 28 while a vacuum is drawn and gas is introduced through the probe 108. Or, a stationary process can be employed in which the puck or vessel holder 50 is moved into a stationary position, at which time the probe 108 is pushed up into the device and then the pump or vacuum source 98 is coupled at the vacuum port 96 and activated to create a vacuum. Once the probe 108 is in place and the vacuum created, plasma can be established inside of the tube or vessel 80 with an external fixed electrode 160 that is independent of the puck or vessel holder 50 and the tube or other vessel 80.

IV.A. FIG. 53 shows additional optional details of the coating station 28 that are usable, for example, with the embodiments of FIGS. 1, 2, 3, 6-10, 12-16, 18, 19, 21, 22, 26-28, 30, 33-35, 37-44, and 52. The coating station 28 can also have a main vacuum valve 574 in its vacuum line 576 leading to the pressure sensor 152. A manual bypass valve 578 is provided in the bypass line 580. A vent valve 582 controls flow at the vent 404.

IV.A. Flow out of the PECVD gas source 144 is controlled by a main reactant gas valve 584 regulating flow through the main reactant feed line 586. One component of the gas source 144 is the organosilicon liquid reservoir 588. The contents of the reservoir 588 are drawn through the organosilicon capillary line 590, which is provided at a suitable length to provide the desired flow rate. Flow of organosilicon vapor is controlled by the organosilicon shut-off valve 592. Pressure is applied to the headspace 614 of the liquid reservoir 588, for example a pressure in the range of 0-15 psi (0 to 78 cm. Hg), from a pressure source 616 such as pressurized air connected to the headspace 614 by a pressure line 618 to establish repeatable organosilicon liquid delivery that is not dependent on atmospheric pressure (and the fluctuations therein). The reservoir 588 is sealed and the capillary connection 620 is at the bottom of the reservoir 588 to ensure that only neat organosilicon liquid (not the pressurized gas from the headspace 614) flows through the capillary tube 590. The organosilicon liquid optionally can be heated above ambient temperature, if necessary or desirable to cause the organosilicon liquid to evaporate, forming an organosilicon vapor. Oxygen is provided from the oxygen tank 594 via an oxygen feed line 596 controlled by a mass flow controller 598 and provided with an oxygen shut-off valve 600.

Figure 7:
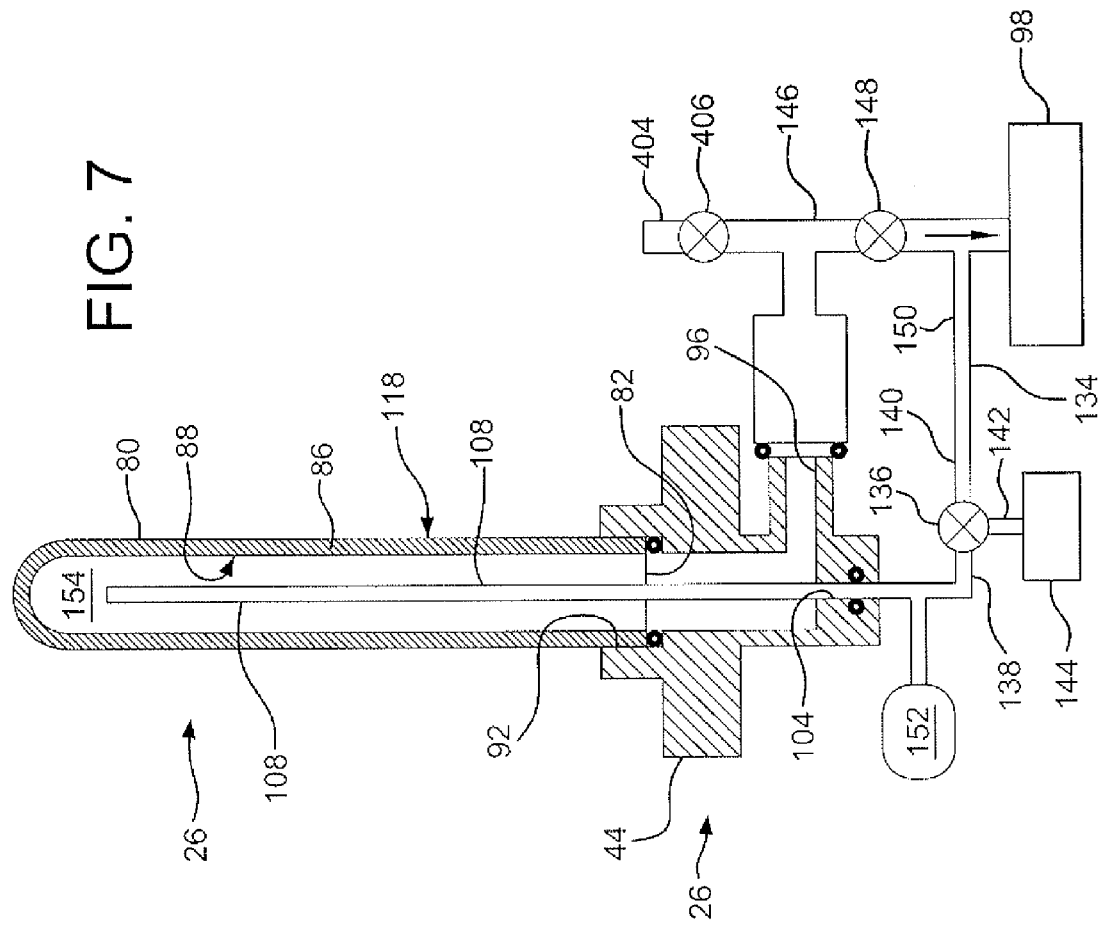
FIG. 7 is a view similar to FIG. 2 of alternative vessel inspection apparatus.

IV.A. In the embodiment of FIG. 7, the station or device 26 can include a vacuum source 98 adapted for seating on the vacuum port 96, a side channel 134 connected to the probe 108, or both (as illustrated). In the illustrated embodiment, the side channel 134 includes a shut-off valve 136 that regulates flow between a probe port 138 and a vacuum port 140. In the illustrated embodiment, the selection valve 136 has at least two states: an evacuation state in which the ports 138 and 140 are connected, providing two parallel paths for gas flow (thus increasing the rate of pumping or decreasing the pumping effort) and a disconnection state in which the ports 138 and 140 are isolated. Optionally, the selection valve 136 can have a third port, such as a PECVD gas inlet port 142, for introducing PECVD reactive and process gases from a gas source 144. This expedient allows the same vacuum supply and probe 108 to be used both for leak or permeation testing and for applying the barrier or other type of coating.

IV.A. In the illustrated embodiments, the vacuum line such as 146 to the vacuum source 98 can also include a shut-off valve 148. The shut-off valves 136 and 148 can be closed when the probe 108 and vacuum source 98 are not connected to a vessel holder such as 44 so the side channel 134 and the vacuum line 146 do not need to be evacuated on the side of the valves 136 and 148 away from the vessel 80 when moved from one vessel holder 44 to another. To facilitate removing the probe 108 axially from the gas inlet port 104, a flexible line 150 can be provided to allow axial movement of the probe 108 independent of the position of the vacuum line 146 relative to the port 96.

IV.A. FIG. 7 also shows another optional feature usable with any embodiment—a vent 404 to ambient air controlled by a valve 406. The valve 406 can be opened to break the vacuum quickly after processing the vessel 80, whether to release the vessel 80 from the vessel holder 44, to release the vessel holder 44 at the vacuum port 96 from the source of vacuum 98, or optionally both.

IV.A. In the illustrated embodiment (still referring to FIG. 7), the probe 108 can also be connected to a pressure gauge 152 and can communicate with the interior 154 of the vessel 80, allowing the pressure within the vessel 80 to be measured.

IV.A. In the apparatus of FIG. 1, the vessel coating station 28 can be, for example, a PECVD apparatus as further described below, operated under suitable conditions to deposit a $SiO_x$ barrier or other type of coating 90 on the interior surface 88 of a vessel 80, as shown in FIG. 2.

IV.A. Referring especially to FIGS. 1 and 2, the processing station 28 can include an electrode 160 fed by a radio frequency power supply 162 for providing an electric field for generating plasma within the vessel 80 during processing. In this embodiment, the probe 108 is also electrically conductive and is grounded, thus providing a counter-electrode within the vessel 80. Alternatively, in any embodiment the outer electrode 160 can be grounded and the probe 108 directly connected to the power supply 162.

Figure 8:
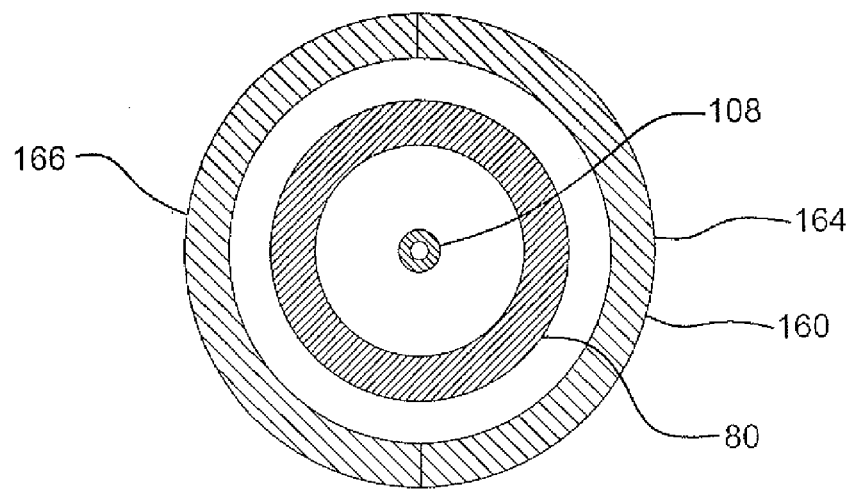
FIG. 8 is a section taken along section lines A-A of FIG. 2.
Figure 9:
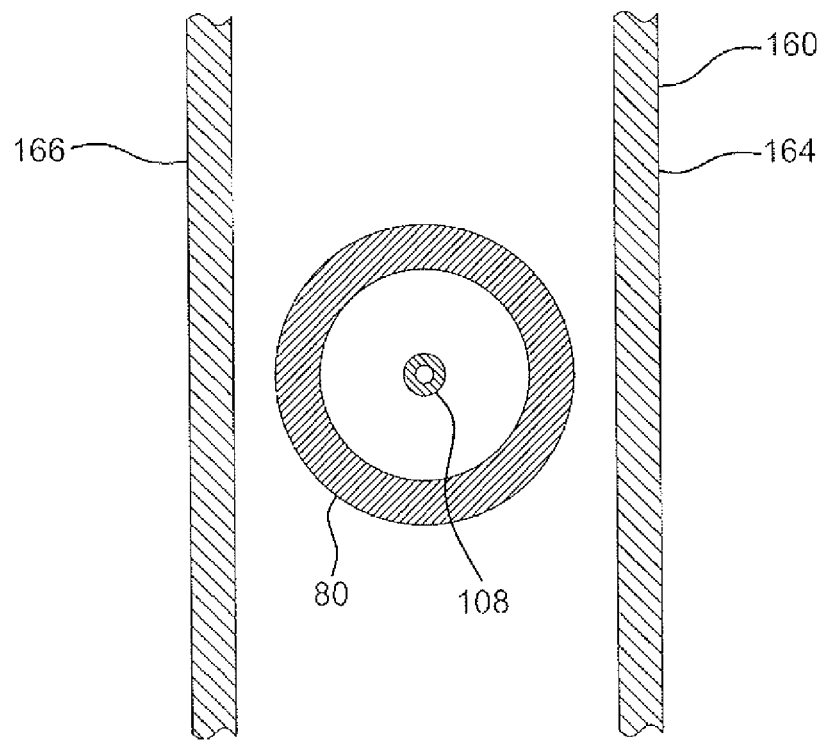
FIG. 9 is an alternative embodiment of the structure shown in FIG. 8.

IV.A. In the embodiment of FIG. 2, the outer electrode 160 can either be generally cylindrical as illustrated in FIGS. 2 and 8 or a generally U-shaped elongated channel as illustrated in FIGS. 2 and 9 (FIGS. 8 and 9 being alternative embodiments of the section taken along section line A-A of FIG. 2). Each illustrated embodiment has one or more sidewalls, such as 164 and 166, and optionally a top end 168, disposed about the vessel 80 in close proximity.

IV.A., IV.B. FIGS. 12 to 19 show other variants of the vessel coating station or device 28 as previously described. Any one or more of these variants can be substituted for the vessel coating station or device 28 shown in FIG. 1-5.

Figure 12:
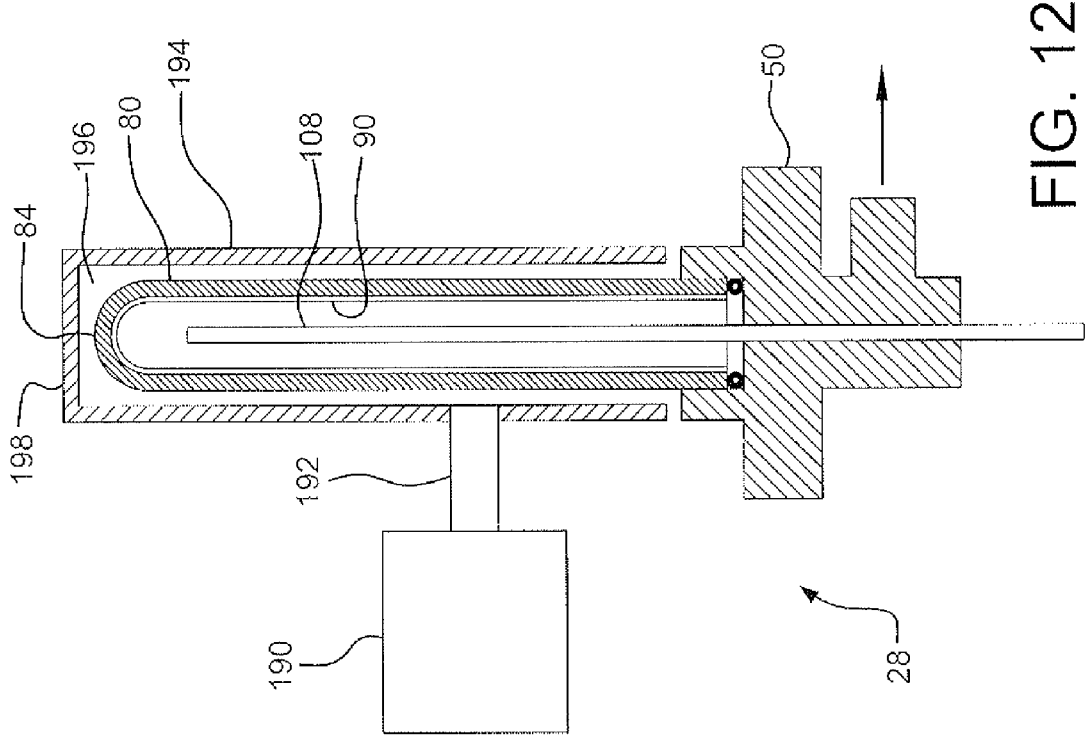
FIG. 12 is a view similar to FIG. 2 of a vessel holder in a coating station according to still another embodiment of the disclosure, employing microwave energy to generate the plasma.

IV.A. FIG. 12 shows an alternative electrode system that can be used (in the same manner as discussed above using the same vessel holder and gas inlet) at frequencies above 1 GHz. At these frequencies the electrical energy from the power supply can be transferred to the interior of the tube through one or more waveguides that are connected to a cavity that either absorbs the energy or resonates the energy. Resonating the energy allows it to couple to the gas. Different cavities can be provided for use with different frequencies and vessels such as 80, since the vessel 80 will interact with the cavity altering its resonation point, creating plasma for coating and/or treatment.

IV.A. FIG. 12 shows that the coating station 28 can include a microwave power supply 190 directing microwaves via a waveguide 192 to a microwave cavity 194 at least partially surrounding the vessel 80 within which plasma can be to be generated. The microwave cavity 194 can be tuned, in relation to the frequency of the microwaves and the partial pressures and selection of gases, to absorb microwaves and couple to the plasma-generating gas. In FIG. 13, as well as any of the illustrated embodiments a small gap 196 can be left between the vessel 80 and the cavity 194 (or electrode, detector, or other surrounding structure) to avoid scratching or otherwise damaging the vessel 80. Also in FIG. 13, the microwave cavity 194 has a flat end wall 198, so the gap 196 is not uniform in width, for example opposite the circular edge of the end wall 198. Optionally, the end 198 can be curved to provide a substantially uniform gap 196. IV.A. FIG. 44 is a view similar to FIG. 2 of an alternative gas delivery tube/inner electrode 470 usable, for example with the embodiments of FIGS. 1, 2, 3, 8, 9, 12-16, 18-19, 21-22, 33, 37-43, 46-49, and 52-54. As shown in FIG. 44, the distal portion 472 of the inner electrode 470 comprises an elongated porous side wall 474 enclosing an internal passage 476 within the inner electrode. The internal passage 476 is connected to the gas feed 144 by the proximal portion 478 of the inner electrode 470 extending outside the vessel 80. The distal end 480 of the inner electrode 470 can also optionally be porous. The porosity of the porous side wall 474 and, if present, the porous distal end 480 allow at least a portion of the reactant gas fed from the gas feed 144 to escape laterally from the passage 476 to supply reactant gas to the adjacent portion of the interior surface 88 of the vessel 80. In this embodiment, the porous portion of the porous side wall 474 extends the entire length of the inner electrode 470 within the vessel 80, although the porous portion could be less extensive, running only a portion of the length of the inner electrode 470. As indicated elsewhere in this specification, the inner electrode 470 could also be longer or shorter, relative to the length of the vessel 80, than is shown in FIG. 44, and the porous portion can be continuous or discontinuous.

IV.A. The outer diameter of the inner electrode 470 can be at least 50% as great, or at least 60% as great, or at least 70% as great, or at least 80% as great, or at least 90% as great, or at least 95% as great as the laterally adjacent inner diameter of the vessel. Employing a larger-diameter inner electrode 470, in relation to the inner diameter of the vessel 80, for example if the electrode 470 is concentric with the vessel 80, reduces the distance between the exterior of the inner electrode 470 and the adjacent interior surface 88 of the vessel 80, confining the plasma to a smaller region within which it can be more uniform. Employing a larger-diameter inner electrode 470 also provides more uniform distribution of the reactant gas and/or carrier gas along the interior surface 80, as fresh gases are introduced to the plasma at closely spaced points along the length of the interior surface 88, very close to the site of initial reaction, as opposed to flowing from a single point relative to the interior surface 88 to form.

IV.A. In one contemplated arrangement, shown in full lines, the power supply 162 has one power connection to the electrode 200, which can be at any point along the electrode 200, and the probe 108 can be grounded. In this configuration a capacitive load can be used to generate the plasma within the vessel 80. In another contemplated arrangement, shown in phantom lines (and eliminating the connections shown in full lines), the respective leads of the power supply 162 are connected to the respective ends of the coil 200, which for convenience can be again referred to as an "electrode" in this specification. In this configuration, an inductive load can be used to generate the plasma within the vessel 80. A combination of inductive and capacitive loads can also be used, in an alternative embodiment.

IV.A. FIGS. 46-48 show an array of two or more gas delivery tubes such as 108 (also shown in FIGS. 2), 510, and 512, which are also inner electrodes. The array can be linear or a carousel. A carousel array allows the electrodes to be reused periodically.

IV.A. FIGS. 46-48 also show an inner electrode extender and retractor 514 for inserting and removing the gas delivery tubes/inner electrodes 108, 510, and 512 into and from one or more vessel holders such as 50 or 48. These features are optional expedients for using the gas delivery tubes.

IV.A. In the illustrated embodiment, referring to FIGS. 46-48 as well as 53, the inner electrodes 108, 510, and 512 are respectively connected by flexible hoses 516, 518, and 520 to a common gas supply 144, via shut-off valves 522, 524, and 526. (The flexible hoses are foreshortened in FIGS. 46-48 by omitting the slack portions). Referring briefly to FIG. 56, the flexible hoses 516, 518, and 520 alternatively can be connected to independent gas sources 144. A mechanism 514 is provided to extend and retract an inner electrode such as 108. The inner electrode extender and retractor is configured for moving an inner electrode among a fully advanced position, an intermediate position, and a retracted position with respect to the vessel holder.

IV.A. In FIGS. 46 and 56, the inner electrode 108 is extended to its operative position within the vessel holder 50 and vessel 80, and its shut-off valve 522 is open. Also in FIG. 46, the idle inner electrodes 510 and 512 are retracted and their shut-off valves 524 and 526 are closed. In the illustrated embodiment, one or more of the idle inner electrodes 510 and 512 are disposed within an electrode cleaning device or station 528. One or more electrodes can be cleaned and others replaced within the station 528, optionally. The cleaning operations can involve chemical reaction or solvent treatment to remove deposits, milling to physically remove deposits, or plasma treatment to essentially burn away accumulated deposits, as non-limiting examples.

IV.A. In FIG. 47, the idle inner electrodes 510 and 512 are as before, while the working inner electrode 108 has been retracted out of the vessel 80, with its distal end remaining within the vessel holder 50, and its valve 522 has been closed. In this condition, the vessel 80 can be removed and a new vessel seated on the vessel holder 50 without any danger of touching the electrode 108 with the vessels 80 being removed and replaced. After the vessel 80 is replaced, the inner electrode 108 can be advanced to the position of FIGS. 46 AND 56 and the shut-off valve 522 can be reopened to commence coating the new vessel 80 using the same inner electrode 108 as before. Thus, in an arrangement in which a series of the vessels 80 are seated on and removed from the vessel holder 50, the inner electrode 108 can be extended and partially retracted numerous times, as the vessel 80 is installed or removed from the vessel holder 50 at the station where the inner electrode 108 is in use IV.A. In FIG. 48, the vessel holder 50 and its vessel 80 have been replaced with a new vessel holder 48 and another vessel 80. Referring to FIG. 1, in this type of embodiment each vessel 80 remains on its vessel holder such as 50 or 48 and an inner electrode such as 108 is inserted into each vessel as its vessel holder reaches the coating station.

IV.A. Additionally in FIG. 48, the inner electrodes 108, 510, and 512 are fully retracted, and the array of inner electrodes 108, 510, and 512 has been moved to the right relative to the vessel holder 48 and electrode cleaning station 528, compared to the positions of each in FIG. 47, so the inner electrode 108 has been moved out of position and the inner electrode 510 has been moved into position with respect to the vessel holder 48.

IV.A. It should be understood that the movement of the array of inner electrodes can be independent of the movement of the vessel holders. They can be moved together or independently, to simultaneously or independently switch to a new vessel holder and/or a new inner electrode.

IV.A. FIGS. 46-48 show an array of two or more gas delivery tubes such as 108 (also shown in FIGS. 2), 510, and 512, which are also inner electrodes. The array can be linear or a carousel. A carousel array allows the electrodes to be reused periodically.

IV.A. FIGS. 46-48 also show an inner electrode extender and retractor 514 for inserting and removing the gas delivery tubes/inner electrodes 108, 510, and 512 into and from one or more vessel holders such as 50 or 48. These features are optional expedients for using the gas delivery tubes.

IV.A. In the illustrated embodiment, referring to FIGS. 46-48 as well as 53, the inner electrodes 108, 510, and 512 are respectively connected by flexible hoses 516, 518, and 520 to a common gas supply 144, via shut-off valves 522, 524, and 526. (The flexible hoses are foreshortened in FIGS. 46-48 by omitting the slack portions). A mechanism 514 is provided to extend and retract an inner electrode such as 108. The inner electrode extender and retractor is configured for moving an inner electrode among a fully advanced position, an intermediate position, and a retracted position with respect to the vessel holder.

IV.A. In FIGS. 46 AND 56, the inner electrode 108 is extended to its operative position within the vessel holder 50 and vessel 80, and its shut-off valve 522 is open. Also in FIGS. 46 AND 56, the idle inner electrodes 510 and 512 are retracted and their shut-off valves 524 and 526 are closed. In the illustrated embodiment, the idle inner electrodes 510 and 512 are disposed within an electrode cleaning or station 528. Some electrodes can be cleaned and others replaced within the station 528, optionally. The cleaning operations can involve chemical reaction or solvent treatment to remove deposits, milling to physically remove deposits, or plasma treatment to essentially burn away accumulated deposits, as non-limiting examples.

IV.A. In FIG. 47, the idle inner electrodes 510 and 512 are as before, while the working inner electrode 108 has been retracted out of the vessel 80, with its distal end remaining within the vessel holder 50, and its valve 522 has been closed. In this condition, the vessel 80 can be removed and a new vessel seated on the vessel holder 50 without any danger of touching the electrode 108 with the vessels 80 being removed and replaced. After the vessel 80 is replaced, the inner electrode 108 can be advanced to the position of FIGS. 46 AND 56 and the shut-off valve 522 can be reopened to commence coating the new vessel 80 using the same inner electrode 108 as before. Thus, in an arrangement in which a series of the vessels 80 are seated on and removed from the vessel holder 50, the inner electrode 108 can be extended and partially retracted numerous times, as the vessel 80 is installed or removed from the vessel holder 50 at the station where the inner electrode 108 is in use IV.A. In FIG. 48, the vessel holder 50 and its vessel 80 have been replaced with a new vessel holder 48 and another vessel 80. Referring to FIG. 1, in this type of embodiment each vessel 80 remains on its vessel holder such as 50 or 48 and an inner electrode such as 108 is inserted into each vessel as its vessel holder reaches the coating station.

IV.A. Additionally in FIG. 48, the inner electrodes 108, 510, and 512 are fully retracted, and the array of inner electrodes 108, 510, and 512 has been moved to the right relative to the vessel holder 48 and electrode cleaning station 528, compared to the positions of each in FIG. 47, so the inner electrode 108 has been moved out of position and the inner electrode 510 has been moved into position with respect to the vessel holder 48.

IV.A. It should be understood that the movement of the array of inner electrodes can be independent of the movement of the vessel holders. They can be moved together or independently, to simultaneously or independently switch to a new vessel holder and/or a new inner electrode.

IV.A. An array of two or more inner electrodes 108, 510, and 512 is useful because the individual combined gas delivery tubes/inner electrodes 108, 510, and 512 will in some instances tend to accumulate polymerized reactant gases or some other type of deposits as they are used to coat a series of vessels such as 80. The deposits can accumulate to the point at which they detract from the coating rate or uniformity produced, which can be undesirable. To maintain a uniform process, the inner electrodes can be periodically removed from service, replaced or cleaned, and a new or cleaned electrode can be put into service. For example, going from FIG. 46 to FIG. 48, the inner electrode 108 has been replaced with a fresh or reconditioned inner electrode 510, which is ready to be extended into the vessel holder 48 and the vessel 80 to apply an interior coating to the new vessel.

IV.A. Thus, an inner electrode drive 530 is operable in conjunction with the inner electrode extender and retractor 514 for removing a first inner electrode 108 from its extended position to its retracted position, substituting a second inner electrode 510 for the first inner electrode 108, and advancing the second inner electrode 510 to its extended position (analogous to FIGS. 46 and 56 except for the substitution of electrode).

IV.A. The array of gas delivery tubes of FIGS. 46-48 and inner electrode drive 530 are usable, for example, with the embodiments of FIGS. 1, 2, 3, 8, 9, 12-16, 18-19, 21-22, 26-28, 33-35, 37-45, 49, and 52-54. The extending and retracting mechanism 514 of FIGS. 46-48 is usable, for example, with the gas delivery tube embodiments of FIGS. 2, 3, 8, 9, 12-16, 18-19, 21-22, 26-28, 33-35, 37-45, 49, and 52-54, as well as with the probes of the vessel inspection apparatus of FIGS. 6 and 7.

IV.A The electrode 160 shown in FIG. 2 can be shaped like a "U" channel with its length into the page and the puck or vessel holder 50 can move through the activated (powered) electrode during the treatment/coating process. Note that since external and internal electrodes are used, this apparatus can employ a frequency between 50 Hz and 1 GHz applied from a power supply 162 to the U channel electrode 160. The probe 108 can be grounded to complete the electrical circuit, allowing current to flow through the low-pressure gas(es) inside of the vessel 80. The current creates plasma to allow the selective treatment and/or coating of the interior surface 88 of the device.

IV.A The electrode in FIG. 2 can also be powered by a pulsed power supply. Pulsing allows for depletion of reactive gases and then removal of by-products prior to activation and depletion (again) of the reactive gases. Pulsed power systems are typically characterized by their duty cycle which determines the amount of time that the electric field (and therefore the plasma) is present. The power-on time is relative to the power-off time. For example a duty cycle of 10% can correspond to a power on time of 10% of a cycle where the power was off for 90% of the time. As a specific example, the power might be on for 0.1 second and off for 1 second. Pulsed power systems reduce the effective power input for a given power supply 162, since the off-time results in increased processing time. When the system is pulsed, the resulting coating can be very pure (no by products or contaminants). Another result of pulsed systems is the possibility to achieve atomic layer deposition (ALD). In this case, the duty cycle can be adjusted so that the power-on time results in the deposition of a single layer of a desired material. In this manner, a single atomic layer is contemplated to be deposited in each cycle. This approach can result in highly pure and highly structured coatings (although at the temperatures required for deposition on polymeric surfaces, temperatures optionally are kept low (<100° C.) and the low-temperature coatings can be amorphous).

IV.A. An alternative coating station is disclosed in FIG. 12, employing a microwave cavity instead of an outer electrode. The energy applied can be a microwave frequency, for example 2.45 GHz.

Figure 15:
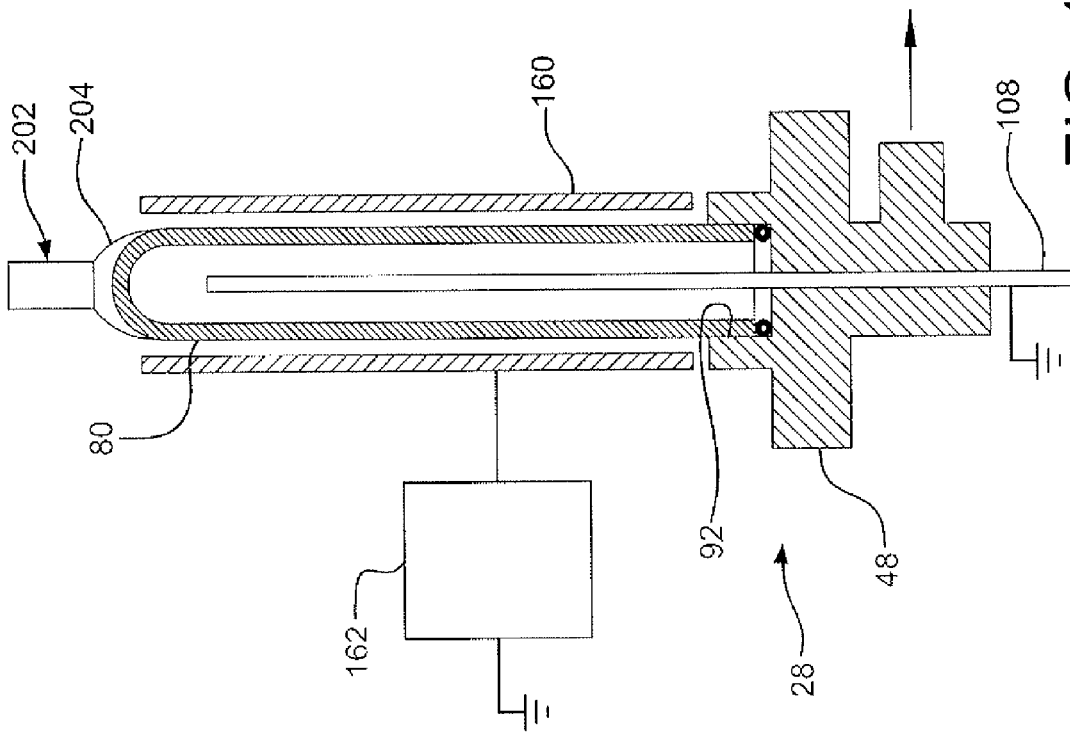
FIG. 15 is a view similar to FIG. 2 of a vessel holder in a coating station according to another embodiment of the disclosure, employing a tube transport to move a vessel to and from the coating station.
Figure 16:
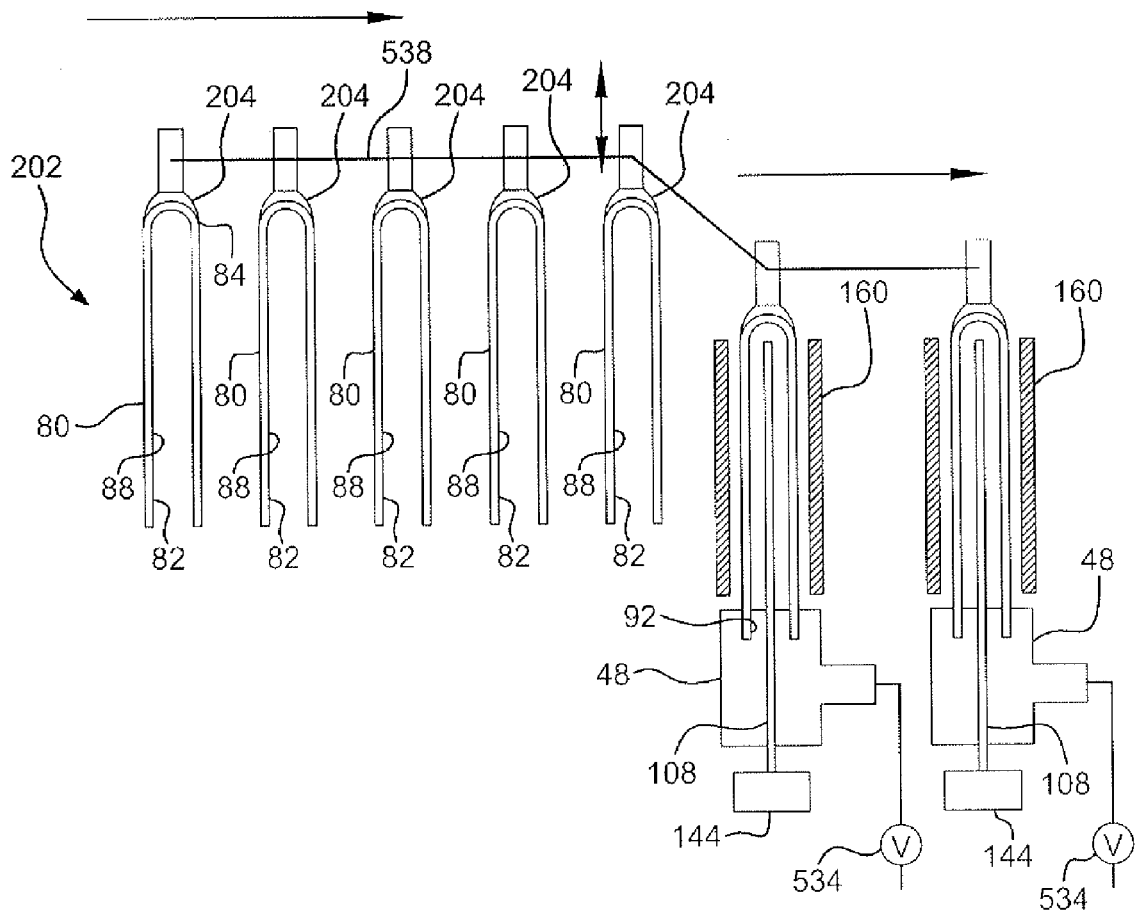
FIG. 16 is a diagrammatic view of the operation of a vessel transport system, such as the one shown in FIG. 15, to place and hold a vessel in a process station.
Figure 17:
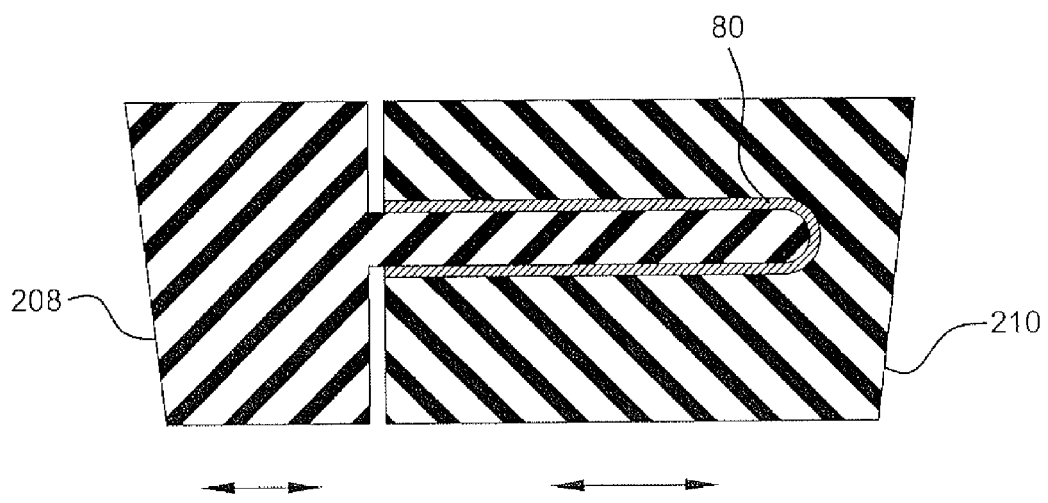
FIG. 17 is a diagrammatic view of a mold and mold cavity for forming a vessel according to an aspect of the present disclosure.
Figure 18:
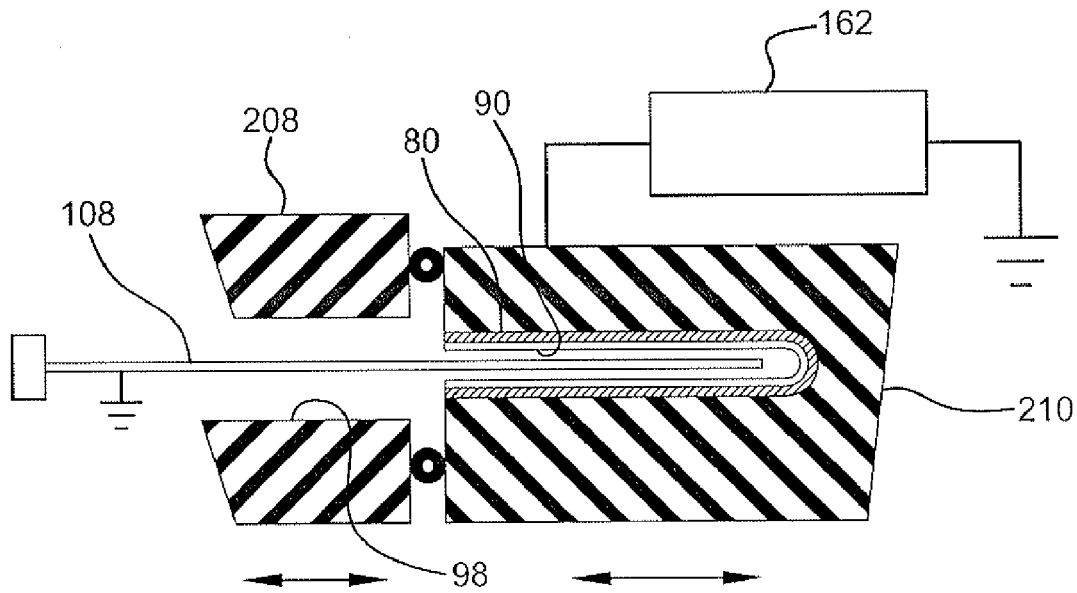
FIG. 18 is a diagrammatic view of the mold cavity of FIG. 17 provided with a vessel coating device according to an aspect of the present disclosure.
Figure 19:
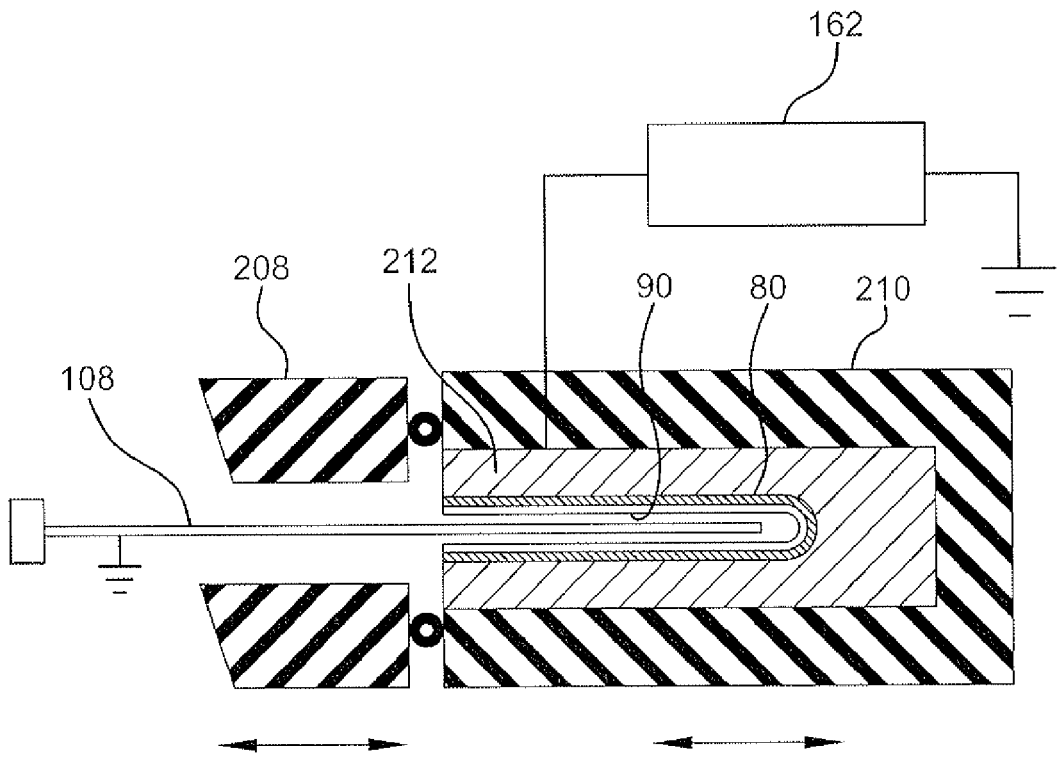
FIG. 19 is a view similar to FIG. 17 provided with an alternative vessel coating device according to an aspect of the present disclosure.

IV.B. PECVD Apparatus Using Gripper for Transporting Tube to and from Coating Station IV.B. Another embodiment is an apparatus for PECVD treatment of a vessel, employing a gripper as previously described. FIGS. 15 and 16 show apparatus generally indicated at 202 for PECVD treatment of a first vessel 80 having an open end 82, a closed end 84, and an interior space defined by the surface 88. This embodiment includes a vessel holder 48, at least a first gripper 204 (in this embodiment, for example, a suction cup), a seat defined by the vessel port 92 on the vessel holder 48, a reactant supply 144, a plasma generator represented by the electrodes 108 and 160, a vessel release, which can be a vent valve such as 534, and either the same gripper 204 or a second one (in effect, optionally a second gripper 204).

IV.B. The first gripper 204, and as illustrated any of the grippers 204, is configured for selectively holding and releasing the closed end 84 of a vessel 80. While gripping the closed end 84 of the vessel, the first gripper 204 can transport the vessel to the vicinity of the vessel holder 48. In the illustrated embodiment, the transportation function is facilitated by a series conveyor 538 to which the grippers 204 are attached in a series.

IV.B. The vessel holder 48 has previously been described in connection with other embodiments, and is configured for seating to the open end 82 of a vessel 80. The seat defined by the vessel port 92 has previously been described in connection with other embodiments, and is configured for establishing sealed communication between the vessel holder 48 and the interior space 88 of the first vessel, and in this case any of the vessels 80. The reactant supply 144 has previously been described in connection with other embodiments, and is operatively connected for introducing at least one gaseous reactant within the first vessel 80 through the vessel holder 48. The plasma generator defined by the electrodes 108 and 160 has previously been described in connection with other embodiments, and is configured for forming plasma within the first vessel under conditions effective to form a reaction product of the reactant on the interior surface of the first vessel.

IV.B. The vessel release 534 or other expedients, such as introducing within the seated vessel 80 a reactant gas, a carrier gas, or an inexpensive gas such as compressed nitrogen or air, can be used for unseating the first vessel 80 from the vessel holder 48.

IV.B. The grippers 204 are configured for axially transporting the first vessel 80 away from the vessel holder 48 and then releasing the first vessel 80, as by releasing suction from between the gripper 48 and the vessel end 84.

IV.B. FIGS. 15 and 16 also show a method of PECVD treatment of a first vessel, comprising several steps. A first vessel 80 is provided having an open end 82, a closed end 84, and an interior surface 88. At least a first gripper 204 is provided that is configured for selectively holding and releasing the closed end 84 of the first vessel 80. The closed end 84 of the first vessel 80 is gripped with the first gripper 204 and thereby transported to the vicinity of a vessel holder 48 configured for seating to the open end of the first vessel. In the embodiment of FIG. 16, two vessel holders 48 are provided, allowing the vessels 80 to be advanced and seated on the vessel holders 48 two at a time, thus doubling the effective production rate. Next, the first gripper 204 is used for axially advancing the first vessel 80 and seating its open end 82 on the vessel holder 48, establishing sealed communication between the vessel holder 48 and the interior of the first vessel. Next, at least one gaseous reactant is introduced within the first vessel through the vessel holder, optionally as explained for previous embodiments.

IV.B. Continuing, plasma is formed within the first vessel under conditions effective to form a reaction product of the reactant on the interior surface of the first vessel, optionally as explained for previous embodiments. The first vessel is unseated from the vessel holder, optionally as explained for previous embodiments. The first gripper or another gripper is used, optionally as explained for previous embodiments, to axially transport the first vessel away from the vessel holder. The first vessel can then be released from the gripper used to axially transport it away from the vessel holder, optionally as explained for previous embodiments.

IV.B. Further optional steps that can be carried out according to this method include providing a reaction vessel different from the first vessel, the reaction vessel having an open end and an interior space, and seating the open end of the reaction vessel on the vessel holder, establishing sealed communication between the vessel holder and the interior space of the reaction vessel. A PECVD reactant conduit can be provided within the interior space. Plasma can be formed within the interior space of the reaction vessel under conditions effective to remove at least a portion of a deposit of a PECVD reaction product from the reactant conduit. These reaction conditions have been explained in connection with a previously described embodiment. The reaction vessel then can be unseated from the vessel holder and transported away from the vessel holder.

IV.B. Further optional steps that can be carried out according to any embodiment of this method include:
  providing at least a second gripper;
  operatively connecting at least the first and second grippers to a series conveyor;
  providing a second vessel having an open end, a closed end, and an interior surface;
  providing a gripper configured for selectively holding and releasing the closed end of the second vessel;
  gripping the closed end of the second vessel with the gripper;
  using the gripper, transporting the second vessel to the vicinity of a vessel holder configured for seating to the open end of the second vessel;
  using the gripper, axially advancing the second vessel and seating its open end on the vessel holder, establishing sealed communication between the vessel holder and the interior of the second vessel;
  introducing at least one gaseous reactant within the second vessel through the vessel holder;
  forming plasma within the second vessel under conditions effective to form a reaction product of the reactant on the interior surface of the second vessel;
  unseating the second vessel from the vessel holder; and
  using the second gripper or another gripper, axially transporting the second vessel away from the vessel holder; and
  releasing the second vessel from the gripper used to axially transport it away from the vessel holder.

IV.B. FIG. 16 is an example of using a suction cup type device to hold the end of a sample collection tube (in this example) that can move through a production line/system. The specific example shown here is one possible step (of many possible steps as outlined above and below) of coating/treatment. The tube can move into the coating step/area and the tube can be lowered into the vessel holder and (in this example) the cylindrical electrode. The vessel holder, sample collection tube and suction cup can then move together to the next step where the electrode is powered and the treatment/coating take place. Any of the above types of electrodes can be utilized in this example.

IV.B. Thus, FIGS. 15 and 16 show a vessel holder 48 in a coating station 28 similar to FIG. 13, employing a vessel transport generally indicated as 202 to move the vessel 80 to and from the coating station 28. The vessel transport 202 can be provided with a grip 204, which in the illustrated transport 202 can be a suction cup. An adhesive pad, active vacuum source (with a pump to draw air from the grip, actively creating a vacuum) or other expedient can also be employed as the grip. The vessel transport 202 can be used, for example, to lower the vessel 80 into a seated position in the vessel port 92 to position the vessel 80 for coating. The vessel transport 202 can also be used to lift the vessel 80 away from the vessel port 92 after processing at the station 28 can be complete. The vessel transport 202 also can be used to seat the vessel 80 before the vessel 80 and vessel transport 48 are advanced together to a station. The vessel transport can also be used to urge the vessel 80 against its seat on the vessel port 92. Also, although FIG. 15 can be oriented to show vertical lifting of the vessel 80 from above, an inverted orientation can be or contemplated in which the vessel transport 202 is below the vessel 80 and supports it from beneath.

IV.B. FIG. 16 shows an embodiment of a method in which vessel transports 202 such as suction cups 204 convey the vessels 80 horizontally, as from one station to the next, as well as (or instead of) vertically into and out of a station such as 28. The vessels 80 can be lifted and transported in any orientation. FIG. 16 thus represents a method of PECVD treatment of a first vessel 80, comprising several steps.

IV.B. In the embodiment of FIG. 13, the outer electrode 160 can be generally cylindrical with open ends, and can be stationary. The vessel 80 can be advanced through the outer electrode 160 until the opening 82 is seated on the vessel port 96. In this embodiment, the probe 108 optionally can be permanently molded or otherwise secured into the gas inlet port 104, as opposed to a wiping seal allowing relative motion between the port 104 and the probe 108.

Figure 14:
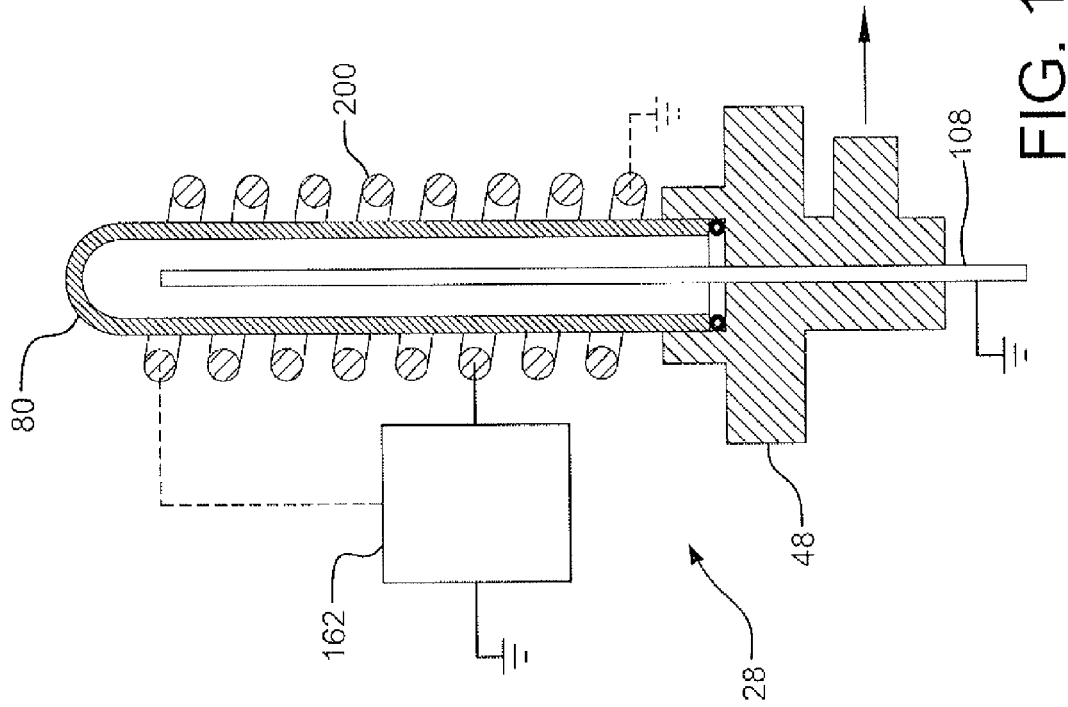
FIG. 14 is a view similar to FIG. 2 of a vessel holder in a coating station according to even another embodiment of the disclosure, in which the electrode can be configured as a coil.

IV.B. FIG. 14 shows an additional alternative for coupling electrical energy into the plasma at 50 Hz-1 GHz. This can consist of a coil that can be either lowered into position or the vessel holder (with device) can be pushed up into position. Coiled electrodes are referred to as inductive coupling devices and can impart a magnetic component to the inside of the device where the plasma can be created.

IV.B. A probe 108 can still be used as discussed in FIG. 2 and FIG. 13. Other aspects of the vessel holder or vessel holder 48 discussed above can remain the same.

IV.B. As FIG. 49 for example shows, a reaction vessel 532 different from the first vessel 80 can be provided, also having an open end 540 and an interior space defined by the interior surface 542. Like the vessels 80, the reaction vessel 532 can have its open end 540 on the vessel holder 48 and establish sealed communication between the vessel holder 48 and the interior space 542 of the reaction vessel.

Figure 49:
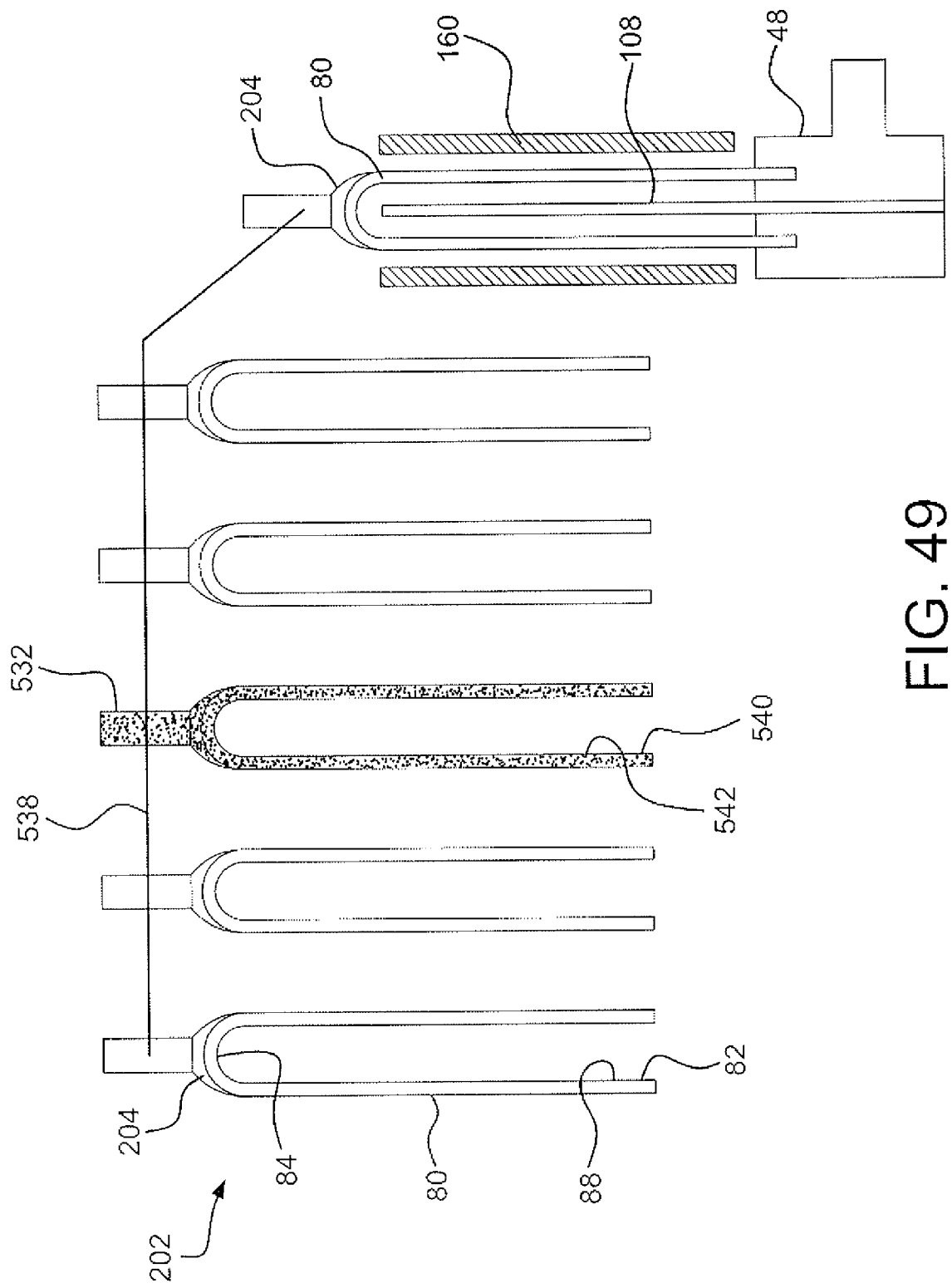
FIG. 49 is a view similar to FIG. 16 showing a mechanism for delivering vessels to be treated and a cleaning reactor to a PECVD coating apparatus. The mechanism of FIG. 49 is usable with the vessel inspection apparatus of FIGS. 1, 9, 15, and 16, for example.

IV.B. FIG. 49 is a view similar to FIG. 16 showing a mechanism for delivering vessels 80 to be treated and a cleaning reactor 532 to a PECVD coating apparatus. In this embodiment, the inner electrode 108 optionally can be cleaned without removing it from the vessel holder 48.

IV.B. FIG. 49 shows that the PECVD reactant conduit 108 as previously described is positioned to be located within the interior space 542 of the reaction vessel 532 when the reaction vessel is seated on the vessel holder 48 in place of a vessel 80 which is provided for coating as described previously. FIG. 49 shows the reactant conduit 108 in this configuration, even though the conduit 108 has an exterior portion, as well as an interior distal end. It suffices for this purpose and the present claims if the reactant conduit 108 extends at least partially into the vessel 80 or 532.

IV.B. The mechanism of FIG. 49 as illustrated is usable with the embodiments of at least FIGS. 1 and 15-16, for example. The cleaning reactor 532 can also be provided as a simple vessel seated and transported on a vessel holder such as 48, in an alternative embodiment. In this configuration, the cleaning reactor 532 can be used with the apparatus of at least FIGS. 1-3, 8, 9, 12-15, 18, 19, 21, 22, 26-28, 33-35, 37-48, and 52-54, for example.

IV.B. The plasma generator defined by the electrodes 108 and 160 is configurable for forming plasma within the interior space of the reaction vessel 532 under conditions effective to remove at least a portion of a deposit of a PECVD reaction product from the reactant conduit 108. It is contemplated above that the inner electrode and gas source 108 can be a conductive tube, for example a metallic tube, and that the reaction vessel 532 can be made of any suitable, optionally heat-resistant material such as ceramic, quartz, glass or other materials that can withstand more heat than a thermoplastic vessel. The material of the reaction vessel 532 also can desirably be chemical or plasma resistant to the conditions used in the reaction vessel to remove deposits of reaction products. Optionally, the reaction vessel 532 can be made of electrically conductive material and itself serve as a special-purpose outer electrode for the purpose of removing deposits from the reactant conduit 108. As yet another alternative, the reaction vessel 532 can be configured as a cap that seats on the outer electrode 160, in which case the outer electrode 160 would optionally be seated on the vessel holder 48 to define a closed cleaning reaction chamber.

IV.B. It is contemplated that the reaction conditions effective to remove at least a portion of a deposit of a PECVD reaction product from the reactant conduit 108 include introduction of a substantial portion of an oxidizing reactant such as oxygen or ozone (either generated separately or by the plasma apparatus), a higher power level than is used for deposition of coatings, a longer cycle time than is used for deposition of coatings, or other expedients known for removing the type of unwanted deposit encountered on the reaction conduit 108. For another example, mechanical milling can also be used to remove unwanted deposits. Or, solvents or other agents can be forced through the reactant conduit 108 to clear obstructions. These conditions can be far more severe than what the vessels 80 to be coated can withstand, since the reaction vessel 532 does not need to be suitable for the normal uses of the vessel 80. Optionally, however, a vessel 80 can be used as the reaction vessel, and if the deposit removing conditions are too severe the vessel 80 employed as a reaction vessel can be discarded, in an alternative embodiment.

V. PECVD Methods for Making Vessels

V.1 Precursors for PECVD Coating

The precursor for the PECVD coating of the present invention is broadly defined as an organometallic precursor. An organometallic precursor is defined in this specification as comprehending compounds of metal elements from Group III and/or Group IV of the Periodic Table having organic residues, e.g. hydrocarbon, aminocarbon or oxycarbon residues. Organometallic compounds as presently defined include any precursor having organic moieties bonded to silicon or other Group III/IV metal atoms directly, or optionally bonded through oxygen or nitrogen atoms. The relevant elements of Group III of the Periodic Table are Boron, Aluminum, Gallium, Indium, Thallium, Scandium, Yttrium, and Lanthanum, Aluminum and Boron being preferred. The relevant elements of Group IV of the Periodic Table are Silicon, Germanium, Tin, Lead, Titanium, Zirconium, Hafnium, and Thorium, with Silicon and Tin being preferred. Other volatile organic compounds can also be contemplated. However, organosilicon compounds are preferred for performing present invention.

An organosilicon precursor is contemplated, where an "organosilicon precursor" is defined throughout this specification most broadly as a compound having at least one of the linkages:

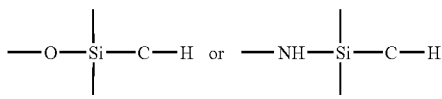

The first structure immediately above is a tetravalent silicon atom connected to an oxygen atom and an organic carbon atom (an organic carbon atom being a carbon atom bonded to at least one hydrogen atom). The second structure immediately above is a tetravalent silicon atom connected to an —NH— linkage and an organic carbon atom (an organic carbon atom being a carbon atom bonded to at least one hydrogen atom). Optionally, the organosilicon precursor is selected from the group consisting of a linear siloxane, a monocyclic siloxane, a polycyclic siloxane, a polysilsesquioxane, a linear silazane, a monocyclic silazane, a polycyclic silazane, a polysilsesquiazane, and a combination of any two or more of these precursors. Also contemplated as a precursor, though not within the two formulas immediately above, is an alkyl trimethoxysilane. If an oxygen-containing precursor (e.g. a siloxane) is used, a representative predicted empirical composition resulting from PECVD under conditions forming a hydrophobic or lubricating coating would be $Si_wO_xC_yH_z$ as defined in the Definition Section, while a representative predicted empirical composition resulting from PECVD under conditions forming a barrier coating would be $SiO_x$, where x in this formula is from about 1.5 to about 2.9. If a nitrogen-containing precursor (e.g. a silazane) is used, the predicted composition would be $Si_w*N_x*C_y*H_z*$, i.e. in $Si_wO_xC_yH_z$ as specified in the Definition Section, O is replaced by N and the indices are adapted to the higher valency of N as compared to O (3 instead of 2). The latter adaptation will generally follow the ratio of w, x, y and z in a siloxane to the corresponding indices in its aza counterpart. In a particular aspect of the invention, $Si_w*N_x*C_y*H_z*$ in which w*, x*, y*, and z* are defined the same as w, x, y, and z for the siloxane counterparts, but for an optional deviation in the number of hydrogen atoms.

One type of precursor starting material having the above empirical formula is a linear siloxane, for example a material having the following formula:

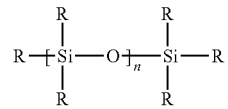

in which each R is independently selected from alkyl, for example methyl, ethyl, propyl, isopropyl, butyl, isobutyl, t-butyl, vinyl, alkyne, or others, and n is 1, 2, 3, 4, or greater, optionally two or greater. Several examples of contemplated linear siloxanes are hexamethyldisiloxane (HMDSO),
octamethyltrisiloxane,
decamethyltetrasiloxane,
dodecamethylpentasiloxane, or combinations of two or more of these. The analogous silazanes in which —NH— is substituted for the oxygen atom in the above structure are also useful for making analogous coatings. Several examples of contemplated linear silazanes are octamethyltrisilazane, decamethyltetrasilazane, or combinations of two or more of these.

V.C. Another type of precursor starting material is a monocyclic siloxane, for example a material having the following structural formula:

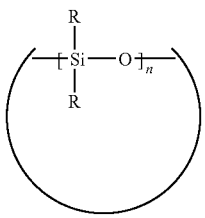

in which R is defined as for the linear structure and "a" is from 3 to about 10, or the analogous monocyclic silazanes. Several examples of contemplated hetero-substituted and unsubstituted monocyclic siloxanes and silazanes include 1,3,5-trimethyl-1,3,5-tris(3,3,3-trifluoropropyl)methyl] cyclotrisiloxane
2,4,6,8-tetramethyl-2,4,6,8-tetravinylcyclotetrasiloxane,
pentamethylcyclopentasiloxane,
pentavinylpentamethylcyclopentasiloxane,
hexamethylcyclotrisiloxane,
hexaphenylcyclotrisiloxane,
octamethylcyclotetrasiloxane (OMCTS),
octaphenylcyclotetrasiloxane,
decamethylcyclopentasiloxane
dodecamethylcyclohexasiloxane,
methyl(3,3,3-trifluoropropl)cyclosiloxane,
Cyclic organosilazanes are also contemplated, such as
Octamethylcyclotetrasilazane,
1,3,5,7-tetravinyl-1,3,5,7-tetramethylcyclotetrasilazane
hexamethylcyclotrisilazane,
octamethylcyclotetrasilazane,
decamethylcyclopentasilazane,
dodecamethylcyclohexasilazane, or
combinations of any two or more of these.

V.C. Another type of precursor starting material is a polycyclic siloxane, for example a material having one of the following structural formulas:

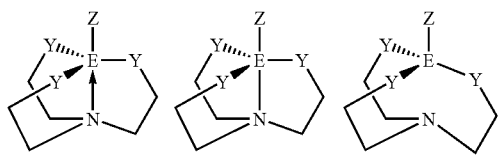

in which Y can be oxygen or nitrogen, E is silicon, and Z is a hydrogen atom or an organic substituent, for example alkyl such as methyl, ethyl, propyl, isopropyl, butyl, isobutyl, t-butyl, vinyl, alkyne, or others. When each Y is oxygen, the respective structures, from left to right, are a silatrane, a silquasilatrane, and a silproatrane. When Y is nitrogen, the respective structures are an azasilatrane, an azasilquasilatrane, and an azasilproatrane.

V.C. Another type of polycyclic siloxane precursor starting material is a polysilsesquioxane, with the empirical formula $RSiO_{1.5}$ and the structural formula:

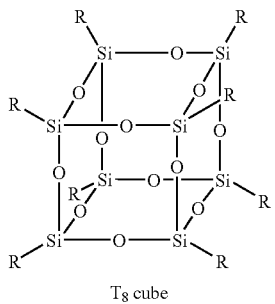

$T_8$ cube in which each R is a hydrogen atom or an organic substituent, for example alkyl such as methyl, ethyl, propyl, isopropyl, butyl, isobutyl, t-butyl, vinyl, alkyne, or others. Two commercial materials of this sort are SST-eM01 poly(methylsilsesquioxane), in which each R is methyl, and SST-3MH1.1 poly(Methyl-Hydridosilsesquioxane), in which 90% of the R groups are methyl, 10% are hydrogen atoms. This material is available in a 10% solution in tetrahydrofuran, for example. Combinations of two or more of these are also contemplated. Other examples of a contemplated precursor are methylsilatrane, CAS No. 2288-13-3, in which each Y is oxygen and Z is methyl, methylazasilatrane, SST-eM01 poly(methylsilsesquioxane), in which each R optionally can be methyl, SST-3MH1.1 poly(Methyl-Hydridosilsesquioxane), in which 90% of the R groups are methyl and 10% are hydrogen atoms, or a combination of any two or more of these.

V.C. The analogous polysilsesquiazanes in which —NH— is substituted for the oxygen atom in the above structure are also useful for making analogous coatings. Examples of contemplated polysilsesquiazanes are a poly(methylsilsesquiazane), in which each R is methyl, and a poly(Methyl-Hydridosilsesquiazane, in which 90% of the R groups are methyl, 10% are hydrogen atoms. Combinations of two or more of these are also contemplated.

V.C. One particularly contemplated precursor for the lubricity layer according to the present invention is a monocyclic siloxane, for example is octamethylcyclotetrasiloxane.

One particularly contemplated precursor for the hydrophobic layer according to the present invention is a monocyclic siloxane, for example is octamethylcyclotetrasiloxane.

One particularly contemplated precursor for the barrier coating according to the present invention is a linear siloxane, for example is HMDSO.

V.C. In any of the coating methods according to the present invention, the applying step optionally can be carried out by vaporizing the precursor and providing it in the vicinity of the substrate. E.g., OMCTS is usually vaporized by heating it to about 50° C. before applying it to the PECVD apparatus.

V.2 General PECVD Method

In the context of the present invention, the following PECVD method is generally applied, which contains the following steps:
 (a) providing a gaseous reactant comprising a precursor as defined herein, optionally an organosilicon precursor, and optionally $O_2$ in the vicinity of the substrate surface; and
 (b) generating a plasma from the gaseous reactant, thus forming a coating on the substrate surface by plasma enhanced chemical vapor deposition (PECVD).

In the method, the coating characteristics are advantageously set by one or more of the following conditions: the plasma properties, the pressure under which the plasma is applied, the power applied to generate the plasma, the presence and relative amount of $O_2$ in the gaseous reactant, the plasma volume, and the organosilicon precursor. Optionally, the coating characteristics are set by the presence and relative amount of $O_2$ in the gaseous reactant and/or the power applied to generate the plasma.

In all embodiments of the present invention, the plasma is in an optional aspect a non-hollow-cathode plasma.

In a further preferred aspect, the plasma is generated at reduced pressure (as compared to the ambient or atmospheric pressure). Optionally, the reduced pressure is less than 300 mTorr, optionally less than 200 mTorr, even optionally less than 100 mTorr.

The PECVD optionally is performed by energizing the gaseous reactant containing the precursor with electrodes powered at a frequency at microwave or radio frequency, and optionally at a radio frequency. The radio frequency preferred to perform an embodiment of the invention will also be addressed as "RF frequency". A typical radio frequency range for performing the present invention is a frequency of from 10 kHz to less than 300 MHz, optionally from 1 to 50 MHz, even optionally from 10 to 15 MHz. A frequency of 13.56 MHz is most preferred, this being a government sanctioned frequency for conducting PECVD work.

There are several advantages for using a RF power source versus a microwave source: Since RF operates a lower power, there is less heating of the substrate/vessel. Because the focus of the present invention is putting a plasma coating on plastic substrates, lower processing temperature are desired to prevent melting/distortion of the substrate. To prevent substrate overheating when using microwave PECVD, the microwave PECVD is applied in short bursts, by pulsing the power. The power pulsing extends the cycle time for the coating, which is undesired in the present invention. The higher frequency microwave can also cause offgassing of volatile substances like residual water, oligomers and other materials in the plastic substrate. This offgassing can interfere with the PECVD coating. A major concern with using microwave for PECVD is delamination of the coating from the substrate. Delamination occurs because the microwaves change the surface of the substrate prior to depositing the coating layer. To mitigate the possibility of delamination, interface coating layers have been developed for microwave PECVD to achieve good bonding between the coating and the substrate. No such interface coating layer is needed with RF PECVD as there is no risk of delamination. Finally, the lubricity layer and hydrophobic layer according to the present invention are advantageously applied using lower power. RF power operates at lower power and provides more control over the PECVD process than microwave power. Nonetheless, microwave power, though less preferred, is usable under suitable process conditions.

Furthermore, for all PECVD methods described herein, there is a specific correlation between the power (in Watts) used to generate the plasma and the volume of the lumen wherein the plasma is generated. Typically, the lumen is the lumen of a vessel coated according to the present invention. The RF power should scale with the volume of the vessel if the same electrode system is employed. Once the composition of a gaseous reactant, for example the ratio of the precursor to $O_2$, and all other parameters of the PECVD coating method but the power have been set, they will typically not change when the geometry of a vessel is maintained and only its volume is varied. In this case, the power will be directly proportional to the volume. Thus, starting from the power to volume ratios provided by present description, the power which has to be applied in order to achieve the same or a similar coating in a vessel of same geometry, but different size, can easily be found. The influence of the vessel geometry on the power to be applied is illustrated by the results of the Examples for tubes in comparison to the Examples for syringe barrels.

For any coating of the present invention, the plasma is generated with electrodes powered with sufficient power to form a coating on the substrate surface. For a lubricity layer or hydrophobic layer, in the method according to an embodiment of the invention the plasma is optionally generated
(i) with electrodes supplied with an electric power of from 0.1 to 25 W, optionally from 1 to 22 W, optionally from 3 to 17 W, even optionally from 5 to 14 W, optionally from 7 to 11 W, for example of 8 W; and/or (ii) wherein the ratio of the electrode power to the plasma volume is less than 10 W/ml, optionally is from 5 W/ml to 0.1 W/ml, optionally is from 4 W/ml to 0.1 W/ml, optionally from 2 W/ml to 0.2 W/ml. For a barrier coating or SiOx coating, the plasma is optionally generated (i) with electrodes supplied with an electric power of from 8 to 500 W, optionally from 20 to 400 W, optionally from 35 to 350 W, even optionally from 44 to 300 W, optionally from 44 to 70 W; and/or
(ii) the ratio of the electrode power to the plasma volume is equal or more than 5 W/ml, optionally is from 6 W/ml to 150 W/ml, optionally is from 7 W/ml to 100 W/ml, optionally from 7 W/ml to 20 W/ml.

The vessel geometry can also influence the choice of the gas inlet used for the PECVD coating. In a particular aspect, a syringe can be coated with an open tube inlet, and a tube can be coated with a gas inlet having small holes which is extended into the tube.

The power (in Watts) used for PECVD also has an influence on the coating properties. Typically, an increase of the power will increase the barrier properties of the coating, and a decrease of the power will increase the lubricity and hydrophobicity of the coating. E.g., for a coating on the inner wall of syringe barrel having a volume of about 3 ml, a power of less than 30 W will lead to a coating which is predominantly a barrier coating, while a power of more than 30 W will lead to a coating which is predominantly a lubricity layer (see Examples).

A further parameter determining the coating properties is the ratio of $O_2$ (or another oxidizing agent) to the precursor (e.g. organosilicon precursor) in the gaseous reactant used for generating the plasma. Typically, an increase of the $O_2$ ratio in the gaseous reactant will increase the barrier properties of the coating, and a decrease of the $O_2$ ratio will increase the lubricity and hydrophobicity of the coating.

If a lubricity layer is desired, then $O_2$ is optionally present in a volume-volume ratio to the gaseous reactant of from 0:1 to 5:1, optionally from 0:1 to 1:1, even optionally from 0:1 to 0.5:1 or even from 0:1 to 0.1:1. Most advantageously, essentially no oxygen is present in the gaseous reactant. Thus, the gaseous reactant should comprise less than 1 vol % $O_2$, for example less than 0.5 vol % $O_2$, and optionally is $O_2$-free. The same applies to a hydrophobic layer.

If, on the other hand, a barrier or $SiO_x$ coating is desired, then the $O_2$ is optionally present in a volume:volume ratio to the gaseous reactant of from 1:1 to 100:1 in relation to the silicon containing precursor, optionally in a ratio of from 5:1 to 30:1, optionally in a ratio of from 10:1 to 20:1, even optionally in a ratio of 15:1.

V.A. PECVD to Apply $SiO_x$ Barrier Coating, Using Plasma that is Substantially Free of Hollow Cathode Plasma V.A. A specific embodiment is a method of applying a barrier coating of $SiO_x$, defined in this specification (unless otherwise specified in a particular instance) as a coating containing silicon, oxygen, and optionally other elements, in which x, the ratio of oxygen to silicon atoms, is from about 1.5 to about 2.9, or 1.5 to about 2.6, or about 2. These alternative definitions of x apply to any use of the term $SiO_x$ in this specification. The barrier coating is applied to the interior of a vessel, for example a sample collection tube, a syringe barrel, or another type of vessel. The method includes several steps.

V.A. A vessel wall is provided, as is a reaction mixture comprising plasma forming gas, i.e. an organosilicon compound gas, optionally an oxidizing gas, and optionally a hydrocarbon gas.

V.A. Plasma is formed in the reaction mixture that is substantially free of hollow cathode plasma. The vessel wall is contacted with the reaction mixture, and the coating of $SiO_x$ is deposited on at least a portion of the vessel wall.

V.A. In certain embodiments, the generation of a uniform plasma throughout the portion of the vessel to be coated is contemplated, as it has been found in certain instances to generate an SiO$_x$ coating providing a better barrier against oxygen. Uniform plasma means regular plasma that does not include a substantial amount of hollow cathode plasma (which has a higher emission intensity than regular plasma and is manifested as a localized area of higher intensity interrupting the more uniform intensity of the regular plasma).

V.A. The hollow cathode effect is generated by a pair of conductive surfaces opposing each other with the same negative potential with respect to a common anode. If the spacing is made (depending on the pressure and gas type) such that the space charge sheaths overlap, electrons start to oscillate between the reflecting potentials of the opposite wall sheaths leading to multiple collisions as the electrons are accelerated by the potential gradient across the sheath region. The electrons are confined in the space charge sheath overlap which results in very high ionization and high ion density plasmas. This phenomenon is described as the hollow cathode effect. Those skilled in the art are able to vary the processing conditions, such as the power level and the feed rates or pressure of the gases, to form uniform plasma throughout or to form plasma including various degrees of hollow cathode plasma.

V.A. In an alternate method, using for example the apparatus of FIG. 12 previously described, microwave energy can be used to generate the plasma in a PECVD process. The processing conditions can be different, however, as microwave energy applied to a thermoplastic vessel will excite (vibrate) water molecules. Since there is a small amount of water in all plastic materials, the microwaves will heat the plastic. As the plastic heats, the large driving force created by the vacuum inside of the device relative to atmospheric pressure outside the device will pull free or easily desorb materials to the interior surface 88 where they will either become volatile or will be weakly bound to the surface. The weakly bound materials will then create an interface that can hinder subsequent coatings (deposited from the plasma) from adhering to the plastic interior surface 88 of the device.

V.A. As one way to negate this coating hindering effect, a coating can be deposited at very low power (in the example above 5 to 20 Watts at 2.45 GHz) creating a cap onto which subsequent coatings can adhere. This results in a two-step coating process (and two coating layers). In the example above, the initial gas flows (for the capping layer) can be changed to 2 sccm ("standard cubic centimeters per minute") HMDSO and 20 sccm oxygen with a process power of 5 to 20 Watts for approximately 2-10 seconds. Then the gases can be adjusted to the flows in the example above and the power level increased to 20-50 Watts so that an SiO$_x$ coating, in which x in this formula is from about 1.5 to about 2.9, alternatively from about 1.5 to about 2.6, alternatively about 2, can be deposited. Note that the capping layer might provide little to no functionality in certain embodiments, except to stop materials from migrating to the vessel interior surface 88 during the higher power SiO$_x$ coating deposition. Note also that migration of easily desorbed materials in the device walls typically is not an issue at lower frequencies such as most of the RF range, since the lower frequencies do not excite (vibrate) molecular species.

V.A. As another way to negate the coating hindering effect described above, the vessel 80 can be dried to remove embedded water before applying microwave energy. Desiccation or drying of the vessel 80 can be accomplished, for example, by thermally heating the vessel 80, as by using an electric heater or forced air heating. Desiccation or drying of the vessel 80 also can be accomplished by exposing the interior of the vessel 80, or gas contacting the interior of the vessel 80, to a desiccant. Other expedients for drying the vessel, such as vacuum drying, can also be used. These expedients can be carried out in one or more of the stations or devices illustrated or by a separate station or device.

V.A. Additionally, the coating hindering effect described above can be addressed by selection or processing of the resin from which the vessels 80 are molded to minimize the water content of the resin.

V.B. PECVD Coating Restricted Opening of Vessel (Syringe Capillary)

Figure 26:
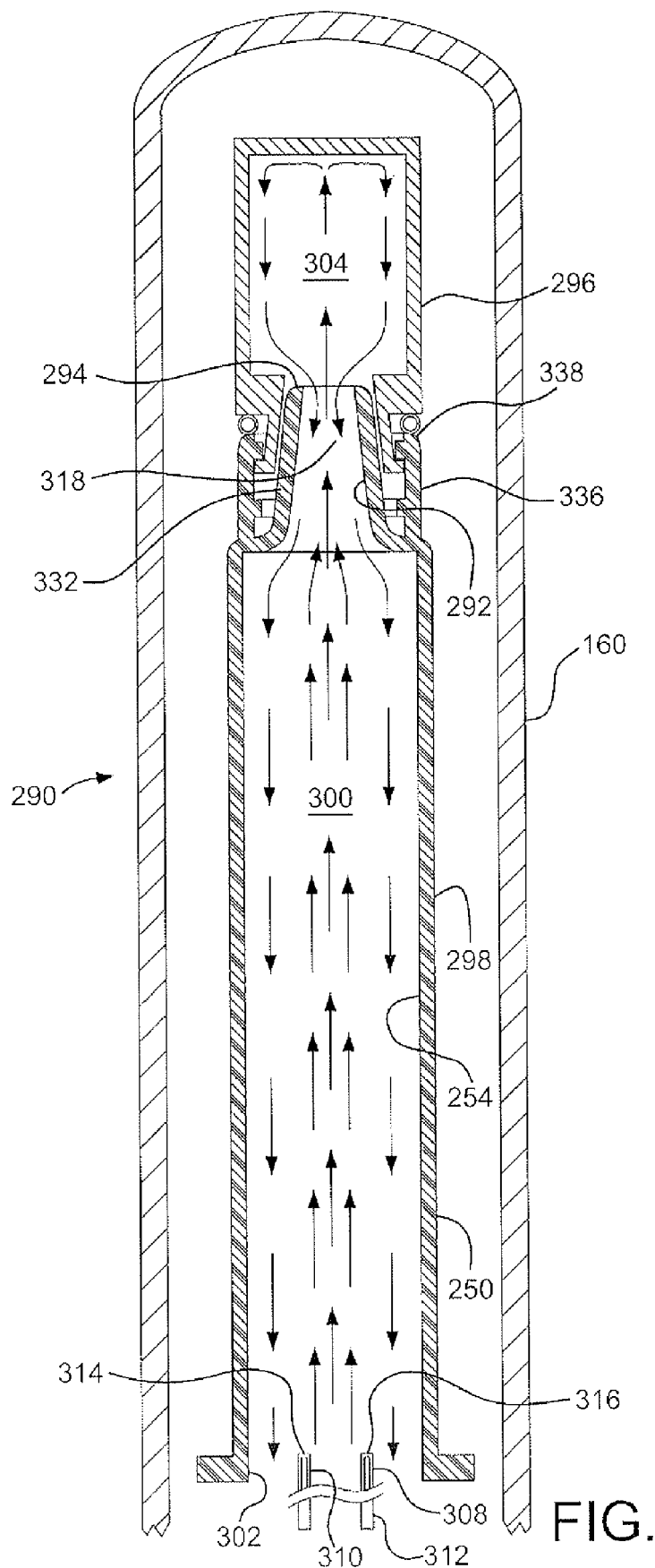
FIG. 26 is a view similar to FIG. 22 of another embodiment of the invention for processing syringe barrels and other vessels.
Figure 27:
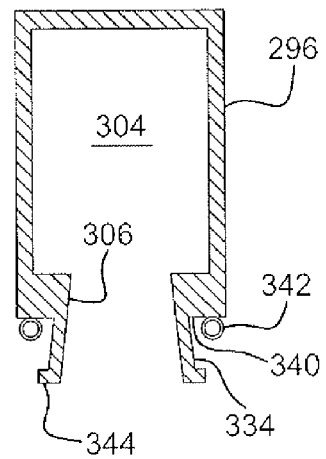
FIG. 27 is an enlarged detail view of the processing vessel of FIG. 26.
Figure 28:
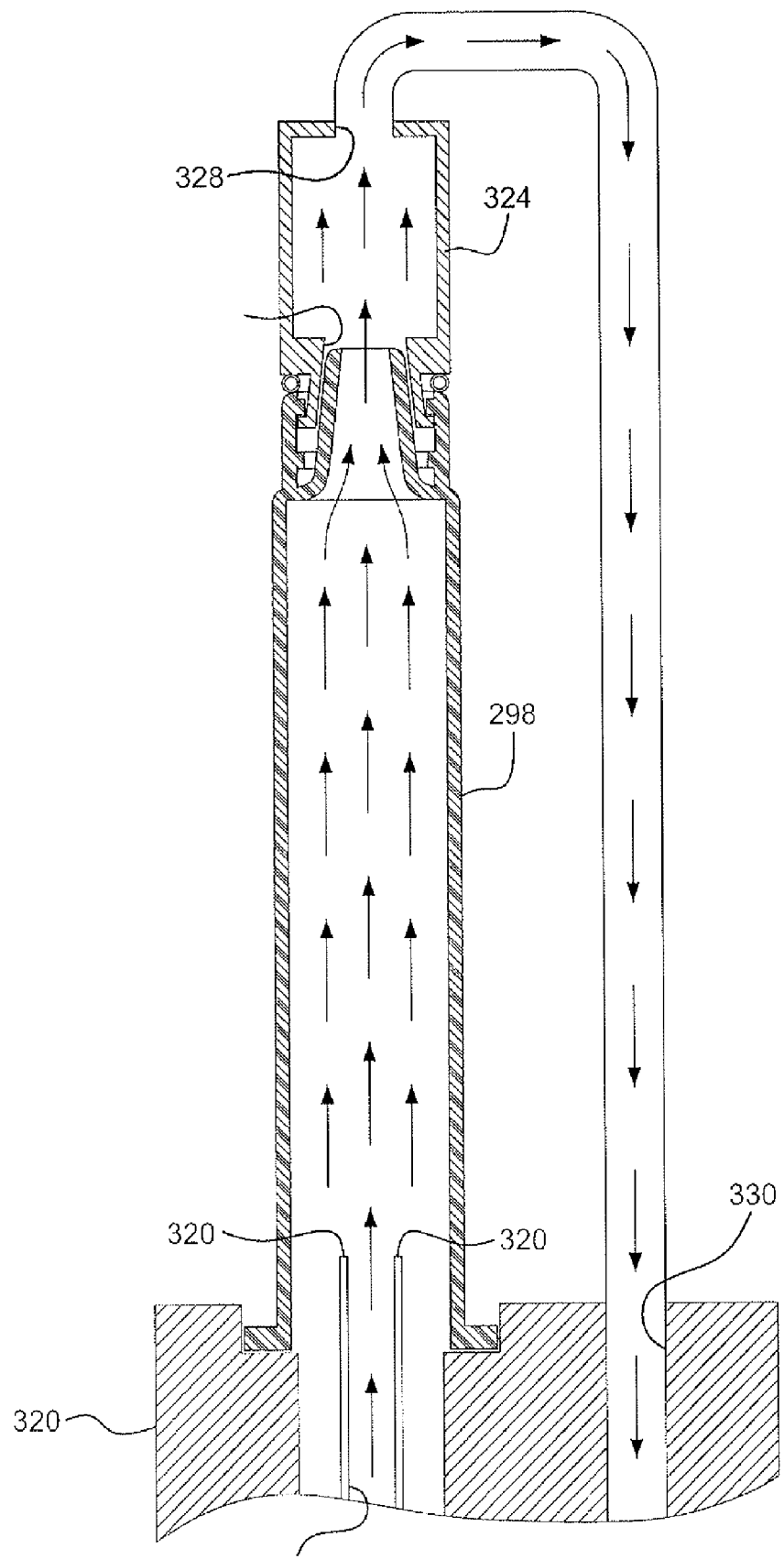
FIG. 28 is a schematic view of an alternative processing vessel.

V.B. FIGS. 26 and 27 show a method and apparatus generally indicated at 290 for coating an inner surface 292 of a restricted opening 294 of a generally tubular vessel 250 to be processed, for example the restricted front opening 294 of a syringe barrel 250, by PECVD. The previously described process is modified by connecting the restricted opening 294 to a processing vessel 296 and optionally making certain other modifications.

V.B. The generally tubular vessel 250 to be processed includes an outer surface 298, an inner or interior surface 254 defining a lumen 300, a larger opening 302 having an inner diameter, and a restricted opening 294 that is defined by an inner surface 292 and has an inner diameter smaller than the inner diameter of the larger opening 302.

V.B. The processing vessel 296 has a lumen 304 and a processing vessel opening 306, which optionally is the only opening, although in other embodiments a second opening can be provided that optionally is closed off during processing. The processing vessel opening 306 is connected with the restricted opening 294 of the vessel 250 to be processed to establish communication between the lumen 300 of the vessel 250 to be processed and the processing vessel lumen via the restricted opening 294.

V.B. At least a partial vacuum is drawn within the lumen 300 of the vessel 250 to be processed and lumen 304 of the processing vessel 296. A PECVD reactant is flowed from the gas source 144 (see FIG. 7) through the first opening 302, then through the lumen 300 of the vessel 250 to be processed, then through the restricted opening 294, then into the lumen 304 of the processing vessel 296.

V.B. The PECVD reactant can be introduced through the larger opening 302 of the vessel 250 by providing a generally tubular inner electrode 308 having an interior passage 310, a proximal end 312, a distal end 314, and a distal opening 316, in an alternative embodiment multiple distal openings can be provided adjacent to the distal end 314 and communicating with the interior passage 310. The distal end of the electrode 308 can be placed adjacent to or into the larger opening 302 of the vessel 250 to be processed. A reactant gas can be fed through the distal opening 316 of the electrode 308 into the lumen 300 of the vessel 250 to be processed. The reactant will flow through the restricted opening 294, then into the lumen 304, to the extent the PECVD reactant is provided at a higher pressure than the vacuum initially drawn before introducing the PECVD reactant.

V.B. Plasma 318 is generated adjacent to the restricted opening 294 under conditions effective to deposit a coating of a PECVD reaction product on the inner surface 292 of the restricted opening 294. In the embodiment shown in FIG. 26, the plasma is generated by feeding RF energy to the generally U-shaped outer electrode 160 and grounding the inner electrode 308. The feed and ground connections to the electrodes could also be reversed, though this reversal can introduce complexity if the vessel 250 to be processed, and thus also the inner electrode 308, are moving through the U-shaped outer electrode while the plasma is being generated.

V.B. The plasma 318 generated in the vessel 250 during at least a portion of processing can include hollow cathode plasma generated inside the restricted opening 294 and/or the processing vessel lumen 304. The generation of hollow cathode plasma 318 can contribute to the ability to successfully apply a barrier coating at the restricted opening 294, although the invention is not limited according to the accuracy or applicability of this theory of operation. Thus, in one contemplated mode of operation, the processing can be carried out partially under conditions generating a uniform plasma throughout the vessel 250 and the gas inlet, and partially under conditions generating a hollow cathode plasma, for example adjacent to the restricted opening 294.

V.B. The process is desirably operated under such conditions, as explained here and shown in the drawings, that the plasma 318 extends substantially throughout the syringe lumen 300 and the restricted opening 294. The plasma 318 also desirably extends substantially throughout the syringe lumen 300, the restricted opening 294, and the lumen 304 of the processing vessel 296. This assumes that a uniform coating of the interior 254 of the vessel 250 is desired. In other embodiments non-uniform plasma can be desired.

V.B. It is generally desirable that the plasma 318 have a substantially uniform color throughout the syringe lumen 300 and the restricted opening 294 during processing, and optionally a substantially uniform color substantially throughout the syringe lumen 300, the restricted opening 294, and the lumen 304 of the processing vessel 296. The plasma desirably is substantially stable throughout the syringe lumen 300 and the restricted opening 294, and optionally also throughout the lumen 304 of the processing vessel 296.

V.B. The order of steps in this method is not contemplated to be critical.

V.B. In the embodiment of FIGS. 26 and 27, the restricted opening 294 has a first fitting 332 and the processing vessel opening 306 has a second fitting 334 adapted to seat to the first fitting 332 to establish communication between the lumen 304 of the processing vessel 296 and the lumen 300 of the vessel 250 to be processed.

V.B. In the embodiment of FIGS. 26 and 27, the first and second fittings are male and female Luer lock fittings 332 and 334, respectively integral with the structure defining the restricted opening 294 and the processing vessel opening 306. One of the fittings, in this case the male Luer lock fitting 332, comprises a locking collar 336 with a threaded inner surface and defining an axially facing, generally annular first abutment 338 and the other fitting 334 comprises an axially facing, generally annular second abutment 340 facing the first abutment 338 when the fittings 332 and 334 are engaged.

V.B. In the illustrated embodiment a seal, for example an O-ring 342 can be positioned between the first and second fittings 332 and 334. For example, an annular seal can be engaged between the first and second abutments 338 and 340. The female Luer fitting 334 also includes dogs 344 that engage the threaded inner surface of the locking collar 336 to capture the O-ring 342 between the first and second fittings 332 and 334. Optionally, the communication established between the lumen 300 of the vessel 250 to be processed and the lumen 304 of the processing vessel 296 via the restricted opening 294 is at least substantially leak proof.

V.B. As a further option, either or both of the Luer lock fittings 332 and 334 can be made of electrically conductive material, for example stainless steel. This construction material forming or adjacent to the restricted opening 294 might contribute to formation of the plasma in the restricted opening 294.

V.B. The desirable volume of the lumen 304 of the processing vessel 296 is contemplated to be a trade-off between a small volume that will not divert much of the reactant flow away from the product surfaces desired to be coated and a large volume that will support a generous reactant gas flow rate through the restricted opening 294 before filling the lumen 304 sufficiently to reduce that flow rate to a less desirable value (by reducing the pressure difference across the restricted opening 294). The contemplated volume of the lumen 304, in an embodiment, is less than three times the volume of the lumen 300 of the vessel 250 to be processed, or less than two times the volume of the lumen 300 of the vessel 250 to be processed, or less than the volume of the lumen 300 of the vessel 250 to be processed, or less than 50% of the volume of the lumen 300 of the vessel 250 to be processed, or less than 25% of the volume of the lumen 300 of the vessel 250 to be processed. Other effective relationships of the volumes of the respective lumens are also contemplated.

V.B. The inventors have found that the uniformity of coating can be improved in certain embodiments by repositioning the distal end of the electrode 308 relative to the vessel 250 so it does not penetrate as far into the lumen 300 of the vessel 250 as the position of the inner electrode shown in previous Figures. For example, although in certain embodiments the distal opening 316 can be positioned adjacent to the restricted opening 294, in other embodiments the distal opening 316 can be positioned less than ⅞ the distance, optionally less than ¾ the distance, optionally less than half the distance to the restricted opening 294 from the larger opening 302 of the vessel to be processed while feeding the reactant gas. Or, the distal opening 316 can be positioned less than 40%, less than 30%, less than 20%, less than 15%, less than 10%, less than 8%, less than 6%, less than 4%, less than 2%, or less than 1% of the distance to the restricted opening 294 from the larger opening of the vessel to be processed while feeding the reactant gas.

V.B. Or, the distal end of the electrode 308 can be positioned either slightly inside or outside or flush with the larger opening 302 of the vessel 250 to be processed while communicating with, and feeding the reactant gas to, the interior of the vessel 250. The positioning of the distal opening 316 relative to the vessel 250 to be processed can be optimized for particular dimensions and other conditions of treatment by testing it at various positions. One particular position of the electrode 308 contemplated for treating syringe barrels 250 is with the distal end 314 penetrating about a quarter inch (about 6 mm) into the vessel lumen 300 above the larger opening 302.

V.B. The inventors presently contemplate that it is advantageous to place at least the distal end 314 of the electrode 308 within the vessel 250 so it will function suitably as an electrode, though that is not necessarily a requirement. Surprisingly, the plasma 318 generated in the vessel 250 can be made more uniform, extending through the restricted opening 294 into the processing vessel lumen 304, with less penetration of the electrode 308 into the lumen 300 than has previously been employed. With other arrangements, such as processing a closed-ended vessel, the distal end 314 of the electrode 308 commonly is placed closer to the closed end of the vessel than to its entrance.

V.B. Or, the distal end 314 of the electrode 308 can be positioned at the restricted opening 294 or beyond the restricted opening 294, for example within the processing vessel lumen 304, as illustrated for example in FIG. 33. Various expedients can optionally be provided, such as shaping the processing vessel 296 to improve the gas flow through the restricted opening 294.

V.B. As another alternative, illustrated in FIGS. 34-35, the composite inner electrode and gas supply tube 398 can have distal gas supply openings such as 400, optionally located near the larger opening 302, and an extension electrode 402 extending distal of the distal gas supply openings 400, optionally extending to a distal end adjacent to the restricted opening 294, and optionally further extending into the processing vessel 324. This construction is contemplated to facilitate formation of plasma within the inner surface 292 adjacent to the restricted opening 294.

V.B. In yet another contemplated embodiment, the inner electrode 308, as in FIG. 26, can be moved during processing, for example, at first extending into the processing vessel lumen 304, then being withdrawn progressively proximally as the process proceeds. This expedient is particularly contemplated if the vessel 250, under the selected processing conditions, is long, and movement of the inner electrode facilitates more uniform treatment of the interior surface 254. Using this expedient, the processing conditions, such as the gas feed rate, the vacuum draw rate, the electrical energy applied to the outer electrode 160, the rate of withdrawing the inner electrode 308, or other factors can be varied as the process proceeds, customizing the process to different parts of a vessel to be treated.

V.B. Conveniently, as in the other processes described in this specification, the larger opening of the generally tubular vessel 250 to be processed can be placed on a vessel support 320, as by seating the larger opening 302 of the vessel 250 to be processed on a port 322 of the vessel support 320. Then the inner electrode 308 can be positioned within the vessel 250 seated on the vessel support 320 before drawing at least a partial vacuum within the lumen 300 of the vessel 250 to be processed.

V.B. In an alternative embodiment, illustrated in FIG. 28, the processing vessel 324 can be provided in the form of a conduit having a first opening 306 secured to the vessel 250 to be processed, as shown in FIG. 26, and a second opening 328 communicating with a vacuum port 330 in the vessel support 320. In this embodiment, the PECVD process gases can flow into the vessel 250, then via the restricted opening 294 into the processing vessel 324, then return via the vacuum port 330. Optionally, the vessel 250 can be evacuated through both openings 294 and 302 before applying the PECVD reactants.

Figure 22:
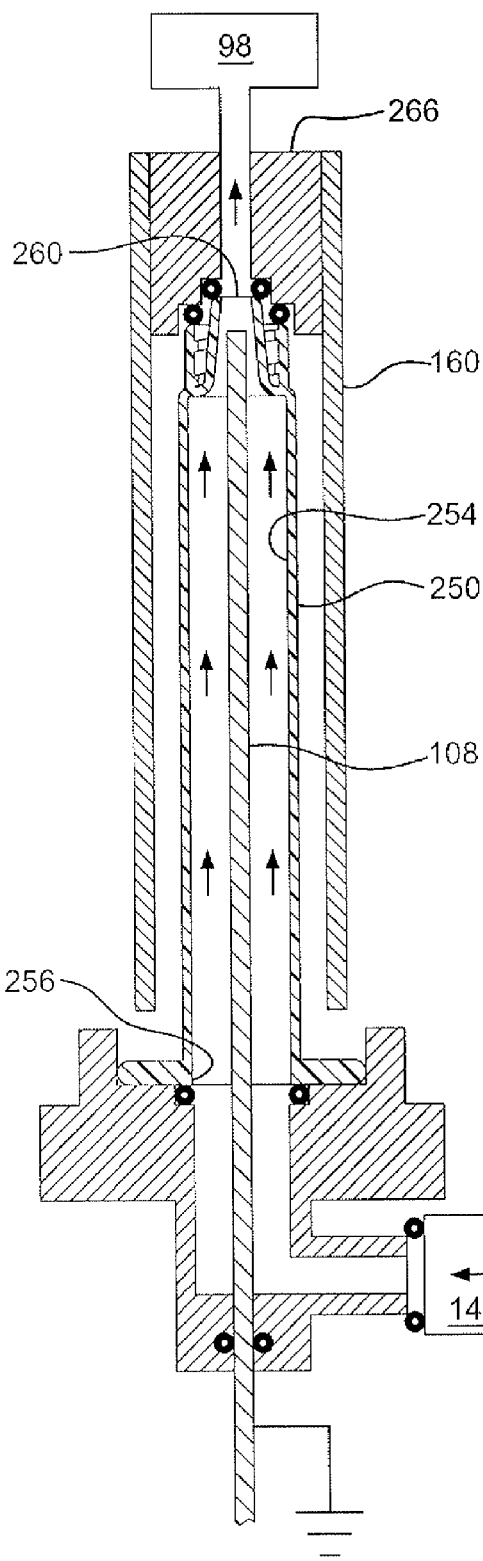
FIG. 22 is a view generally similar to FIG. 21 showing an uncapped syringe barrel and vessel holder in a coating station according to yet another embodiment of the invention.

V.B. Or, an uncapped syringe barrel 250, as shown in FIG. 22, can be provided with an interior coating of $SiO_x$, in which x in this formula is from about 1.5 to about 2.9, alternatively from about 1.5 to about 2.6, alternatively about 2, barrier or other type of PECVD coating by introducing the reactants from the source 144 through the opening at the back end 256 of the barrel 250 and drawing a vacuum using the vacuum source 98 drawing through the opening at the front end 260 of the barrel. For example, the vacuum source 98 can be connected through a second fitting 266 seated on the front end 260 of the syringe barrel 250. Using this expedient, the reactants can flow through the barrel 250 in a single direction (upward as shown in FIG. 22, though the orientation is not critical), and there is no need to convey the reactants through a probe that separates the fed gas from the exhausted gas within the syringe barrel 250. The front and back ends 260 and 256 of the syringe barrel 250 can also be reversed relative to the coating apparatus, in an alternative arrangement. The probe 108 can act simply as an electrode, and can either be tubular or a solid rod in this embodiment. As before, the separation between the interior surface 254 and the probe 108 can be uniform over at least most of the length of the syringe barrel 250.

Figure 37:
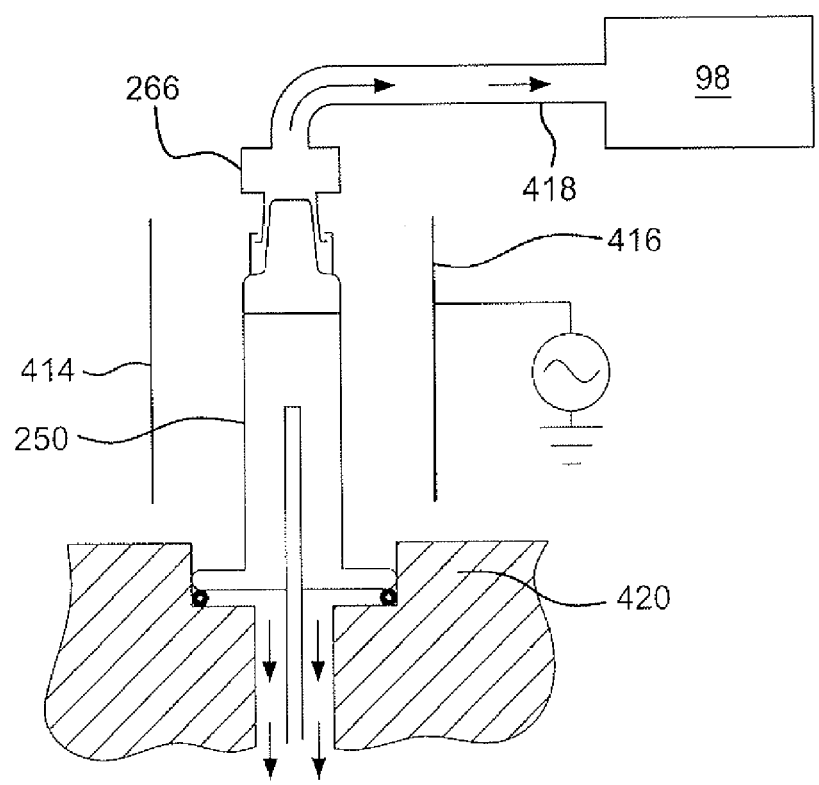
FIG. 37 is a view similar to FIG. 22 showing another embodiment.

V.B. FIG. 37 is a view similar to FIG. 22 showing another embodiment in which the fitting 266 is independent of and not attached to the plate electrodes 414 and 416. The fitting 266 can have a Luer lock fitting adapted to be secured to the corresponding fitting of the syringe barrel 250. This embodiment allows the vacuum conduit 418 to pass over the electrode 416 while the vessel holder 420 and attached vessel 250 move between the electrodes 414 and 416 during a coating step.

Figure 38:
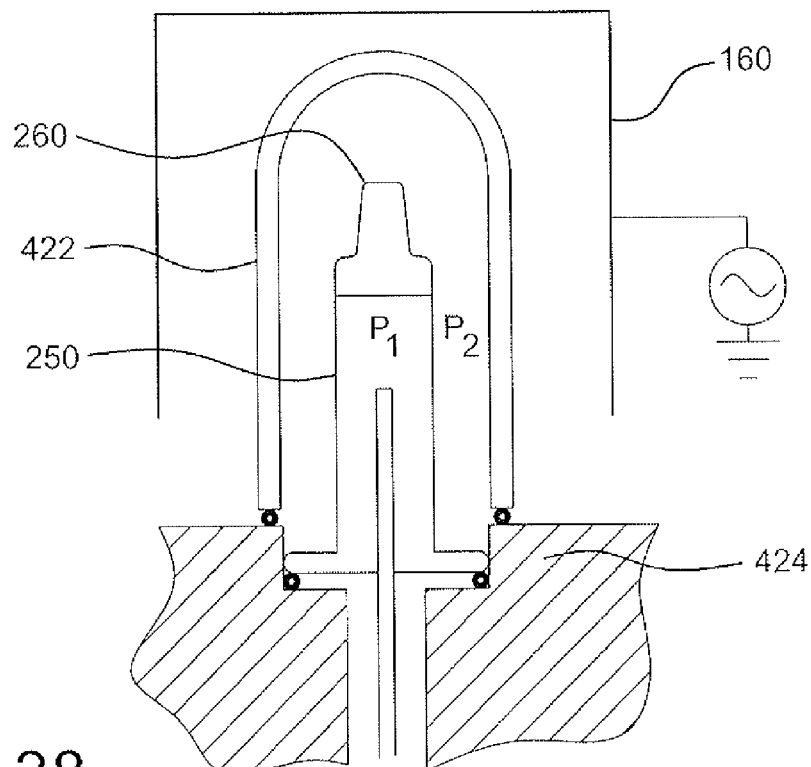
FIG. 38 is a view similar to FIG. 22 showing still another embodiment.

V.B. FIG. 38 is a view similar to FIG. 22 showing still another embodiment in which the front end 260 of the syringe barrel 250 is open and the syringe barrel 250 is enclosed by a vacuum chamber 422 seated on the vessel holder 424. In this embodiment the pressures P1 within the syringe barrel 250 and within the vacuum chamber 422 are approximately identical, and the vacuum in the vacuum chamber 422 optionally is drawn through the front end 260 of the syringe barrel 250. When the process gases flow into the syringe barrel 250, they flow through the front end 260 of the syringe barrel 250 until a steady composition is provided within the syringe barrel 250, at which time the electrode 160 is energized to form the coating. It is contemplated that due to the larger volume of the vacuum chamber 422 relative to the syringe barrel 250, and the location of the counter electrode 426 within the syringe barrel 250, the process gases passing through the front end 260 will not form substantial deposits on the walls of the vacuum chamber 422.

Figure 39:
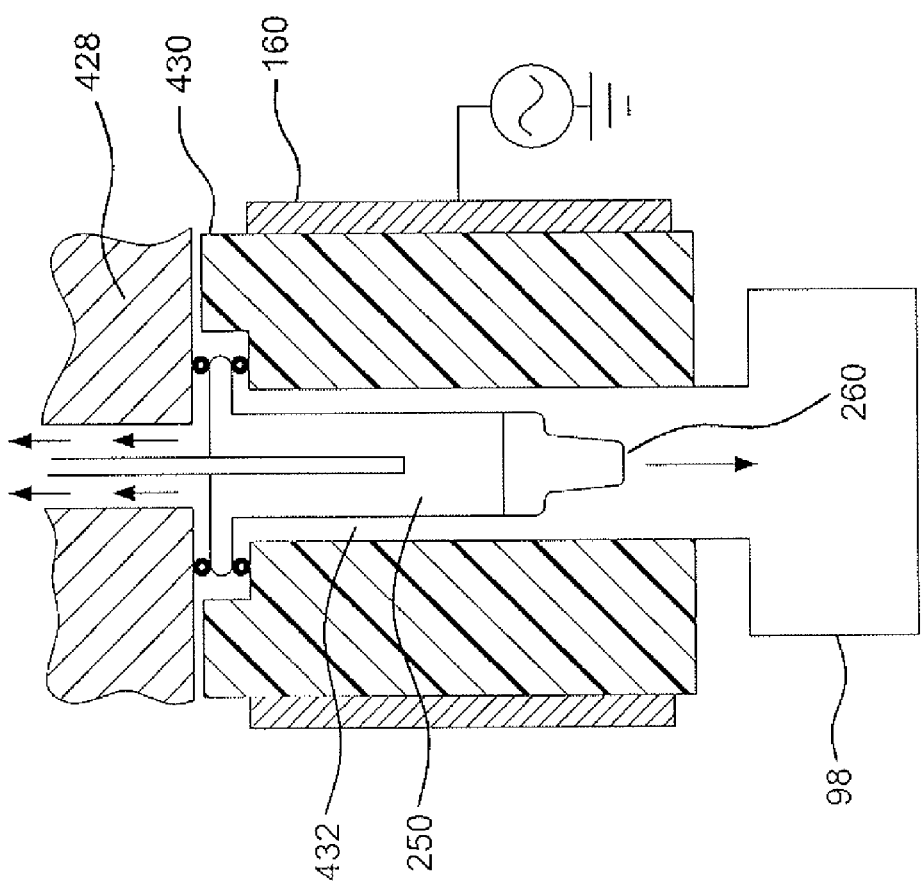
FIG. 39 is a view similar to FIG. 22 showing yet another embodiment.

V.B. FIG. 39 is a view similar to FIG. 22 showing yet another embodiment in which the back flange of the syringe barrel 250 is clamped between a vessel holder 428 and an electrode assembly 430 to which a cylindrical electrode or pair of plate electrodes indicated as 160 and a vacuum source 98 are secured. The volume generally indicated as 432 enclosed outside the syringe barrel 250 is relatively small in this embodiment to minimize the pumping needed to evacuate the volume 432 and the interior of the syringe barrel 250 to operate the PECVD process.

Figure 40:
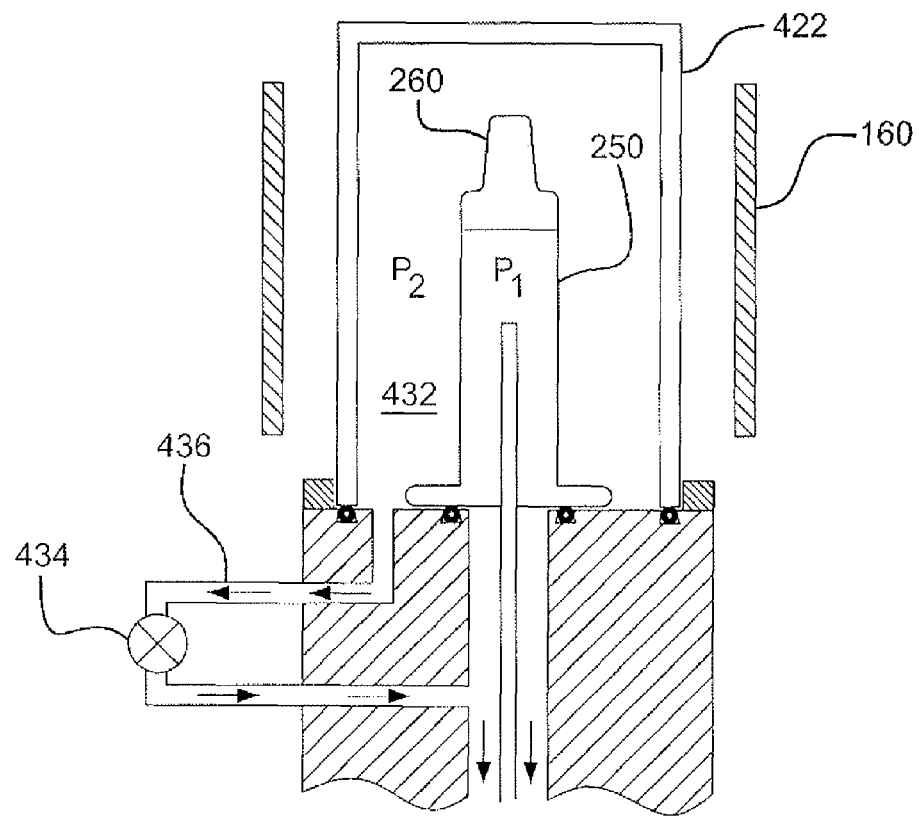
FIG. 40 is a view similar to FIG. 22 showing even another embodiment.
Figure 41:
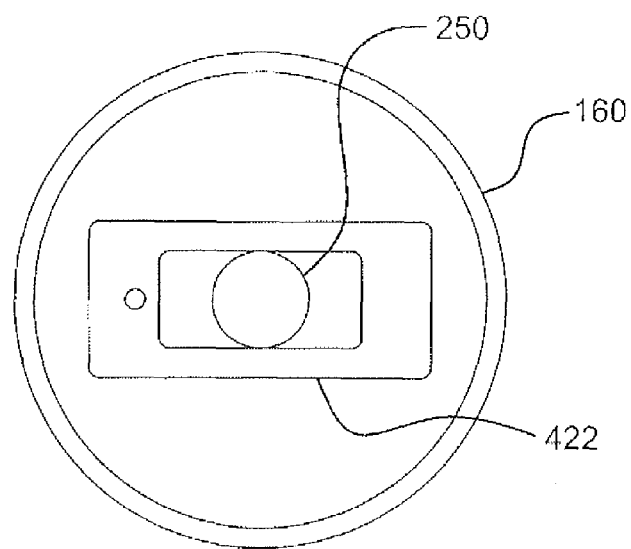
FIG. 41 is a plan view of the embodiment of FIG. 40.

V.B. FIG. 40 is a view similar to FIG. 22 and FIG. 41 is a plan view showing even another embodiment as an alternative to FIG. 38 in which the ratio of pressures P1/P2 is maintained at a desired level by providing a pressure proportioning valve 434. It is contemplated that P1 can be a lower vacuum, i.e. a higher pressure, than P2 during a PECVD process so the waste process gases and by-products will pass through the front end 260 of the syringe barrel 250 and be exhausted. Also, the provision of a separate vacuum chamber conduit 436 to serve the vacuum chamber 422 allows the use of a separate vacuum pump to evacuate the greater enclosed volume 432 more quickly.

V.B. FIG. 41 is a plan view of the embodiment of FIG. 40, also showing the electrode 160 removed from FIG. 40.

V.C. Method of Applying a Lubricity Layer

V.C. Another embodiment is a method of applying a lubricity layer derived from an organosilicon precursor. A "lubricity layer" or any similar term is generally defined as a coating that reduces the frictional resistance of the coated surface, relative to the uncoated surface. If the coated object is a syringe (or syringe part, e.g. syringe barrel) or any other item generally containing a plunger or movable part in sliding contact with the coated surface, the frictional resistance has two main aspects—breakout force and plunger sliding force.

The plunger sliding force test is a specialized test of the coefficient of sliding friction of the plunger within a syringe, accounting for the fact that the normal force associated with a coefficient of sliding friction as usually measured on a flat surface is addressed by standardizing the fit between the plunger or other sliding element and the tube or other vessel within which it slides. The parallel force associated with a coefficient of sliding friction as usually measured is comparable to the plunger sliding force measured as described in this specification. Plunger sliding force can be measured, for example, as provided in the ISO 7886-1:1993 test.

The plunger sliding force test can also be adapted to measure other types of frictional resistance, for example the friction retaining a stopper within a tube, by suitable variations on the apparatus and procedure. In one embodiment, the plunger can be replaced by a closure and the withdrawing force to remove or insert the closure can be measured as the counterpart of plunger sliding force.

Also or instead of the plunger sliding force, the breakout force can be measured. The breakout force is the force required to start a stationary plunger moving within a syringe barrel, or the comparable force required to unseat a seated, stationary closure and begin its movement. The breakout force is measured by applying a force to the plunger that starts at zero or a low value and increases until the plunger begins moving. The breakout force tends to increase with storage of a syringe, after the prefilled syringe plunger has pushed away the intervening lubricant or adhered to the barrel due to decomposition of the lubricant between the plunger and the barrel. The breakout force is the force needed to overcome "sticktion," an industry term for the adhesion between the plunger and barrel that needs to be overcome to break out the plunger and allow it to begin moving.

V.C. Some utilities of coating a vessel in whole or in part with a lubricity layer, such as selectively at surfaces contacted in sliding relation to other parts, is to ease the insertion or removal of a stopper or passage of a sliding element such as a piston in a syringe or a stopper in a sample tube. The vessel can be made of glass or a polymer material such as polyester, for example polyethylene terephthalate (PET), a cyclic olefin copolymer (COC), an olefin such as polypropylene, or other materials. Applying a lubricity layer by PECVD can avoid or reduce the need to coat the vessel wall or closure with a sprayed, dipped, or otherwise applied organosilicon or other lubricant that commonly is applied in a far larger quantity than would be deposited by a PECVD process.

V.C. In any of the above embodiments V.C., a plasma, optionally a non-hollow-cathode plasma, optionally can be formed in the vicinity of the substrate V.C. In any of embodiments V.C., the precursor optionally can be provided in the substantial absence of oxygen. V.C. In any of embodiments V.C., the precursor optionally can be provided in the substantial absence of a carrier gas. V.C. In any of embodiments V.C., in which the precursor optionally can be provided in the substantial absence of nitrogen. V.C. In any of embodiments V.C., in which the precursor optionally can be provided at less than 1 Torr absolute pressure.

V.C. In any of embodiments V.C., the precursor optionally can be provided to the vicinity of a plasma emission.

V.C. In any of embodiments V.C., the coating optionally can be applied to the substrate at a thickness of 1 to 5000 nm, or 10 to 1000 nm, or 10-200 nm, or 20 to 100 nm thick. The thickness of this and other coatings can be measured, for example, by transmission electron microscopy (TEM).

V.C. The TEM can be carried out, for example, as follows. Samples can be prepared for Focused Ion Beam (FIB) cross-sectioning in two ways. Either the samples can be first coated with a thin layer of carbon (50-100 nm thick) and then coated with a sputtered layer of platinum (50-100 nm thick) using a K575X Emitech coating system, or the samples can be coated directly with the protective sputtered Pt layer. The coated samples can be placed in an FEI FIB200 FIB system. An additional layer of platinum can be FIB-deposited by injection of an oregano-metallic gas while rastering the 30 kV gallium ion beam over the area of interest. The area of interest for each sample can be chosen to be a location half way down the length of the syringe barrel. Thin cross sections measuring approximately 15 μm ("micrometers") long, 2 μm wide and 15 μm deep can be extracted from the die surface using a proprietary in-situ FIB lift-out technique. The cross sections can be attached to a 200 mesh copper TEM grid using FIB-deposited platinum. One or two windows in each section, measuring ~8 μm wide, can be thinned to electron transparency using the gallium ion beam of the FEI FIB.

V.C. Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| | |
|---|---|
| 1. Instrument | Scanning Transmission Electron Microscope |
| Manufacturer/Model | Hitachi HD2300 |
| Accelerating Voltage | 200 kV |
| Objective Aperture | #2 |
| Condenser Lens 1 Setting | 1.672 |
| Condenser Lens 2 Setting | 1.747 |
| Approximate Objective Lens Setting | 5.86 |
| ZC Mode Projector Lens | 1.149 |
| TE Mode Projector Lens | 0.7 |
| Image Acquisition | |
| Pixel Resolution | 1280 × 960 |
| Acquisition Time | 20 sec. (x4) |

V.C. For TEM analysis the sample grids can be transferred to a Hitachi HF2000 transmission electron microscope. Transmitted electron images can be acquired at appropriate magnifications. The relevant instrument settings used during image acquisition can be those given below.

| | |
|---|---|
| Instrument | Transmission Electron Microscope |
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | #1 |
| Objective Lens Aperture for imaging | #3 |
| Selective Area Aperture for SAD | N/A |

V.C. In any of embodiments V.C., the substrate can comprise glass or a polymer, for example a polycarbonate polymer, an olefin polymer, a cyclic olefin copolymer, a polypropylene polymer, a polyester polymer, a polyethylene terephthalate polymer or a combination of any two or more of these.

V.C. In any of embodiments V.C., the PECVD optionally can be performed by energizing the gaseous reactant containing the precursor with electrodes powered at a RF frequency as defined above, for example a frequency from 10 kHz to less than 300 MHz, optionally from 1 to 50 MHz, even optionally from 10 to 15 MHz, optionally a frequency of 13.56 MHz.

V.C. In any of embodiments V.C., the plasma can be generated by energizing the gaseous reactant comprising the precursor with electrodes supplied with electric power sufficient to form a lubricity layer. Optionally, the plasma is generated by energizing the gaseous reactant containing the precursor with electrodes supplied with an electric power of from 0.1 to 25 W, optionally from 1 to 22 W, optionally from 3 to 17 W, even optionally from 5 to 14 W, optionally from 7 to 11 W, optionally 8 W. The ratio of the electrode power to the plasma volume can be less than 10 W/ml, optionally is from 5 W/ml to 0.1 W/ml, optionally is from 4 W/ml to 0.1 W/ml, optionally from 2 W/ml to 0.2 W/ml. These power levels are suitable for applying lubricity coatings to syringes and sample tubes and vessels of similar geometry having a void volume of 1 to 3 mL in which PECVD plasma is generated. It is contemplated that for larger or smaller objects the power applied should be increased or reduced accordingly to scale the process to the size of the substrate.

V.C. One contemplated product optionally can be a syringe having a barrel treated by the method of any one or more of embodiments V.C.

V.D. Liquid-Applied Coatings

V.D. Another example of a suitable barrier or other type of coating, usable in conjunction with PECVD-applied coatings or other PECVD treatment as disclosed here, can be a liquid barrier, lubricant, surface energy tailoring, or other type of coating 90 applied to the interior surface of a vessel, either directly or with one or more intervening PECVD-applied coatings described in this specification, for example $SiO_x$, a lubricity layer characterized as defined in the Definition Section, or both.

V.D. Suitable liquid barriers or other types of coatings 90 also optionally can be applied, for example, by applying a liquid monomer or other polymerizable or curable material to the interior surface of the vessel 80 and curing, polymerizing, or crosslinking the liquid monomer to form a solid polymer. Suitable liquid barrier or other types of coatings 90 can also be provided by applying a solvent-dispersed polymer to the surface 88 and removing the solvent.

V.D. Either of the above methods can include as a step forming a coating 90 on the interior 88 of a vessel 80 via the vessel port 92 at a processing station or device 28. One example is applying a liquid coating, for example of a curable monomer, prepolymer, or polymer dispersion, to the interior surface 88 of a vessel 80 and curing it to form a film that physically isolates the contents of the vessel 80 from its interior surface 88. The prior art describes polymer coating technology as suitable for coating plastic blood collection tubes. For example, the acrylic and polyvinylidene chloride (PVdC) coating materials and coating methods described in U.S. Pat. No. 6,165,566, which is hereby incorporated by reference, optionally can be used.

V.D. Either of the above methods can also or include as a step forming a coating on the exterior outer wall of a vessel 80. The coating optionally can be a barrier coating, optionally an oxygen barrier coating, or optionally a water barrier coating. One example of a suitable coating is polyvinylidene chloride, which functions both as a water barrier and an oxygen barrier. Optionally, the barrier coating can be applied as a water-based coating. The coating optionally can be applied by dipping the vessel in it, spraying it on the vessel, or other expedients. A vessel having an exterior barrier coating as described above is also contemplated.

VI. Vessel Inspection

VI. One station or device shown in FIG. 1 is the processing station or device 30, which can be configured to inspect the interior surface of a vessel 80 for defects, as by measuring the air pressure loss or mass flow rate or volume flow rate through a vessel wall or outgassing of a vessel wall. The device 30 can operate similarly to the device 26, except that better performance (less leakage or permeation at given process conditions) can be required of the vessel to pass the inspection provided by the device 30, since in the illustrated embodiment a barrier or other type of coating has been applied by the station or device 28 before the station or device 30 is reached. In an embodiment, this inspection of the coated vessel 80 can be compared to the inspection of the same vessel 80 at the device or station 26. Less leakage or permeation at the station or device 30 indicates that the barrier coating is functioning at least to a degree.

VI. The identity of a vessel 80 measured at two different stations or by two different devices can be ascertained by placing individual identifying characteristics, such as a bar code, other marks, or a radio frequency identification (RFID) device or marker, on each of the vessel holders 38-68 and matching up the identity of vessels measured at two or more different points about the endless conveyor shown in FIG. 1. Since the vessel holders can be reused, they can be registered in a computer database or other data storage structure as they reach the position of the vessel holder 40 in FIG. 1, just after a new vessel 80 has been seated on the vessel holder 40, and removed from the data register at or near the end of the process, for example as or after they reach the position of the vessel holder 66 in FIG. 1 and the processed vessel 80 is removed by the transfer mechanism 74.

VI. The processing station or device 32 can be configured to inspect a vessel, for example a barrier or other type of coating applied to the vessel, for defects. In the illustrated embodiment, the station or device 32 determines the optical source transmission of the coating, as a measurement of the thickness of the coating. The barrier or other type of coating, if suitably applied, can make the vessel 80 more transparent, even though additional material has been applied, as it provides a more uniform surface.

VI. Other measures of the thickness of the coating are also contemplated, as by using interference measurements to determine the difference in travel distance between an energy wave that bounces off the inside of the coating 90 (interfacing with the atmosphere within the vessel interior 154) and an energy wave that bounces off the interior surface 88 of the vessel 80 (interfacing with the outside of the coating 90). As is well known, the difference in travel distance can be determined directly, as by measuring the time of arrival of the respective waves with high precision, or indirectly, as by determining what wavelengths of the incident energy are reinforced or canceled, in relation to the test conditions.

VI. Another measurement technique that can be carried out to check coating integrity is an ellipsometric measurement on the device. In this case, a polarized laser beam can be projected either from the inside or the outside of the vessel 80. In the case of a laser beam projected from the inside, the laser beam can be pointed orthogonally at the surface and then either the transmitted or reflected beam can be measured. The change in beam polarity can be measured. Since a coating or treatment on the surface of the device will impact (change) the polarization of the laser beam, changes in the polarity can be the desired result. The changes in the polarity are a direct result of the existence of a coating or treatment on the surface and the amount of change is related to the amount of treatment or coating.

VI. If the polarized beam is projected from the outside of the device, a detector can be positioned on the inside to measure the transmitted component of the beam (and the polarity determined as above). Or, a detector can be placed outside of the device in a position that can correspond to the reflection point of the beam from the interface between the treatment/coating (on the inside of the device). The polarity change(s) can then be determined as detailed above.

VI. In addition to measuring optical properties and/or leak rates as described above, other probes and/or devices can be inserted into the inside of the device and measurements made with a detector apparatus. This apparatus is not limited by the measurement technique or method. Other test methods that employ mechanical, electrical, or magnetic properties, or any other physical, optical, or chemical property, can be utilized.

VI. During the plasma treatment setup, an optical detection system optionally can be used to record the plasma emission spectrum (wavelength and intensity profile), which corresponds to the unique chemical signature of the plasma environment. This characteristic emission spectrum provides confirmation that the coating has been applied and treated. The system also offers a real-time precision measurement and data archive tool for each part processed.

Figure 11:
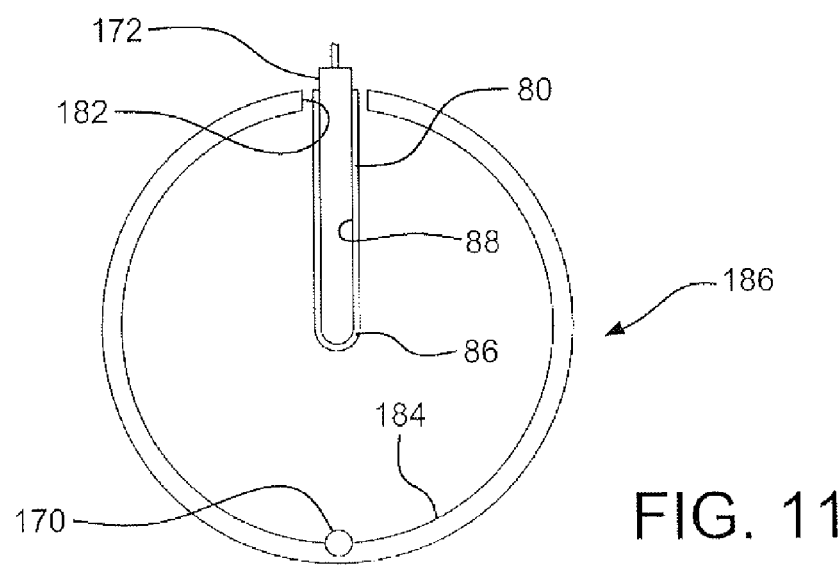
FIG. 11 is a detail view similar to FIG. 10 of a light source and detector that are reversed compared to the corresponding parts of FIG. 6.

VI. Any of the above methods can include as a step inspecting the interior surface 88 of a vessel 80 for defects at a processing station such as 24, 26, 30, 32, or 34. Inspecting can be carried out, as at the stations 24, 32, and 34, by inserting a detection probe 172 into the vessel 80 via the vessel port 92 and detecting the condition of the vessel interior surface 88 or a barrier or other type of coating 90 using the probe 172. Inspecting can be carried out, as shown in FIG. 11, by radiating energy inward through the vessel wall 86 and vessel interior surface 88 and detecting the energy with the probe 172. Or, inspecting can be carried out by reflecting the radiation from the vessel interior surface 88 and detecting the energy with a detector located inside the vessel 80. Or, inspecting can be carried out by detecting the condition of the vessel interior surface 88 at numerous, closely spaced positions on the vessel interior surface.

VI. Any of the above methods can include carrying out the inspecting step at a sufficient number of positions throughout the vessel interior surface 88 to determine that the barrier or other type of coating 90 will be effective to prevent the pressure within the vessel, when it is initially evacuated and its wall is exposed to the ambient atmosphere, from increasing to more than 20% of the ambient atmospheric pressure during a shelf life of a year.

VI. Any of the above methods can include carrying out the inspecting step within an elapsed time of 30 or fewer seconds per vessel, or 25 or fewer seconds per vessel, or 20 or fewer seconds per vessel, or 15 or fewer seconds per vessel, or 10 or fewer seconds per vessel, or 5 or fewer seconds per vessel, or 4 or fewer seconds per vessel, or 3 or fewer seconds per vessel, or 2 or fewer seconds per vessel, or 1 or fewer seconds per vessel. This can be made possible, for example, by measuring the efficacy of the barrier or other type of coated vessel wall, as shown in FIG. 7, which can involve one measurement for the entire vessel 80, or by inspecting many or even all the points to be inspected in parallel, as by using the charge coupled device as the detector 172 shown or substitutable in FIGS. 6, 10, and 11. The latter step can be used for detecting the condition of the barrier or other type of coating at numerous, closely spaced positions on the vessel interior surface 88 in a very short overall time.

VI. In any embodiment of the method, a multi-point vessel inspection can be further expedited, if desired, by collecting data using a charge coupled device 172, transporting away the vessel 80 that has just been inspected, and processing the collected data shortly thereafter, while the vessel 80 is moving downstream. If a defect in the vessel 80 is later ascertained due to the data processing, the vessel 80 that is defective can be moved off line at a point downstream of the detection station such as 34 (FIG. 10).

VI. In any of the above embodiments, the inspecting step can be carried out at a sufficient number of positions throughout the vessel 80 interior surface 88 to determine that the barrier or other type of coating 90 will be effective to prevent the initial vacuum level (i.e. initial reduction of pressure versus ambient) within the vessel 80, when it is initially evacuated and its wall 86 is exposed to the ambient atmosphere, from decreasing more than 20%, optionally more than 15%, optionally more than 10%, optionally more than 5%, optionally more than 2%, during a shelf life of at least 12 months, or at least 18 months, or at least two years.

VI. The initial vacuum level can be a high vacuum, i.e. a remaining pressure of less than 10 Torr, or a lesser vacuum such as less than 20 Torr of positive pressure (i.e. the excess pressure over a full vacuum), or less than 50 Torr, or less than 100 Torr, or less than 150 Torr, or less than 200 Torr, or less than 250 Torr, or less than 300 Torr, or less than 350 Torr, or less than 380 Torr of positive pressure. The initial vacuum level of evacuated blood collection tubes, for example, is in many instances determined by the type of test the tube is to be used for, and thus the type and appropriate amount of a reagent that is added to the tube at the time of manufacture. The initial vacuum level is commonly set to draw the correct volume of blood to combine with the reagent charge in the tube.

VI. In any of the above embodiments, the barrier or other type of coating 90 inspecting step can be carried out at a sufficient number of positions throughout the vessel interior surface 88 to determine that the barrier or other type of coating 90 will be effective to prevent the pressure within the vessel 80, when it is initially evacuated and its wall is exposed to the ambient atmosphere, from increasing to more than 15%, or more than 10%, of the ambient atmospheric pressure of the ambient atmospheric pressure during a shelf life of at least one year.

VI.A. Vessel Processing Including Pre-Coating and Post-Coating Inspection

VI.A. Even another embodiment is a vessel processing method for processing a molded plastic vessel having an opening and a wall defining an interior surface. The method is carried out by inspecting the interior surface of the vessel as molded or just before coating for defects; applying a coating to the interior surface of the vessel after inspecting the vessel as molded; and inspecting the coating for defects.

VI.A. Another embodiment is a vessel processing method in which a barrier coating is applied to the vessel after inspecting the vessel as molded, and the interior surface of the vessel is inspected for defects after applying the barrier coating.

VI.A. In an embodiment, the station or device 26 (which can also function as the station or device 28 for applying a coating) can be used as follows for barometric vessel inspection. With either or both of the valves 136 and 148 open, the vessel 80 can be evacuated to a desired degree, optionally to a very low pressure such as less than 10 Torr, optionally less than 1 Torr. Whichever of the valves 136 and 148 is initially open can then be closed, isolating the evacuated interior 154 of the vessel 80 and the pressure gauge 152 from ambient conditions and from the vacuum source 98. The change in pressure over a measurement time, whether due to the ingress of gas through the vessel wall or outgassing from the material of the wall and/or a coating on the vessel wall, can then be sensed and used to calculate the rate of ingress of ambient gas into the vessel 80 as mounted on the vessel holder 44. For the present purpose, outgassing is defined as the release of adsorbed or occluded gases or water vapor from the vessel wall, optionally in at least a partial vacuum.

VI.A. Another optional modification can be to provide the ambient gas at a higher pressure than atmospheric pressure. This again can increase the rate of gas transfer through a barrier or other type of layer, providing a measurable difference in a shorter time than if a lower ambient pressure were provided. Or, gas can be introduced into the vessel 80 at a higher than atmospheric pressure, again increasing the transfer rate through the wall 86.

VI.A. Optionally, the vessel inspection at the station or by the device 26 can be modified by providing an inspection gas, such as helium, on an upstream side with respect to the substrate, either within or outside the vessel 80, and detecting it on the downstream side. A low-molecular-weight gas, such as hydrogen, or a less expensive or more available gas, such as oxygen or nitrogen, can also be used as an inspection gas.

VI.A. Helium is contemplated as an inspection gas that can increase the rate of leak or permeation detection, as it will pass through an imperfect barrier or other type of coating, or past a leaking seal, much more quickly than the usual ambient gases such as nitrogen and oxygen in ordinary air. Helium has a high transfer rate through many solid substrates or small gaps because it: (1) is inert, so it is not adsorbed by the substrate to any great degree, (2) is not ionized easily, so its molecules are very compact due to the high level of attraction between its electrons and nucleus, and (3) has a molecular weight of 4, as opposed to nitrogen (molecular weight 28) and oxygen (molecular weight 32), again making the molecules more compact and easily passed through a porous substrate or gap. Due to these factors, helium will travel through a barrier having a given permeability much more quickly than many other gases. Also, the atmosphere contains an extremely small proportion of helium naturally, so the presence of additional helium can be relatively easy to detect, particularly if the helium is introduced within the vessel 80 and detected outside the vessel 80 to measure leakage and permeation. The helium can be detected by a pressure drop upstream of the substrate or by other means, such as spectroscopic analysis of the downstream gas that has passed through the substrate.

VI.A. An example of barometric vessel inspection by determining the oxygen concentration from $O_2$ fluorescence detection follows.

VI.A. An Excitation Source (Ocean Optics USB-LS-450 Pulsed Blue LED), fiber assembly (Ocean Optics QBIF6000-VIS-NIR), a spectrometer (USB4000-FL Fluorescence Spectrometer), an oxygen sensor probe (Ocean Optics FOXY-R), and a vacuum feed through adaptor (like VFT-1000-VIS-275) connected to a vacuum source are used. A vacuum can be applied to remove the ambient air, and when the vessel is at a defined pressure any oxygen content that has leaked or permeated in to refill the vessel from the ambient air can be determined using the detection system. A coated tube replaces the uncoated tube and $O_2$ concentration measurement can be taken. The coated tube will demonstrate reproducibly different atmospheric oxygen content than the uncoated sample due to differential $O_2$ surface absorption on the coated tube (an $SiO_x$ surface, versus the uncoated PET or glass surface) and/or a change in $O_2$ diffusion rate from the surface. Detection time can be less than one second.

VI.A. These barometric methods should not be considered limited to a specific gas sensed (helium detection or other gases can be considered) or a specific apparatus or arrangement.

VI.A. The processing station or device 34 also can be configured to inspect a barrier or other type of coating for defects. In the embodiment of FIGS. 1 and 10, the processing station or device 34 can be another optical inspection, this time intended to scan or separately measure the properties of at least a portion of the barrier or other type of coating 90, or substantially the entire barrier or other type of coating 90, at numerous, closely spaced positions on the barrier or other type of coating 90. The numerous, closely spaced positions can be, for example, spaced about 1 micron apart, or about 2 microns apart, or about 3 microns apart, or about 4 microns apart, or about 5 microns apart, or about 6 microns apart, or about 7 microns apart, either in every case or on average over at least part of the surface, thus separately measuring some or all small portions of the barrier or other type of coating 90. In an embodiment, a separate scan of each small area of the coating can be useful to find individual pinholes or other defects, and to distinguish the local effects of pinhole defects from more general defects, such as a large area with a coating that is too thin or porous.

VI.A. The inspection by the station or device 34 can be carried out by inserting a radiation or light source 170 or any other suitable radio frequency, microwave, infrared, visible light, ultraviolet, x-ray, or electron beam source, for example, into the vessel 80 via the vessel port 92 and detecting the condition of the vessel interior surface, for example the barrier coating 90, by detecting radiation transmitted from the radiation source using a detector.

VI.A. The above vessel holder system can also be used for testing the device. For example, the probe 108 of FIG. 2 having a gas delivery port 110 can be replaced by a light source 170 (FIG. 10). The light source 170 can irradiate the inside of the tube and then subsequent testing can be completed outside of the tube, measuring transmission or other properties. The light source 170 can be extended into the inside of the tube in the same manner that the probe 108 is pushed into the puck or vessel holder 62, although a vacuum and seals are not necessarily required. The light source 170 can be an optical fiber source, a laser, a point (such as an LED) source or any other radiation source. The source can radiate at one or more frequencies from the deep UV (100 nm) into the far infra red (100 microns) and all frequencies in between. There is no limitation on the source that can be used.

VI.A. As a specific example see FIG. 10. In FIG. 10 the tube or vessel 80 is positioned in the puck or vessel holder 62 and a light source 170 at the end of the probe 108 has been inserted into the tube. The light source 170 in this case can be a blue LED source of sufficient intensity to be received by the detector 172 surrounding the outside of the vessel 80. The light source 170 can be, for example, a three dimensional charge-coupled-device (CCD) comprising an array of pixels such as 174 on its interior surface 176. The pixels such as 174 receive and detect the illumination radiated through the barrier or other type of coating 90 and vessel wall 86. In this embodiment the detector 172 has a larger inner diameter relative to the vessel 80 than the separation of the electrode 164 and vessel 80 of FIG. 2, and has a cylindrical top portion adjacent to the closed end 84 instead of a hemispherical top portion. The outside detector 172 or can have a smaller radial gap from the vessel 80 and a gap of more uniform dimension at its top portion adjacent to the closed end 84. This can be accomplished, for example, by providing a common center of curvature for the closed end 84 and the top of the detector 172 when the vessel 80 is seated. This variation might provide more uniform inspection of the curved closed end 84 of the vessel 80, although either variation is contemplated to be suitable.

VI.A. Prior to the light source being turned on, the CCD is measured and the resulting value stored as a background (which can be subtracted from subsequent measurements). The light source 170 is then turned on and measurements taken with the CCD. The resulting measurements can then be used to compute total light transmission (and compared to an uncoated tube to determine the average coating thickness) and defect density (by taking individual photon counts on each element of the CCD and comparing them to a threshold value—if the photon count is lower, then this corresponds to not enough light being transmitted). Low light transmission likely is the result of no or too-thin coating—a defect in the coating on the tube. By measuring the number of adjacent elements that have a low photon count, the defect size can be estimated. By summing the size and number of defects, the tube's quality can be assessed, or other properties determined that might be specific to the frequency of the radiation from the light source 170.

VI.A. In the embodiment of FIG. 10, energy can be radiated outward through the vessel interior surface, such as through the coating 90 and the vessel wall 86, and detected with a detector 172 located outside the vessel. Various types of detectors 172 can be used.

VI.A. Since the incident radiation from the source 170 transmitted through the barrier or other type of coating 90 and vessel wall 80 can be greater for a lower angle of incidence (compared to a reference line normal to the vessel wall 80 at any given point), the pixels such as 174 lying on a normal line through the vessel wall 86 will receive more of the radiation than neighboring pixels, though more than one pixel can receive some of the light passing through a given portion of the barrier or other type of coating, and the light passing through more than one given portion of the barrier or other type of coating 90 and vessel wall 80 will be received by a particular pixel such as 174.

VI.A. The degree of resolution of the pixels such as 174 for detecting radiation passing through a particular portion of the barrier or other type of coating 90 and vessel wall 86 can be increased by placing the CCD so its array of pixels such as 174 is very close to and closely conforms to the contours of the vessel wall 86. The degree of resolution can also be increased by selecting a smaller or essentially point source of light, as shown diagrammatically in FIG. 6, to illuminate the interior of the vessel 80. Using smaller pixels will also improve the resolution of the array of pixels in the CCD.

Figure 6:
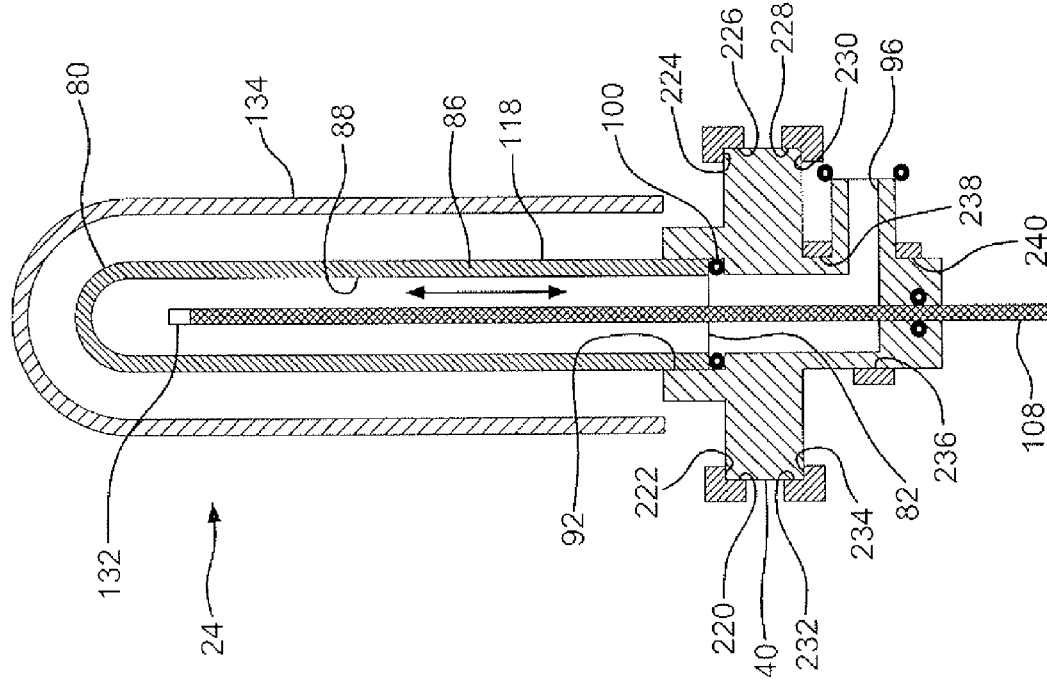
FIG. 6 is a view similar to FIG. 2 of vessel inspection apparatus.

VI.A. In FIG. 6 a point light source 132 (laser or LED) is positioned at the end of a rod or probe. ("Point source" refers either to light emanating from a small-volume source resembling a mathematical point, as can be generated by a small LED or a diffusing tip on an optical fiber radiating light in all directions, or to light emanated as a small-cross-section beam, such as coherent light transmitted by a laser.) The point source of light 132 can be either stationary or movable, for example axially movable, while the characteristics of the barrier or other type of coating 90 and vessel wall 80 are being measured. If movable, the point light source 132 can be moved up and down inside of the device (tube) 80. In a similar manner described above, the interior surface 88 of the vessel 80 can be scanned and subsequent measurements made by an external detector apparatus 134 to determine coating integrity. An advantage of this approach is that a linearly polarized or similar coherent light source with specific directionality can be used.

VI.A. The position of the point source of light 132 can be indexed to the pixels such as 174 so the illumination of the detectors can be determined at the time the detector is at a normal angle with respect to a particular area of the coating 90. In the embodiment of FIG. 10, a cylindrical detector 172, optionally with a curved end matching the curve (if any) of the closed end 84 of a vessel 80, can be used to detect the characteristics of a cylindrical vessel 80.

VI.A. It will be understood, with reference to FIG. 10, that the inspection station or device 24 or 34 can be modified by reversing the positions of the light or other radiation source 170 and detector 172 so the light radiates through the vessel wall 86 from the exterior to the interior of the vessel 80. If this expedient is selected, in an embodiment a uniform source of incident light or other radiation can be provided by inserting the vessel 80 into an aperture 182 through the wall 184 of an integrating sphere light source 186. An integrating sphere light source will disperse the light or radiation from the source 170 outside the vessel 80 and inside the integrating sphere, so the light passing through the respective points of the wall 86 of the vessel 80 will be relatively uniform. This will tend to reduce the distortions caused by artifacts relating to portions of the wall 86 having different shapes.

VI.A. In the embodiment of FIG. 11, the detector 172 can be shown to closely conform to the barrier or other type of coating 90 or interior surface 88 of the vessel 80. Since the detector 172 can be on the same side of the vessel wall 86 as the barrier or other type of coating 80, this proximity will tend to increase the resolution of the pixels such as 174, though in this embodiment the detector 172 optionally will be precisely positioned relative to the barrier or other type of coating 90 to avoid scraping one against the other, possibly damaging either the coating or the CCD array. Placing the detector 172 immediately adjacent to the coating 90 also can reduce the effects of refraction by the vessel wall 86, which in the embodiment of FIG. 10 occurs after the light or other radiation passes through the barrier or other type of coating 90, so the signal to be detected can be differentially refracted depending on the local shape of the vessel 80 and the angle of incidence of the light or other radiation.

VI.A. Other barrier or other type of coating inspection techniques and devices can also, or, be used. For example, fluorescence measurements can be used to characterize the treatment/coating on the device. Using the same apparatus described in FIGS. 10 and 6, a light source 132 or 170 (or other radiation source) can be selected that can interact with the polymer material of the wall 86 and/or a dopant in the polymer material of the wall 86. Coupled with a detection system, this can be used to characterize a range of properties including defects, thicknesses and other performance factors.

VI.A. Yet another example of inspection is to use x-rays to characterize the treatment/coating and/or the polymer itself. In FIG. 10 or 6, the light source can be replaced with an x-radiation source and the external detector can be of a type to measure the x-ray intensity. Elemental analysis of the barrier or other type of coating can be carried out using this technique.

VI.A. After molding a device 80, as at the station 22, several potential issues can arise that will render any subsequent treatment or coating imperfect, and possibly ineffective. If the devices are inspected prior to coating for these issues, the devices can be coated with a highly optimized, optionally up to 6-sigma controlled process that will ensure a desired result (or results).

VI.A. Some of the potential problems that can interfere with treatment and coating include (depending on the nature of the coated article to be produced):

VI.A. 1. Large density of particulate contamination defects (for example, each more than 10 micrometers in its longest dimension), or a smaller density of large particulate contamination (for example, each more than 10 micrometers in its longest dimension).

VI.A. 2. Chemical or other surface contamination (for example silicone mold release or oil).

VI.A. 3. High surface roughness, characterized by either a high/large number of sharp peaks and/or valleys. This can also be characterized by quantifying the average roughness (Ra) which should be less than 100 nm.

VI.A. 4. Any defect in the device such as a hole that will not allow a vacuum to be created.

VI.A. 5. Any defect on the surface of the device that will be used to create a seal (for example the open end of a sample collection tube).

VI.A. 6. Large wall thickness non-uniformities which can impede or modify power coupling through the thickness during treatment or coating.

VI.A. 7. Other defects that will render the barrier or other type of coating ineffective.

VI.A. To assure that the treatment/coating operation is successful using the parameters in the treatment/coating operation, the device can be pre-inspected for one or more of the above potential issues or other issues. Previously, an apparatus was disclosed for holding a device (a puck or vessel holder such as 38-68) and moving it through a production process, including various tests and a treatment/coating operation. Several possible tests can be implemented to ensure that a device will have the appropriate surface for treatment/coating. These include:

VI.A. 1. Optical Inspection, for example, transmission of radiation through the device, reflection of radiation from the inside of the device or from the outside, absorption of radiation by the device, or interference with radiation by the device.

VI.A. 2. Digital Inspection—for example, using a digital camera that can measure specific lengths and geometries (for example how "round" or otherwise evenly or correctly shaped the open end of a sample collection tube is relative to a reference).

VI.A. 3. Vacuum leak checking or pressure testing.

VI.A. 4. Sonic (ultra sonic) testing of the device.

VI.A. 5. X-ray analysis.

VI.A. 6. Electrical conductivity of the device (the plastic tube material and $SiO_x$ have different electrical resistance— on the order of 1020 Ohm-cm for quartz as a bulk material and on the order of 1014 Ohm-cm for polyethylene terephthalate, for example).

VI.A. 7. Thermal conductivity of the device (for example, the thermal conductivity of quartz as a bulk material is about 1.3 W-° K/m, while the thermal conductivity of polyethylene terephthalate is 0.24 W-° K/m).

VI.A. 8. Outgassing of the vessel wall, which optionally can be measured as described below under post-coating inspection to determine an outgassing baseline.

VI.A. The above testing can be conducted in a station 24 as shown in FIG. 6. In this figure the device (for example a sample collection tube 80) can be held in place and a light source (or other source) 132 can be inserted into the device and an appropriate detector 134 positioned outside of the device to measure the desired result.

VI.A. In the case of vacuum leak detection, the vessel holder and device can be coupled to a vacuum pump and a measuring device inserted into the tube. The testing can also be conducted as detailed elsewhere in the specification.

VI.A. The processing station or device 24 can be a visual inspection station, and can be configured to inspect one or more of the interior surface 88 of a vessel, its exterior surface 118, or the interior of its vessel wall 86 between its surfaces 88 and 118 for defects. The inspection of the exterior surface 118, the interior surface 88, or the vessel wall 86 can be carried out from outside the vessel 80, particularly if the vessel is transparent or translucent to the type of radiation and wavelength used for inspection. The inspection of the interior surface 88 can or be facilitated, if desired, by providing an optical fiber probe inserted into the vessel 80 via the vessel port 92, so a view of the inside of the vessel 80 can be obtained from outside the vessel 80. An endoscope or borescope can be used in this environment, for example.

VI.A. Another expedient illustrated in FIG. 6 can be to insert a light source 132 within a vessel 80. The light transmitted through the vessel wall 86, and artifacts of the vessel 80 made apparent by the light, can be detected from outside the vessel 80, as by using a detector measuring apparatus 134. This station or device 24 can be used, for example, to detect and correct or remove misaligned vessels 80 not properly seated on the vessel port 96 or vessels 80 that have a visible distortion, impurity, or other defect in the wall 86. Visual inspection of the vessel 80 also can be conducted by a worker viewing the vessel 80, instead or in addition to machine inspection.

VI.A. The processing station or device 26, shown in more detail in FIG. 7, can be optionally configured to inspect the interior surface 88 of a vessel 80 for defects, and for example to measure the gas pressure loss through the vessel wall 86, which can be done before a barrier or other type of coating is provided. This test can be carried out by creating a pressure difference between the two sides of the barrier coating 90, as by pressurizing or evacuating the interior of the vessel 80, isolating the interior 154 of the vessel 80 so the pressure will remain constant absent leakage around the seal or permeation of gas through the vessel wall, and measuring the pressure change per unit time accumulating from these problems. This measurement will not only reveal any gas coming through the vessel wall 86, but will also detect a leaking seal between the mouth 82 of the vessel and the O-ring or other seal 100, which might indicate either a problem with the alignment of the vessel 80 or with the function of the seal 100. In either case, the tube mis-seating can be corrected or the tube taken out of the processing line, saving time in attempting to achieve or maintain the proper processing vacuum level and preventing the dilution of the process gases by air drawn through a malfunctioning seal.

VI.A. The above systems can be integrated into a manufacturing and inspection method comprising multiple steps.

VI.A. FIG. 1 as previously described shows a schematic layout of the steps of one possible method (although this invention is not limited to a single concept or approach). First the vessel 80 is visually inspected at the station or by the device 24, which can include dimensional measurement of the vessel 80. If there are any defects found, the device or vessel 80 is rejected and the puck or vessel holder such as 38 is inspected for defects, recycled or removed.

VI.A. Next the leak rate or other characteristics of the assembly of a vessel holder 38 and seated vessel 80 is tested, as at the station 26, and stored for comparison after coating. The puck or vessel holder 38 then moves, for example, into the coating step 28. The device or vessel 80 is coated with a $SiO_x$ or other barrier or other type of coating at a power supply frequency of, for example, 13.56 MHz. Once coated, the vessel holder is retested for its leak rate or other characteristics (this can be carried out as a second test at the testing station 26 or a duplicate or similar station such as 30—the use of a duplicate station can increase the system throughput).

VI.A. The coated measurement can be compared to the uncoated measurement. If the ratio of these values exceeds a pre-set required level, indicating an acceptable overall coating performance, the vessel holder and device move on. An optical testing station 32, for example, follows with a blue light source and an external integrating sphere detector to measure the total light transmitted through the tube. The value can be required to exceed a pre-set limit at which the device is rejected or recycled for additional coating. Next (for devices that are not rejected), a second optical testing station 34 can be used. In this case a point light source can be inserted inside of the tube or vessel 80 and pulled out slowly while measurements are taken with a tubular CCD detector array outside of the tube. The data is then computationally analyzed to determine the defect density distribution. Based on the measurements the device is either approved for final packaging or rejected.

VI.A. The above data optionally can be logged and plotted (for example, electronically) using statistical process control techniques to ensure up to 6-sigma quality.

VI.B. Vessel Inspection by Detecting Outgassing of Container Wall Through Barrier Layer VI.B. Another embodiment is a method for inspecting a barrier or other type of layer on a material that outgasses a vapor, having several steps. A sample of material that outgasses a gas and has at least a partial barrier layer is provided. Optionally, a pressure differential can be provided across the barrier layer, such that at least some of the material that outgasses is on the higher-pressure side of the barrier layer. In another option, the outgassed gas can be allowed to diffuse without providing a pressure difference. The outgassed gas is measured. If a pressure differential is provided across the barrier layer, the outgassing can be measured on the higher-pressure or lower-pressure side of the barrier layer.

VI.B. In addition a measurement of the efficacy of the interior coating (applied above) can be made by measuring the diffusion rate of a specific species or adsorbed materials in the wall of the device (prior to coating). When compared to an uncoated (untreated) tube, this type of measurement can provide a direct measurement of the barrier or other type of properties of the coating or treatment, or the presence or absence of the coating or treatment. The coating or treatment detected, in addition to or instead of being a barrier layer, can be a lubricity layer, a hydrophobic layer, a decorative coating, or other types of layers that modify the outgassing of the substrate, either by increasing or decreasing it.

VI.B. As a specific example using the vessel holder from FIG. 2 and referring again to FIG. 7, a device or vessel 80 can be inserted into the puck or vessel holder 44 (the test can also be carried out on a seated vessel 80 carried in a puck or vessel holder such as 44 moving from another operation such as coating/treatment). Once the vessel holder moves into the barrier testing area, the measurement tube or probe 108 can be inserted into the inside (in a similar manner as the gas tube for coating, although the measurement tube does not need to extend as far into the tube). Valves 136 and 148 can both be opened and the interior of the tube can be evacuated (a vacuum created).

VI.B. Once a desired measurement pressure is reached, the valves 136 and 148 can be closed and the pressure gauge 152 can begin measuring the pressure. By measuring the time that a particular pressure (higher than the starting pressure) is reached or by measuring the pressure reached after a given amount of time, the rate of rise (or leak-rate) of the tube, vessel holder, pump channel and all other parts connected to the interior volume but isolated by valve 1 and 2 can be measured. If this value is then compared to an uncoated tube, the ratio of the two measurements (the coated tube value divided by the uncoated tube value) can yield a measurement of the leak rate through the coated surface of the tube. This measurement technique can require the minimization of the interior volume of the vessel holder, pump channel and all other parts connected to the interior volume but isolated by valve 1 and 2 (except the tube/device) to minimize the impact of gas permeation or outgassing from these surfaces.

VI.B. Distinctions are made in this disclosure among "permeation," "leakage," and "surface diffusion" or "outgassing."

Figure 29:
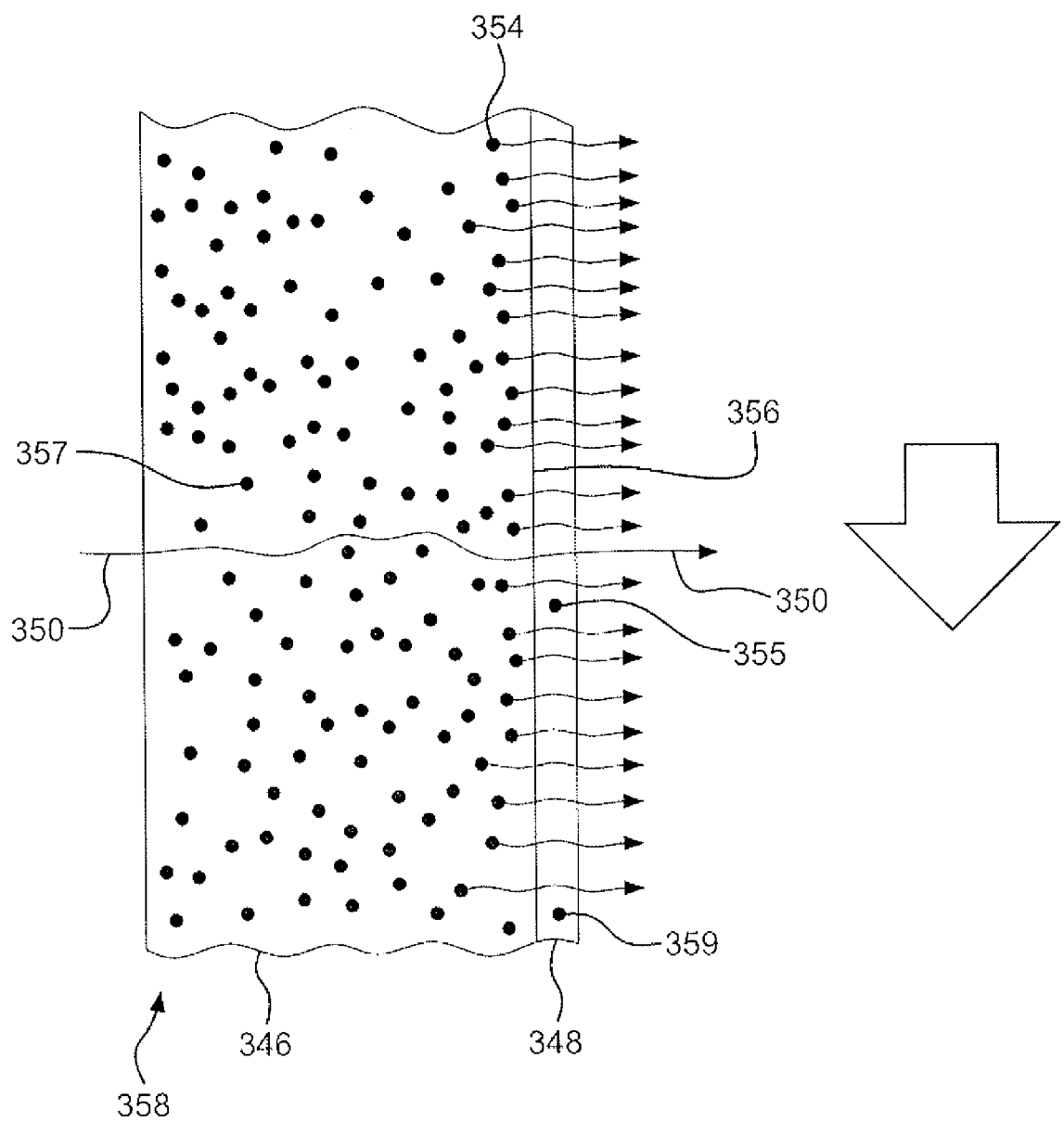
FIG. 29 is a schematic view showing outgassing of a material through a coating.
Figure 30:
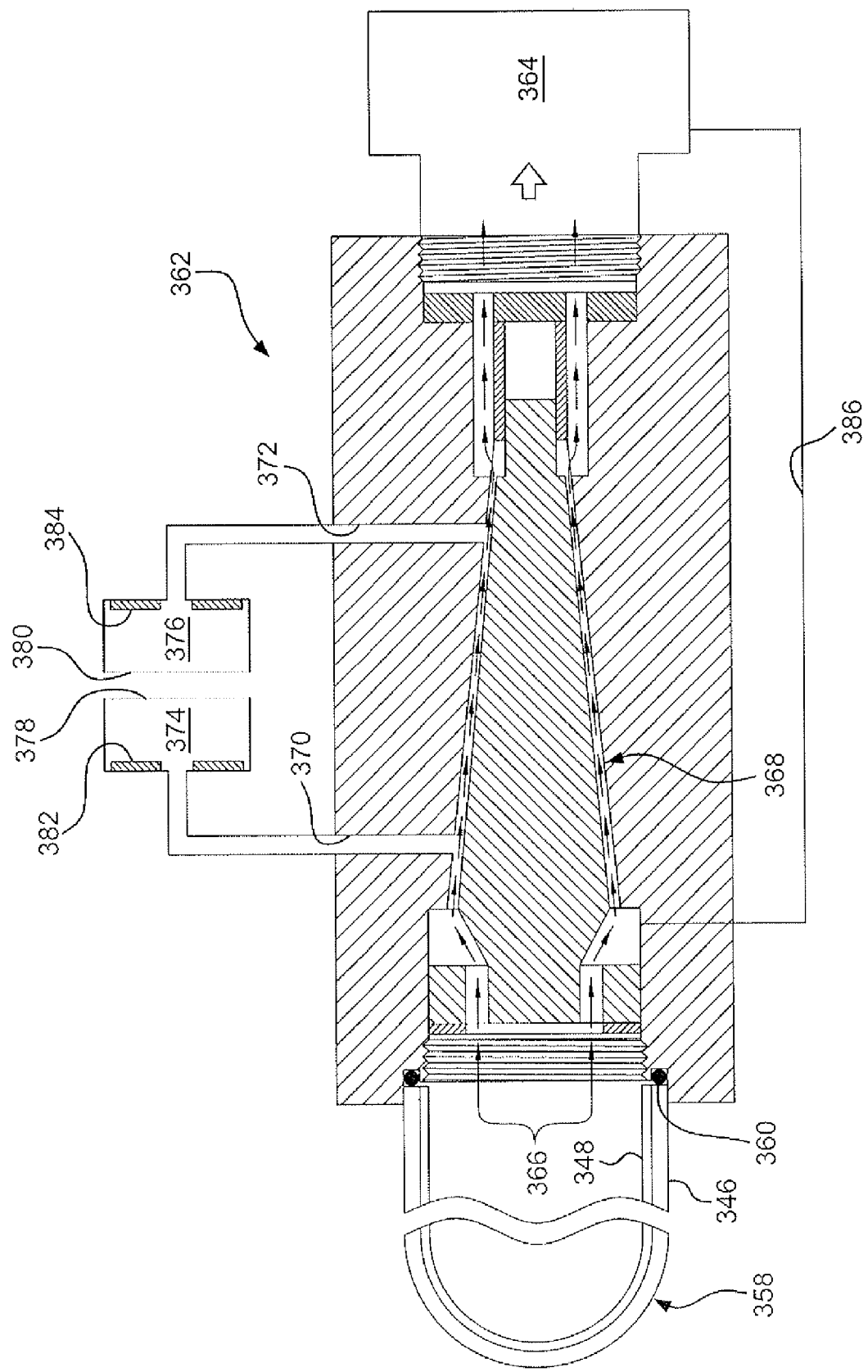
FIG. 30 is a schematic sectional view of a test set-up for causing outgassing of the wall of a vessel to the interior of the vessel and measurement of the outgassing using a measurement cell interposed between the vessel and a source of vacuum.

"Permeation" as used here in reference to a vessel is traverse of a material through a wall 346 or other obstruction, as from the outside of the vessel to the inside or vice versa along the path 350 in FIG. 29 or the reverse of that path.

Outgassing refers to the movement of an absorbed or adsorbed material such as the gas molecule 354 or 357 or 359 outward from within the wall 346 or coating 348 in FIG. 29, for example through the coating 348 (if present) and into the vessel 358 (to the right in FIG. 29). Outgassing can also refer to movement of a material such as 354 or 357 out of the wall 346, to the left as shown in FIG. 29, thus to the outside of the vessel 357 as illustrated. Outgassing can also refer to the removal of adsorbed material from the surface of an article, for example the gas molecule 355 from the exposed surface of the barrier coating 90.

Leakage refers to the movement of a material around the obstruction represented by the wall 346 and coating 348 rather than through or off the surface of the obstruction, as by passing between a closure and the wall of a vessel closed with a closure.

VI.B. Permeation is indicative of the rate of gas movement through a material, devoid of gaps/defects and not relating to leaks or outgassing. Referring to FIG. 29, which shows a vessel wall or other substrate 346 having a barrier coating 348, permeation is traverse of a gas entirely through the substrate 346 and coating 348 along the path 350 through both layers. Permeation is regarded as a thermodynamic, thus relatively slow, process.

VI.B. Permeation measurements are very slow, as the permeating gas must past entirely through an unbroken wall of the plastic article. In the case of evacuated blood collection tubes, a measurement of permeation of gas through its wall is conventionally used as a direct indication of the propensity of the vessel to lose vacuum over time, but commonly is an extremely slow measurement, commonly requiring a test duration of six days, thus not fast enough to support on-line coating inspection. Such testing is ordinarily used for off-line testing of a sample of vessels.

VI.B. Permeation testing also is not a very sensitive measurement of the barrier efficacy of a thin coating on a thick substrate. Since all the gas flow is through both the coating and the substrate, variations in flow through the thick substrate will introduce variation that is not due to the barrier efficacy of the coating per se.

VI.B. The inventors have found a much quicker and potentially more sensitive way of measuring the barrier properties of a coating—measuring outgassing of quickly-separated air or other gaseous or volatile constituents in the vessel wall through the coating. The gaseous or volatile constituents can be any material that in fact outgasses, or can be selected from one or more specific materials to be detected. The constituents can include, but are not limited to, oxygen, nitrogen, air, carbon dioxide, water vapor, helium, volatile organic materials such as alcohols, ketones, hydrocarbons, coating precursors, substrate components, by-products of the preparation of the coating such as volatile organosilicons, by-products of the preparation of the coated substrate, other constituents that happen to be present or are introduced by spiking the substrate, or mixtures or combinations of any of these.

Surface diffusion and outgassing are synonyms. Each term refers to fluid initially adsorbed on or absorbed in a wall 346, such as the wall of a vessel, and caused to pass into the adjacent space by some motivating force, such as drawing a vacuum (creating air movement indicated by the arrow 352 of FIG. 29) within a vessel having a wall to force fluid out of the wall into the interior of the vessel. Outgassing or diffusion is regarded as a kinetic, relatively quick process. It is contemplated that, for a wall 346 having substantial resistance to permeation along the path 350, outgassing will quickly dislodge the molecules such as 354 that are closest to the interface 356 between the wall 346 and the barrier layer 348. This differential outgassing is suggested by the large number of molecules such as 354 near the interface 356 shown as outgassing, and by the large number of other molecules such as 358 that are further from the interface 356 and are not shown as outgassing.

VI.B. Accordingly, yet another method is contemplated for inspecting a barrier layer on a material that outgasses a vapor, including several steps. A sample of material is provided that outgasses a gas and has at least a partial barrier layer. A pressure differential is provided across the barrier layer, such that at least some of the material that outgasses initially is on the higher-pressure side of the barrier layer. The outgassed gas transported to the lower-pressure side of the barrier layer during a test is measured to determine such information as whether the barrier is present or how effective it is as a barrier.

VI.B. In this method, the material that outgasses a gas can include a polymeric compound, a thermoplastic compound, or one or more compounds having both properties. The material that outgasses a gas can include polyester, for example polyethylene terephthalate. The material that outgasses a gas can include a polyolefin, for two examples polypropylene, a cyclic olefin copolymer, or a combination of these. The material that outgasses a gas can be a composite of two different materials, at least one of which outgasses a vapor. One example is a two layer structure of polypropylene and polyethylene terephthalate. Another example is a two layer structure of cyclic olefin copolymer and polyethylene terephthalate. These materials and composites are exemplary; any suitable material or combination of materials can be used.

VI.B. Optionally, the material that outgasses a gas is provided in the form of a vessel having a wall having an outer surface and an inner surface, the inner surface enclosing a lumen. In this embodiment, the barrier layer optionally is disposed on the vessel wall, optionally on the inner surface of the vessel wall. The barrier layer could or also be disposed on the outer surface of the vessel wall. Optionally, the material that outgasses a gas can be provided in the form of a film.

VI.B. The barrier layer can be a full or partial coating of any of the presently described barrier layers. The barrier layer can be less than 500 nm thick, or less than 300 nm thick, or less than 100 nm thick, or less than 80 nm thick, or less than 60 nm thick, or less than 50 nm thick, or less than 40 nm thick, or less than 30 nm thick, or less than 20 nm thick, or less than 10 nm thick, or less than 5 nm thick.

VI.B. In the case of a coated wall, the inventors have found that diffusion/outgassing can be used to determine the coating integrity. Optionally, a pressure differential can be provided across the barrier layer by at least partially evacuating the lumen or interior space of the vessel. This can be done, for example, by connecting the lumen via a duct to a vacuum source to at least partially evacuate the lumen. For example, an uncoated PET wall 346 of a vessel that has been exposed to ambient air will outgas from its interior surface a certain number of oxygen and other gas molecules such as 354 for some time after a vacuum is drawn. If the same PET wall is coated on the interior with a barrier coating 348, the barrier coating will stop, slow down, or reduce this outgassing. This is true for example of an $SiO_x$ barrier coating 348, which outgasses less than a plastic surface. By measuring this differential of outgassing between coated and uncoated PET walls, the barrier effect of the coating 348 for the outgassed material can be rapidly determined.

VI.B. If the barrier coating 348 is imperfect, due to known or theoretical holes, cracks, gaps or areas of insufficient thickness or density or composition, the PET wall will outgas preferentially through the imperfections, thus increasing the total amount of outgassing. The primary source of the collected gas is from the dissolved gas or vaporizable constituents in the (sub)surface of the plastic article next to the coating, not from outside the article. The amount of outgassing beyond a basic level (for example the amount passed or released by a standard coating with no imperfections, or the least attainable degree of imperfection, or an average and acceptable degree of imperfection) can be measured in various ways to determine the integrity of the coating.

VI.B. The measurement can be carried out, for example, by providing an outgassing measurement cell communicating between the lumen and the vacuum source.

VI.B. The measurement cell can implement any of a variety of different measurement technologies. One example of a suitable measurement technology is micro-flow technology. For example, the mass flow rate of outgassed material can be measured. The measurement can be carried out in a molecular flow mode of operation. An exemplary measurement is a determination of the volume of gas outgassed through the barrier layer per interval of time.

VI.B. The outgassed gas on the lower-pressure side of the barrier layer can be measured under conditions effective to distinguish the presence or absence of the barrier layer. Optionally, the conditions effective to distinguish the presence or absence of the barrier layer include a test duration of less than one minute, or less than 50 seconds, or less than 40 seconds, or less than 30 seconds, or less than 20 seconds, or less than 15 seconds, or less than 10 seconds, or less than 8 seconds, or less than 6 seconds, or less than 4 seconds, or less than 3 seconds, or less than 2 seconds, or less than 1 second.

VI.B. Optionally, the measurement of the presence or absence of the barrier layer can be confirmed to at least a six-sigma level of certainty within any of the time intervals identified above.

VI.B. Optionally, the outgassed gas on the lower-pressure side of the barrier layer is measured under conditions effective to determine the barrier improvement factor (BIF) of the barrier layer, compared to the same material without a barrier layer. A BIF can be determined, for example, by providing two groups of identical containers, adding a barrier layer to one group of containers, testing a barrier property (such as the rate of outgassing in micrograms per minute or another suitable measure) on containers having a barrier, doing the same test on containers lacking a barrier, and taking a ratio of the properties of the materials with versus without a barrier. For example, if the rate of outgassing through the barrier is one-third the rate of outgassing without a barrier, the barrier has a BIF of 3.

VI.B. Optionally, outgassing of a plurality of different gases can be measured, in instances where more than one type of gas is present, such as both nitrogen and oxygen in the case of outgassed air. Optionally, outgassing of substantially all or all of the outgassed gases can be measured. Optionally, outgassing of substantially all of the outgassed gases can be measured simultaneously, as by using a physical measurement like the combined mass flow rate of all gases.

VI.B. Measuring the number or partial pressure of individual gas species (such as oxygen or helium) outgassed from the sample can be done more quickly than barometric testing, but the rate of testing is reduced to the extent that only a fraction of the outgassing is of the measured species. For example, if nitrogen and oxygen are outgassed from the PET wall in the approximately 4:1 proportion of the atmosphere, but only oxygen outgassing is measured, the test would need to be run five times as long as an equally sensitive test (in terms of number of molecules detected to obtain results of sufficient statistical quality) that measures all the species outgassed from the vessel wall.

VI.B. For a given level of sensitivity, it is contemplated that a method that accounts for the volume of all species outgassed from the surface will provide the desired level of confidence more quickly than a test that measures outgassing of a specific species, such as oxygen atoms. Consequently, outgassing data having practical utility for in-line measurements can be generated. Such in-line measurements can optionally be carried out on every vessel manufactured, thus reducing the number of idiosyncratic or isolated defects and potentially eliminating them (at least at the time of measurement).

VI.B. In a practical measurement, a factor changing the apparent amount of outgassing is leakage past an imperfect seal, such as the seal of the vessel seated on a vacuum receptacle as the vacuum is drawn in the outgassing test. Leakage means a fluid bypassing a solid wall of the article, for example fluid passing between a blood tube and its closure, between a syringe plunger and syringe barrel, between a container and its cap, or between a vessel mouth and a seal upon which the vessel mouth is seated (due to an imperfect or mis-seated seal). The word "leakage" is usually indicative of the movement of gas/gas through an opening in the plastic article.

VI.B. Leakage and (if necessary in a given situation) permeation can be factored into the basic level of outgassing, so an acceptable test result assures both that the vessel is adequately seated on the vacuum receptacle (thus its seated surfaces are intact and properly formed and positioned), the vessel wall does not support an unacceptable level of permeation (thus the vessel wall is intact and properly formed), and the coating has sufficient barrier integrity.

VI.B. Outgassing can be measured in various ways, as by barometric measurement (measuring the pressure change within the vessel in a given amount of time after the initial vacuum is drawn) or by measuring the partial pressure or flow rate of gas outgassed from the sample. Equipment is available that measures a mass flow rate in a molecular flow mode of operation. An example of commercially available equipment of this type employing Micro-Flow Technology is available from ATC, Inc., Indianapolis, Ind. See U.S. Pat. Nos. 5,861, 546, 6,308,556, 6,584,828 and EP1356260, which are incorporated by reference here, for a further description of this known equipment. See also Example 8 in this specification, showing an example of outgassing measurement to distinguish barrier coated polyethylene terephthalate (PET) tubes from uncoated tubes very rapidly and reliably.

Figure 31:
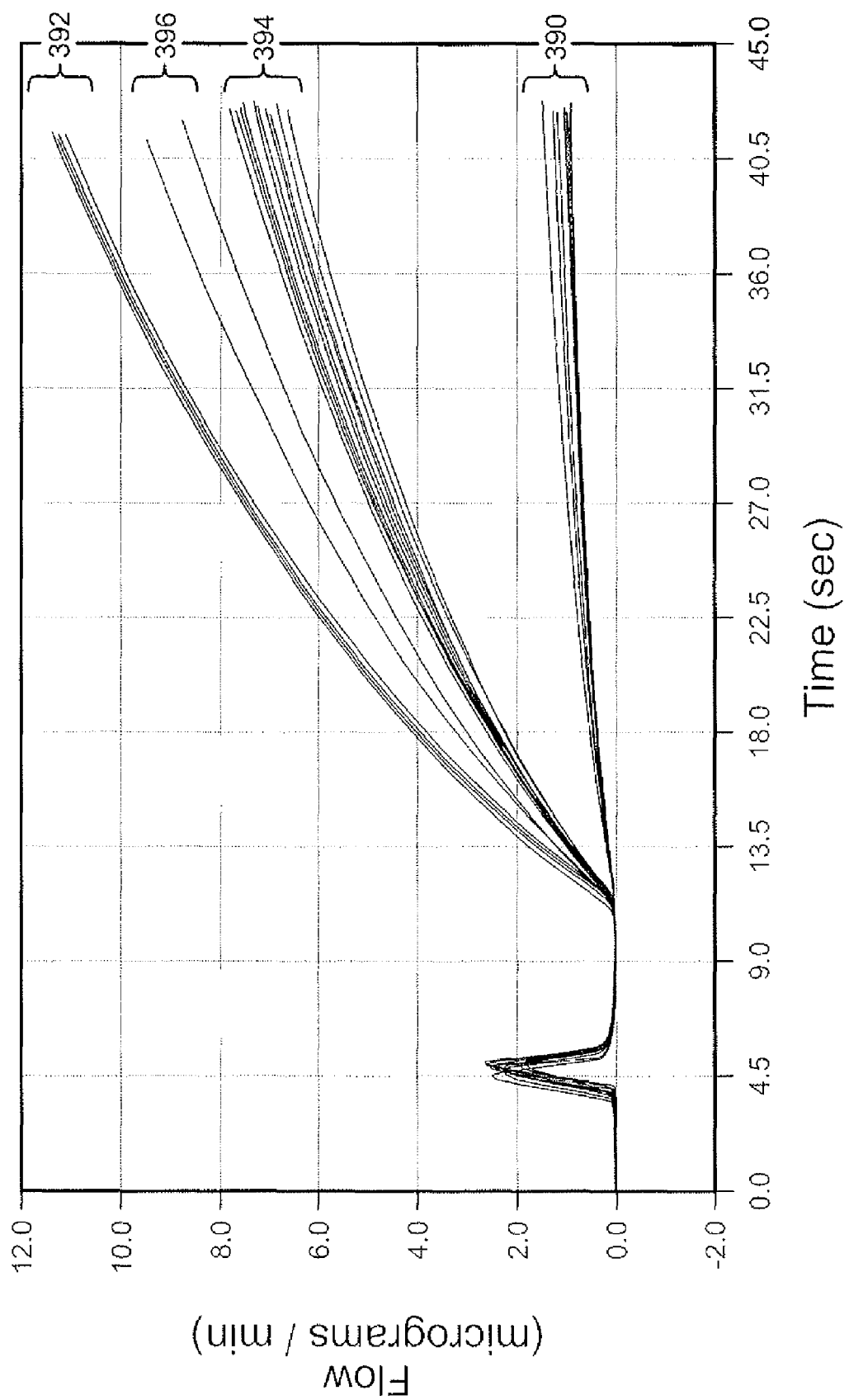
FIG. 31 is a plot of outgassing mass flow rate measured on the test-set-up of FIG. 30 for multiple vessels.

VI.B. For a vessel made of polyethylene terephthalate (PET), the microflow rate is much different for the $SiO_x$ coated surface versus an uncoated surface. For example, in Working Example 8 in this specification, the microflow rate for PET was 8 or more micrograms after the test had run for 30 seconds, as shown in FIG. 31. This rate for uncoated PET was much higher than the measured rate for $SiO_x$-coated PET, which was less than 6 micrograms after the test had run for 30 sec, again as shown in FIG. 31.

VI.B. One possible explanation for this difference in flow rate is that uncoated PET contains roughly 0.7 percent equilibrium moisture; this high moisture content is believed to cause the observed high microflow rate. With an $SiO_x$-coated PET plastic, the $SiO_x$ coating can have a higher level of surface moisture than an uncoated PET surface. Under the testing conditions, however, the barrier coating is believed to prevent additional desorption of moisture from the bulk PET plastic, resulting in a lower microflow rate. The microflow rates of oxygen or nitrogen from the uncoated PET plastic versus the $SiO_x$ coated PET would also be expected to be distinguishable.

VI.B. Modifications of the above test for a PET tube might be appropriate when using other materials. For example, polyolefin plastics tend to have little moisture content. An example of a polyolefin having low moisture content is TOPAS® cyclic olefin copolymer (COC), having an equilibrium moisture content (0.01 percent) and moisture permeation rate much lower than for PET. In the case of COC, uncoated COC plastic can have microflow rate similar to, or even less than, $SiO_x$-coated COC plastic. This is most likely due to the higher surface moisture content of the $SiO_x$-coating and the lower equilibrium bulk moisture content and lower permeation rate of an uncoated COC plastic surface. This makes differentiation of uncoated and coated COC articles more difficult.

The present invention shows that exposure of the to-be-tested surfaces of COC articles to moisture (uncoated and coated) results in improved and consistent microflow separation between uncoated and $SiO_x$-coated COC plastics. This is shown in Example 19 in this specification and FIG. 57. The moisture exposure can be simply exposure to relative humidity ranging from 35%-100%, either in a controlled relative humidity room or direct exposure to a warm (humidifier) or cold (vaporizer) moisture source, with the latter preferred.

VI.B. While the validity and scope of the invention are not limited according to the accuracy of this theory, it appears the moisture doping or spiking of the uncoated COC plastic increases its moisture or other outgassable content relative to the already saturated $SiO_x$-coated COC surface. This can also be accomplished by exposing the coated and uncoated tubes to other gases including oxygen, nitrogen, or their mixtures, for example air.

VI.B Thus, before measuring the outgassed gas, the barrier layer can be contacted with water, for example water vapor. Water vapor can be provided, for example, by contacting the barrier layer with air at a relative humidity of 35% to 100%, alternatively 40% to 100%, alternatively 40% to 50%. Instead of or in addition to water, the barrier layer can be contacted with oxygen, nitrogen or a mixture of oxygen and nitrogen, for example ambient air. The contacting time can be from 10 seconds to one hour, alternatively from one minute to thirty minutes, alternatively from 5 minutes to 25 minutes, alternatively from 10 minutes to 20 minutes.

Alternatively, the wall 346 which will be outgassing can be spiked or supplemented from the side opposite a barrier layer 348, for example by exposing the left side of the wall 346 as shown in FIG. 11 to a material that will ingas into the wall 346, then outgas either to the left or to the right as shown in FIG. 29. Spiking a wall or other material such as 346 from the left by ingassing, then measuring outgassing of the spiked material from the right (or vice versa) is distinguished from permeation measurement because the material spiked is within the wall 346 at the time outgassing is measured, as opposed to material that travels the full path 350 through the wall at the time gas presented through the coating is being measured. The ingassing can take place over a long period of time, as one embodiment before the coating 348 is applied, and as another embodiment after the coating 348 is applied and before it is tested for outgassing.

VI.B. Another potential method to increase separation of microflow response between uncoated and $SiO_x$-coated plastics is to modify the measurement pressure and/or temperature. Increasing the pressure or decreasing the temperature when measuring outgassing can result in greater relative binding of water molecules in $SiO_x$-coated COC than in uncoated COC. Thus, the outgassed gas can be measured at a pressure from 0.1 Torr to 100 Torr, alternatively from 0.2 Torr to 50 Torr, alternatively from 0.5 Torr to 40 Torr, alternatively from 1 Torr to 30 Torr, alternatively from 5 Torr to 100 Torr, alternatively from 10 Torr to 80 Torr, alternatively from 15 Torr to 50 Torr. The outgassed gas can be measured at a temperature from 0° C. to 50° C., alternatively from 0° C. to 21° C., alternatively from 5° C. to 20° C.

VI.B. Another way contemplated for measuring outgassing, in any embodiment of the present disclosure, is to employ a microcantilever measurement technique. Such a technique is contemplated to allow measurement of smaller mass differences in outgassing, potentially on the order of $10^{-12}$ g. (picograms) to $10^{-15}$ g. (femtograms). This smaller mass detection permits differentiation of coated versus uncoated surfaces as well as different coatings in less than a second, optionally less than 0.1 sec., optionally a matter of microseconds.

VI.B. Microcantilever (MCL) sensors in some instances can respond to the presence of an outgassed or otherwise provided material by bending or otherwise moving or changing shape due to the absorption of molecules. Microcantilever (MCL) sensors in some instances can respond by shifting in resonance frequency. In other instances, the MCL sensors can change in both these ways or in other ways. They can be operated in different environments such as gaseous environment, liquids, or vacuum. In gas, microcantilever sensors can be operated as an artificial nose, whereby the bending pattern of a microfabricated array of eight polymer-coated silicon cantilevers is characteristic of the different vapors from solvents, flavors, and beverages. The use of any other type of electronic nose, operated by any technology, is also contemplated.

Several MCL electronic designs, including piezoresistive, piezoelectric, and capacitive approaches, have been applied and are contemplated to measure the movement, change of shape, or frequency change of the MCLs upon exposure to chemicals.

VI.B. One specific example of measuring outgassing can be carried out as follows. At least one microcantilever is provided that has the property, when in the presence of an outgassed material, of moving or changing to a different shape. The microcantilever is exposed to the outgassed material under conditions effective to cause the microcantilever to move or change to a different shape. The movement or different shape is then detected.

VI.B. As one example, the movement or different shape can be detected by reflecting an energetic incident beam from a portion of the microcantilever that moves or changes shape, before and after exposing the microcantilever to outgassing, and measuring the resulting deflection of the reflected beam at a point spaced from the cantilever. The shape is optionally measured at a point spaced from the cantilever because the amount of deflection of the beam under given conditions is proportional to the distance of the point of measurement from the point of reflection of the beam.

VI.B. Several suitable examples of an energetic incident beam are a beam of photons, a beam of electrons, or a combination of two or more of these. Alternatively, two or more different beams can be reflected from the MCL along different incident and/or reflected paths, to determine movement or shape change from more than one perspective. One specifically contemplated type of energetic incident beam is a beam of coherent photons, such as a laser beam. "Photons" as discussed in this specification are inclusively defined to include wave energy as well as particle or photon energy per se.

VI.B. An alternative example of measurement takes advantage of the property of certain MCLs of changing in resonant frequency when encountering an environmental material in an effective amount to accomplish a change in resonant frequency. This type of measurement can be carried out as follows. At least one microcantilever is provided that resonates at a different frequency when in the presence of an outgassed material. The microcantilever can be exposed to the outgassed material under conditions effective to cause the microcantilever to resonate at a different frequency. The different resonant frequency is then detected by any suitable means.

VI.B. As one example, the different resonant frequency can be detected by inputting energy to the microcantilever to induce it to resonate before and after exposing the microcantilever to outgassing. The differences between the resonant frequencies of the MCL before and after exposure to outgassing are determined. Alternatively, instead of determining the difference in resonant frequency, an MCL can be provided that is known to have a certain resonant frequency when in the presence of a sufficient concentration or quantity of an outgassed material. The different resonant frequency or the resonant frequency signaling the presence of a sufficient quantity of the outgassed material is detected using a harmonic vibration sensor.

As one example of using MCL technology for measuring outgassing, an MCL device can be incorporated into a quartz vacuum tube linked to a vessel and vacuum pump. A harmonic vibration sensor using a commercially available piezoresistive cantilever, Wheatstone bridge circuits, a positive feedback controller, an exciting piezoactuator and a phase-locked loop (PLL) demodulator can be constructed. See, e.g., Hayato Sone, Yoshinori Fujinuma and Sumio Hosaka *Picogram Mass Sensor Using Resonance Frequency Shift of Cantilever*, Jpn. J. Appl. Phys. 43 (2004) 3648;

Hayato Sone, Ayumi Ikeuchi, Takashi Izumi, Haruki Okano and Sumio Hosaka Femtogram Mass Biosensor Using Self-Sensing Cantilever for Allergy Check, Jpn. J. Appl. Phys. 43 (2006) 2301).

To prepare the MCL for detection, one side of the microcantilever can be coated with gelatin. See, e.g., Hans Peter Lang, Christoph Gerber, STM and AFM Studies on (Bio)molecular Systems: Unraveling the Nanoworld, Topics in Current Chemistry, Volume 285/2008. Water vapor desorbing from the evacuated coated vessel surface binds with the gelatin, causing the cantilever to bend and its resonant frequency to change, as measured by laser deflection from a surface of the cantilever. The change in mass of an uncoated vs coated vessel is contemplated to be resolvable in fractions of seconds and be highly reproducible. The articles cited above in connection with cantilever technology are incorporated here by reference for their disclosures of specific MCLs and equipment arrangements that can be used for detecting and quantifying outgassed species.

Alternative coatings for moisture detection (phosphoric acid) or oxygen detection can be applied to MCLs in place of or in addition to the gelatin coating described above.

VI.B. It is further contemplated that any of the presently contemplated outgassing test set-ups can be combined with an $SiO_x$ coating station. In such an arrangement, the measurement cell 362 could be as illustrated above, using the main vacuum channel for PECVD as the bypass 386. In an embodiment, the measurement cell generally indicated as 362 of FIG. 30 can be incorporated in a vessel holder such as 50 in which the bypass channel 386 is configured as the main vacuum duct 94 and the measurement cell 362 is a side channel.

VI.B. This combination of the measurement cell 362 with the vessel holder 50 would optionally allow the outgassing measurement to be conducted without breaking the vacuum used for PECVD. Optionally, the vacuum pump for PECVD would be operated for a short, optionally standardized amount of time to pump out some or all of the residual reactant gases remaining after the coating step (a pump-down of less than one Torr, with a further option of admitting a small amount of air, nitrogen, oxygen, or other gas to flush out or dilute the process gases before pumping down). This would expedite the combined processes of coating the vessel and testing the coating for presence and barrier level.

VI.B. It will be further appreciated by those skilled in the art, after review of this specification, that outgassing measurements and all the other described barrier measurement techniques can be used for many purposes other than or in addition to determining the efficacy of a barrier layer. For one example, the test can be used on uncoated or coated vessels to determine the degree of outgassing of the vessel walls. This test can be used, for example, in cases in which an uncoated polymer is required to outgas less than a specified amount.

VI.B. For another example, these outgassing measurements and all the other described barrier measurement techniques can be used on barrier coated or uncoated films, either as a static test or as an in-line test to measure variations in outgassing of a film as it traverses the measurement cell. The test can be used for determining the continuity or barrier efficacy of other types of coatings, such as aluminum coatings or EVOH barrier coatings or layers of packaging films.

VI.B. These outgassing measurements and all the other described barrier measurement techniques can be used to determine the efficacy of a barrier layer applied on the side of a vessel wall, film, or the like opposite the measurement cell, such as a barrier layer applied on the outside of a vessel wall and interrogated for outgassing to the interior of the vessel wall. In this instance, the flow differential would be for permeation through the barrier coating followed by permeation through the substrate film or wall. This measurement would be particularly useful in instances where the substrate film or wall is quite permeable, such as a very thin or porous film or wall.

VI.B. These outgassing measurements and all the other described barrier measurement techniques can be used to determine the efficacy of a barrier layer which is an interior layer of a vessel wall, film, or the like, in which case the measurement cell would detect any outgassing through the layer adjacent to the measurement cell plus outgassing, through the barrier layer, of the layer or layers more remote from the measurement cell than the barrier layer.

VI.B. These outgassing measurements and all the other described barrier measurement techniques can be used to determine the percentage of coverage of a pattern of barrier material over a material that outgasses, as by determining the degree of outgassing of the partially barrier coated material as a proportion of the amount of outgassing expected if no barrier were present over any part of the material.

VI.B. One test technique that can be used to increase the rate of testing for outgassing of a vessel, usable with any outgassing test embodiment in the specification, is to reduce the void volume of the vessel, as by inserting a plunger or closure into the vessel to reduce the void volume of the portion of the vessel tested. Decreasing the void volume allows the vessel to be pumped down more quickly to a given vacuum level, thus decreasing the test interval.

VI.B. Many other applications for the presently described outgassing measurements and all the other described barrier measurement techniques will be evident to the skilled person after reviewing this specification.

VII. PECVD Treated Vessels

VII. Vessels are contemplated having a barrier coating 90 (shown in FIG. 2, for example), which can be an $SiO_x$ coating applied to a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The coating can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated. The thickness of the $SiO_x$ or other coating can be measured, for example, by transmission electron microscopy (TEM), and its composition can be measured by X-ray photoelectron spectroscopy (XPS).

VII. It is contemplated that the choice of the material to be barred from permeating the coating and the nature of the $SiO_x$ coating applied can affect its barrier efficacy. For example, two examples of material commonly intended to be barred are oxygen and water/water vapor. Materials commonly are a better barrier to one than to the other. This is believed to be so at least in part because oxygen is transmitted through the coating by a different mechanism than water is transmitted.

VII. Oxygen transmission is affected by the physical features of the coating, such as its thickness, the presence of cracks, and other physical details of the coating. Water transmission, on the other hand, is believed to commonly be affected by chemical factors, i.e. the material of which the coating is made, more than physical factors. The inventors also believe that at least one of these chemical factors is a substantial concentration of OH moieties in the coating, which leads to a higher transmission rate of water through the barrier. An $SiO_x$ coating often contains OH moieties, and thus a physically sound coating containing a high proportion of OH moieties is a better barrier to oxygen than to water. A physically sound carbon-based barrier, such as amorphous carbon or diamond-like carbon (DLC) commonly is a better barrier to water than is a $SiO_x$ coating because the carbon-based barrier more commonly has a lower concentration of OH moieties.

VII. Other factors lead to a preference for an $SiO_x$ coating, however, such as its oxygen barrier efficacy and its close chemical resemblance to glass and quartz. Glass and quartz (when used as the base material of a vessel) are two materials long known to present a very high barrier to oxygen and water transmission as well as substantial inertness to many materials commonly carried in vessels. Thus, it is commonly desirable to optimize the water barrier properties such as the water vapor transmission rate (WVTR) of an $SiO_x$ coating, rather than choosing a different or additional type of coating to serve as a water transmission barrier.

VII. Several ways contemplated to improve the WVTR of an $SiO_x$ coating are as follow.

VII. The concentration ratio of organic moieties (carbon and hydrogen compounds) to OH moieties in the deposited coating can be increased. This can be done, for example, by increasing the proportion of oxygen in the feed gases (as by increasing the oxygen feed rate or by lowering the feed rate of one or more other constituents). The lowered incidence of OH moieties is believed to result from increasing the degree of reaction of the oxygen feed with the hydrogen in the silicone source to yield more volatile water in the PECVD exhaust and a lower concentration of OH moieties trapped or incorporated in the coating.

VII. Higher energy can be applied in the PECVD process, either by raising the plasma generation power level, by applying the power for a longer period, or both. An increase in the applied energy must be employed with care when used to coat a plastic tube or other device, as it also has a tendency to distort the vessel being treated, to the extent the tube absorbs the plasma generation power. This is why RF power is contemplated in the context of present application. Distortion of the medical devices can be reduced or eliminated by employing the energy in a series of two or more pulses separated by cooling time, by cooling the vessels while applying energy, by applying the coating in a shorter time (commonly thus making it thinner), by selecting a frequency of the applied coating that is absorbed minimally by the base material selected for being coated, and/or by applying more than one coating, with time in between the respective energy application steps. For example, high power pulsing can be used with a duty cycle of 1 millisecond on, 99 milliseconds off, while continuing to feed the process gas. The process gas is then the coolant, as it keeps flowing between pulses. Another alternative is to reconfigure the power applicator, as by adding magnets to confine the plasma increase the effective power application (the power that actually results in incremental coating, as opposed to waste power that results in heating or unwanted coating). This expedient results in the application of more coating-formation energy per total Watt-hour of energy applied. See for example U.S. Pat. No. 5,904,952.

VII. An oxygen post-treatment of the coating can be applied to remove OH moieties from the previously-deposited coating. This treatment is also contemplated to remove residual volatile organosilicon compounds or silicones or oxidize the coating to form additional $SiO_x$.

VII. The plastic base material tube can be preheated.

VII. A different volatile source of silicon, such as hexamethyldisilazane (HMDZ), can be used as part or all of the silicone feed. It is contemplated that changing the feed gas to HMDZ will address the problem because this compound has no oxygen moieties in it, as supplied. It is contemplated that one source of OH moieties in the HMDSO-sourced coating is hydrogenation of at least some of the oxygen atoms present in unreacted HMDSO.

VII. A composite coating can be used, such as a carbon-based coating combined with $SiO_x$. This can be done, for example, by changing the reaction conditions or by adding a substituted or unsubstituted hydrocarbon, such as an alkane, alkene, or alkyne, to the feed gas as well as an organosilicon-based compound. See for example U.S. Pat. No. 5,904,952, which states in relevant part: "For example, inclusion of a lower hydrocarbon such as propylene provides carbon moieties and improves most properties of the deposited films (except for light transmission), and bonding analysis indicates the film to be silicon dioxide in nature. Use of methane, methanol, or acetylene, however, produces films that are silicone in nature. The inclusion of a minor amount of gaseous nitrogen to the gas stream provides nitrogen moieties in the deposited films and increases the deposition rate, improves the transmission and reflection optical properties on glass, and varies the index of refraction in response to varied amounts of $N_2$. The addition of nitrous oxide to the gas stream increases the deposition rate and improves the optical properties, but tends to decrease the film hardness."

VII. A diamond-like carbon (DLC) coating can be formed as the primary or sole coating deposited. This can be done, for example, by changing the reaction conditions or by feeding methane, hydrogen, and helium to a PECVD process. These reaction feeds have no oxygen, so no OH moieties can be formed. For one example, an $SiO_x$ coating can be applied on the interior of a tube or syringe barrel and an outer DLC coating can be applied on the exterior surface of a tube or syringe barrel. Or, the $SiO_x$ and DLC coatings can both be applied as a single layer or plural layers of an interior tube or syringe barrel coating.

VII. Referring to FIG. 2, the barrier or other type of coating 90 reduces the transmission of atmospheric gases into the vessel 80 through its interior surface 88. Or, the barrier or other type of coating 90 reduces the contact of the contents of the vessel 80 with the interior surface 88. The barrier or other type of coating can comprise, for example, $SiO_x$, amorphous (for example, diamond-like) carbon, or a combination of these.

VII. Any coating described herein can be used for coating a surface, for example a plastic surface. It can further be used as a barrier layer, for example as a barrier against a gas or liquid, optionally against water vapor, oxygen and/or air. It can also be used for preventing or reducing mechanical and/or chemical effects which the coated surface would have on a compound or composition if the surface were uncoated. For example, it can prevent or reduce the precipitation of a compound or composition, for example insulin precipitation or blood clotting or platelet activation.

VII.A. Evacuated Blood Collection Vessels

VII.A.1. Tubes

VII.A.I. Referring to FIG. 2, more details of the vessel such as 80 are shown. The illustrated vessel 80 can be generally tubular, having an opening 82 at one end of the vessel, opposed by a closed end 84. The vessel 80 also has a wall 86 defining an interior surface 88. One example of the vessel 80 is a medical sample tube, such as an evacuated blood collection tube, as commonly is used by a phlebotomist for receiving a venipuncture sample of a patient's blood for use in a medical laboratory.

VII.A.1. The vessel 80 can be made, for example, of thermoplastic material. Some examples of suitable thermoplastic material are polyethylene terephthalate or a polyolefin such as polypropylene or a cyclic polyolefin copolymer.

VII.A.1. The vessel 80 can be made by any suitable method, such as by injection molding, by blow molding, by machining, by fabrication from tubing stock, or by other suitable means. PECVD can be used to form a coating on the internal surface of $SiO_x$.

VII.A.1. If intended for use as an evacuated blood collection tube, the vessel 80 desirably can be strong enough to withstand a substantially total internal vacuum substantially without deformation when exposed to an external pressure of 760 Torr or atmospheric pressure and other coating processing conditions. This property can be provided, in a thermoplastic vessel 80, by providing a vessel 80 made of suitable materials having suitable dimensions and a glass transition temperature higher than the processing temperature of the coating process, for example a cylindrical wall 86 having sufficient wall thickness for its diameter and material.

VII.A.1. Medical vessels or containers like sample collection tubes and syringes are relatively small and are injection molded with relatively thick walls, which renders them able to be evacuated without being crushed by the ambient atmospheric pressure. They are thus stronger than carbonated soft drink bottles or other larger or thinner-walled plastic containers. Since sample collection tubes designed for use as evacuated vessels typically are constructed to withstand a full vacuum during storage, they can be used as vacuum chambers.

VII.A.1. Such adaptation of the vessels to be their own vacuum chambers might eliminate the need to place the vessels into a vacuum chamber for PECVD treatment, which typically is carried out at very low pressure. The use of a vessel as its own vacuum chamber can result in faster processing time (since loading and unloading of the parts from a separate vacuum chamber is not necessary) and can lead to simplified equipment configurations. Furthermore, a vessel holder is contemplated, for certain embodiments, that will hold the device (for alignment to gas tubes and other apparatus), seal the device (so that the vacuum can be created by attaching the vessel holder to a vacuum pump) and move the device between molding and subsequent processing steps.

VII.A.1. A vessel 80 used as an evacuated blood collection tube should be able to withstand external atmospheric pressure, while internally evacuated to a reduced pressure useful for the intended application, without a substantial volume of air or other atmospheric gas leaking into the tube (as by bypassing the closure) or permeating through the wall 86 during its shelf life. If the as-molded vessel 80 cannot meet this requirement, it can be processed by coating the interior surface 88 with a barrier or other type of coating 90. It is desirable to treat and/or coat the interior surfaces of these devices (such as sample collection tubes and syringe barrels) to impart various properties that will offer advantages over existing polymeric devices and/or to mimic existing glass products. It is also desirable to measure various properties of the devices before and/or after treatment or coating.

VII.A.1.a. Coating Deposited from an Organosilicon Precursor Made by In Situ Polymerizing Organosilicon Precursor VII.A.1.a. A process is contemplated for applying a lubricity layer characterized as defined in the Definition Section on a substrate, for example the interior of the barrel of a syringe, comprising applying one of the described precursors on or in the vicinity of a substrate at a thickness of 1 to 5000 nm, optionally 10 to 1000 nm, optionally 10-200 nm, optionally 20 to 100 nm thick and crosslinking or polymerizing (or both) the coating, optionally in a PECVD process, to provide a lubricated surface. The coating applied by this process is also contemplated to be new.

VII.A.1.a. A coating of $Si_wO_xC_yH_z$ as defined in the Definition Section can have utility as a hydrophobic layer. Coatings of this kind are contemplated to be hydrophobic, independent of whether they function as lubricity layers. A coating or treatment is defined as "hydrophobic" if it lowers the wetting tension of a surface, compared to the corresponding uncoated or untreated surface. Hydrophobicity is thus a function of both the untreated substrate and the treatment.

VII.A.1.a. The degree of hydrophobicity of a coating can be varied by varying its composition, properties, or deposition method. For example, a coating of SiOx having little or no hydrocarbon content is more hydrophilic than a coating of $Si_wO_xC_yH_z$ as defined in the Definition Section. Generally speaking, the higher the C—$H_x$ (e.g. CH, $CH_2$, or $CH_3$) moiety content of the coating, either by weight, volume, or molarity, relative to its silicon content, the more hydrophobic the coating.

VII.A.1.a. A hydrophobic layer can be very thin, having a thickness of at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The coating can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated.

VII.A.1.a. One utility for such a hydrophobic layer is to isolate a thermoplastic tube wall, made for example of polyethylene terephthalate (PET), from blood collected within the tube. The hydrophobic layer can be applied on top of a hydrophilic $SiO_x$ coating on the internal surface of the tube. The $SiO_x$ coating increases the barrier properties of the thermoplastic tube and the hydrophobic layer changes the surface energy of blood contact surface with the tube wall. The hydrophobic layer can be made by providing a precursor selected from those identified in this specification. For example, the hydrophobic layer precursor can comprise hexamethyldisiloxane (HMDSO) or octamethylcyclotetrasiloxane (OMCTS).

VII.A.1.a. Another use for a hydrophobic layer is to prepare a glass cell preparation tube. The tube has a wall defining a lumen, a hydrophobic layer in the internal surface of the glass wall, and contains a citrate reagent. The hydrophobic layer can be made by providing a precursor selected from those identified elsewhere in this specification. For another example, the hydrophobic layer precursor can comprise hexamethyldisiloxane (HMDSO) or octamethylcyclotetrasiloxane (OMCTS). Another source material for hydrophobic layers is an alkyl trimethoxysilane of the formula:

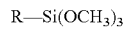

$$R—Si(OCH_3)_3$$

in which R is a hydrogen atom or an organic substituent, for example methyl, ethyl, propyl, isopropyl, butyl, isobutyl, t-butyl, vinyl, alkyne, epoxide, or others. Combinations of two or more of these are also contemplated.

VII.A.1.a. Combinations of acid or base catalysis and heating, using an alkyl trimethoxysilane precursor as described above, can condense the precursor (removing ROH by-products) to form crosslinked polymers, which can optionally be further crosslinked via an alternative method. One specific example is by Shimojima et. al. J. Mater. Chem., 2007, 17, 658-663.

VII.A.1.a. A lubricity layer, characterized as defined in the Definition Section, can be applied as a subsequent coating after applying an $SiO_x$ barrier coating to the interior surface 88 of the vessel 80 to provide a lubricity layer, particularly if the lubricity layer is a liquid organosiloxane compound at the end of the coating process.

VII.A.1.a. Optionally, after the lubricity layer is applied, it can be post-cured after the PECVD process. Radiation curing approaches, including UV-initiated (free radial or cationic), electron-beam (E-beam), and thermal as described in Development Of Novel Cycloaliphatic Siloxanes For Thermal And UV-Curable Applications (Ruby Chakraborty Dissertation, can 2008) be utilized.

VII.A.1.a. Another approach for providing a lubricity layer is to use a silicone demolding agent when injection-molding the thermoplastic vessel to be lubricated. For example, it is contemplated that any of the demolding agents and latent monomers causing in-situ thermal lubricity layer formation during the molding process can be used. Or, the aforementioned monomers can be doped into traditional demolding agents to accomplish the same result.

VII.A.1.a. A lubricity layer, characterized as defined in the Definition Section, is particularly contemplated for the internal surface of a syringe barrel as further described below. A lubricated internal surface of a syringe barrel can reduce the plunger sliding force needed to advance a plunger in the barrel during operation of a syringe, or the breakout force to start a plunger moving after the prefilled syringe plunger has pushed away the intervening lubricant or adhered to the barrel, for example due to decomposition of the lubricant between the plunger and the barrel. As explained elsewhere in this specification, a lubricity layer also can be applied to the interior surface 88 of the vessel 80 to improve adhesion of a subsequent coating of $SiO_x$.

VII.A.1.a. Thus, the coating 90 can comprise a layer of $SiO_x$ and a lubricity layer and/or hydrophobic layer, characterized as defined in the Definition Section. The lubricity layer and/or hydrophobic layer of $Si_wO_xC_yH_z$ can be deposited between the layer of $SiO_x$ and the interior surface of the vessel. Or, the layer of $SiO_x$ can be deposited between the lubricity layer and/or hydrophobic layer and the interior surface of the vessel. Or, three or more layers, either alternating or graduated between these two coating compositions: (1) a layer of $SiO_x$ and (2) the lubricity layer and/or hydrophobic layer; can also be used. The layer of $SiO_x$ can be deposited adjacent to the lubricity layer and/or hydrophobic layer or remotely, with at least one intervening layer of another material. The layer of $SiO_x$ can be deposited adjacent to the interior surface of the vessel. Or, the lubricity layer and/or hydrophobic layer can be deposited adjacent to the interior surface of the vessel.

VII.A.1.a. Another expedient contemplated here, for adjacent layers of $SiO_x$ and a lubricity layer and/or hydrophobic layer, is a graded composite of $Si_wO_xC_yH_z$, as defined in the Definition Section. A graded composite can be separate layers of a lubricity layer and/or hydrophobic layer and $SiO_x$ with a transition or interface of intermediate composition between them, or separate layers of a lubricity layer and/or hydrophobic layer and $SiO_x$ with an intermediate distinct layer of intermediate composition between them, or a single layer that changes continuously or in steps from a composition of a lubricity layer and/or hydrophobic layer to a composition more like $SiO_x$, going through the coating in a normal direction.

VII.A.1.a. The grade in the graded composite can go in either direction. For example, the a lubricity layer and/or hydrophobic layer can be applied directly to the substrate and graduate to a composition further from the surface of $SiO_x$. Or, the composition of $SiO_x$ can be applied directly to the substrate and graduate to a composition further from the surface of a lubricity layer and/or hydrophobic layer. A graduated coating is particularly contemplated if a coating of one composition is better for adhering to the substrate than the other, in which case the better-adhering composition can, for example, be applied directly to the substrate. It is contemplated that the more distant portions of the graded coating can be less compatible with the substrate than the adjacent portions of the graded coating, since at any point the coating is changing gradually in properties, so adjacent portions at nearly the same depth of the coating have nearly identical composition, and more widely physically separated portions at substantially different depths can have more diverse properties. It is also contemplated that a coating portion that forms a better barrier against transfer of material to or from the substrate can be directly against the substrate, to prevent the more remote coating portion that forms a poorer barrier from being contaminated with the material intended to be barred or impeded by the barrier.

VII.A.1.a. The coating, instead of being graded, optionally can have sharp transitions between one layer and the next, without a substantial gradient of composition. Such coatings can be made, for example, by providing the gases to produce a layer as a steady state flow in a non-plasma state, then energizing the system with a brief plasma discharge to form a coating on the substrate. If a subsequent coating is to be applied, the gases for the previous coating are cleared out and the gases for the next coating are applied in a steady-state fashion before energizing the plasma and again forming a distinct layer on the surface of the substrate or its outermost previous coating, with little if any gradual transition at the interface.

VII.A.1.b. Citrate Blood Tube Having Wall Coated with Hydrophobic Layer Deposited from an Organosilicon Precursor VII.A.1.b. Another embodiment is a cell preparation tube having a wall provided with a hydrophobic layer on its inside surface and containing an aqueous sodium citrate reagent. The hydrophobic layer can be also be applied on top of a hydrophilic $SiO_x$ coating on the internal surface of the tube. The $SiO_x$ coating increases the barrier properties of the thermoplastic tube and the hydrophobic layer changes the surface energy of blood contact surface with the tube wall.

VII.A.1.b. The wall is made of thermoplastic material having an internal surface defining a lumen.

VII.A.1.b. A blood collection tube according to the embodiment VII.A.1.b can have a first layer of $SiO_x$ on the internal surface of the tube, applied as explained in this specification, to function as an oxygen barrier and extend the shelf life of an evacuated blood collection tube made of thermoplastic material. A second layer of a hydrophobic layer, characterized as defined in the Definition Section, can then be applied over the barrier layer on the internal surface of the tube to provide a hydrophobic surface. The coating is effective to reduce the platelet activation of blood plasma treated with a sodium citrate additive and exposed to the inner surface, compared to the same type of wall uncoated.

VII.A.1.b. PECVD is used to form a hydrophobic layer on the internal surface, characterized as defined in the Definition Section. Unlike conventional citrate blood collection tubes, the blood collection tube having a hydrophobic layer, characterized as defined in the Definition Section does not require a coating of baked on silicone on the vessel wall, as is conventionally applied to make the surface of the tube hydrophobic.

VII.A.1.b. Both layers can be applied using the same precursor, for example HMDSO or OMCTS, and different PECVD reaction conditions.

VII.A.1.b. A sodium citrate anticoagulation reagent is then placed within the tube and it is evacuated and sealed with a closure to produce an evacuated blood collection tube. The components and formulation of the reagent are known to those skilled in the art. The aqueous sodium citrate reagent is disposed in the lumen of the tube in an amount effective to inhibit coagulation of blood introduced into the tube.

VII.A.1.c. $SiO_x$ Barrier Coated Double Wall Plastic Vessel—COC, PET, $SiO_x$ Layers VII.A.1.c. Another embodiment is a vessel having a wall at least partially enclosing a lumen. The wall has an interior polymer layer enclosed by an exterior polymer layer. One of the polymer layers is a layer at least 0.1 mm thick of a cyclic olefin copolymer (COC) resin defining a water vapor barrier. Another of the polymer layers is a layer at least 0.1 mm thick of a polyester resin.

VII.A.1.c. The wall includes an oxygen barrier layer of $SiO_x$ having a thickness of from about 10 to about 500 angstroms.

VII.A.1.c. In an embodiment, illustrated in FIG. 36, the vessel 80 can be a double-walled vessel having an inner wall 408 and an outer wall 410, respectively made of the same or different materials. One particular embodiment of this type can be made with one wall molded from a cyclic olefin copolymer (COC) and the other wall molded from a polyester such as polyethylene terephthalate (PET), with an $SiO_x$ coating as previously described on the interior surface 412. As needed, a tie coating or layer can be inserted between the inner and outer walls to promote adhesion between them. An advantage of this wall construction is that walls having different properties can be combined to form a composite having the respective properties of each wall.

VII.A.1.c. As one example, the inner wall 408 can be made of PET coated on the interior surface 412 with an $SiO_x$ barrier layer, and the outer wall 410 can be made of COC. PET coated with $SiO_x$, as shown elsewhere in this specification, is an excellent oxygen barrier, while COC is an excellent barrier for water vapor, providing a low water vapor transition rate (WVTR). This composite vessel can have superior barrier properties for both oxygen and water vapor. This construction is contemplated, for example, for an evacuated medical sample collection tube that contains an aqueous reagent as manufactured, and has a substantial shelf life, so it should have a barrier preventing transfer of water vapor outward or transfer of oxygen or other gases inward through its composite wall during its shelf life.

VII.A.1.c. As another example, the inner wall 408 can be made of COC coated on the interior surface 412 with an $SiO_x$ barrier layer, and the outer wall 410 can be made of PET. This construction is contemplated, for example, for a prefilled syringe that contains an aqueous sterile fluid as manufactured. The $SiO_x$ barrier will prevent oxygen from entering the syringe through its wall. The COC inner wall will prevent ingress or egress of other materials such as water, thus preventing the water in the aqueous sterile fluid from leaching materials from the wall material into the syringe. The COC inner wall is also contemplated to prevent water derived from the aqueous sterile fluid from passing out of the syringe (thus undesirably concentrating the aqueous sterile fluid), and will prevent non-sterile water or other fluids outside the syringe from entering through the syringe wall and causing the contents to become non-sterile. The COC inner wall is also contemplated to be useful for decreasing the breaking force or friction of the plunger against the inner wall of a syringe.

VII.A.1.d. Method of Making Double Wall Plastic Vessel—COG, PET, $SiO_x$ Layers

VII.A.1.d. Another embodiment is a method of making a vessel having a wall having an interior polymer layer enclosed by an exterior polymer layer, one layer made of COC and the other made of polyester. The vessel is made by a process including introducing COC and polyester resin layers into an injection mold through concentric injection nozzles.

VII.A.1.d. An optional additional step is applying an amorphous carbon coating to the vessel by PECVD, as an inside coating, an outside coating, or as an interlayer coating located between the layers.

VII.A.1.d. An optional additional step is applying an $SiO_x$ barrier layer to the inside of the vessel wall, where $SiO_x$ is defined as before. Another optional additional step is post-treating the $SiO_x$ layer with a process gas consisting essentially of oxygen and essentially free of a volatile silicon compound.

VII.A.1.d. Optionally, the $SiO_x$ coating can be formed at least partially from a silazane feed gas.

VII.A.1.d. The vessel 80 shown in FIG. 36 can be made from the inside out, for one example, by injection molding the inner wall in a first mold cavity, then removing the core and molded inner wall from the first mold cavity to a second, larger mold cavity, then injection molding the outer wall against the inner wall in the second mold cavity. Optionally, a tie layer can be provided to the exterior surface of the molded inner wall before over-molding the outer wall onto the tie layer.

VII.A.1.d. Or, the vessel 80 shown in FIG. 36 can be made from the outside in, for one example, by inserting a first core in the mold cavity, injection molding the outer wall in the mold cavity, then removing the first core from the molded first wall and inserting a second, smaller core, then injection molding the inner wall against the outer wall still residing in the mold cavity. Optionally, a tie layer can be provided to the interior surface of the molded outer wall before over-molding the inner wall onto the tie layer.

VII.A.1.d. Or, the vessel 80 shown in FIG. 36 can be made in a two shot mold. This can be done, for one example, by injection molding material for the inner wall from an inner nozzle and the material for the outer wall from a concentric outer nozzle. Optionally, a tie layer can be provided from a third, concentric nozzle disposed between the inner and outer nozzles. The nozzles can feed the respective wall materials simultaneously. One useful expedient is to begin feeding the outer wall material through the outer nozzle slightly before feeding the inner wall material through the inner nozzle. If there is an intermediate concentric nozzle, the order of flow can begin with the outer nozzle and continue in sequence from the intermediate nozzle and then from the inner nozzle. Or, the order of beginning feeding can start from the inside nozzle and work outward, in reverse order compared to the preceding description.

VII.A.1.e. Barrier Coating Made of Glass

VII.A.1.e. Another embodiment is a vessel including a vessel, a barrier coating, and a closure. The vessel is generally tubular and made of thermoplastic material. The vessel has a mouth and a lumen bounded at least in part by a wall having an inner surface interfacing with the lumen. There is an at least essentially continuous barrier coating made of glass on the inner surface of the wall. A closure covers the mouth and isolates the lumen of the vessel from ambient air.

VII.A.1.e. The vessel 80 can also be made, for example of glass of any type used in medical or laboratory applications, such as soda-lime glass, borosilicate glass, or other glass formulations. Other vessels having any shape or size, made of any material, are also contemplated for use in the system 20. One function of coating a glass vessel can be to reduce the ingress of ions in the glass, either intentionally or as impurities, for example sodium, calcium, or others, from the glass to the contents of the vessel, such as a reagent or blood in an evacuated blood collection tube. Another function of coating a glass vessel in whole or in part, such as selectively at surfaces contacted in sliding relation to other parts, is to provide lubricity to the coating, for example to ease the insertion or removal of a stopper or passage of a sliding element such as a piston in a syringe. Still another reason to coat a glass vessel is to prevent a reagent or intended sample for the vessel, such as blood, from sticking to the wall of the vessel or an increase in the rate of coagulation of the blood in contact with the wall of the vessel.

VII.A.1.e.i. A related embodiment is a vessel as described in the previous paragraph, in which the barrier coating is made of soda lime glass, borosilicate glass, or another type of glass.

VII.A.2. Stoppers

Figure 23:
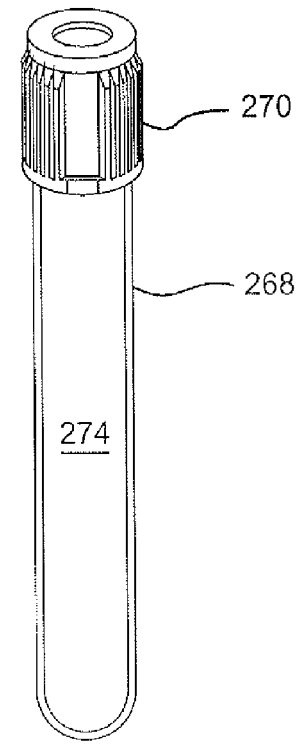
FIG. 23 is a perspective view of a blood collection tube assembly having a closure according to still another embodiment of the invention.
Figure 24:
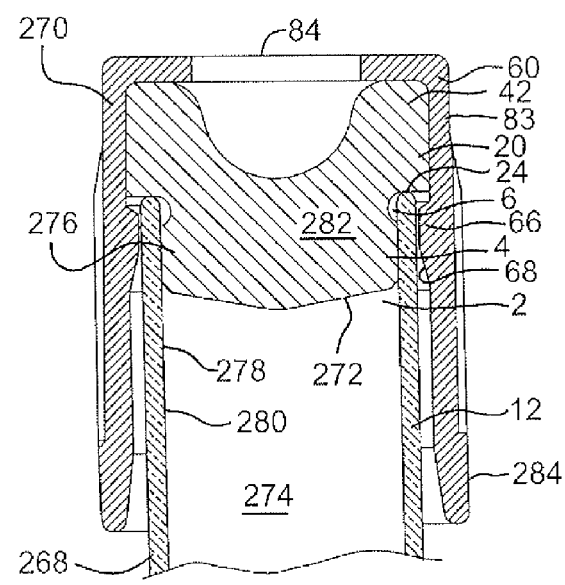
FIG. 24 is a fragmentary section of the blood collection tube and closure assembly of FIG. 23.
Figure 25:
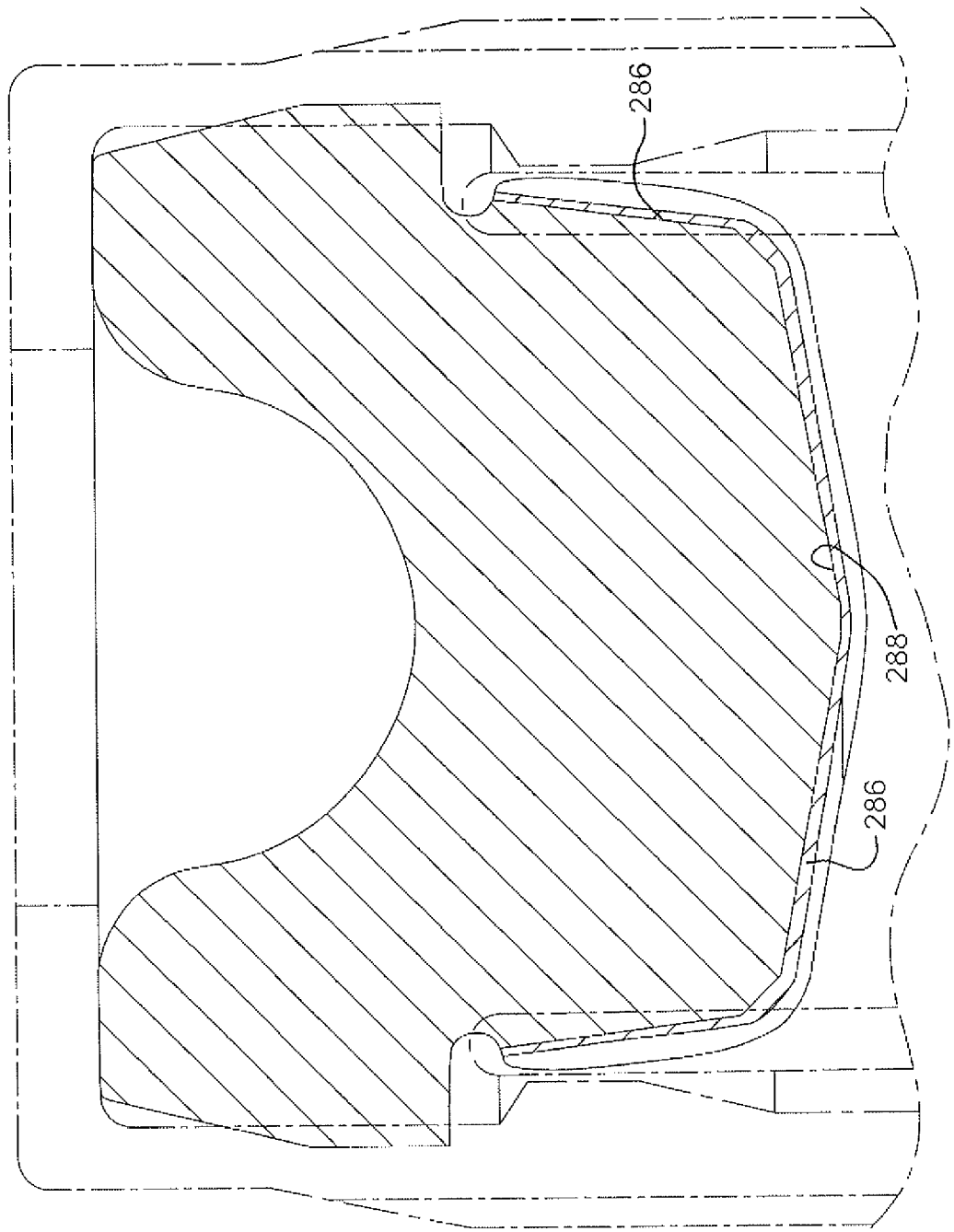
FIG. 25 is an isolated section of an elastomeric insert of the closure of FIGS. 23 and 24.

VII.A.2. FIGS. 23-25 illustrate a vessel 268, which can be an evacuated blood collection tube, having a closure 270 to isolate the lumen 274 from the ambient environment. The closure 270 comprises a interior-facing surface 272 exposed to the lumen 274 of the vessel 268 and a wall-contacting surface 276 that is in contact with the inner surface 278 of the vessel wall 280. In the illustrated embodiment the closure 270 is an assembly of a stopper 282 and a shield 284.

VII.A.2.a. Method of Applying Lubricity Layer to Stopper in Vacuum Chamber

VII.A.2.a. Another embodiment is a method of applying a coating on an elastomeric stopper such as 282. The stopper 282, separate from the vessel 268, is placed in a substantially evacuated chamber. A reaction mixture is provided including plasma forming gas, i.e. an organosilicon compound gas, optionally an oxidizing gas, and optionally a hydrocarbon gas. Plasma is formed in the reaction mixture, which is contacted with the stopper. A lubricity and/or hydrophobic layer, characterized as defined in the Definition Section, is deposited on at least a portion of the stopper.

VII.A.2.a. In the illustrated embodiment, the wall-contacting surface 276 of the closure 270 is coated with a lubricity layer 286.

VII.A.2.a. In some embodiments, the lubricity and/or hydrophobic layer, characterized as defined in the Definition Section, is effective to reduce the transmission of one or more constituents of the stopper, such as a metal ion constituent of the stopper, or of the vessel wall, into the vessel lumen. Certain elastomeric compositions of the type useful for fabricating a stopper 282 contain trace amounts of one or more metal ions. These ions sometimes should not be able to migrate into the lumen 274 or come in substantial quantities into contact with the vessel contents, particularly if the sample vessel 268 is to be used to collect a sample for trace metal analysis. It is contemplated for example that coatings containing relatively little organic content, i.e. where y and z of $Si_wO_xC_yH_z$ as defined in the Definition Section are low or zero, are particularly useful as a metal ion barrier in this application. Regarding silica as a metal ion barrier see, for example, Anupama Mallikarjunan, Jasbir Juneja, Guangrong Yang, Shyam P. Murarka, and Toh-Ming Lu, The Effect of Interfacial Chemistry on Metal Ion Penetration into Polymeric Films, Mat. Res. Soc. Symp. Proc., Vol. 734, pp. B9.60.1 to B9.60.6 (Materials Research Society, 2003); U.S. Pat. Nos. 5,578,103 and 6,200,658, and European Appl. EP0697378 A2, which are all incorporated here by reference. It is contemplated, however, that some organic content can be useful to provide a more elastic coating and to adhere the coating to the elastomeric surface of the stopper 282.

VII.A.2.a. In some embodiments, the lubricity and/or hydrophobic layer, characterized as defined in the Definition Section, can be a composite of material having first and second layers, in which the first or inner layer 288 interfaces with the elastomeric stopper 282 and is effective to reduce the transmission of one or more constituents of the stopper 282 into the vessel lumen. The second layer 286 can interface with the inner wall 280 of the vessel and is effective as a lubricity layer to reduce friction between the stopper 282 and the inner wall 280 of the vessel when the stopper 282 is seated on or in the vessel 268. Such composites are described in connection with syringe coatings elsewhere in this specification.

VII.A.2.a. Or, the first and second layers 288 and 286 are defined by a coating of graduated properties, in which the values of y and z defined in the Definition Section are greater in the first layer than in the second layer.

VII.A.2.a. The lubricity and/or hydrophobic layer can be applied, for example, by PECVD substantially as previously described. The lubricity and/or hydrophobic layer can be, for example, between 0.5 and 5000 nm (5 to 50,000 Angstroms) thick, or between 1 and 5000 nm thick, or between 5 and 5000 nm thick, or between 10 and 5000 nm thick, or between 20 and 5000 nm thick, or between 50 and 5000 nm thick, or between 100 and 5000 nm thick, or between 200 and 5000 nm thick, or between 500 and 5000 nm thick, or between 1000 and 5000 nm thick, or between 2000 and 5000 nm thick, or between 3000 and 5000 nm thick, or between 4000 and 10,000 nm thick.

VII.A.2.a. Certain advantages are contemplated for plasma coated lubricity layers, versus the much thicker (one micron or greater) conventional spray applied silicone lubricants. Plasma coatings have a much lower migratory potential to move into blood versus sprayed or micron-coated silicones, both because the amount of plasma coated material is much less and because it can be more intimately applied to the coated surface and better bonded in place.

VII.A.2.a. Nanocoatings, as applied by PECVD, are contemplated to offer lower resistance to sliding of an adjacent surface or flow of an adjacent fluid than micron coatings, as the plasma coating tends to provide a smoother surface.

VII.A.2.a. Still another embodiment is a method of applying a coating of a lubricity and/or hydrophobic layer on an elastomeric stopper. The stopper can be used, for example, to close the vessel previously described. The method includes several parts. A stopper is placed in a substantially evacuated chamber. A reaction mixture is provided comprising plasma forming gas, i.e. an organosilicon compound gas, optionally an oxidizing gas, and optionally a hydrocarbon gas. Plasma is formed in the reaction mixture. The stopper is contacted with the reaction mixture, depositing the coating of a lubricity and/or hydrophobic layer on at least a portion of the stopper.

VII.A.2.a. In practicing this method, to obtain higher values of y and z as defined in the Definition Section, it is contemplated that the reaction mixture can comprise a hydrocarbon gas, as further described above and below. Optionally, the reaction mixture can contain oxygen, if lower values of y and z or higher values of x are contemplated. Or, particularly to reduce oxidation and increase the values of y and z, the reaction mixture can be essentially free of an oxidizing gas.

VII.A.2.a. In practicing this method to coat certain embodiments of the stopper such as the stopper 282, it is contemplated to be unnecessary to project the reaction mixture into the concavities of the stopper. For example, the wall-contacting and interior facing surfaces 276 and 272 of the stopper 282 are essentially convex, and thus readily treated by a batch process in which a multiplicity of stoppers such as 282 can be located and treated in a single substantially evacuated reaction chamber. It is further contemplated that in some embodiments the coatings 286 and 288 do not need to present as formidable a barrier to oxygen or water as the barrier coating on the interior surface 280 of the vessel 268, as the material of the stopper 282 can serve this function to a large degree.

VII.A.2.a. Many variations of the stopper and the stopper coating process are contemplated. The stopper 282 can be contacted with the plasma. Or, the plasma can be formed upstream of the stopper 282, producing plasma product, and the plasma product can be contacted with the stopper 282. The plasma can be formed by exciting the reaction mixture with electromagnetic energy and/or microwave energy.

VII.A.2.a. Variations of the reaction mixture are contemplated. The plasma forming gas can include an inert gas. The inert gas can be, for example, argon or helium, or other gases described in this disclosure. The organosilicon compound gas can be, or include, HMDSO, OMCTS, any of the other organosilicon compounds mentioned in this disclosure, or a combination of two or more of these. The oxidizing gas can be oxygen or the other gases mentioned in this disclosure, or a combination of two or more of these. The hydrocarbon gas can be, for example, methane, methanol, ethane, ethylene, ethanol, propane, propylene, propanol, acetylene, or a combination of two or more of these.

VII.A.2.b. Applying by PECVD a Coating of Group III or IV Element and Carbon on a Stopper VII.A.2.b. Another embodiment is a method of applying a coating of a composition including carbon and one or more elements of Groups III or IV on an elastomeric stopper. To carry out the method, a stopper is located in a deposition chamber.

VII.A.2.b. A reaction mixture is provided in the deposition chamber, including a plasma forming gas with a gaseous source of a Group III element, a Group IV element, or a combination of two or more of these. The reaction mixture optionally contains an oxidizing gas and optionally contains a gaseous compound having one or more C—H bonds. Plasma is formed in the reaction mixture, and the stopper is contacted with the reaction mixture. A coating of a Group III element or compound, a Group IV element or compound, or a combination of two or more of these is deposited on at least a portion of the stopper.

VII.A.3. Stoppered Plastic Vessel Having Barrier Coating Effective to Provide 95% Vacuum Retention for 24 Months VII.A.3. Another embodiment is a vessel including a vessel, a barrier coating, and a closure. The vessel is generally tubular and made of thermoplastic material. The vessel has a mouth and a lumen bounded at least in part by a wall. The wall has an inner surface interfacing with the lumen. An at least essentially continuous barrier coating is applied on the inner surface of the wall. The barrier coating is effective to provide a substantial shelf life. A closure is provided covering the mouth of the vessel and isolating the lumen of the vessel from ambient air.

VII.A.3. Referring to FIGS. 23-25, a vessel 268 such as an evacuated blood collection tube or other vessel is shown.

VII.A.3. The vessel is, in this embodiment, a generally tubular vessel having an at least essentially continuous barrier coating and a closure. The vessel is made of thermoplastic material having a mouth and a lumen bounded at least in part by a wall having an inner surface interfacing with the lumen. The barrier coating is deposited on the inner surface of the wall, and is effective to maintain at least 95%, or at least 90%, of the initial vacuum level of the vessel for a shelf life of at least 24 months, optionally at least 30 months, optionally at least 36 months. The closure covers the mouth of the vessel and isolates the lumen of the vessel from ambient air.

VII.A.3. The closure, for example the closure 270 illustrated in the Figures or another type of closure, is provided to maintain a partial vacuum and/or to contain a sample and limit or prevent its exposure to oxygen or contaminants. FIGS. 23-25 are based on figures found in U.S. Pat. No. 6,602,206, but the present discovery is not limited to that or any other particular type of closure.

VII.A.3. The closure 270 comprises a interior-facing surface 272 exposed to the lumen 274 of the vessel 268 and a wall-contacting surface 276 that is in contact with the inner surface 278 of the vessel wall 280. In the illustrated embodiment the closure 270 is an assembly of a stopper 282 and a shield 284.

VII.A.3. In the illustrated embodiment, the stopper 282 defines the wall-contacting surface 276 and the inner surface 278, while the shield is largely or entirely outside the stoppered vessel 268, retains and provides a grip for the stopper 282, and shields a person removing the closure 270 from being exposed to any contents expelled from the vessel 268, such as due to a pressure difference inside and outside of the vessel 268 when the vessel 268 is opened and air rushes in or out to equalize the pressure difference.

VII.A.3. It is further contemplated that the coatings on the vessel wall 280 and the wall contacting surface 276 of the stopper can be coordinated. The stopper can be coated with a lubricity silicone layer, and the vessel wall 280, made for example of PET or glass, can be coated with a harder $SiO_x$ layer, or with an underlying $SiO_x$ layer and a lubricity overcoat.

VII.B. Syringes

VII.B. The foregoing description has largely addressed applying a barrier coating to a tube with one permanently closed end, such as a blood collection tube or, more generally, a specimen receiving tube 80. The apparatus is not limited to such a device.

VII.B. Another example of a suitable vessel, shown in FIGS. 20-22, is a syringe barrel 250 for a medical syringe 252. Such syringes 252 are sometimes supplied prefilled with saline solution, a pharmaceutical preparation, or the like for use in medical techniques. Pre-filled syringes 252 are also contemplated to benefit from an $SiO_x$ barrier or other type of coating on the interior surface 254 to keep the contents of the prefilled syringe 252 out of contact with the plastic of the syringe, for example of the syringe barrel 250 during storage. The barrier or other type of coating can be used to avoid leaching components of the plastic into the contents of the barrel through the interior surface 254.

VII.B. A syringe barrel 250 as molded commonly can be open at both the back end 256, to receive a plunger 258, and at the front end 260, to receive a hypodermic needle, a nozzle, or tubing for dispensing the contents of the syringe 252 or for receiving material into the syringe 252. But the front end 260 can optionally be capped and the plunger 258 optionally can be fitted in place before the prefilled syringe 252 is used, closing the barrel 250 at both ends. A cap 262 can be installed either for the purpose of processing the syringe barrel 250 or assembled syringe, or to remain in place during storage of the prefilled syringe 252, up to the time the cap 262 is removed and (optionally) a hypodermic needle or other delivery conduit is fitted on the front end 260 to prepare the syringe 252 for use.

VII.B.1. Assemblies

VII.B.1. FIG. 42 also shows an alternative syringe barrel construction usable, for example, with the embodiments of FIGS. 21, 26, 28, 30, and 34 and adapted for use with the vessel holder 450 of that Figure.

Figure 50:
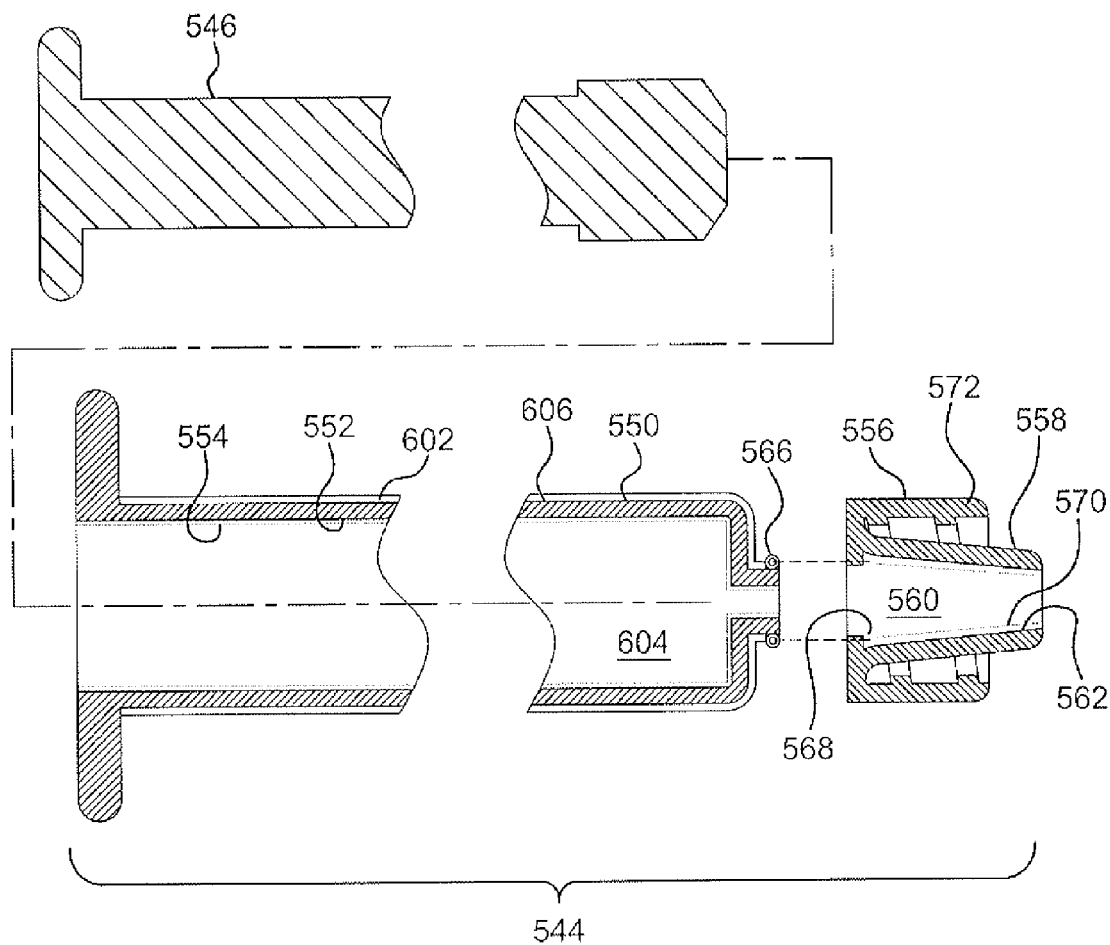
FIG. 50 is an exploded view of a two-piece syringe barrel and Luer lock fitting. The syringe barrel is usable with the vessel treatment and inspection apparatus of FIGS. 1-22, 26-28, 33-35, 37-39, 44, and 53-54.
Figure 51:
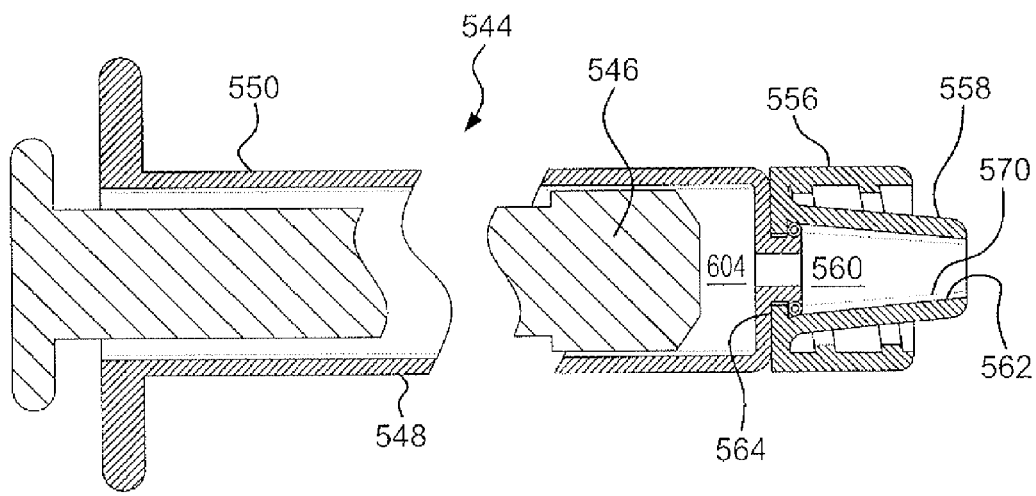
FIG. 51 is an assembled view of the two-piece syringe barrel and Luer lock fitting of FIG. 50.

VII.B.1. FIG. 50 is an exploded view and FIG. 51 is an assembled view of a syringe. The syringe barrel can be processed with the vessel treatment and inspection apparatus of FIGS. 1-22, 26-28, 33-35, 37-39, 44, and 53-54.

VII.B.1. The installation of a cap 262 makes the barrel 250 a closed-end vessel that can be provided with an $SiO_x$ barrier or other type of coating on its interior surface 254 in the previously illustrated apparatus, optionally also providing a coating on the interior 264 of the cap and bridging the interface between the cap interior 264 and the barrel front end 260. Suitable apparatus adapted for this use is shown, for example, in FIG. 21, which is analogous to FIG. 2 except for the substitution of the capped syringe barrel 250 for the vessel 80 of FIG. 2. VII.B.

Figure 52:
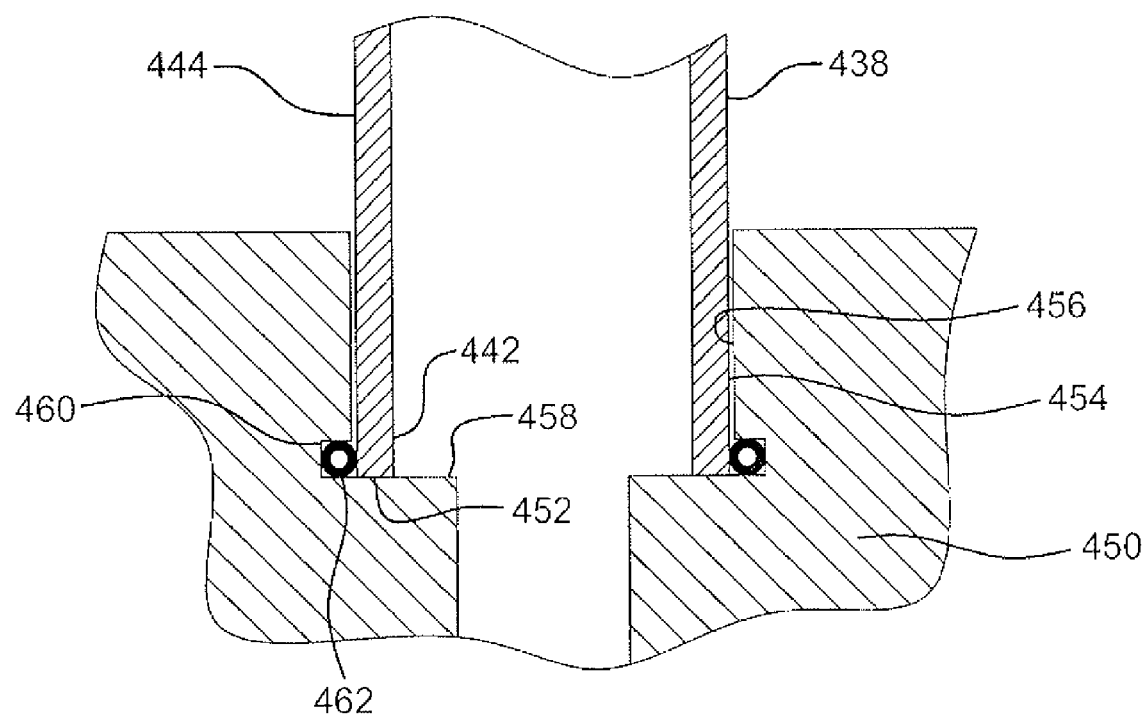
FIG. 52 is a view similar to FIG. 42 showing a syringe barrel being treated that has no flange or finger stops 440. The syringe barrel is usable with the vessel treatment and inspection apparatus of FIGS. 1-19, 27, 33, 35, 44-51, and 53-54.
Figure 53:
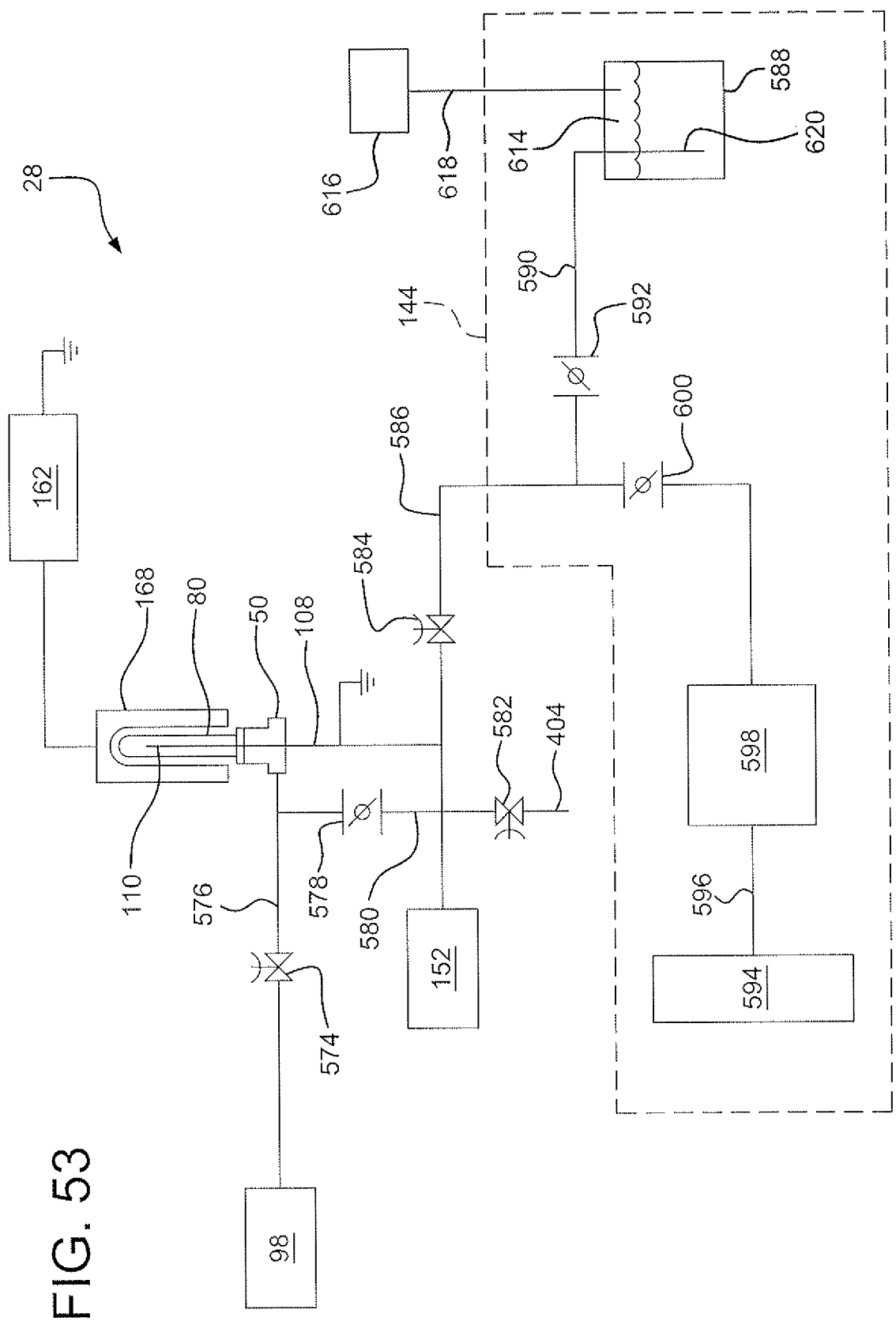
FIG. 53 is a schematic view of an assembly for treating vessels. The assembly is usable with the apparatus of FIGS. 1-3, 8-9, 12-16, 18-22, 26-28, 33-35, and 37-49.
Figure 54:
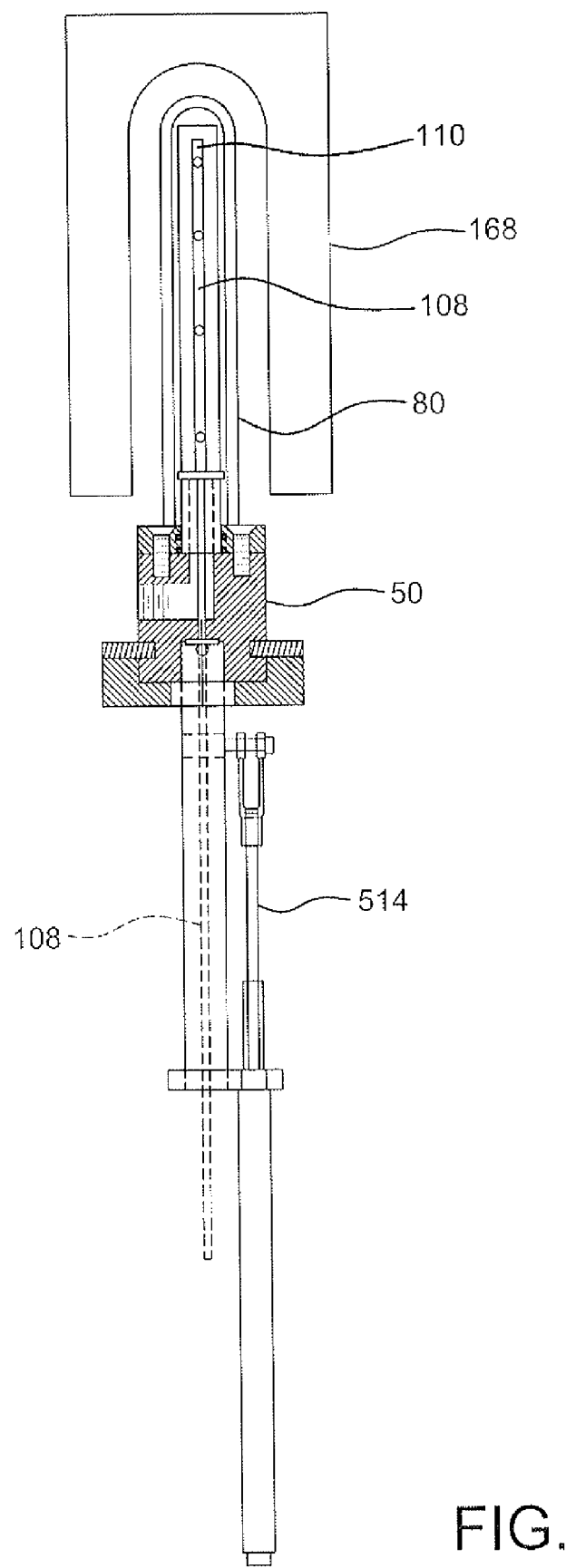
FIG. 54 is a diagrammatic view of the embodiment of FIG. 53.

VII.B.1 FIG. 52 is a view similar to FIG. 42, but showing a syringe barrel being treated that has no flange or finger stops 440. The syringe barrel is usable with the vessel treatment and inspection apparatus of FIGS. 1-19, 27, 33, 35, 44-51, and 53-54.

VII.B.1.a. Syringe Having Barrel Coated with Lubricity Layer Deposited from an Organosilicon Precursor VII.B.1.a. Still another embodiment is a vessel having a lubricity layer, characterized as defined in the Definition Section, of the type made by the following process.

VII.B.1.a. A precursor is provided as defined above.

VII.B.1.a. The precursor is applied to a substrate under conditions effective to form a coating. The coating is polymerized or crosslinked, or both, to form a lubricated surface having a lower plunger sliding force or breakout force than the untreated substrate.

VII.B.1.a. Respecting any of the Embodiments VII and sub-parts, optionally the applying step is carried out by vaporizing the precursor and providing it in the vicinity of the substrate.

VII.B.1.a. Respecting any of the Embodiments VII.A.1.a.i, optionally a plasma, optionally a non-hollow-cathode plasma, is formed in the vicinity of the substrate. Optionally, the precursor is provided in the substantial absence of oxygen. Optionally, the precursor is provided in the substantial absence of a carrier gas. Optionally, the precursor is provided in the substantial absence of nitrogen. Optionally, the precursor is provided at less than 1 Torr absolute pressure. Optionally, the precursor is provided to the vicinity of a plasma emission. Optionally, the precursor its reaction product is applied to the substrate at a thickness of 1 to 5000 nm thick, or 10 to 1000 nm thick, or 10-200 nm thick, or 20 to 100 nm thick. Optionally, the substrate comprises glass. Optionally, the substrate comprises a polymer, optionally a polycarbonate polymer, optionally an olefin polymer, optionally a cyclic olefin copolymer, optionally a polypropylene polymer, optionally a polyester polymer, optionally a polyethylene terephthalate polymer.

VII.B.1.a. Optionally, the plasma is generated by energizing the gaseous reactant containing the precursor with electrodes powered, for example, at a RF frequency as defined above, for example a frequency of from 10 kHz to less than 300 MHz, optionally from 1 to 50 MHz, even optionally from 10 to 15 MHz, optionally a frequency of 13.56 MHz.

VII.B.1.a. Optionally, the plasma is generated by energizing the gaseous reactant containing the precursor with electrodes supplied with an electric power of from 0.1 to 25 W, optionally from 1 to 22 W, optionally from 3 to 17 W, even optionally from 5 to 14 W, optionally from 7 to 11 W, optionally 8 W. The ratio of the electrode power to the plasma volume can be less than 10 W/ml, optionally is from 5 W/ml to 0.1 W/ml, optionally is from 4 W/ml to 0.1 W/ml, optionally from 2 W/ml to 0.2 W/ml. These power levels are suitable for applying lubricity layers to syringes and sample tubes and vessels of similar geometry having a void volume of 1 to 3 mL in which PECVD plasma is generated. It is contemplated that for larger or smaller objects the power applied should be increased or reduced accordingly to scale the process to the size of the substrate.

VII.B.1.a. Another embodiment is a lubricity layer, characterized as defined in the Definition Section, on the inner wall of a syringe barrel. The coating is produced from a PECVD process using the following materials and conditions. A cyclic precursor is optionally employed, selected from a monocyclic siloxane, a polycyclic siloxane, or a combination of two or more of these, as defined elsewhere in this specification for lubricity layers. One example of a suitable cyclic precursor comprises octamethylcyclotetrasiloxane (OMCTS), optionally mixed with other precursor materials in any proportion. Optionally, the cyclic precursor consists essentially of octamethycyclotetrasiloxane (OMCTS), meaning that other precursors can be present in amounts which do not change the basic and novel properties of the resulting lubricity layer, i.e. its reduction of the plunger sliding force or breakout force of the coated surface.

VII.B.1.a. At least essentially no oxygen. as defined in the Definition Section is added to the process.

VII.B.1.a. A sufficient plasma generation power input, for example any power level successfully used in one or more working examples of this specification or described in the specification, is provided to induce coating formation.

VII.B.1.a. The materials and conditions employed are effective to reduce the syringe plunger sliding force or breakout force moving through the syringe barrel at least 25 percent, alternatively at least 45 percent, alternatively at least 60 percent, alternatively greater than 60 percent, relative to an uncoated syringe barrel. Ranges of plunger sliding force or breakout force reduction of from 20 to 95 percent, alternatively from 30 to 80 percent, alternatively from 40 to 75 percent, alternatively from 60 to 70 percent, are contemplated.

VII.B.1.a. Another embodiment is a vessel having a hydrophobic layer, characterized as defined in the Definition Section, on the inside wall. The coating is made as explained for the lubricant coating of similar composition, but under conditions effective to form a hydrophobic surface having a higher contact angle than the untreated substrate.

VII.B.1.a. Respecting any of the Embodiments VII.A.1.a.ii, optionally the substrate comprises glass or a polymer. The glass optionally is borosilicate glass. The polymer is optionally a polycarbonate polymer, optionally an olefin polymer, optionally a cyclic olefin copolymer, optionally a polypropylene polymer, optionally a polyester polymer, optionally a polyethylene terephthalate polymer.

VII.B.1.a. Another embodiment is a syringe including a plunger, a syringe barrel, and a lubricity layer, characterized as defined in the Definition Section. The syringe barrel includes an interior surface receiving the plunger for sliding. The lubricity layer is disposed on the interior surface of the syringe barrel. The lubricity layer is less than 1000 nm thick and effective to reduce the breakout force or the plunger sliding force necessary to move the plunger within the barrel. Reducing the plunger sliding force is alternatively expressed as reducing the coefficient of sliding friction of the plunger within the barrel or reducing the plunger force; these terms are regarded as having the same meaning in this specification.

VII.B.1.a. The syringe 544 of FIGS. 50-51 comprises a plunger 546 and a syringe barrel 548. The syringe barrel 548 has an interior surface 552 receiving the plunger for sliding 546. The interior surface 552 of the syringe barrel 548 further comprises a lubricity layer 554, characterized as defined in the Definition Section. The lubricity layer is less than 1000 nm thick, optionally less than 500 nm thick, optionally less than 200 nm thick, optionally less than 100 nm thick, optionally less than 50 nm thick, and is effective to reduce the breakout force necessary to overcome adhesion of the plunger after storage or the plunger sliding force necessary to move the plunger within the barrel after it has broken away. The lubricity layer is characterized by having a plunger sliding force or breakout force lower than that of the uncoated surface.

VII.B.1.a. Any of the above precursors of any type can be used alone or in combinations of two or more of them to provide a lubricity layer.

VII.B.1.a. In addition to utilizing vacuum processes, low temperature atmospheric (non-vacuum) plasma processes can also be utilized to induce molecular ionization and deposition through precursor monomer vapor delivery optionally in a non-oxidizing atmosphere such as helium or argon. Separately, thermal CVD can be considered via flash thermolysis deposition.

VII.B.1.a. The approaches above are similar to vacuum PECVD in that the surface coating and crosslinking mechanisms can occur simultaneously.

VII.B.1.a. Yet another expedient contemplated for any coating or coatings described here is a coating that is not uniformly applied over the entire interior 88 of a vessel. For example, a different or additional coating can be applied selectively to the cylindrical portion of the vessel interior, compared to the hemispherical portion of the vessel interior at its closed end 84, or vice versa. This expedient is particularly contemplated for a syringe barrel or a sample collection tube as described below, in which a lubricity layer might be provided on part or all of the cylindrical portion of the barrel, where the plunger or piston or closure slides, and not elsewhere.

VII.B.1.a. Optionally, the precursor can be provided in the presence, substantial absence, or absence of oxygen, in the presence, substantial absence, or absence of nitrogen, or in the presence, substantial absence, or absence of a carrier gas. In one contemplated embodiment, the precursor alone is delivered to the substrate and subjected to PECVD to apply and cure the coating.

VII.B.1.a. Optionally, the precursor can be provided at less than 1 Torr absolute pressure.

VII.B.1.a. Optionally, the precursor can be provided to the vicinity of a plasma emission.

VII.B.1.a. Optionally, the precursor its reaction product can be applied to the substrate at a thickness of 1 to 5000 nm, or 10 to 1000 nm., or 10-200 nm, or 20 to 100 nm.

VII.B.1.a. In any of the above embodiments, the substrate can comprise glass, or a polymer, for example one or more of a polycarbonate polymer, an olefin polymer (for example a cyclic olefin copolymer or a polypropylene polymer), or a polyester polymer (for example, a polyethylene terephthalate polymer).

VII.B.1.a. In any of the above embodiments, the plasma is generated by energizing the gaseous reactant containing the precursor with electrodes powered at a RF frequency as defined in this description.

VII.B.1.a. In any of the above embodiments, the plasma is generated by energizing the gaseous reactant containing the precursor with electrodes supplied with sufficient electric power to generate a lubricity layer. Optionally, the plasma is generated by energizing the gaseous reactant containing the precursor with electrodes supplied with an electric power of from 0.1 to 25 W, optionally from 1 to 22 W, optionally from 3 to 17 W, even optionally from 5 to 14 W, optionally from 7 to 11 W, optionally 8 W. The ratio of the electrode power to the plasma volume can be less than 10 W/ml, optionally is from 5 W/ml to 0.1 W/ml, optionally is from 4 W/ml to 0.1 W/ml, optionally from 2 W/ml to 0.2 W/ml. These power levels are suitable for applying lubricity layers to syringes and sample tubes and vessels of similar geometry having a void volume of 1 to 3 mL in which PECVD plasma is generated. It is contemplated that for larger or smaller objects the power applied should be increased or reduced accordingly to scale the process to the size of the substrate.

VII.B.1.a. The coating can be cured, as by polymerizing or crosslinking the coating, or both, to form a lubricated surface having a lower plunger sliding force or breakout force than the untreated substrate. Curing can occur during the application process such as PECVD, or can be carried out or at least completed by separate processing.

VII.B.1.a. Although plasma deposition has been used herein to demonstrate the coating characteristics, alternate deposition methods can be used as long as the chemical composition of the starting material is preserved as much as possible while still depositing a solid film that is adhered to the base substrate.

VII.B.1.a. For example, the coating material can be applied onto the syringe barrel (from the liquid state) by spraying the coating or dipping the substrate into the coating, where the coating is either the neat precursor a solvent-diluted precursor (allowing the mechanical deposition of a thinner coating). The coating optionally can be crosslinked using thermal energy, UV energy, electron beam energy, plasma energy, or any combination of these.

VII.B.1.a. Application of a silicone precursor as described above onto a surface followed by a separate curing step is also contemplated. The conditions of application and curing can be analogous to those used for the atmospheric plasma curing of pre-coated polyfluoroalkyl ethers, a process practiced under the trademark TriboGlide®. More details of this process can be found at http://www.triboglide.com/process.htm.

VII.B.1.a. In such a process, the area of the part to be coated can optionally be pre-treated with an atmospheric plasma. This pretreatment cleans and activates the surface so that it is receptive to the lubricant that is sprayed in the next step.

VII.B.1.a. The lubrication fluid, in this case one of the above precursors or a polymerized precursor, is then sprayed on to the surface to be treated. For example, IVEK precision dispensing technology can be used to accurately atomize the fluid and create a uniform coating.

VII.B.1.a. The coating is then bonded or crosslinked to the part, again using an atmospheric plasma field. This both immobilizes the coating and improves the lubricant's performance.

VII.B.1.a. Optionally, the atmospheric plasma can be generated from ambient air in the vessel, in which case no gas feed and no vacuum drawing equipment is needed. Optionally, however, the vessel is at least substantially closed while plasma is generated, to minimize the power requirement and prevent contact of the plasma with surfaces or materials outside the vessel.

VII.B.1.a.i. Lubricity Layer: $SiO_x$ Barrier, Lubricity Layer, Surface Treatment Surface Treatment VII.B.1.a.i. Another embodiment is a syringe comprising a barrel defining a lumen and having an interior surface slidably receiving a plunger, i.e. receiving a plunger for sliding contact to the interior surface.

VII.B.1.a.i. The syringe barrel is made of thermoplastic base material.

VII.B.1.a.i. Optionally, the interior surface of the barrel is coated with an $SiO_x$ barrier layer as described elsewhere in this specification.

VII.B.1.a.i. A lubricity layer is applied to the barrel interior surface, the plunger, or both, or to the previously applied $SiO_x$ barrier layer. The lubricity layer can be provided, applied, and cured as set out in embodiment VII.B.1.a or elsewhere in this specification.

VII.B.1.a.i. For example, the lubricity layer can be applied, in any embodiment, by PECVD. The lubricity layer is deposited from an organosilicon precursor, and is less than 1000 nm thick.

VII.B.1.a.i. A surface treatment is carried out on the lubricity layer in an amount effective to reduce the leaching or extractables of the lubricity layer, the thermoplastic base material, or both. The treated surface can thus act as a solute retainer. This surface treatment can result in a skin coating, e.g. a skin coating which is at least 1 nm thick and less than 100 nm thick, or less than 50 nm thick, or less than 40 nm thick, or less than 30 nm thick, or less than 20 nm thick, or less than 10 nm thick, or less than 5 nm thick, or less than 3 nm thick, or less than 2 nm thick, or less than 1 nm thick, or less than 0.5 nm thick.

VII.B.1.a.i. As used herein, "leaching" refers to material transferred out of a substrate, such as a vessel wall, into the contents of a vessel, for example a syringe. Commonly, leachables are measured by storing the vessel filled with intended contents, then analyzing the contents to determine what material leached from the vessel wall into the intended contents. "Extraction" refers to material removed from a substrate by introducing a solvent or dispersion medium other than the intended contents of the vessel, to determine what material can be removed from the substrate into the extraction medium under the conditions of the test.

VII.B.1.a.i. The surface treatment resulting in a solute retainer optionally can be a $SiO_x$ layer as previously defined in this specification or a hydrophobic layer, characterized as defined in the Definition Section. In one embodiment, the surface treatment can be applied by PECVD deposit of $SiO_x$ or a hydrophobic layer. Optionally, the surface treatment can be applied using higher power or stronger oxidation conditions than used for creating the lubricity layer, or both, thus providing a harder, thinner, continuous solute retainer 539. Surface treatment can be less than 100 nm deep, optionally less than 50 nm deep, optionally less than 40 nm deep, optionally less than 30 nm deep, optionally less than 20 nm deep, optionally less than 10 nm deep, optionally less than 5 nm deep, optionally less than 3 nm deep, optionally less than 1 nm deep, optionally less than 0.5 nm deep, optionally between 0.1 and 50 nm deep in the lubricity layer.

VII.B.1.a.i. The solute retainer is contemplated to provide low solute leaching performance to the underlying lubricity and other layers, including the substrate, as required. This retainer would only need to be a solute retainer to large solute molecules and oligomers (for example siloxane monomers such as HMDSO, OMCTS, their fragments and mobile oligomers derived from lubricants, for example a "leachables retainer") and not a gas ($O_2/N_2/CO_2$/water vapor) barrier layer. A solute retainer can, however, also be a gas barrier (e.g. the SiOx coating according to present invention. One can create a good leachable retainer without gas barrier performance, either by vacuum or atmospheric-based PECVD processes. It is desirable that the "leachables barrier" will be sufficiently thin that, upon syringe plunger movement, the plunger will readily penetrate the "solute retainer" exposing the sliding plunger nipple to the lubricity layer immediately below to form a lubricated surface having a lower plunger sliding force or breakout force than the untreated substrate.

VII.B.1.a.i. In another embodiment, the surface treatment can be performed by oxidizing the surface of a previously applied lubricity layer, as by exposing the surface to oxygen in a plasma environment. The plasma environment described in this specification for forming $SiO_x$ coatings can be used. Or, atmospheric plasma conditions can be employed in an oxygen-rich environment.

VII.B.1.a.i. The lubricity layer and solute retainer, however formed, optionally can be cured at the same time. In another embodiment, the lubricity layer can be at least partially cured, optionally fully cured, after which the surface treatment can be provided, applied, and the solute retainer can be cured.

VII.B.1.a.i. The lubricity layer and solute retainer are composed, and present in relative amounts, effective to provide a breakout force, plunger sliding force, or both that is less than the corresponding force required in the absence of the lubricity layer and surface treatment. In other words, the thickness and composition of the solute retainer are such as to reduce the leaching of material from the lubricity layer into the contents of the syringe, while allowing the underlying lubricity layer to lubricate the plunger. It is contemplated that the solute retainer will break away easily and be thin enough that the lubricity layer will still function to lubricate the plunger when it is moved.

VII.B.1.a.i. In one contemplated embodiment, the lubricity and surface treatments can be applied on the barrel interior surface. In another contemplated embodiment, the lubricity and surface treatments can be applied on the plunger. In still another contemplated embodiment, the lubricity and surface treatments can be applied both on the barrel interior surface and on the plunger. In any of these embodiments, the optional $SiO_x$ barrier layer on the interior of the syringe barrel can either be present or absent.

VII.B.1.a.i. One embodiment contemplated is a plural-layer, e.g. a 3-layer, configuration applied to the inside surface of a syringe barrel. Layer 1 can be an $SiO_x$ gas barrier made by PECVD of HMDSO, OMCTS, or both, in an oxidizing atmosphere. Such an atmosphere can be provided, for example, by feeding HMDSO and oxygen gas to a PECVD coating apparatus as described in this specification. Layer 2 can be a lubricity layer using OMCTS applied in a non-oxidizing atmosphere. Such a non-oxidizing atmosphere can be provided, for example, by feeding OMCTS to a PECVD coating apparatus as described in this specification, optionally in the substantial or complete absence of oxygen. A subsequent solute retainer can be formed by a treatment forming a thin skin layer of $SiO_x$ or a hydrophobic layer as a solute retainer using higher power and oxygen using OMCTS and/or HMDSO.

VII.B.1.a.i. Certain of these plural-layer coatings are contemplated to have one or more of the following optional advantages, at least to some degree. They can address the reported difficulty of handling silicone, since the solute retainer can confine the interior silicone and prevent if from migrating into the contents of the syringe or elsewhere, resulting in fewer silicone particles in the deliverable contents of the syringe and less opportunity for interaction between the lubricity layer and the contents of the syringe. They can also address the issue of migration of the lubricity layer away from the point of lubrication, improving the lubricity of the interface between the syringe barrel and the plunger. For example, the break-free force can be reduced and the drag on the moving plunger can be reduced, or optionally both.

VII.B.1.a.i. It is contemplated that when the solute retainer is broken, the solute retainer will continue to adhere to the lubricity layer and the syringe barrel, which can inhibit any particles from being entrained in the deliverable contents of the syringe.

VII.B.1.a.i. Certain of these coatings will also provide manufacturing advantages, particularly if the barrier coating, lubricity layer and surface treatment are applied in the same apparatus, for example the illustrated PECVD apparatus. Optionally, the $SiO_x$ barrier coating, lubricity layer, and surface treatment can all be applied in one PECVD apparatus, thus greatly reducing the amount of handling necessary.

Further advantages can be obtained by forming the barrier coating, lubricity layer, and solute retainer using the same precursors and varying the process. For example, an $SiO_x$ gas barrier layer can be applied using an OMCTS precursor under high power/high $O_2$ conditions, followed by applying a lubricity layer applied using an OMCTS precursor under low power and/or in the substantial or complete absence of oxygen, finishing with a surface treatment using an OMCTS precursor under intermediate power and oxygen.

VII.B.1.b Syringe Having Barrel with $SiO_x$ Coated Interior and Barrier Coated Exterior VII.B.1.b. Still another embodiment, illustrated in FIG. 50, is a syringe 544 including a plunger 546, a barrel 548, and interior and exterior barrier coatings 554 and 602. The barrel 548 can be made of thermoplastic base material defining a lumen 604. The barrel 548 can have an interior surface 552 receiving the plunger for sliding 546 and an exterior surface 606. A barrier coating 554 of $SiO_x$, in which x is from about 1.5 to about 2.9, can be provided on the interior surface 552 of the barrel 548. A barrier coating 602 of a resin can be provided on the exterior surface 606 of the barrel 548.

VII.B.1.b. In any embodiment, the thermoplastic base material optionally can include a polyolefin, for example polypropylene or a cyclic olefin copolymer (for example the material sold under the trademark TOPAS®), a polyester, for example polyethylene terephthalate, a polycarbonate, for example a bisphenol A polycarbonate thermoplastic, or other materials. Composite syringe barrels are contemplated having any one of these materials as an outer layer and the same or a different one of these materials as an inner layer. Any of the material combinations of the composite syringe barrels or sample tubes described elsewhere in this specification can also be used.

VII.B.1.b. In any embodiment, the resin optionally can include polyvinylidene chloride in homopolymer or copolymer form. For example, the PVdC homopolymers (trivial name: Saran) or copolymers described in U.S. Pat. No. 6,165,566, incorporated here by reference, can be employed. The resin optionally can be applied onto the exterior surface of the barrel in the form of a latex or other dispersion.

VII.B.1.b. In any embodiment, the syringe barrel 548 optionally can include a lubricity layer disposed between the plunger and the barrier coating of $SiO_x$. Suitable lubricity layers are described elsewhere in this specification.

VII.B.1.b. In any embodiment, the lubricity layer optionally can be applied by PECVD and optionally can include material characterized as defined in the Definition Section.

VII.B.1.b. In any embodiment, the syringe barrel 548 optionally can include a surface treatment covering the lubricity layer in an amount effective to reduce the leaching of the lubricity layer, constituents of the thermoplastic base material, or both into the lumen 604.

VII.B.1.c Method of Making Syringe Having Barrel with $SiO_x$ Coated Interior and Barrier Coated Exterior VII.B.1.c. Even another embodiment is a method of making a syringe as described in any of the embodiments of part VII.B.1.b, including a plunger, a barrel, and interior and exterior barrier coatings. A barrel is provided having an interior surface for receiving the plunger for sliding and an exterior surface. A barrier coating of $SiO_x$ is provided on the interior surface of the barrel by PECVD. A barrier coating of a resin is provided on the exterior surface of the barrel. The plunger and barrel are assembled to provide a syringe.

VII.B.1.c. For effective coating (uniform wetting) of the plastic article with the aqueous latex, it is contemplated to be useful to match the surface tension of the latex to the plastic substrate. This can be accomplished by several approaches, independently or combined, for example, reducing the surface tension of the latex (with surfactants or solvents), and/or corona pretreatment of the plastic article, and/or chemical priming of the plastic article.

VII.B.1.c. The resin optionally can be applied via dip coating of the latex onto the exterior surface of the barrel, spray coating of the latex onto the exterior surface of the barrel, or both, providing plastic-based articles offering improved gas and vapor barrier performance. Polyvinylidene chloride plastic laminate articles can be made that provide significantly improved gas barrier performance versus the non-laminated plastic article.

VII.B.1.c. In any embodiment, the resin optionally can be heat cured. The resin optionally can be cured by removing water. Water can be removed by heat curing the resin, exposing the resin to a partial vacuum or low-humidity environment, catalytically curing the resin, or other expedients.

VII.B.1.c. An effective thermal cure schedule is contemplated to provide final drying to permit PVdC crystallization, offering barrier performance. Primary curing can be carried out at an elevated temperature, for example between 180-310° F. (82-154° C.), of course depending on the heat tolerance of the thermoplastic base material. Barrier performance after the primary cure optionally can be about 85% of the ultimate barrier performance achieved after a final cure.

VII.B.1.c. A final cure can be carried out at temperatures ranging from ambient temperature, such as about 65-75° F. (18-24° C.) for a long time (such as 2 weeks) to an elevated temperature, such as 122° F. (50° C.), for a short time, such as four hours.

VII.B.1.c. The PVdC-plastic laminate articles, in addition to superior barrier performance, are optionally contemplated to provide one or more desirable properties such as colorless transparency, good gloss, abrasion resistance, printability, and mechanical strain resistance.

VII.B.2. Plungers

VII.B.2.a. With Barrier Coated Piston Front Face

VII.B.2.a. Another embodiment is a plunger for a syringe, including a piston and a push rod. The piston has a front face, a generally cylindrical side face, and a back portion, the side face being configured to movably seat within a syringe barrel. The front face has a barrier coating. The push rod engages the back portion and is configured for advancing the piston in a syringe barrel.

VII.B.2.b. With Lubricity Layer Interfacing with Side Face

VII.B.2.b. Yet another embodiment is a plunger for a syringe, including a piston, a lubricity layer, and a push rod. The piston has a front face, a generally cylindrical side face, and a back portion. The side face is configured to movably seat within a syringe barrel. The lubricity layer interfaces with the side face. The push rod engages the back portion of the piston and is configured for advancing the piston in a syringe barrel.

VII.B.3. Two Piece Syringe and Luer Fitting

VII.B.3. Another embodiment is a syringe including a plunger, a syringe barrel, and a Luer fitting. The syringe includes a barrel having an interior surface receiving the plunger for sliding. The Luer fitting includes a Luer taper having an internal passage defined by an internal surface. The Luer fitting is formed as a separate piece from the syringe barrel and joined to the syringe barrel by a coupling. The internal passage of the Luer taper has a barrier coating of $SiO_x$.

VII.B.3. Referring to FIGS. 50-51, the syringe 544 optionally can include a Luer fitting 556 comprising a Luer taper 558 to receive a cannula mounted on a complementary Luer taper (not shown, conventional). The Luer taper 558 has an internal passage 560 defined by an internal surface 562. The Luer fitting 556 optionally is formed as a separate piece from the syringe barrel 548 and joined to the syringe barrel 548 by a coupling 564. As illustrated in FIGS. 50 and 51, the coupling 564 in this instance has a male part 566 and a female part 568 that snap together to secure the Luer fitting in at least substantially leak proof fashion to the barrel 548. The internal surface 562 of the Luer taper can include a barrier coating 570 of $SiO_x$. The barrier coating can be less than 100 nm thick and effective to reduce the ingress of oxygen into the internal passage of the Luer fitting. The barrier coating can be applied before the Luer fitting is joined to the syringe barrel. The syringe of FIGS. 50-51 also has an optional locking collar 572 that is internally threaded so to lock the complementary Luer taper of a cannula in place on the taper 558.

VII.B.4. Lubricant Compositions—Lubricity Layer Deposited from an Organosilicon Precursor Made by In Situ Polymerizing Organosilicon Precursor VII.B.4.a. Product By Process and Lubricity VII.B.4.a. Still another embodiment is a lubricity layer. This coating can be of the type made by the following process.

VII.B.4.a. Any of the precursors mentioned elsewhere in this specification can be used, alone or in combination. The precursor is applied to a substrate under conditions effective to form a coating. The coating is polymerized or crosslinked, or both, to form a lubricated surface having a lower plunger sliding force or breakout force than the untreated substrate.

VII.B.4.a. Another embodiment is a method of applying a lubricity layer. An organosilicon precursor is applied to a substrate under conditions effective to form a coating. The coating is polymerized or crosslinked, or both, to form a lubricated surface having a lower plunger sliding force or breakout force than the untreated substrate.

VII.B.4.b. Product by Process and Analytical Properties

VII.B.4.b. Even another aspect of the invention is a lubricity layer deposited by PECVD from a feed gas comprising an organometallic precursor, optionally an organosilicon precursor, optionally a linear siloxane, a linear silazane, a monocyclic siloxane, a monocyclic silazane, a polycyclic siloxane, a polycyclic silazane, or any combination of two or more of these. The coating has a density between 1.25 and 1.65 g/cm³ optionally between 1.35 and 1.55 g/cm³, optionally between 1.4 and 1.5 g/cm³, optionally between 1.44 and 1.48 g/cm³ as determined by X-ray reflectivity (XRR).

VII.B.4.b. Still another aspect of the invention is a lubricity layer deposited by PECVD from a feed gas comprising an organometallic precursor, optionally an organosilicon precursor, optionally a linear siloxane, a linear silazane, a monocyclic siloxane, a monocyclic silazane, a polycyclic siloxane, a polycyclic silazane, or any combination of two or more of these. The coating has as an outgas component one or more oligomers containing repeating -(Me)$_2$SiO— moieties, as determined by gas chromatography/mass spectrometry. Optionally, the coating meets the limitations of any of embodiments VII.B.4.a or VII.B.4.b.A.585h. Optionally, the coating outgas component as determined by gas chromatography/mass spectrometry is substantially free of trimethylsilanol.

VII.B.4.b. Optionally, the coating outgas component can be at least 10 ng/test of oligomers containing repeating -(Me)$_2$SiO— moieties, as determined by gas chromatography/mass spectrometry using the following test conditions:

| | |
|---|---|
| GC Column: | 30 m × 0.25 mm DB-5MS (J&W Scientific), 0.25 μm film thickness |
| Flow rate: | 1.0 ml/min, constant flow mode |
| Detector: | Mass Selective Detector (MSD) |
| Injection Mode: | Split injection (10:1 split ratio) |
| Outgassing Conditions: | 1½" (37 mm) Chamber, purge for three hour at 85° C., flow 60 ml/min |
| Oven temperature: | 40° C. (5 min.) to 300° C. at 10° C./min.; hold for 5 min. at 300° C. |

VII.B.4.b. Optionally, the outgas component can include at least 20 ng/test of oligomers containing repeating -(Me)$_2$SiO— moieties.

VII.B.4.b. Optionally, the feed gas comprises a monocyclic siloxane, a monocyclic silazane, a polycyclic siloxane, a polycyclic silazane, or any combination of two or more of these, for example a monocyclic siloxane, a monocyclic silazane, or any combination of two or more of these, for example octamethylcyclotetrasiloxane.

VII.B.4.b. The lubricity layer of any embodiment can have a thickness measured by transmission electron microscopy (TEM) between 1 and 500 nm, optionally between 10 and 500 nm, optionally between 20 and 200 nm, optionally between 20 and 100 nm, optionally between 30 and 100 nm.

VII.B.4.b. Another aspect of the invention is a lubricity layer deposited by PECVD from a feed gas comprising a monocyclic siloxane, a monocyclic silazane, a polycyclic siloxane, a polycyclic silazane, or any combination of two or more of these. The coating has an atomic concentration of carbon, normalized to 100% of carbon, oxygen, and silicon, as determined by X-ray photoelectron spectroscopy (XPS), greater than the atomic concentration of carbon in the atomic formula for the feed gas. Optionally, the coating meets the limitations of embodiments VII.B.4.a or VII.B.4.b.A.

VII.B.4.b. Optionally, the atomic concentration of carbon increases by from 1 to 80 atomic percent (as calculated and based on the XPS conditions in Example 15), alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

VII.B.4.b. An additional aspect of the invention is a lubricity layer deposited by PECVD from a feed gas comprising a monocyclic siloxane, a monocyclic silazane, a polycyclic siloxane, a polycyclic silazane, or any combination of two or more of these. The coating has an atomic concentration of silicon, normalized to 100% of carbon, oxygen, and silicon, as determined by X-ray photoelectron spectroscopy (XPS), less than the atomic concentration of silicon in the atomic formula for the feed gas. Optionally, the coating meets the limitations of embodiments VII.B.4.a or VII.B.4.b.A.

VII.B.4.b. Optionally, the atomic concentration of silicon decreases by from 1 to 80 atomic percent (as calculated and based on the XPS conditions in Example 15), alternatively from 10 to 70 atomic percent, alternatively from 20 to 60 atomic percent, alternatively from 30 to 55 atomic percent, alternatively from 40 to 50 atomic percent, alternatively from 42 to 46 atomic percent.

VII.B.4.b. Lubricity layers having combinations of any two or more properties recited in Section VII.B.4 are also expressly contemplated.

VII.C. Vessels Generally

VII.C. A coated vessel or container as described herein and/or prepared according to a method described herein can be used for reception and/or storage and/or delivery of a compound or composition. The compound or composition can be sensitive, for example air-sensitive, oxygen-sensitive, sensitive to humidity and/or sensitive to mechanical influences. It can be a biologically active compound or composition, for example a medicament like insulin or a composition comprising insulin. In another aspect, it can be a biological fluid, optionally a bodily fluid, for example blood or a blood fraction. In certain aspects of the present invention, the compound or composition is a product to be administrated to a subject in need thereof, for example a product to be injected, like blood (as in transfusion of blood from a donor to a recipient or reintroduction of blood from a patient back to the patient) or insulin.

VII.C. A coated vessel or container as described herein and/or prepared according to a method described herein can further be used for protecting a compound or composition contained in its interior space against mechanical and/or chemical effects of the surface of the uncoated vessel material. For example, it can be used for preventing or reducing precipitation and/or clotting or platelet activation of the compound or a component of the composition, for example insulin precipitation or blood clotting or platelet activation.

VII.C. It can further be used for protecting a compound or composition contained in its interior against the environment outside of the vessel, for example by preventing or reducing the entry of one or more compounds from the environment surrounding the vessel into the interior space of the vessel. Such environmental compound can be a gas or liquid, for example an atmospheric gas or liquid containing oxygen, air, and/or water vapor.

VII.C. A coated vessel as described herein can also be evacuated and stored in an evacuated state. For example, the coating allows better maintenance of the vacuum in comparison to a corresponding uncoated vessel. In one aspect of this embodiment, the coated vessel is a blood collection tube. The tube can also contain an agent for preventing blood clotting or platelet activation, for example EDTA or heparin.

VII.C. Any of the above-described embodiments can be made, for example, by providing as the vessel a length of tubing from about 1 cm to about 200 cm, optionally from about 1 cm to about 150 cm, optionally from about 1 cm to about 120 cm, optionally from about 1 cm to about 100 cm, optionally from about 1 cm to about 80 cm, optionally from about 1 cm to about 60 cm, optionally from about 1 cm to about 40 cm, optionally from about 1 cm to about 30 cm long, and processing it with a probe electrode as described below. Particularly for the longer lengths in the above ranges, it is contemplated that relative motion between the probe and the vessel can be useful during coating formation. This can be done, for example, by moving the vessel with respect to the probe or moving the probe with respect to the vessel.

VII.C. In these embodiments, it is contemplated that the coating can be thinner or less complete than can be preferred for a barrier coating, as the vessel in some embodiments will not require the high barrier integrity of an evacuated blood collection tube.

VII.C. As an optional feature of any of the foregoing embodiments the vessel has a central axis.

VII.C. As an optional feature of any of the foregoing embodiments the vessel wall is sufficiently flexible to be flexed at least once at 20° C., without breaking the wall, over a range from at least substantially straight to a bending radius at the central axis of not more than 100 times as great as the outer diameter of the vessel.

VII.C. As an optional feature of any of the foregoing embodiments the bending radius at the central axis is not more than 90 times as great as, or not more than 80 times as great as, or not more than 70 times as great as, or not more than 60 times as great as, or not more than 50 times as great as, or not more than 40 times as great as, or not more than 30 times as great as, or not more than 20 times as great as, or not more than 10 times as great as, or not more than 9 times as great as, or not more than 8 times as great as, or not more than 7 times as great as, or not more than 6 times as great as, or not more than 5 times as great as, or not more than 4 times as great as, or not more than 3 times as great as, or not more than 2 times as great as, or not more than, the outer diameter of the vessel.

VII.C. As an optional feature of any of the foregoing embodiments the vessel wall can be a fluid-contacting surface made of flexible material.

VII.C. As an optional feature of any of the foregoing embodiments the vessel lumen can be the fluid flow passage of a pump.

VII.C. As an optional feature of any of the foregoing embodiments the vessel can be a blood bag adapted to maintain blood in good condition for medical use.

VII.C., VII.D. As an optional feature of any of the foregoing embodiments the polymeric material can be a silicone elastomer or a thermoplastic polyurethane, as two examples, or any material suitable for contact with blood, or with insulin.

VII.C., VII.D. In an optional embodiment, the vessel has an inner diameter of at least 2 mm, or at least 4 mm.

VII.C. As an optional feature of any of the foregoing embodiments the vessel is a tube.

VII.C. As an optional feature of any of the foregoing embodiments the lumen has at least two open ends.

VII.C.1. Vessel Containing Viable Blood, Having a Coating Deposited from an Organosilicon Precursor VII.C.1. Even another embodiment is a blood containing vessel. Several non-limiting examples of such a vessel are a blood transfusion bag, a blood sample collection vessel in which a sample has been collected, the tubing of a heart-lung machine, a flexible-walled blood collection bag, or tubing used to collect a patient's blood during surgery and reintroduce the blood into the patient's vasculature. If the vessel includes a pump for pumping blood, a particularly suitable pump is a centrifugal pump or a peristaltic pump. The vessel has a wall; the wall has an inner surface defining a lumen. The inner surface of the wall has an at least partial coating of a hydrophobic layer, characterized as defined in the Definition Section. The coating can be as thin as monomolecular thickness or as thick as about 1000 nm. The vessel contains blood viable for return to the vascular system of a patient disposed within the lumen in contact with the hydrophobic layer.

VII.C.1. An embodiment is a blood containing vessel including a wall and having an inner surface defining a lumen. The inner surface has an at least partial coating of a hydrophobic layer. The coating can also comprise or consist essentially of $SiO_x$, where x is as defined in this specification. The thickness of the coating is within the range from monomolecular thickness to about 1000 nm thick on the inner surface. The vessel contains blood viable for return to the vascular system of a patient disposed within the lumen in contact with the hydrophobic layer.

VII.C.2. Coating Deposited from an Organosilicon Precursor Reduces Clotting or Platelet Activation of Blood in the Vessel VII.C.2. Another embodiment is a vessel having a wall. The wall has an inner surface defining a lumen and has an at least partial coating of a hydrophobic layer, where optionally w, x, y, and z are as previously defined in the Definition Section. The thickness of the coating is from monomolecular thickness to about 1000 nm thick on the inner surface. The coating is effective to reduce the clotting or platelet activation of blood exposed to the inner surface, compared to the same type of wall uncoated with a hydrophobic layer.

VII.C.2. It is contemplated that the incorporation of a hydrophobic layer will reduce the adhesion or clot forming tendency of the blood, as compared to its properties in contact with an unmodified polymeric or $SiO_x$ surface. This property is contemplated to reduce or potentially eliminate the need for treating the blood with heparin, as by reducing the necessary blood concentration of heparin in a patient undergoing surgery of a type requiring blood to be removed from the patient and then returned to the patient, as when using a heart-lung machine during cardiac surgery. It is contemplated that this will reduce the complications of surgery involving the passage of blood through such a vessel, by reducing the bleeding complications resulting from the use of heparin.

VII.C.2. Another embodiment is a vessel including a wall and having an inner surface defining a lumen. The inner surface has an at least partial coating of a hydrophobic layer, the thickness of the coating being from monomolecular thickness to about 1000 nm thick on the inner surface, the coating being effective to reduce the clotting or platelet activation of blood exposed to the inner surface.

VII.C.3. Vessel Containing Viable Blood, Having a Coating of Group III or IV Element VII.C.3. Another embodiment is a blood containing vessel having a wall having an inner surface defining a lumen. The inner surface has an at least partial coating of a composition comprising one or more elements of Group III, one or more elements of Group IV, or a combination of two or more of these. The thickness of the coating is between monomolecular thickness and about 1000 nm thick, inclusive, on the inner surface. The vessel contains blood viable for return to the vascular system of a patient disposed within the lumen in contact with the hydrophobic layer.

VII.C.4. Coating of Group III or IV Element Reduces Clotting or Platelet Activation of Blood in the Vessel VII.C.4. Optionally, in the vessel of the preceding paragraph, the coating of the Group III or IV Element is effective to reduce the clotting or platelet activation of blood exposed to the inner surface of the vessel wall.

VII.D. Pharmaceutical Delivery Vessels

VII.D. A coated vessel or container as described herein can be used for preventing or reducing the escape of a compound or composition contained in the vessel into the environment surrounding the vessel.

Further uses of the coating and vessel as described herein, which are apparent from any part of the description and claims, are also contemplated.

VII.D.1. Vessel Containing Insulin, Having a Coating Deposited from an Organosilicon Precursor VII.D.1. Another embodiment is an insulin containing vessel including a wall having an inner surface defining a lumen. The inner surface has an at least partial coating of a hydrophobic layer, characterized as defined in the Definition Section. The coating can be from monomolecular thickness to about 1000 nm thick on the inner surface. Insulin is disposed within the lumen in contact with the $Si_wO_xC_yH_z$ coating.

VII.D.1. Still another embodiment is an insulin containing vessel including a wall and having an inner surface defining a lumen. The inner surface has an at least partial coating of a hydrophobic layer, characterized as defined in the Definition Section, the thickness of the coating being from monomolecular thickness to about 1000 nm thick on the inner surface. Insulin, for example pharmaceutical insulin FDA approved for human use, is disposed within the lumen in contact with the hydrophobic layer.

VII.D.1. It is contemplated that the incorporation of a hydrophobic layer, characterized as defined in the Definition Section, will reduce the adhesion or precipitation forming tendency of the insulin in a delivery tube of an insulin pump, as compared to its properties in contact with an unmodified polymeric surface. This property is contemplated to reduce or potentially eliminate the need for filtering the insulin passing through the delivery tube to remove a solid precipitate.

VII.D.2. Coating Deposited from an Organosilicon Precursor Reduces Precipitation of Insulin in the Vessel VII.D.2. Optionally, in the vessel of the preceding paragraph, the coating of a hydrophobic layer is effective to reduce the formation of a precipitate from insulin contacting the inner surface, compared to the same surface absent the hydrophobic layer.

VII.D.2. Even another embodiment is a vessel again comprising a wall and having an inner surface defining a lumen. The inner surface includes an at least partial coating of a hydrophobic layer. The thickness of the coating is in the range from monomolecular thickness to about 1000 nm thick on the inner surface. The coating is effective to reduce the formation of a precipitate from insulin contacting the inner surface.

VII.D.3. Vessel Containing Insulin, Having a Coating of Group III or IV Element

VII.D.3. Another embodiment is an insulin containing vessel including a wall having an inner surface defining a lumen. The inner surface has an at least partial coating of a composition comprising carbon, one or more elements of Group III, one or more elements of Group IV, or a combination of two or more of these. The coating can be from monomolecular thickness to about 1000 nm thick on the inner surface. Insulin is disposed within the lumen in contact with the coating.

VII.D.4. Coating of Group III or IV Element Reduces Precipitation of Insulin in the Vessel VII.D.4. Optionally, in the vessel of the preceding paragraph, the coating of a composition comprising carbon, one or more elements of Group III, one or more elements of Group IV, or a combination of two or more of these, is effective to reduce the formation of a precipitate from insulin contacting the inner surface, compared to the same surface absent the coating.

Working Examples

Example 0

Basic Protocols for Forming and Coating Tubes and Syringe Barrels

The vessels tested in the subsequent working examples were formed and coated according to the following exemplary protocols, except as otherwise indicated in individual examples. Particular parameter values given in the following basic protocols, e.g. the electric power and process gas flow, are typical values. Whenever parameter values were changed in comparison to these typical values, this will be indicated in the subsequent working examples. The same applies to the type and composition of the process gas.

Protocol for Forming COC Tube (Used, e.g., in Examples 1, 19)

Cyclic olefin copolymer (COC) tubes of the shape and size commonly used as evacuated blood collection tubes ("COC tubes") were injection molded from Topas® 8007-04 cyclic olefin copolymer (COC) resin, available from Hoechst AG, Frankfurt am Main, Germany, having these dimensions: 75 mm length, 13 mm outer diameter, and 0.85 mm wall thickness, each having a volume of about 7.25 cm³ and a closed, rounded end.

Protocol for Forming PET Tube (Used, e.g., in Examples 2, 4, 8, 9, 10)

Polyethylene terephthalate (PET) tubes of the type commonly used as evacuated blood collection tubes ("PET tubes") were injection molded in the same mold used for the Protocol for Forming COC Tube, having these dimensions: 75 mm length, 13 mm outer diameter, and 0.85 mm wall thickness, each having a volume of about 7.25 cm³ and a closed, rounded end.

Protocol for Coating Tube Interior with $SiO_x$ (Used, e.g., in Examples 1, 2, 4, 8, 9, 10, 18, 19)

The apparatus as shown in FIG. 2 with the sealing mechanism of FIG. 45, which is a specific contemplated embodiment, was used. The vessel holder 50 was made from Delrin® acetal resin, available from E.I. du Pont de Nemours and Co., Wilmington Del., USA, with an outside diameter of 1.75 inches (44 mm) and a height of 1.75 inches (44 mm). The vessel holder 50 was housed in a Delrin® structure that allowed the device to move in and out of the electrode (160).

The electrode 160 was made from copper with a Delrin® shield. The Delrin® shield was conformal around the outside of the copper electrode 160. The electrode 160 measured approximately 3 inches (76 mm) high (inside) and was approximately 0.75 inches (19 mm) wide.

The tube used as the vessel 80 was inserted into the vessel holder 50 base sealing with Viton® O-rings 490, 504 (Viton® is a trademark of DuPont Performance Elastomers LLC, Wilmington Del., USA) around the exterior of the tube (FIG. 45). The tube 80 was carefully moved into the sealing position over the extended (stationary) ⅛-inch (3-mm) diameter brass probe or counter electrode 108 and pushed against a copper plasma screen.

The copper plasma screen 610 was a perforated copper foil material (K&S Engineering, Chicago Ill., USA, Part #LXMUW5 copper mesh) cut to fit the outside diameter of the tube, and was held in place by a radially extending abutment surface 494 that acted as a stop for the tube insertion (see FIG. 45). Two pieces of the copper mesh were fit snugly around the brass probe or counter electrode 108, insuring good electrical contact.

The brass probe or counter electrode 108 extended approximately 70 mm into the interior of the tube and had an array of #80 wire (diameter=0.0135 inch or 0.343 mm). The brass probe or counter electrode 108 extended through a Swagelok® fitting (available from Swagelok Co., Solon Ohio, USA) located at the bottom of the vessel holder 50, extending through the vessel holder 50 base structure. The brass probe or counter electrode 108 was grounded to the casing of the RF matching network.

The gas delivery port 110 was 12 holes in the probe or counter electrode 108 along the length of the tube (three on each of four sides oriented 90 degrees from each other) and two holes in the aluminum cap that plugged the end of the gas delivery port 110. The gas delivery port 110 was connected to a stainless steel assembly comprised of Swagelok® fittings incorporating a manual ball valve for venting, a thermocouple pressure gauge and a bypass valve connected to the vacuum pumping line. In addition, the gas system was connected to the gas delivery port 110 allowing the process gases, oxygen and hexamethyldisiloxane (HMDSO) to be flowed through the gas delivery port 110 (under process pressures) into the interior of the tube.

The gas system was comprised of a Aalborg® GFC17 mass flow meter (Part #EW-32661-34, Cole-Parmer Instrument Co., Barrington Ill. USA) for controllably flowing oxygen at 90 sccm (or at the specific flow reported for a particular example) into the process and a polyether ether ketone ("PEEK") capillary (outside diameter, "OD" 1/16-inch (1.5-mm.), inside diameter, "ID" 0.004 inch (0.1 mm)) of length 49.5 inches (1.26 m). The PEEK capillary end was inserted into liquid hexamethyldisiloxane ("HMDSO," Alfa Aesar® Part Number L16970, NMR Grade, available from Johnson Matthey PLC, London). The liquid HMDSO was pulled through the capillary due to the lower pressure in the tube during processing. The HMDSO was then vaporized into a vapor at the exit of the capillary as it entered the low pressure region.

To ensure no condensation of the liquid HMDSO past this point, the gas stream (including the oxygen) was diverted to the pumping line when it was not flowing into the interior of the tube for processing via a Swagelok® 3-way valve. Once the tube was installed, the vacuum pump valve was opened to the vessel holder 50 and the interior of the tube.

An Alcatel rotary vane vacuum pump and blower comprised the vacuum pump system. The pumping system allowed the interior of the tube to be reduced to pressure(s) of less than 200 mTorr while the process gases were flowing at the indicated rates.

Once the base vacuum level was achieved, the vessel holder 50 assembly was moved into the electrode 160 assembly. The gas stream (oxygen and HMDSO vapor) was flowed into the brass gas delivery port 110 (by adjusting the 3-way valve from the pumping line to the gas delivery port 110). Pressure inside the tube was approximately 300 mTorr as measured by a capacitance manometer (MKS) installed on the pumping line near the valve that controlled the vacuum. In addition to the tube pressure, the pressure inside the gas delivery port 110 and gas system was also measured with the thermocouple vacuum gauge that was connected to the gas system. This pressure was typically less than 8 Torr.

Once the gas was flowing to the interior of the tube, the RF power supply was turned on to its fixed power level. A ENI ACG-6 600 Watt RF power supply was used (at 13.56 MHz) at a fixed power level of approximately 50 Watts. The output power was calibrated in this and all following Protocols and Examples using a Bird Corporation Model 43 RF Watt meter connected to the RF output of the power supply during operation of the coating apparatus. The following relationship was found between the dial setting on the power supply and the output power: RF Power Out=55×Dial Setting. In the priority applications to the present application, a factor 100 was used, which was incorrect. The RF power supply was connected to a COMDEL CPMX1000 auto match which matched the complex impedance of the plasma (to be created in the tube) to the 50 ohm output impedance of the ENI ACG-6 RF power supply. The forward power was 50 Watts (or the specific amount reported for a particular example) and the reflected power was 0 Watts so that the applied power was delivered to the interior of the tube. The RF power supply was controlled by a laboratory timer and the power on time set to 5 seconds (or the specific time period reported for a particular example). Upon initiation of the RF power, a uniform plasma was established inside the interior of the tube. The plasma was maintained for the entire 5 seconds until the RF power was terminated by the timer. The plasma produced a silicon oxide coating of approximately 20 nm thickness (or the specific thickness reported in a particular example) on the interior of the tube surface.

After coating, the gas flow was diverted back to the vacuum line and the vacuum valve was closed. The vent valve was then opened, returning the interior of the tube to atmospheric pressure (approximately 760 Torr). The tube was then carefully removed from the vessel holder 50 assembly (after moving the vessel holder 50 assembly out of the electrode 160 assembly).

Protocol for Coating Tube Interior with Hydrophobic Layer (Used, e.g., in Example 9)

The apparatus as shown in FIG. 2 with the sealing mechanism of FIG. 45, which is a specific contemplated embodiment, was used. The vessel holder 50 was made from Delrin® acetal resin, available from E.I. du Pont de Nemours and Co., Wilmington Del., USA, with an outside diameter of 1.75 inches (44 mm) and a height of 1.75 inches (44 mm). The vessel holder 50 was housed in a Delrin® structure that allowed the device to move in and out of the electrode (160).

The electrode 160 was made from copper with a Delrin® shield. The Delrin® shield was conformal around the outside of the copper electrode 160. The electrode 160 measured approximately 3 inches (76 mm) high (inside) and was approximately 0.75 inches (19 mm) wide.

The tube used as the vessel 80 was inserted into the vessel holder 50 base sealing with Viton® O-rings 490, 504 (Viton® is a trademark of DuPont Performance Elastomers LLC, Wilmington Del., USA) around the exterior of the tube (FIG. 45). The tube 80 was carefully moved into the sealing position over the extended (stationary) ⅛-inch (3-mm) diameter brass probe or counter electrode 108 and pushed against a copper plasma screen.

The copper plasma screen 610 was a perforated copper foil material (K&S Engineering, Chicago Ill., USA, Part #LXMUW5 copper mesh) cut to fit the outside diameter of the tube, and was held in place by a radially extending abutment surface 494 that acted as a stop for the tube insertion (see FIG. 45). Two pieces of the copper mesh were fit snugly around the brass probe or counter electrode 108, insuring good electrical contact.

The brass probe or counter electrode 108 extended approximately 70 mm into the interior of the tube and had an array of #80 wire (diameter=0.0135 inch or 0.343 mm). The brass probe or counter electrode 108 extended through a Swagelok® fitting (available from Swagelok Co., Solon Ohio, USA) located at the bottom of the vessel holder 50, extending through the vessel holder 50 base structure. The brass probe or counter electrode 108 was grounded to the casing of the RF matching network.

The gas delivery port 110 was 12 holes in the probe or counter electrode 108 along the length of the tube (three on each of four sides oriented 90 degrees from each other) and two holes in the aluminum cap that plugged the end of the gas delivery port 110. The gas delivery port 110 was connected to a stainless steel assembly comprised of Swagelok® fittings incorporating a manual ball valve for venting, a thermocouple pressure gauge and a bypass valve connected to the vacuum pumping line. In addition, the gas system was connected to the gas delivery port 110 allowing the process gases, oxygen and hexamethyldisiloxane (HMDSO) to be flowed through the gas delivery port 110 (under process pressures) into the interior of the tube.

The gas system was comprised of a Aalborg® GFC17 mass flow meter (Part #EW-32661-34, Cole-Parmer Instrument Co., Barrington Ill. USA) for controllably flowing oxygen at 60 sccm (or at the specific flow reported for a particular example) into the process and a polyether ether ketone ("PEEK") capillary (outside diameter, "OD" 1/16-inch (1.5-mm.), inside diameter, "ID" 0.004 inch (0.1 mm)) of length 49.5 inches (1.26 m). The PEEK capillary end was inserted into liquid hexamethyldisiloxane ("HMDSO," Alfa Aesar® Part Number L16970, NMR Grade, available from Johnson Matthey PLC, London). The liquid HMDSO was pulled through the capillary due to the lower pressure in the tube during processing. The HMDSO was then vaporized into a vapor at the exit of the capillary as it entered the low pressure region.

To ensure no condensation of the liquid HMDSO past this point, the gas stream (including the oxygen) was diverted to the pumping line when it was not flowing into the interior of the tube for processing via a Swagelok® 3-way valve. Once the tube was installed, the vacuum pump valve was opened to the vessel holder 50 and the interior of the tube.

An Alcatel rotary vane vacuum pump and blower comprised the vacuum pump system. The pumping system allowed the interior of the tube to be reduced to pressure(s) of less than 200 mTorr while the process gases were flowing at the indicated rates.

Once the base vacuum level was achieved, the vessel holder 50 assembly was moved into the electrode 160 assembly. The gas stream (oxygen and HMDSO vapor) was flowed into the brass gas delivery port 110 (by adjusting the 3-way valve from the pumping line to the gas delivery port 110). Pressure inside the tube was approximately 270 mTorr as measured by a capacitance manometer (MKS) installed on the pumping line near the valve that controlled the vacuum. In addition to the tube pressure, the pressure inside the gas delivery port 110 and gas system was also measured with the thermocouple vacuum gauge that was connected to the gas system. This pressure was typically less than 8 Torr.

Once the gas was flowing to the interior of the tube, the RF power supply was turned on to its fixed power level. A ENI ACG-6 600 Watt RF power supply was used (at 13.56 MHz) at a fixed power level of approximately 39 Watts. The RF power supply was connected to a COMDEL CPMX1000 auto match which matched the complex impedance of the plasma (to be created in the tube) to the 50 ohm output impedance of the ENI ACG-6 RF power supply. The forward power was 39 Watts (or the specific amount reported for a particular example) and the reflected power was 0 Watts so that the applied power was delivered to the interior of the tube. The RF power supply was controlled by a laboratory timer and the power on time set to 7 seconds (or the specific time period reported for a particular example). Upon initiation of the RF power, a uniform plasma was established inside the interior of the tube. The plasma was maintained for the entire 7 seconds until the RF power was terminated by the timer. The plasma produced a silicon oxide coating of approximately 20 nm thickness (or the specific thickness reported in a particular example) on the interior of the tube surface.

After coating, the gas flow was diverted back to the vacuum line and the vacuum valve was closed. The vent valve was then opened, returning the interior of the tube to atmospheric pressure (approximately 760 Torr). The tube was then carefully removed from the vessel holder 50 assembly (after moving the vessel holder 50 assembly out of the electrode 160 assembly).

Protocol for Forming COC Syringe Barrel (Used, e.g., in Examples 3, 5, 11-18, 20)

Syringe barrels ("COC syringe barrels"), CV Holdings Part 11447, each having a 2.8 mL overall volume (excluding the Luer fitting) and a nominal 1 mL delivery volume or plunger displacement, Luer adapter type, were injection molded from Topas® 8007-04 cyclic olefin copolymer (COC) resin, available from Hoechst AG, Frankfurt am Main, Germany, having these dimensions: about 51 mm overall length, 8.6 mm inner syringe barrel diameter and 1.27 mm wall thickness at the cylindrical portion, with an integral 9.5 millimeter length needle capillary Luer adapter molded on one end and two finger flanges molded near the other end.

Protocol for Coating COC Syringe Barrel Interior with $SiO_x$ (Used, e.g. in Examples 3, 5, 18)

An injection molded COC syringe barrel was interior coated with SiOx. The apparatus as shown in FIG. 2 with the sealing mechanism of FIG. 45 was modified to hold a COC syringe barrel with butt sealing at the base of the COC syringe barrel. Additionally a cap was fabricated out of a stainless steel Luer fitting and a polypropylene cap that sealed the end of the COC syringe barrel (illustrated in FIG. 26), allowing the interior of the COC syringe barrel to be evacuated.

The vessel holder 50 was made from Delrin® with an outside diameter of 1.75 inches (44 mm) and a height of 1.75 inches (44 mm). The vessel holder 50 was housed in a Delrin® structure that allowed the device to move in and out of the electrode 160.

The electrode 160 was made from copper with a Delrin® shield. The Delrin® shield was conformal around the outside of the copper electrode 160. The electrode 160 measured approximately 3 inches (76 mm) high (inside) and was approximately 0.75 inches (19 mm) wide. The COC syringe barrel was inserted into the vessel holder 50, base sealing with an Viton® O-rings.

The COC syringe barrel was carefully moved into the sealing position over the extended (stationary) ⅛-inch (3-mm.) diameter brass probe or counter electrode 108 and pushed against a copper plasma screen. The copper plasma screen was a perforated copper foil material (K&S Engineering Part #LXMUW5 Copper mesh) cut to fit the outside diameter of the COC syringe barrel and was held in place by a abutment surface 494 that acted as a stop for the COC syringe barrel insertion. Two pieces of the copper mesh were fit snugly around the brass probe or counter electrode 108 insuring good electrical contact.

The probe or counter electrode 108 extended approximately 20 mm into the interior of the COC syringe barrel and was open at its end. The brass probe or counter electrode 108 extended through a Swagelok® fitting located at the bottom of the vessel holder 50, extending through the vessel holder 50 base structure. The brass probe or counter electrode 108 was grounded to the casing of the RF matching network.

The gas delivery port 110 was connected to a stainless steel assembly comprised of Swagelok® fittings incorporating a manual ball valve for venting, a thermocouple pressure gauge and a bypass valve connected to the vacuum pumping line. In addition, the gas system was connected to the gas delivery port 110 allowing the process gases, oxygen and hexamethyldisiloxane (HMDSO) to be flowed through the gas delivery port 110 (under process pressures) into the interior of the COC syringe barrel.

The gas system was comprised of a Aalborg® GFC17 mass flow meter (Cole Parmer Part #EW-32661-34) for controllably flowing oxygen at 90 sccm (or at the specific flow reported for a particular example) into the process and a PEEK capillary (OD 1/16-inch (3-mm) ID 0.004 inches (0.1 mm)) of length 49.5 inches (1.26 m). The PEEK capillary end was inserted into liquid hexamethyldisiloxane (Alfa Aesar® Part Number L16970, NMR Grade). The liquid HMDSO was pulled through the capillary due to the lower pressure in the COC syringe barrel during processing. The HMDSO was then vaporized into a vapor at the exit of the capillary as it entered the low pressure region.

To ensure no condensation of the liquid HMDSO past this point, the gas stream (including the oxygen) was diverted to the pumping line when it was not flowing into the interior of the COC syringe barrel for processing via a Swagelok® 3-way valve.

Once the COC syringe barrel was installed, the vacuum pump valve was opened to the vessel holder 50 and the interior of the COC syringe barrel. An Alcatel rotary vane vacuum pump and blower comprised the vacuum pump system. The pumping system allowed the interior of the COC syringe barrel to be reduced to pressure(s) of less than 150 mTorr while the process gases were flowing at the indicated rates. A lower pumping pressure was achievable with the COC syringe barrel, as opposed to the tube, because the COC syringe barrel has a much smaller internal volume.

After the base vacuum level was achieved, the vessel holder 50 assembly was moved into the electrode 160 assembly. The gas stream (oxygen and HMDSO vapor) was flowed into the brass gas delivery port 110 (by adjusting the 3-way valve from the pumping line to the gas delivery port 110). The pressure inside the COC syringe barrel was approximately 200 mTorr as measured by a capacitance manometer (MKS) installed on the pumping line near the valve that controlled the vacuum. In addition to the COC syringe barrel pressure, the pressure inside the gas delivery port 110 and gas system was also measured with the thermocouple vacuum gauge that was connected to the gas system. This pressure was typically less than 8 Torr.

When the gas was flowing to the interior of the COC syringe barrel, the RF power supply was turned on to its fixed power level. A ENI ACG-6 600 Watt RF power supply was used (at 13.56 MHz) at a fixed power level of approximately 30 Watts. The RF power supply was connected to a COMDEL CPMX1000 auto match that matched the complex impedance of the plasma (to be created in the COC syringe barrel) to the 50 ohm output impedance of the ENI ACG-6 RF power supply. The forward power was 30 Watts (or whatever value is reported in a working example) and the reflected power was 0 Watts so that the power was delivered to the interior of the COC syringe barrel. The RF power supply was controlled by a laboratory timer and the power on time set to 5 seconds (or the specific time period reported for a particular example).

Upon initiation of the RF power, a uniform plasma was established inside the interior of the COC syringe barrel. The plasma was maintained for the entire 5 seconds (or other coating time indicated in a specific example) until the RF power was terminated by the timer. The plasma produced a silicon oxide coating of approximately 20 nm thickness (or the thickness reported in a specific example) on the interior of the COC syringe barrel surface.

After coating, the gas flow was diverted back to the vacuum line and the vacuum valve was closed. The vent valve was then opened, returning the interior of the COC syringe barrel to atmospheric pressure (approximately 760 Torr). The COC syringe barrel was then carefully removed from the vessel holder 50 assembly (after moving the vessel holder 50 assembly out of the electrode 160 assembly).

Protocol for Coating COC Syringe Barrel Interior with OMCTS Lubricity Layer (Used, e.g., in Examples 11, 12, 15-18, 20)

COC syringe barrels as previously identified were interior coated with a lubricity layer. The apparatus as shown in FIG.

2 with the sealing mechanism of FIG. 45 was modified to hold a COC syringe barrel with butt sealing at the base of the COC syringe barrel. Additionally a cap was fabricated out of a stainless steel Luer fitting and a polypropylene cap that sealed the end of the COC syringe barrel (illustrated in FIG. 26). The installation of a Buna-N O-ring onto the Luer fitting allowed a vacuum tight seal, allowing the interior of the COC syringe barrel to be evacuated.

The vessel holder 50 was made from Delrin® with an outside diameter of 1.75 inches (44 mm) and a height of 1.75 inches (44 mm). The vessel holder 50 was housed in a Delrin® structure that allowed the device to move in and out of the electrode 160.

The electrode 160 was made from copper with a Delrin® shield. The Delrin® shield was conformal around the outside of the copper electrode 160. The electrode 160 measured approximately 3 inches (76 mm) high (inside) and was approximately 0.75 inches (19 mm) wide. The COC syringe barrel was inserted into the vessel holder 50, base sealing with Viton® O-rings around the bottom of the finger flanges and lip of the COC syringe barrel.

The COC syringe barrel was carefully moved into the sealing position over the extended (stationary) ⅛-inch (3-mm.) diameter brass probe or counter electrode 108 and pushed against a copper plasma screen. The copper plasma screen was a perforated copper foil material (K&S Engineering Part #LXMUW5 Copper mesh) cut to fit the outside diameter of the COC syringe barrel and was held in place by a abutment surface 494 that acted as a stop for the COC syringe barrel insertion. Two pieces of the copper mesh were fit snugly around the brass probe or counter electrode 108 insuring good electrical contact.

The probe or counter electrode 108 extended approximately 20 mm (unless otherwise indicated) into the interior of the COC syringe barrel and was open at its end. The brass probe or counter electrode 108 extended through a Swagelok® fitting located at the bottom of the vessel holder 50, extending through the vessel holder 50 base structure. The brass probe or counter electrode 108 was grounded to the casing of the RF matching network.

The gas delivery port 110 was connected to a stainless steel assembly comprised of Swagelok® fittings incorporating a manual ball valve for venting, a thermocouple pressure gauge and a bypass valve connected to the vacuum pumping line. In addition, the gas system was connected to the gas delivery port 110 allowing the process gas, octamethylcyclotetrasiloxane (OMCTS) (or the specific process gas reported for a particular example) to be flowed through the gas delivery port 110 (under process pressures) into the interior of the COC syringe barrel.

The gas system was comprised of a commercially available Horiba VC1310/SEF8240 OMCTS 10SC 4CR heated mass flow vaporization system that heated the OMCTS to about 100° C. The Horiba system was connected to liquid octamethylcyclotetrasiloxane (Alfa Aesar® Part Number A12540, 98%) through a ⅛-inch (3-mm) outside diameter PFA tube with an inside diameter of 1/16 in (1.5 mm). The OMCTS flow rate was set to 1.25 sccm (or the specific organosilicon precursor flow reported for a particular example). To ensure no condensation of the vaporized OMCTS flow past this point, the gas stream was diverted to the pumping line when it was not flowing into the interior of the COC syringe barrel for processing via a Swagelok® 3-way valve.

Once the COC syringe barrel was installed, the vacuum pump valve was opened to the vessel holder 50 and the interior of the COC syringe barrel. An Alcatel rotary vane vacuum pump and blower comprised the vacuum pump system. The pumping system allowed the interior of the COC syringe barrel to be reduced to pressure(s) of less than 100 mTorr while the process gases were flowing at the indicated rates. A lower pressure could be obtained in this instance, compared to the tube and previous COC syringe barrel examples, because the overall process gas flow rate is lower in this instance.

Once the base vacuum level was achieved, the vessel holder 50 assembly was moved into the electrode 160 assembly. The gas stream (OMCTS vapor) was flowed into the brass gas delivery port 110 (by adjusting the 3-way valve from the pumping line to the gas delivery port 110). Pressure inside the COC syringe barrel was approximately 140 mTorr as measured by a capacitance manometer (MKS) installed on the pumping line near the valve that controlled the vacuum. In addition to the COC syringe barrel pressure, the pressure inside the gas delivery port 110 and gas system was also measured with the thermocouple vacuum gauge that was connected to the gas system. This pressure was typically less than 6 Torr.

Once the gas was flowing to the interior of the COC syringe barrel, the RF power supply was turned on to its fixed power level. A ENI ACG-6 600 Watt RF power supply was used (at 13.56 MHz) at a fixed power level of approximately 7.5 Watts (or other power level indicated in a specific example). The RF power supply was connected to a COMDEL CPMX1000 auto match which matched the complex impedance of the plasma (to be created in the COC syringe barrel) to the 50 ohm output impedance of the ENI ACG-6 RF power supply. The forward power was 7.5 Watts and the reflected power was 0 Watts so that 7.5 Watts of power (or a different power level delivered in a given example) was delivered to the interior of the COC syringe barrel. The RF power supply was controlled by a laboratory timer and the power on time set to 10 seconds (or a different time stated in a given example).

Upon initiation of the RF power, a uniform plasma was established inside the interior of the COC syringe barrel. The plasma was maintained for the entire coating time, until the RF power was terminated by the timer. The plasma produced a lubricity layer on the interior of the COC syringe barrel surface.

After coating, the gas flow was diverted back to the vacuum line and the vacuum valve was closed. The vent valve was then opened, returning the interior of the COC syringe barrel to atmospheric pressure (approximately 760 Torr). The COC syringe barrel was then carefully removed from the vessel holder 50 assembly (after moving the vessel holder 50 assembly out of the electrode 160 assembly).

Protocol for Coating COC Syringe Barrel Interior with HMDSO Coating (Used, e.g., in Examples 12, 15, 16, 17)

The Protocol for Coating COC Syringe Barrel Interior with OMCTS Lubricity layer was also used for applying an HMDSO coating, except substituting HMDSO for OMCTS.

Example 1

V. In the following test, hexamethyldisiloxane (HMDSO) was used as the organosilicon ("O—Si") feed to PECVD apparatus of FIG. 2 to apply an $SiO_x$ coating on the internal surface of a cyclic olefin copolymer (COC) tube as described in the Protocol for Forming COC Tube. The deposition conditions are summarized in the Protocol for Coating Tube Interior with $SiO_x$ and Table 1. The control was the same type of tube to which no barrier coating was applied. The coated and uncoated tubes were then tested for their oxygen transmission rate (OTR) and their water vapor transmission rate (WVTR).

V. Referring to Table 1, the uncoated COC tube had an OTR of 0.215 cc/tube/day. Tubes A and B subjected to PECVD for 14 seconds had an average OTR of 0.0235 cc/tube/day. These results show that the $SiO_x$ coating provided an oxygen transmission BIF over the uncoated tube of 9.1. In other words, the $SiO_x$ barrier coating reduced the oxygen transmission through the tube to less than one ninth its value without the coating.

V. Tube C subjected to PECVD for 7 seconds had an OTR of 0.026. This result shows that the $SiO_x$ coating provided an OTR BIF over the uncoated tube of 8.3. In other words, the $SiO_x$ barrier coating applied in 7 seconds reduced the oxygen transmission through the tube to less than one eighth of its value without the coating.

V. The relative WVTRs of the same barrier coatings on COC tubes were also measured. The uncoated COC tube had a WVTR of 0.27 mg/tube/day. Tubes A and B subjected to PECVD for 14 seconds had an average WVTR of 0.10 mg/tube/day or less. Tube C subjected to PECVD for 7 seconds had a WVTR of 0.10 mg/tube/day. This result shows that the $SiO_x$ coating provided a water vapor transmission barrier improvement factor (WVTR BIF) over the uncoated tube of about 2.7. This was a surprising result, since the uncoated COC tube already has a very low WVTR.

Example 2

V. A series of PET tubes, made according to the Protocol for Forming PET Tube, were coated with $SiO_x$ according to the Protocol for Coating Tube Interior with $SiO_x$ under the conditions reported in Table 2. Controls were made according to the Protocol for Forming PET Tube, but left uncoated. OTR and WVTR samples of the tubes were prepared by epoxy-sealing the open end of each tube to an aluminum adaptor.

V. In a separate test, using the same type of coated PET tubes, mechanical scratches of various lengths were induced with a steel needle through the interior coating, and the OTR BIF was tested. Controls were either left uncoated or were the same type of coated tube without an induced scratch. The OTR BIF, while diminished, was still improved over uncoated tubes (Table 2A).

V. Tubes were tested for OTR as follows. Each sample/adaptor assembly was fitted onto a MOCON® Oxtran 2/21 Oxygen Permeability Instrument. Samples were allowed to equilibrate to transmission rate steady state (1-3 days) under the following test conditions:

| Test Gas: | Oxygen |
|---|---|
| Test Gas Concentration: | 100% |
| Test Gas Humidity: | 0% relative humidity |
| Test Gas Pressure: | 760 mmHg |
| Test Temperature: | 23.0° C. (73.4° F.) |
| Carrier Gas: | 98% nitrogen, 2% hydrogen |
| Carrier Gas Humidity: | 0% relative humidity |

V. The OTR is reported as average of two determinations in Table 2.

V. Tubes were tested for WVTR as follows. The sample/adaptor assembly was fitted onto a MOCON® Permatran-W 3/31 Water Vapor Permeability Instrument. Samples were allowed to equilibrate to transmission rate steady state (1-3 days) under the following test conditions:

| Test Gas: | Water Vapor |
|---|---|
| Test Gas Concentration: | NA |
| Test Gas Humidity: | 100% relative humidity |
| Test Gas Temperature: | 37.8(° C.) 100.0(° F.) |
| Carrier Gas: | Dry nitrogen |
| Carrier Gas Humidity: | 0% relative humidity |

V. The WVTR is reported as average of two determinations in Table 2.

Example 3

A series of syringe barrels were made according to the Protocol for Forming COC Syringe barrel. The syringe barrels were either barrier coated with $SiO_x$ or not under the conditions reported in the Protocol for Coating COC Syringe barrel Interior with $SiO_x$ modified as indicated in Table 3.

OTR and WVTR samples of the syringe barrels were prepared by epoxy-sealing the open end of each syringe barrel to an aluminum adaptor. Additionally, the syringe barrel capillary ends were sealed with epoxy. The syringe-adapter assemblies were tested for OTR or WVTR in the same manner as the PET tube samples, again using a MOCON® Oxtran 2/21 Oxygen Permeability Instrument and a MOCON® Permatran-W 3/31 Water Vapor Permeability Instrument. The results are reported in Table 3.

Example 4

Composition Measurement of Plasma Coatings Using X-Ray Photoelectron Spectroscopy (XPS)/Electron Spectroscopy for Chemical Analysis (ESCA) Surface Analysis V.A. PET tubes made according to the Protocol for Forming PET Tube and coated according to the Protocol for Coating Tube Interior with $SiO_x$ were cut in half to expose the inner tube surface, which was then analyzed using X-ray photoelectron spectroscopy (XPS).

V.A. The XPS data was quantified using relative sensitivity factors and a model which assumes a homogeneous layer. The analysis volume is the product of the analysis area (spot size or aperture size) and the depth of information. Photoelectrons are generated within the X-ray penetration depth (typically many microns), but only the photoelectrons within the top three photoelectron escape depths are detected. Escape depths are on the order of 15-35 Å, which leads to an analysis depth of ~50-100 Å. Typically, 95% of the signal originates from within this depth.

V.A. Table 5 provides the atomic ratios of the elements detected. The analytical parameters used in for XPS are as follows:

| Instrument | PHI Quantum 2000 |
|---|---|
| X-ray source | Monochromated $Alk_\alpha$ 1486.6 eV |
| Acceptance Angle | ±23° |
| Take-off angle | 45° |
| Analysis area | 600 μm |
| Charge Correction | C1s 284.8 eV |
| Ion Gun Conditions | $Ar^+$, 1 keV, 2 × 2 mm raster |
| Sputter Rate | 15.6 Å/min ($SiO_2$ Equivalent) |

V.A. XPS does not detect hydrogen or helium. Values given are normalized to Si=1 for the experimental number (last row) using the elements detected, and to O=1 for the uncoated polyethylene terephthalate calculation and example. Detection limits are approximately 0.05 to 1.0 atomic percent. Values given are alternatively normalized to 100% Si+O+C atoms.

V.A. The Inventive Example has an Si/O ratio of 2.4 indicating an $SiO_x$ composition, with some residual carbon from incomplete oxidation of the coating. This analysis demonstrates the composition of an $SiO_x$ barrier layer applied to a polyethylene terephthalate tube according to the present invention.

V.A. Table 4 shows the thickness of the $SiO_x$ samples, determined using TEM according to the following method. Samples were prepared for Focused Ion Beam (FIB) cross-sectioning by coating the samples with a sputtered layer of platinum (50-100 nm thick) using a K575X Emitech coating system. The coated samples were placed in an FEI FIB200 FIB system. An additional layer of platinum was FIB-deposited by injection of an organo-metallic gas while rastering the 30 kV gallium ion beam over the area of interest. The area of interest for each sample was chosen to be a location halfway down the length of the tube. Thin cross sections measuring approximately 15 μm ("micrometers") long, 2 μm wide and 15 μm deep were extracted from the die surface using a proprietary in-situ FIB lift-out technique. The cross sections were attached to a 200 mesh copper TEM grid using FIB-deposited platinum. One or two windows in each section, measuring about 8 μm wide, were thinned to electron transparency using the gallium ion beam of the FEI FIB.

V.C. Cross-sectional image analysis of the prepared samples was performed utilizing a Transmission Electron Microscope (TEM). The imaging data was recorded digitally.

The sample grids were transferred to a Hitachi HF2000 transmission electron microscope. Transmitted electron images were acquired at appropriate magnifications. The relevant instrument settings used during image acquisition are given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | #1 |
| Objective Lens Aperture for imaging | #3 |
| Selective Area Aperture for SAD | N/A |

Example 5

Plasma Uniformity

V.A. COC syringe barrels made according to the Protocol for Forming COC Syringe barrel were treated using the Protocol for Coating COC Syringe Barrel Interior with $SiO_x$, with the following variations. Three different modes of plasma generation were tested for coating syringe barrels such as 250 with $SiO_x$ films. V.A. In Mode 1, hollow cathode plasma ignition was generated in the gas inlet 310, restricted area 292 and processing vessel lumen 304, and ordinary or non-hollow-cathode plasma was generated in the remainder of the vessel lumen 300.

V.A. In Mode 2, hollow cathode plasma ignition was generated in the restricted area 292 and processing vessel lumen 304, and ordinary or non-hollow-cathode plasma was generated in the remainder of the vessel lumen 300 and gas inlet 310.

V.A. In Mode 3, ordinary or non-hollow-cathode plasma was generated in the entire vessel lumen 300 and gas inlet 310. This was accomplished by ramping up power to quench any hollow cathode ignition. Table 6 shows the conditions used to achieve these modes.

V.A. The syringe barrels 250 were then exposed to a ruthenium oxide staining technique. The stain was made from sodium hypochlorite bleach and $Ru^{(III)}$ chloride hydrate. 0.2 g of $Ru^{(III)}$ chloride hydrate was put into a vial. 10 ml bleach were added and mixed thoroughly until the Ru(III) chloride hydrate dissolved.

V.A. Each syringe barrel was sealed with a plastic Luer seal and 3 drops of the staining mixture were added to each syringe barrel. The syringe barrels were then sealed with aluminum tape and allowed to sit for 30-40 minutes. In each set of syringe barrels tested, at least one uncoated syringe barrel was stained. The syringe barrels were stored with the restricted area 292 facing up.

V.A. Based on the staining, the following conclusions were drawn:

V.A. 1. The stain started to attack the uncoated (or poorly coated) areas within 0.25 hours of exposure.

V.A. 2. Ignition in the restricted area 292 resulted in $SiO_x$ coating of the restricted area 292.

V.A. 3. The best syringe barrel was produced by the test with no hollow cathode plasma ignition in either the gas inlet 310 or the restricted area 292. Only the restricted opening 294 was stained, most likely due to leaking of the stain.

V.A. 4. Staining is a good qualitative tool to guide uniformity work.

V.A. Based on all of the above, we concluded:

V.A. 1. Under the conditions of the test, hollow cathode plasma in either the gas inlet 310 or the restricted area 292 led to poor uniformity of the coating.

V.A. 2. The best uniformity was achieved with no hollow cathode plasma in either the gas inlet 310 or the restricted area 292.

Example 6

Interference Patterns from Reflectance Measurements-Prophetic Example

VI.A. Using a UV-Visible Source (Ocean Optics DH2000-BAL Deuterium Tungsten 200-1000 nm), a fiber optic reflection probe (combination emitter/collector Ocean Optics QR400-7 SR/BX with approximately 3 mm probe area), miniature detector (Ocean Optics HR4000CG UV-NIR Spectrometer), and software converting the spectrometer signal to a transmittance/wavelength graph on a laptop computer, an uncoated PET tube Becton Dickinson (Franklin Lakes, N.J., USA) Product No. 366703 13×75 mm (no additives) is scanned (with the probe emitting and collecting light radially from the centerline of the tube, thus normal to the coated surface) both about the inner circumference of the tube and longitudinally along the inner wall of the tube, with the probe, with no observable interference pattern observed. Then a Becton Dickinson Product No. 366703 13×75 mm (no additives) $SiO_x$ plasma-coated BD 366703 tube is coated with a 20 nanometer thick $SiO_2$ coating as described in Protocol for Coating Tube Interior with $SiO_x$. This tube is scanned in a similar manner as the uncoated tube. A clear interference pattern is observed with the coated tube, in which certain wavelengths were reinforced and others canceled in a periodic pattern, indicating the presence of a coating on the PET tube.

Example 7

Enhanced Light Transmission from Integrating Sphere Detection

VI.A. The equipment used was a Xenon light source (Ocean Optics HL-2000-HP-FHSA-20 W output Halogen Lamp Source (185-2000 nm)), an Integrating Sphere detector (Ocean Optics ISP-80-8-I) machined to accept a PET tube into its interior, and HR2000+ES Enhanced Sensitivity UV.VIS spectrometer, with light transmission source and light receiver fiber optic sources (QP600-2-UV-VIS—600 um Premium Optical FIBER, UV/VIS, 2 m), and signal conversion software (SPECTRASUITE—Cross-platform Spectroscopy Operating SOFTWARE). An uncoated PET tube made according to the Protocol for Forming PET Tube was inserted onto a TEFZEL Tube Holder (Puck), and inserted into the integrating sphere. With the Spectrasuite software in absorbance mode, the absorption (at 615 nm) was set to zero. An SiOx coated tube made according to the Protocol for Forming PET Tube and coated according to the Protocol for Coating Tube Interior with SiOx (except as varied in Table 16) was then mounted on the puck, inserted into the integrating sphere and the absorbance recorded at 615 nm wavelength. The data is recorded in Table 16.

VI.A. With the SiOx coated tubes, an increase in absorption relative to the uncoated article was observed; increased coating times resulted in increased absorption. The measurement took less than one second.

VI.A. These spectroscopic methods should not be considered limited by the mode of collection (for example, reflectance vs. transmittance vs. absorbance), the frequency or type of radiation applied, or other parameters.

Example 8

Outgassing Measurement on PET

VI.B. Present FIG. 30, adapted from FIG. 15 of U.S. Pat. No. 6,584,828, is a schematic view of a test set-up that was used in a working example for measuring outgassing through an $SiO_x$ barrier coating 348 applied according to the Protocol for Coating Tube Interior with $SiO_x$ on the interior of the wall 346 of a PET tube 358 made according to the Protocol for Forming PET Tube seated with a seal 360 on the upstream end of a Micro-Flow Technology measurement cell generally indicated at 362.

VI.B. A vacuum pump 364 was connected to the downstream end of a commercially available measurement cell 362 (an Intelligent Gas Leak System with Leak Test Instrument Model ME2, with second generation IMFS sensor, (10µ/min full range), Absolute Pressure Sensor range: 0-10 Torr, Flow measurement uncertainty: +/−5% of reading, at calibrated range, employing the Leak-Tek Program for automatic data acquisition (with PC) and signatures/plots of leak flow vs. time. This equipment is supplied by ATC Inc.), and was configured to draw gas from the interior of the PET vessel 358 in the direction of the arrows through the measurement cell 362 for determination of the mass flow rate outgassed vapor into the vessel 358 from its walls.

VI.B. The measurement cell 362 shown and described schematically here was understood to work substantially as follows, though this information might deviate somewhat from the operation of the equipment actually used. The cell 362 has a conical passage 368 through which the outgassed flow is directed. The pressure is tapped at two longitudinally spaced lateral bores 370 and 372 along the passage 368 and fed respectively to the chambers 374 and 376 formed in part by the diaphragms 378 and 380. The pressures accumulated in the respective chambers 374 and 376 deflect the respective diaphragms 378 and 380. These deflections are measured in a suitable manner, as by measuring the change in capacitance between conductive surfaces of the diaphragms 378 and 380 and nearby conductive surfaces such as 382 and 384. A bypass 386 can optionally be provided to speed up the initial pump-down by bypassing the measurement cell 362 until the desired vacuum level for carrying out the test is reached.

VI.B. The PET walls 350 of the vessels used in this test were on the order of 1 mm thick, and the coating 348 was on the order of 20 nm (nanometers) thick. Thus, the wall 350 to coating 348 thickness ratio was on the order of 50,000:1.

VI.B. To determine the flow rate through the measurement cell 362, including the vessel seal 360, 15 glass vessels substantially identical in size and construction to the vessel 358 were successively seated on the vessel seal 360, pumped down to an internal pressure of 1 Torr, then capacitance data was collected with the measurement cell 362 and converted to an "outgassing" flow rate. The test was carried out two times on each vessel. After the first run, the vacuum was released with nitrogen and the vessels were allowed recovery time to reach equilibrium before proceeding with the second run. Since a glass vessel is believed to have very little outgassing, and is essentially impermeable through its wall, this measurement is understood to be at least predominantly an indication of the amount of leakage of the vessel and connections within the measurement cell 362, and reflects little if any true outgassing or permeation. The results are in Table 7.

VI.B. The family of plots 390 in FIG. 31 shows the "outgas" flow rate, also in micrograms per minute, of individual tubes corresponding to the second run data in previously-mentioned Table 7. Since the flow rates for the plots do not increase substantially with time, and are much lower than the other flow rates shown, the flow rate is attributed to leakage.

VI.B. Table 8 and the family of plots 392 in FIG. 31 show similar data for uncoated tubes made according to the Protocol for Forming PET Tube.

VI.B. This data for uncoated tubes shows much larger flow rates: the increases are attributed to outgas flow of gases captured on or within the inner region of the vessel wall. There is some spread among the vessels, which is indicative of the sensitivity of the test to small differences among the vessels and/or how they are seated on the test apparatus.

VI.B. Table 9 and the families of plots 394 and 396 in FIG. 31 show similar data for an $SiO_x$ barrier coating 348 applied according to the Protocol for Coating PET Tube Interior with $SiO_x$ on the interior of the wall 346 of a PET tube made according to the Protocol for Forming PET Tube.

VI.B. The family of curves 394 for the $SiO_x$ coated, injection-molded PET tubes of this example shows that the $SiO_x$ coating acts as a barrier to limit outgassing from the PET vessel walls, since the flow rate is consistently lower in this test than for the uncoated PET tubes. (The $SiO_x$ coating itself is believed to outgas very little.) The separation between the curves 394 for the respective vessels indicates that this test is sensitive enough to distinguish slightly differing barrier efficacy of the $SiO_x$ coatings on different tubes. This spread in the family 394 is attributed mainly to variations in gas tightness among the $SiO_x$ coatings, as opposed to variations in outgassing among the PET vessel walls or variations in seating integrity (which have a much tighter family 392 of curves).

The two curves 396 for samples 2 and 4 are outliers, as demonstrated below, and their disparity from other data is believed to show that the $SiO_x$ coatings of these tubes are defective. This shows that the present test can very clearly separate out samples that have been processed differently or damaged.

VI.B. Referring to Tables 8 and 9 previously mentioned and FIG. 32, the data was analyzed statistically to find the mean and the values of the first and third standard deviations above and below the mean (average). These values are plotted in FIG. 32.

VI.B. This statistical analysis first shows that samples 2 and 4 of Table 9 representing coated PET tubes are clear outliers, more than +3 standard deviations away from the mean. These outliers are, however, shown to have some barrier efficacy, as their flow rates are still clearly distinguished from (lower than) those of the uncoated PET tubes.

Figure 32:
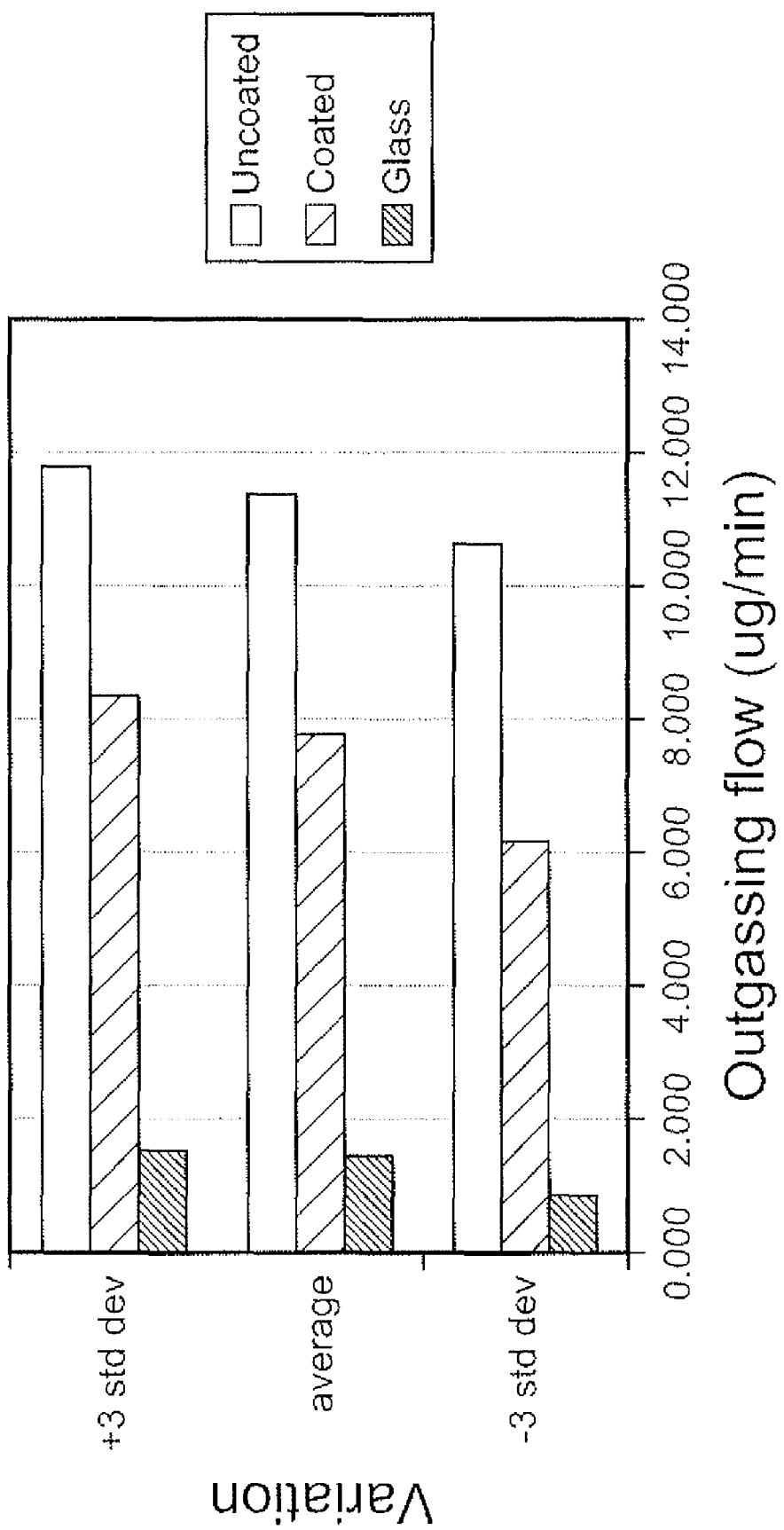
FIG. 32 is a bar graph showing a statistical analysis of the endpoint data shown in FIG. 31.
Figure 33:
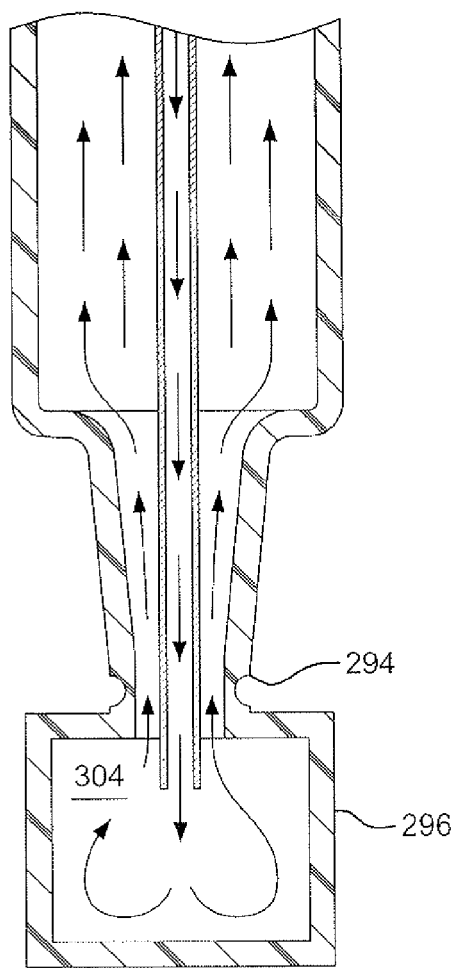
FIG. 33 is a longitudinal section of a combined syringe barrel and gas receiving volume according to another embodiment of the invention.
Figure 35:
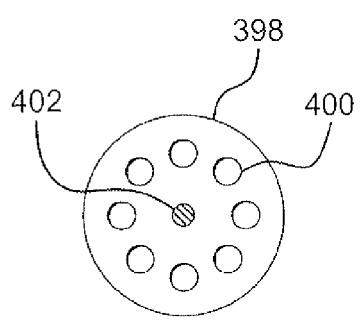
FIG. 35 is a view taken from section lines 35-35 of FIG. 34, showing the distal gas supply openings and extension electrode of FIG. 34.
Figure 34:
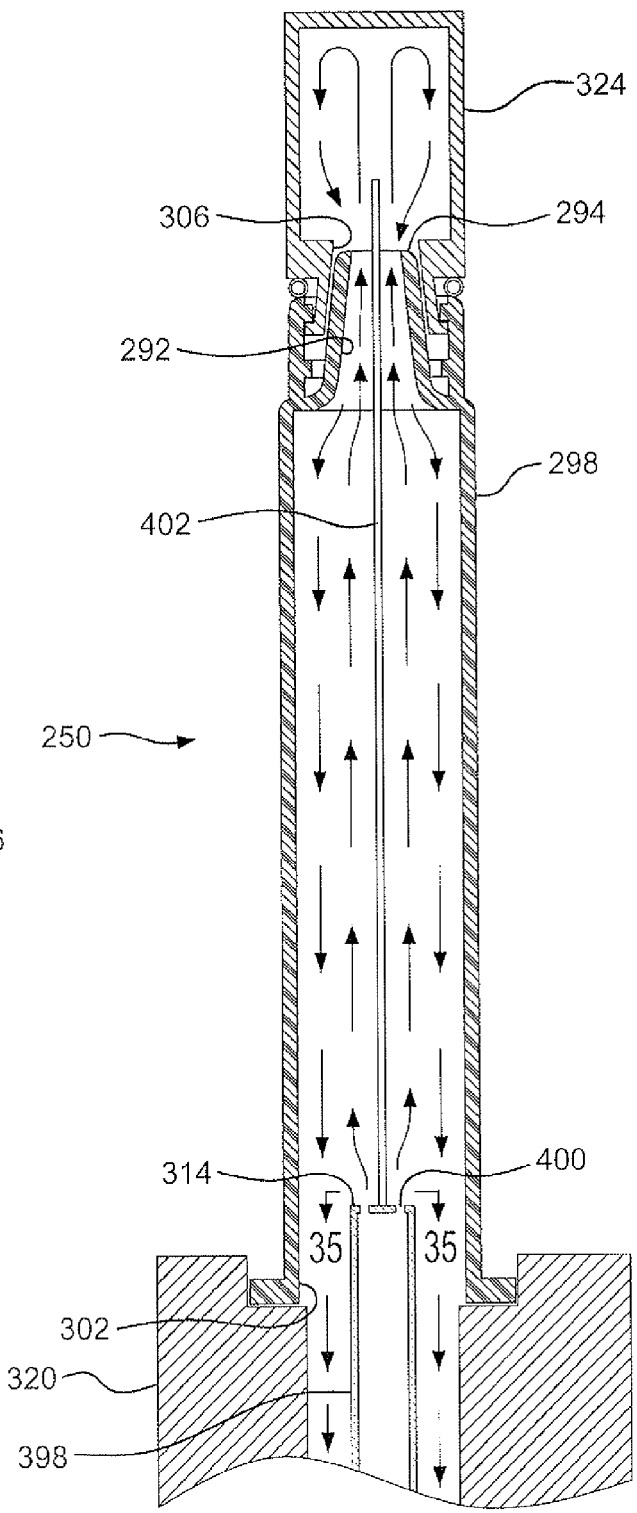
FIG. 34 is a view similar to FIG. 34 of another embodiment of the invention including an electrode extension.

VI.B. This statistical analysis also shows the power of an outgassing measurement to very quickly and accurately analyze the barrier efficacy of nano-thickness barrier coatings and to distinguish coated tubes from uncoated tubes (which are believed to be indistinguishable using the human senses at the present coating thickness). Referring to FIG. 32, coated PET vessels showing a level of outgassing three standard deviations above the mean, shown in the top group of bars, have less outgassing than uncoated PET vessels showing a level of outgassing three standard deviations below the mean, shown in the bottom group of bars. This data shows no overlap of the data to a level of certainty exceeding 6σ (six-sigma).

VI.B. Based on the success of this test, it is contemplated that the presence or absence of an $SiO_x$ coating on these PET vessels can be detected in a much shorter test than this working example, particularly as statistics are generated for a larger number of samples. This is evident, for example from the smooth, clearly separated families of plots even at a time T=12 seconds for samples of 15 vessels, representing a test duration of about one second following the origin at about T=11 seconds.

VI.B. It is also contemplated, based on this data, that a barrier efficacy for $SiO_x$ coated PET vessels approaching that of glass or equal to glass can be obtained by optimizing the $SiO_x$ coating.

Example 9

Wetting Tension-Plasma Coated PET Tube Examples

VII.A.1.a.ii. The wetting tension method is a modification of the method described in ASTM D 2578. Wetting tension is a specific measure for the hydrophobicity or hydrophilicity of a surface. This method uses standard wetting tension solutions (called dyne solutions) to determine the solution that comes nearest to wetting a plastic film surface for exactly two seconds. This is the film's wetting tension.

VII.A.1.a.ii. The procedure utilized is varied from ASTM D 2578 in that the substrates are not flat plastic films, but are tubes made according to the Protocol for Forming PET Tube and (except for controls) coated according to the Protocol for Coating Tube Interior with Hydrophobic layer. A silicone coated glass syringe (Becton Dickinson Hypak® PRTC glass prefillable syringe with Luer-lok® tip) (1 mL) was also tested. The results of this test are listed in Table 10.

VII.A.1.a.ii. Surprisingly, plasma coating of uncoated PET tubes (40 dynes/cm) can achieve either higher (more hydrophilic) or lower (more hydrophobic) energy surfaces using the same hexamethyldisiloxane (HMDSO) feed gas, by varying the plasma process conditions. A thin (approximately 20-40 nanometers) $SiO_x$ coating made according to the Protocol for Coating Tube Interior with $SiO_x$ (data not shown in the tables) provides similar wettability as hydrophilic bulk glass substrates. A thin (less than about 100 nanometers) hydrophobic layer made according to the Protocol for Coating Tube Interior with Hydrophobic layer provides similar non-wettability as hydrophobic silicone fluids (data not shown in the tables).

Example 10

Vacuum Retention Study of Tubes Via Accelerated Ageing

VII.A.3 Accelerated ageing offers faster assessment of long term shelf-life products. Accelerated ageing of blood tubes for vacuum retention is described in U.S. Pat. No. 5,792,940, Column 1, Lines 11-49.

VII.A.3 Three types of polyethylene terephthalate (PET) 13×75 mm (0.85 mm thick walls) molded tubes were tested:
Becton Dickinson Product No. 366703 13×75 mm (no additives) tube (shelf life 545 days or 18 months), closed with Hemogard® system red stopper and uncolored guard [commercial control];
PET tubes made according to the Protocol for Forming PET Tube, closed with the same type of Hemogard® system red stopper and uncolored guard [internal control]; and
injection molded PET 13×75 mm tubes, made according to the Protocol for Forming PET Tube, coated according to the Protocol for Coating Tube Interior with $SiO_x$, closed with the same type of Hemogard® system red stopper and uncolored guard [inventive sample].

VII.A.3 The BD commercial control was used as received. The internal control and inventive samples were evacuated and capped with the stopper system to provide the desired partial pressure (vacuum) inside the tube after sealing. All samples were placed into a three gallon (3.8 L) 304 SS wide mouth pressure vessel (Sterlitech No. 740340). The pressure vessel was pressurized to 48 psi (3.3 atm, 2482 mm.Hg). Water volume draw change determinations were made by (a) removing 3-5 samples at increasing time intervals, (b) permitting water to draw into the evacuated tubes through a 20 gauge blood collection adaptor from a one liter plastic bottle reservoir, (c) and measuring the mass change before and after water draw.

VII.A.3 Results are indicated on Table 11.

VII.A.3 The Normalized Average Decay Rate is calculated by dividing the time change in mass by the number of pressurization days and initial mass draw [mass change/(days× initial mass)]. The Accelerated Time to 10% Loss (months) is also calculated. Both data are listed in Table 12.

VII.A.3 This data indicates that both the commercial control and uncoated internal control have identical vacuum loss rates, and surprisingly, incorporation of a $SiO_x$ coating on the PET interior walls improves vacuum retention time by a factor of 2.1.

Example 11

Lubricity Layers

VII.B.1.a. The following materials were used in this test:
Commercial (BD Hypak® PRTC) glass prefillable syringes with Luer-lok® tip (ca 1 mL)
COC syringe barrels made according to the Protocol for Forming COC Syringe barrel;

Commercial plastic syringe plungers with elastomeric tips taken from Becton Dickinson Product No. 306507 (obtained as saline prefilled syringes);

Normal saline solution (taken from the Becton-Dickinson Product No. 306507 prefilled syringes);

Dillon Test Stand with an Advanced Force Gauge (Model AFG-50N)

Syringe holder and drain jig (fabricated to fit the Dillon Test Stand)

VII.B.1.a. The following procedure was used in this test.

VII.B.1.a. The jig was installed on the Dillon Test Stand. The platform probe movement was adjusted to 6 in/min (2.5 mm/sec) and upper and lower stop locations were set. The stop locations were verified using an empty syringe and barrel. The commercial saline-filled syringes were labeled, the plungers were removed, and the saline solution was drained via the open ends of the syringe barrels for re-use. Extra plungers were obtained in the same manner for use with the COC and glass barrels.

VII.B.1.a. Syringe plungers were inserted into the COC syringe barrels so that the second horizontal molding point of each plunger was even with the syringe barrel lip (about 10 mm from the tip end). Using another syringe and needle assembly, the test syringes were filled via the capillary end with 2-3 milliliters of saline solution, with the capillary end uppermost. The sides of the syringe were tapped to remove any large air bubbles at the plunger/fluid interface and along the walls, and any air bubbles were carefully pushed out of the syringe while maintaining the plunger in its vertical orientation.

VII.B.1.a. Each filled syringe barrel/plunger assembly was installed into the syringe jig. The test was initiated by pressing the down switch on the test stand to advance the moving metal hammer toward the plunger. When the moving metal hammer was within 5 mm of contacting the top of the plunger, the data button on the Dillon module was repeatedly tapped to record the force at the time of each data button depression, from before initial contact with the syringe plunger until the plunger was stopped by contact with the front wall of the syringe barrel.

VII.B.1.a. All benchmark and coated syringe barrels were run with five replicates (using a new plunger and barrel for each replicate).

VII.B.1.a. COC syringe barrels made according to the Protocol for Forming COC Syringe barrel were coated with an OMCTS lubricity layer according to the Protocol for Coating COC Syringe Barrel Interior with OMCTS Lubricity layer, assembled and filled with saline, and tested as described above in this Example for lubricity layers. The polypropylene chamber used per the Protocol for Coating COC Syringe Barrel Interior with OMCTS Lubricity layer allowed the OMCTS vapor (and oxygen, if added—see Table 13) to flow through the syringe barrel and through the syringe capillary into the polypropylene chamber (although a lubricity layer can not be needed in the capillary section of the syringe in this instance). Several different coating conditions were tested, as shown in previously mentioned Table 13. All of the depositions were completed on COC syringe barrels from the same production batch.

The coated samples were then tested using the plunger sliding force test per the protocol of this Example, yielding the results in Table 13, in English and metric force units. The data shows clearly that low power and no oxygen provided the lowest plunger sliding force for COC and coated COC syringes. Note that when oxygen was added at lower power (6 W) (the lower power being a favorable condition) the plunger sliding force increased from 1.09 lb, 0.49 Kg (at Power=11 W) to 2.27 lb., 1.03 Kg. This indicates that the addition of oxygen can not be desirable to achieve the lowest possible plunger sliding force.

VII.B.1.a. Note also that the best plunger sliding force (Power=11 W, plunger sliding force=1.09 lb, 0.49 Kg) was very near the current industry standard of silicone coated glass (plunger sliding force=0.58 lb, 0.26 Kg), while avoiding the problems of a glass syringe such as breakability and a more expensive manufacturing process. With additional optimization, values equal to or better than the current glass with silicone performance are expected to be achieved.

VII.B.1.a. The samples were created by coating COC syringe barrels according to the Protocol for Coating COC Syringe Barrel Interior with OMCTS Lubricity layer. An alternative embodiment of the technology herein, would apply the lubricity layer over another thin film coating, such as $SiO_x$, for example applied according to the Protocol for Coating COC Syringe barrel Interior with $SiO_x$.

Example 12

Improved Syringe Barrel Lubricity Layer

VII.B.1.a. The force required to expel a 0.9 percent saline payload from a syringe through a capillary opening using a plastic plunger was determined for inner wall-coated syringes.

VII.B.1.a. Three types of COC syringe barrels made according to the Protocol for Forming COC Syringe barrel were tested: one type having no internal coating [Uncoated Control], another type with a hexamethyldisiloxane (HMDSO)-based plasma coated internal wall coating [HMDSO Control] according to the Protocol for Coating COC Syringe Barrel Interior with HMDSO Coating, and a third type with an octamethylcyclotetrasiloxane [OMCTS-Inventive Example]-based plasma coated internal wall coating applied according to the Protocol for Coating COC Syringe Barrel Interior with OMCTS Lubricity layer. Fresh plastic plungers with elastomeric tips taken from BD Product Becton-Dickinson Product No. 306507 were used for all examples. Saline from Product No. 306507 was also used.

VII.B.1.a. The plasma coating method and apparatus for coating the syringe barrel inner walls is described in other experimental sections of this application. The specific coating parameters for the HMDSO-based and OMCTS-based coatings are listed in the Protocol for Coating COC Syringe Barrel Interior with HMDSO Coating, the Protocol for Coating COC Syringe barrel Interior with OMCTS Lubricity layer, and Table 14.

VII.B.1.a. The plunger is inserted into the syringe barrel to about 10 millimeters, followed by vertical filling of the experimental syringe through the open syringe capillary with a separate saline-filled syringe/needle system. When the experimental syringe has been filled into the capillary opening, the syringe is tapped to permit any air bubbles adhering to the inner walls to release and rise through the capillary opening.

VII.B.1.a. The filled experimental syringe barrel/plunger assembly is placed vertically into a home-made hollow metal jig, the syringe assembly being supported on the jig at the finger flanges. The jig has a drain tube at the base and is mounted on Dillon Test Stand with Advanced Force Gauge (Model AFG-50N). The test stand has a metal hammer, moving vertically downward at a rate of six inches (152 millimeters) per minute. The metal hammer contacts the extended plunger expelling the saline solution through the capillary.

Once the plunger has contacted the syringe barrel/capillary interface the experiment is stopped.

VII.B.1.a. During downward movement of the metal hammer/extended plunger, resistance force imparted on the hammer as measured on the Force Gauge is recorded on an electronic spreadsheet. From the spreadsheet data, the maximum force for each experiment is identified.

VII.B.1.a. Table 14 lists for each Example the Maximum Force average from replicate coated COC syringe barrels and the Normalized Maximum Force as determined by division of the coated syringe barrel Maximum Force average by the uncoated Maximum Force average.

VII.B.1.a. The data indicates all OMCTS-based inner wall plasma coated COC syringe barrels (Inventive Examples C,E, F,G,H) demonstrate much lower plunger sliding force than uncoated COC syringe barrels (uncoated Control Examples A & D) and surprisingly, also much lower plunger sliding force than HMDSO-based inner wall plasma coated COC syringe barrels (HMDSO control Example B). More surprising, an OMCTS-based coating over a silicon oxide ($SiO_x$) gas barrier coating maintains excellent low plunger sliding force (Inventive Example F). The best plunger sliding force was Example C (Power=8, plunger sliding force=1.1 lb, 0.5 Kg). It was very near the current industry standard of silicone coated glass (plunger sliding force=0.58 lb., 0.26 Kg.), while avoiding the problems of a glass syringe such as breakability and a more expensive manufacturing process. With additional optimization, values equal to or better than the current glass with silicone performance are expected to be achieved.

Example 13

Fabrication of COC Syringe Barrel with Exterior Coating-Prophetic Example

VII.B.1.c. A COC syringe barrel formed according to the Protocol for Forming COC Syringe barrel is sealed at both ends with disposable closures. The capped COC syringe barrel is passed through a bath of Daran® 8100 Saran Latex (Owensboro Specialty Plastics). This latex contains five percent isopropyl alcohol to reduce the surface tension of the composition to 32 dynes/cm). The latex composition completely wets the exterior of the COC syringe barrel. After draining for 30 seconds, the coated COC syringe barrel is exposed to a heating schedule comprising 275° F. (135° C.) for 25 seconds (latex coalescence) and 122° F. (50° C.) for four hours (finish cure) in respective forced air ovens. The resulting PVdC film is 1/10 mil (2.5 microns) thick. The COC syringe barrel and PVdC-COC laminate COC syringe barrel are measured for OTR and WVTR using a MOCON brand Oxtran 2/21 Oxygen Permeability Instrument and Permatran-W 3/31 Water Vapor Permeability Instrument, respectively.

VII.B.1.c. Predicted OTR and WVTR values are listed in Table 15, which shows the expected Barrier Improvement Factor (BIF) for the laminate would be 4.3 (OTR-BIF) and 3.0 (WVTR-BIF), respectively.

Example 15

Atomic Compositions of PECVD Applied OMCTS and HMDSO Coatings

VII.B.4. COC syringe barrel samples made according to the Protocol for Forming COC Syringe barrel, coated with OMCTS (according to the Protocol for Coating COC Syringe Barrel Interior with OMCTS Lubricity layer) or coated with HMDSO according to the Protocol for Coating COC Syringe Barrel Interior with HMDSO Coating were provided. The atomic compositions of the coatings derived from OMCTS or HMDSO were characterized using X-Ray Photoelectron Spectroscopy (XPS).

VII.B.4. XPS data is quantified using relative sensitivity factors and a model that assumes a homogeneous layer. The analysis volume is the product of the analysis area (spot size or aperture size) and the depth of information. Photoelectrons are generated within the X-ray penetration depth (typically many microns), but only the photoelectrons within the top three photoelectron escape depths are detected. Escape depths are on the order of 15-35 Å, which leads to an analysis depth of ~50-100 Å. Typically, 95% of the signal originates from within this depth.

VII.B.4. The following analytical parameters were used:

| | |
|---|---|
| Instrument: | PHI Quantum 2000 |
| x-ray source: | Monochromated Alkα 1486.6 eV |
| Acceptance Angle | +23° |
| Take-off angle | 45° |
| Analysis area | 600 μm |
| Charge Correction | C1s 284.8 eV |
| Ion Gun Conditions | Ar+, 1 keV, 2 × 2 mm raster |
| Sputter Rate | 15.6 Å/min ($SiO_2$ Equivalent) |

VII.B.4. Table 17 provides the atomic concentrations of the elements detected. XPS does not detect hydrogen or helium. Values given are normalized to 100 percent using the elements detected. Detection limits are approximately 0.05 to 1.0 atomic percent.

VII.B.4. From the coating composition results and calculated starting monomer precursor elemental percent in Table 17, while the carbon atom percent of the HMDSO-based coating is decreased relative to starting HMDSO monomer carbon atom percent (54.1% down to 44.4%), surprisingly the OMCTS-based coating carbon atom percent is increased relative to the OMCTS monomer carbon atom percent (34.8% up to 48.4%), an increase of 39 atomic %, calculated as follows:

$$100\% \; [(48.4/34.8)-1]=39 \text{ at. \%}.$$

Also, while the silicon atom percent of the HMDSO-based coating is almost unchanged relative to starting HMDSO monomer silicon atom percent (21.8% to 22.2%), surprisingly the OMCTS-based coating silicon atom percent is significantly decreased relative to the OMCTS monomer silicon atom percent (42.0% down to 23.6%), a decrease of 44 atomic %. With both the carbon and silicon changes, the OMCTS monomer to coating behavior does not trend with that observed in common precursor monomers (e.g. HMDSO). See, e.g., Hans J. Griesser, Ronald C. Chatelier, Chris Martin, Zoran R. Vasic, Thomas R. Gengenbach, George Jessup J. Biomed. Mater. Res. (Appl Biomater) 53: 235-243, 2000.

Example 16

Volatile Components from Plasma Coatings ("Outgassing")

VII.B.4. COC syringe barrel samples made according to the Protocol for Forming COC SyrinRge barrel, coated with OMCTS (according to the Protocol for Coating COC Syringe Barrel Interior with OMCTS Lubricity layer) or with HMDSO (according to the Protocol for Coating COC Syringe Barrel Interior with HMDSO Coating) were provided. Outgassing gas chromatography/mass spectroscopy (GC/MS)

analysis was used to measure the volatile components released from the OMCTS or HMDSO coatings.

VII.B.4. The syringe barrel samples (four COC syringe barrels cut in half lengthwise) were placed in one of the 1½" (37 mm) diameter chambers of a dynamic headspace sampling system (CDS 8400 auto-sampler). Prior to sample analysis, a system blank was analyzed. The sample was analyzed on an Agilent 7890A Gas Chromatograph/Agilent 5975 Mass Spectrometer, using the following parameters, producing the data set out in Table 18:

| | |
|---|---|
| GC Column: | 30 m × 0.25 mm DB-5MS (J&W Scientific), 0.25 µm film thickness |
| Flow rate: | 1.0 ml/min, constant flow mode |
| Detector: | Mass Selective Detector (MSD) |
| Injection Mode: | Split injection (10:1 split ratio) |
| Outgassing Conditions: | 1½ " (37 mm) Chamber, purge for three hour at 85° C., flow 60 ml/min |
| Oven temperature: | 40° C. (5 min.) to 300° C. @10° C./min.; hold for 5 min. at 300° C. |

The outgassing results from Table 18 clearly indicated a compositional differentiation between the HMDSO-based and OMCTS-based lubricity layers tested. HMDSO-based compositions outgassed trimethylsilanol [$(Me)_3SiOH$] but outgassed no measured higher oligomers containing repeating -$(Me)_2SiO$— moieties, while OMCTS-based compositions outgassed no measured trimethylsilanol [$(Me)_3SiOH$] but outgassed higher oligomers containing repeating -$(Me)_2SiO$— moieties. It is contemplated that this test can be useful for differentiating HMDSO-based coatings from OMCTS-based coatings.

Without limiting the invention according to the scope or accuracy of the following theory, it is contemplated that this result can be explained by considering the cyclic structure of OMCTS, with only two methyl groups bonded to each silicon atom, versus the acyclic structure of HMDSO, in which each silicon atom is bonded to three methyl groups. OMCTS is contemplated to react by ring opening to form a diradical having repeating -$(Me)_2SiO$— moieties which are already oligomers, and can condense to form higher oligomers. HMDSO, on the other hand, is contemplated to react by cleaving at one O—Si bond, leaving one fragment containing a single O—Si bond that recondenses as $(Me)_3SiOH$ and the other fragment containing no O—Si bond that recondenses as [$(Me)_3Si$]$_2$.

The cyclic nature of OMCTS is believed to result in ring opening and condensation of these ring-opened moieties with outgassing of higher MW oligomers (26 ng/test). In contrast, HMDSO-based coatings are believed not to provide any higher oligomers, based on the relatively low-molecular-weight fragments from HMDSO.

Example 17

Density Determination of Plasma Coatings Using X-Ray Reflectivity (XRR)

VII. B. 4. Sapphire witness samples (0.5×0.5×0.1 cm) were glued to the inner walls of separate PET tubes, made according to the Protocol for Forming PET tubes. The sapphire witness-containing PET tubes were coated with OMCTS or HMDSO (both according to the Protocol for Coating COC Syringe Barrel Interior with OMCTS Lubricity layer, deviating all with 2× power). The coated sapphire samples were then removed and X-ray reflectivity (XRR) data were acquired on a PANalytical X'Pert diffractometer equipped with a parabolic multilayer incident beam monochromator and a parallel plate diffracted beam collimator. A two layer $Si_wO_xC_yH_z$ model was used to determine coating density from the critical angle measurement results. This model is contemplated to offer the best approach to isolate the true $Si_wO_xC_yH_z$ coating. The results are shown in Table 19.

VII. B. 4. From Table 17 showing the results of Example 15, the lower oxygen (28%) and higher carbon (48.4%) composition of OMCTS versus HMDSO would suggest OMCTS should have a lower density, due to both atomic mass considerations and valency (oxygen=2; carbon=4). Surprisingly, the XRR density results indicate the opposite would be observed, that is, the OMCTS density is higher than HMDSO density.

VII. B. 4. Without limiting the invention according to the scope or accuracy of the following theory, it is contemplated that there is a fundamental difference in reaction mechanism in the formation of the respective HMDSO-based and OMCTS-based coatings. HMDSO fragments can more easily nucleate or react to form dense nanoparticles which then deposit on the surface and react further on the surface, whereas OMCTS is much less likely to form dense gas phase nanoparticles. OMCTS reactive species are much more likely to condense on the surface in a form much more similar to the original OMCTS monomer, resulting in an overall less dense coating.

Example 18

Thickness Uniformity of PECVD Applied Coatings

VII. B. 4. Samples were provided of COC syringe barrels made according to the Protocol for Forming COC Syringe barrel and respectively coated with $SiO_x$ according to the Protocol for Coating COC Syringe Barrel Interior with $SiO_x$ or an OMCTS-based lubricity layer according to the Protocol for Coating COC Syringe Barrel Interior with OMCTS Lubricity layer. Samples were also provided of PET tubes made according to the Protocol for Forming PET Tube, respectively coated and uncoated with $SiO_x$ according to the Protocol for Coating Tube Interior with $SiO_x$ and subjected to an accelerated aging test. Transmission electron microscopy (TEM) was used to measure the thickness of the PECVD-applied coatings on the samples. The previously stated TEM procedure of Example 4 was used. The method and apparatus described by the SiOx and lubricity layer protocols used in this example demonstrated uniform coating as shown in Table 20.

Example 19

Outgassing Measurement on COC

VI.B. COC tubes were made according to the Protocol for Forming COC Tube. Some of the tubes were provided with an interior barrier coating of SiOx according to the Protocol for Coating Tube Interior with $SiO_x$, and other COC tubes were uncoated. Commercial glass blood collection Becton Dickinson 13×75 mm tubes having similar dimensions were also provided as above. The tubes were stored for about 15 minutes in a room containing ambient air at 45% relative humidity and 70° F. (21° C.), and the following testing was done at the same ambient relative humidity. The tubes were tested for outgassing following the ATC microflow measurement procedure and equipment of Example 8 (an Intelligent Gas Leak System with Leak Test Instrument Model ME2, with second generation IMFS sensor, (10µ/min full range), Absolute Pressure Sensor range: 0-10 Torr, Flow measurement uncertainty: +/−5% of reading, at calibrated range, employing the Leak-Tek Program for automatic data acquisition (with PC) and signatures/plots of leak flow vs. time). In the present case each tube was subjected to a 22-second bulk moisture degassing step at a pressure of 1 mm Hg, was pressurized with nitrogen gas for 2 seconds (to 760 millimeters Hg), then the nitrogen gas was pumped down and the microflow measurement step was carried out for about one minute at 1 millimeter Hg pressure.

Figure 57:
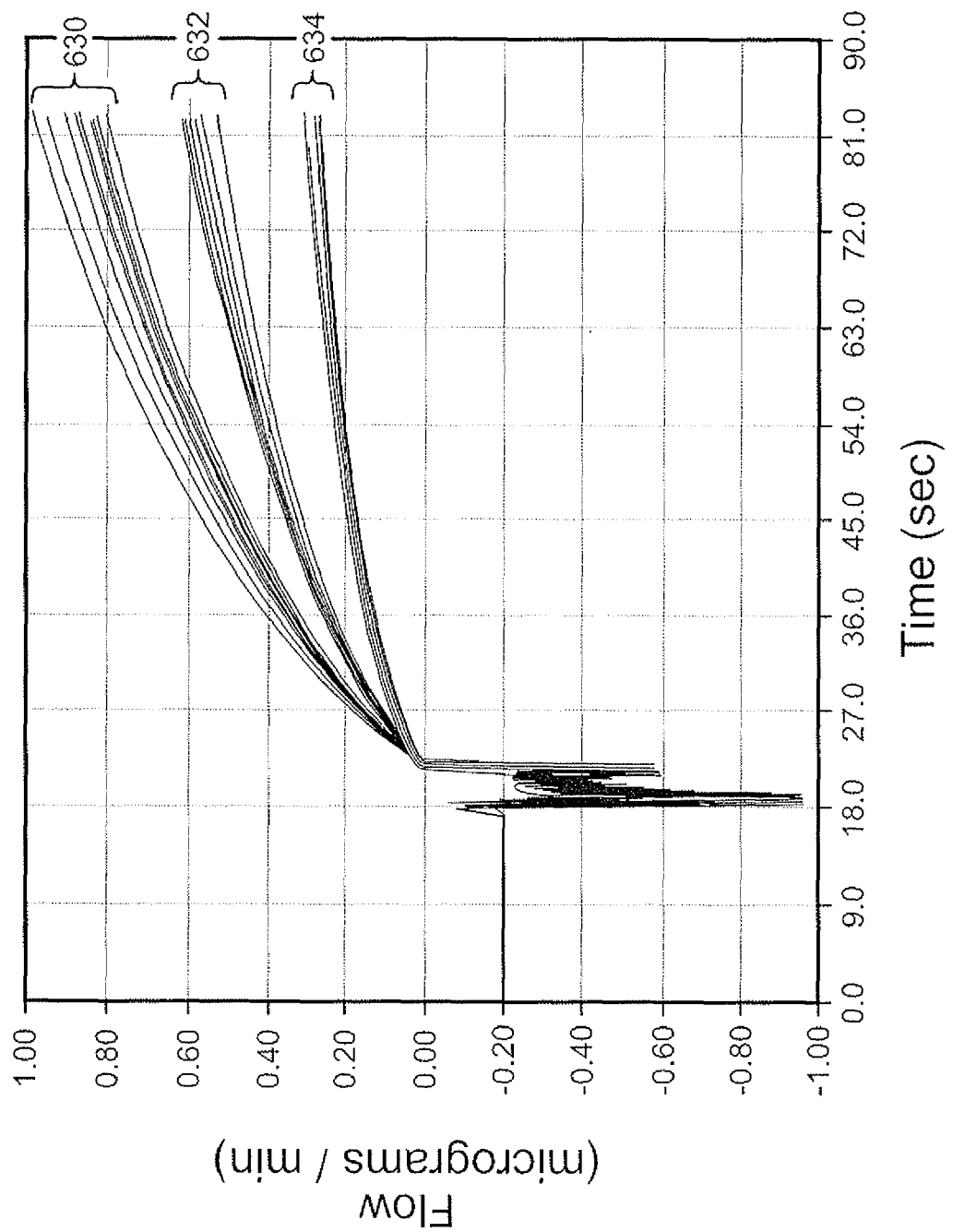
FIG. 57 is a plot of outgassing mass flow rate measured in Example 19.

VI.B. The result is shown in FIG. 57, which is similar to FIG. 31 generated in Example 8. In FIG. 57, the plots for the uncoated COC tubes are at 630, the plots for the SiOx coated COC tubes are at 632, and the plots for the glass tubes used as a control are at 634. Again, the outgassing measurement began at about 4 seconds, and a few seconds later the plots 630 for the uncoated COC tubes and the plots 632 for the SiOx barrier coated tubes clearly diverged, again demonstrating rapid differentiation between barrier coated tubes and uncoated tubes. A consistent separation of uncoated COC (>2 micrograms at 60 seconds) versus $SiO_x$-coated COC (less than 1.6 micrograms at 60 seconds) was realized.

Example 20

Lubricity Layers

VII.B.1.a. COC syringe barrels made according to the Protocol for Forming COC Syringe Barrel were coated with a lubricity layer according to the Protocol for Coating COC Syringe Barrel Interior with OMCTS Lubricity layer. The results are provided in Table 21. The results show that the trend of increasing the power level, in the absence of oxygen, from 8 to 14 Watts was to improve the lubricity of the coating. Further experiments with power and flow rates can provide further enhancement of lubricity.

Example 21

Lubricity Layers—Hypothetical Example

VII. B. 4. Injection molded cyclic olefin copolymer (COC) plastic syringe barrels are made according to the Protocol for Forming COC Syringe Barrel. Some are uncoated ("control") and others are PECVD lubricity coated according to the Protocol for Coating COC Syringe Barrel Interior with OMCTS Lubricity layer ("lubricated syringe"). The lubricated syringes and controls are tested to measure the force to initiate movement of the plunger in the barrel (breakout force) and the force to maintain movement of the plunger in the barrel (plunger sliding force) using a Genesis Packaging Automated Syringe Force Tester, Model AST.

VII. B. 4. The test is a modified version of the ISO 7886-1:1993 test. The following procedure is used for each test. A fresh plastic plunger with elastomeric tip taken from Becton Dickinson Product No. 306507 (obtained as saline prefilled syringes) is removed from the syringe assembly. The elastomeric tip is dried with clean dry compressed air. The elastomeric tip and plastic plunger are then inserted into the COC plastic syringe barrel to be tested with the plunger positioned even with the bottom of the syringe barrel. The filled syringes are then conditioned as necessary to achieve the state to be tested. For example, if the test object is to find out the effect of lubricant coating on the breakout force of syringes after storing the syringes for three months, the syringes are stored for three months to achieve the desired state.

VII. B. 4. The syringe is installed into a Genesis Packaging Automated Syringe Force Tester. The tester is calibrated at the start of the test per the manufacturer's specification. The tester, input variables are Speed=100 mm/minute, Range=10, 000. The start button is pushed on the tester. At completion of the test, the breakout force (to initiate movement of the plunger in the barrel) and the plunger sliding force (to maintain movement) are measured, and are found to be substantially lower for the lubricated syringes than for the control syringes.

Figure 59:
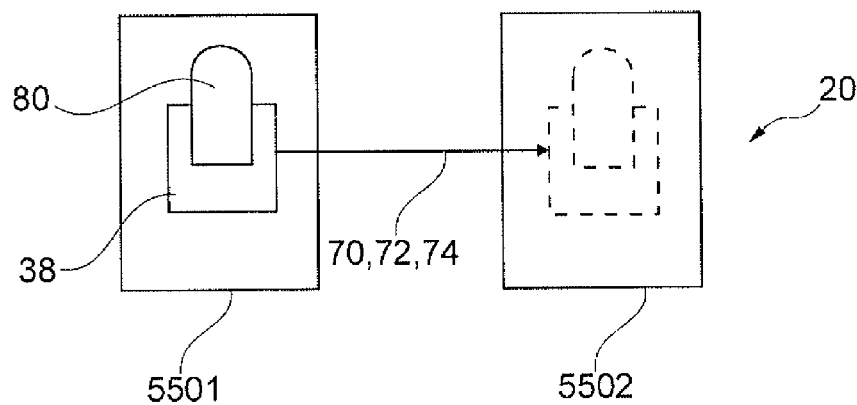
FIG. 59 shows a schematic representation of a vessel processing system according to an exemplary embodiment of the present invention.

I. FIG. 59 shows a vessel processing system 20 according to an exemplary embodiment of the present invention. The vessel processing system 20 comprises, inter alia, a first processing station 5501 and a second processing station 5502. Examples for such processing stations are for example depicted in FIG. 1, reference numerals 24, 26, 28, 30, 32 and 34.

I. The first vessel processing system 5501 contains a vessel holder 38 which holds a seated vessel 80. Although FIG. 59 depicts a blood tube 80, the vessel can also be, for example, a syringe body, a vial, a cuvette, a catheter or a pipette. The vessel can, for example, be made of glass or plastic. In case of plastic vessels, the first processing station can also comprise a mold for molding the plastic vessel.

I. After the first processing at the first processing station (which processing can comprise molding of the vessel, a first inspection of the vessel for defects, coating of the interior surface of the vessel and a second inspection of the vessel for defects, for example of the interior coating), the vessel holder 38 is transported together with the vessel 80 to a second vessel processing station 5502. This transportation is performed by a conveyor arrangement 70, 72, 74. For example, a gripper or several grippers can be provided for gripping the vessel holder 38 and/or the vessel 80 in order to move the vessel/holder combination to the next processing station 5502. Alternatively, only the vessel can be moved without the holder. However, it can be advantageous to move the holder together with the vessel in which case the holder is adapted such that it can be transported by the conveyor arrangement.

Figure 60:
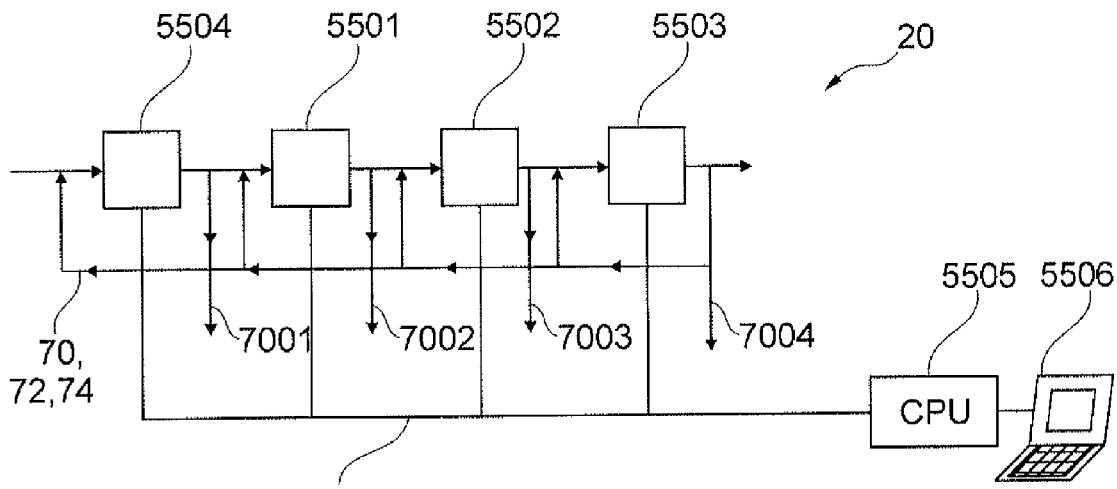
FIG. 60 shows a schematic representation of a vessel processing system according to another exemplary embodiment of the present invention.

I. FIG. 60 shows a vessel processing system 20 according to another exemplary embodiment of the present invention. Again, two vessel processing stations 5501, 5502 are provided. Furthermore, additional vessel processing stations 5503, 5504 are provided which are arranged in series and in which the vessel can be processed, i.e. inspected and/or coated.

I. A vessel can be moved from a stock or holding area to the left processing station 5504. Alternatively, the vessel can be molded in the first processing station 5504. In any case, a first vessel processing step is performed in the processing station 5504, such as molding, inspection and/or coating, which can be followed by a second inspection. Then, the vessel is moved to the next processing station 5501 via the conveyor arrangement 70, 72, 74. Typically, the vessel is moved together with the vessel holder. Additional processing is performed in the second processing station 5501 after which the vessel and holder are moved to the next processing station 5502 in which more processing is performed. The vessel is then moved (again together with the holder) to the fourth processing station 5503 for a fourth processing, after which it is conveyed to storage.

I. Before and after each coating step or molding step or any other step which manipulates the vessel an inspection of the whole vessel, of part of the vessel and for example of an interior surface of the vessel can be performed. The result of each inspection can be transferred to a central processing unit 5505 via a data bus 5507. Each processing station can be connected to the data bus 5507. The processor 5505, which can be adapted in form of a central control and regulation unit, processes the inspection data, analyzes the data and determines whether the last processing step was successful.

I. If it is determined that the last processing step was not successful, because for example the coating comprises gaps or because the surface of the coating is determined to be irregular or not smooth enough, the vessel does not enter the next processing station but is either removed from the production process (see conveyor sections 7001, 7002, 7003, 7004) or conveyed back in order to be re-processed.

I. The processor 5505 is connected to a user interface 5506 for inputting control or regulation parameters.

Figure 61:
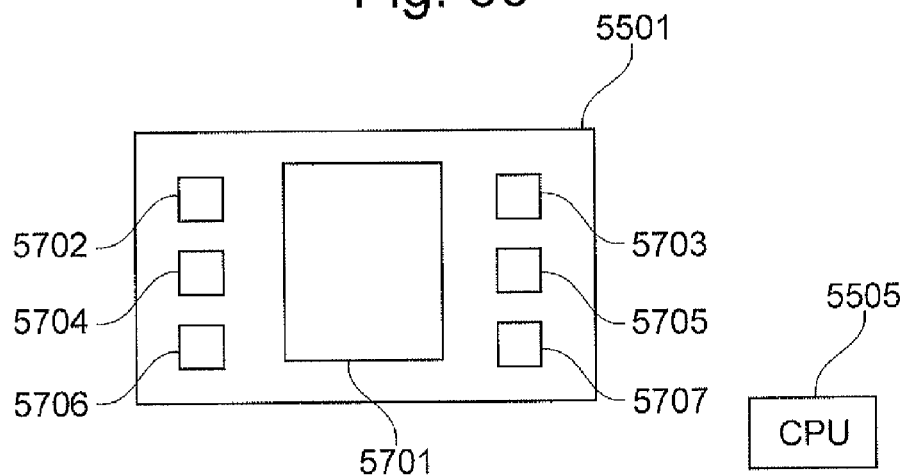
FIG. 61 shows a processing station of a vessel processing system according to an exemplary embodiment of the present invention.
Figure 62:
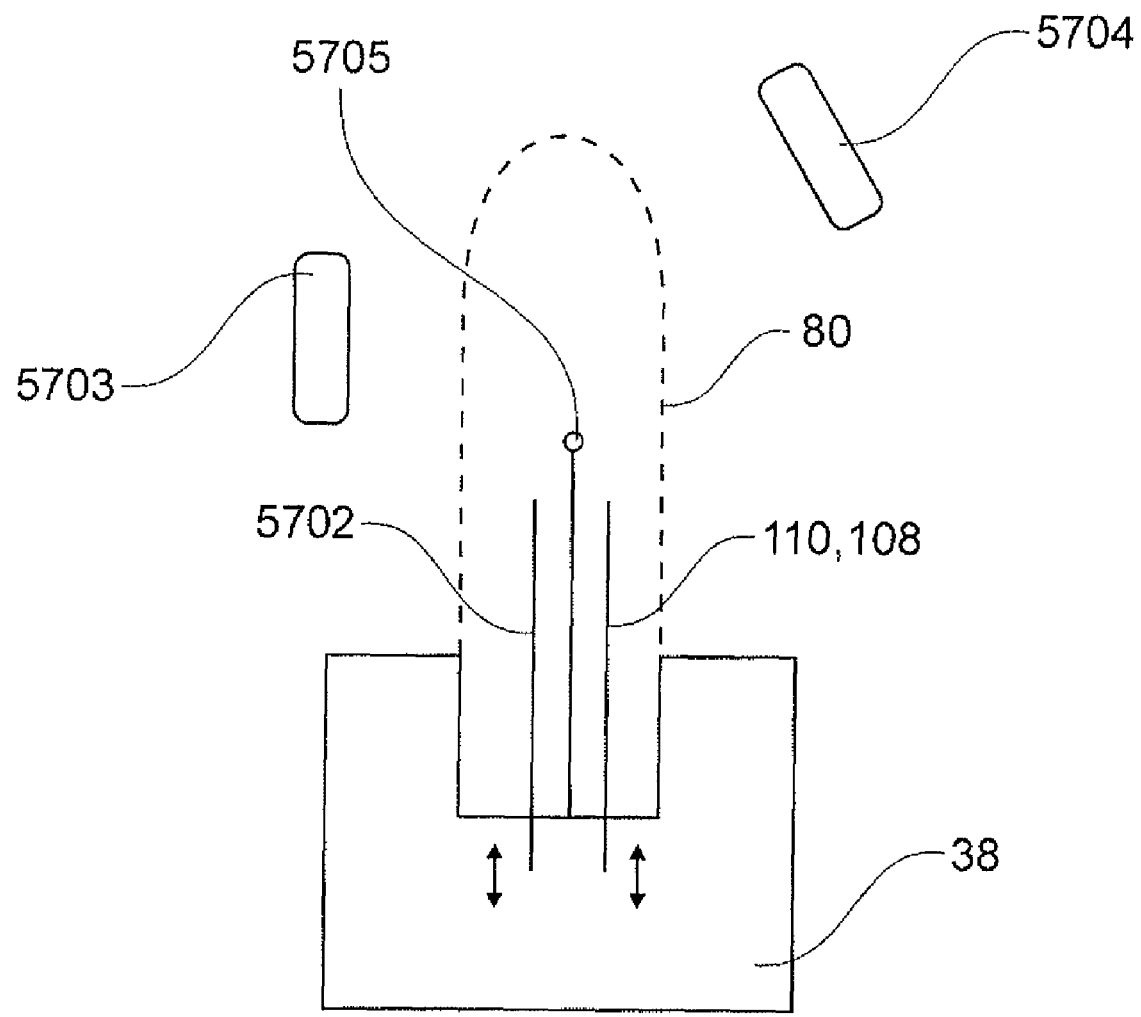
FIG. 62 shows a portable vessel holder according to an exemplary embodiment of the present invention.

I. FIG. 61 shows a vessel processing station 5501 according to an exemplary embodiment of the present invention. The station comprises a PECVD apparatus 5701 for coating an interior surface of the vessel. Furthermore, several detectors 5702-5707 are provided for vessel inspection. Such detectors can for example be electrodes for performing electric measurements, optical detectors, like CCD cameras, gas detectors or pressure detectors.

I. a vessel holder 38 according to an exemplary embodiment of the present invention, together with several detectors 5702, 5703, 5704 and an electrode with gas inlet port 108, 110.

I. The electrode and the detector 5702 can be adapted to be moved into the interior space of the vessel 80 when the vessel is seated on the holder 38.

I. The optical inspection can be performed during a coating step, for example with the help of optical detectors 5703, 5704 which are arranged outside the seated vessel 80 or even with the help of an optical detector 5705 arranged inside the interior space of the vessel 80.

I. The detectors can comprise color filters such that different wavelengths can be detected during the coating process. The processing unit 5505 analyzes the optical data and determines whether the coating was successful or not to a predetermined level of certainty. If it is determined that the coating was most probably unsuccessful, the respective vessel is separated from the processing system or re-processed.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

TABLE 1

COATED COC TUBE OTR AND WVTR MEASUREMENT

| Coating ID | Power (Watts) | O—Si | O—Si Flow (sccm) | $O_2$ Flow (sccm) | Time (sec) | OTR (cc/ Tube. Day) | WVTR (mg/ Tube. Day) |
|---|---|---|---|---|---|---|---|
| No Coating | | | | | | 0.215 | 0.27 |
| A | 50 | HMDSO | 6 | 90 | 14 | 0.023 | 0.07 |
| B | 50 | HMDSO | 6 | 90 | 14 | 0.024 | 0.10 |
| C | 50 | HMDSO | 6 | 90 | 7 | 0.026 | 0.10 |

TABLE 2

COATED PET TUBE OTR AND WVTR MEASUREMENT

| Coating ID | Power (Watts) | O—Si | O—Si Flow (sccm) | $O_2$ Flow (sccm) | Time (sec) | OTR (cc/ Tube. Day) | WVTR (mg/ Tube. Day) | BIF (OTR) | BIF (WVTR) |
|---|---|---|---|---|---|---|---|---|---|
| Uncoated Control | | | | | | 0.0078 | 3.65 | — | — |
| $SiO_x$ | 50 | HMDSO | 6 | 90 | 3 | 0.0035 | 1.95 | 2.2 | 1.9 |

TABLE 2A

COATED PET TUBE OTR WITH MECHANICAL SCRATCH DEFECTS

| Example | O—Si | Power (Watts) | O—Si Flow (sccm) | $O_2$ Flow (sccm) | Treat Time (sec) | Mechanical Scratch Length (mm) | OTR (cc/tube. day)* | OTR BIF |
|---|---|---|---|---|---|---|---|---|
| Uncoated Control | | | | | | | 0.0052 | |
| Inventive | HMDSO | 50 | 6 | 90 | 3 | 0 | 0.0014 | 3.7 |
| Inventive | HMDSO | 50 | 6 | 90 | 3 | 1 | 0.0039 | 1.3 |
| Inventive | HMDSO | 50 | 6 | 90 | 3 | 2 | 0.0041 | 1.3 |
| Inventive | HMDSO | 50 | 6 | 90 | 3 | 10 | 0.0040 | 1.3 |
| Inventive | HMDSO | 50 | 6 | 90 | 3 | 20 | 0.0037 | 1.4 |

*average of two tubes

TABLE 3

COATED COC SYRINGE BARREL OTR AND WVTR MEASUREMENT

| Example | Syringe Coating | O—Si Composition | Power (Watts) | O—Si Flow Rate (sccm) | $O_2$ Flow Rate (sccm) | Coating Time (sec) | OTR (cc/Barrel·Day) | WVTR (mg/Barrel·Day) | BIF (OTR) | BIF (WVTR) |
|---|---|---|---|---|---|---|---|---|---|---|
| A | Uncoated Control | | | | | | 0.032 | 0.12 | | |
| B | $SiO_x$ Inventive Example | HMDSO | 44 | 6 | 90 | 7 | 0.025 | 0.11 | 1.3 | 1.1 |
| C | $SiO_x$ Inventive Example | HMDSO | 44 | 6 | 105 | 7 | 0.021 | 0.11 | 1.5 | 1.1 |
| D | $SiO_x$ Inventive Example | HMDSO | 50 | 6 | 90 | 7 | 0.026 | 0.10 | 1.2 | 1.2 |
| E | $SiO_x$ Inventive Example | HMDSO | 50 | 6 | 90 | 14 | 0.024 | 0.07 | 1.3 | 1.7 |
| F | $SiO_x$ Inventive Example | HMDSO | 52 | 6 | 97.5 | 7 | 0.022 | 0.12 | 1.5 | 1.0 |
| G | $SiO_x$ Inventive Example | HMDSO | 61 | 6 | 105 | 7 | 0.022 | 0.11 | 1.4 | 1.1 |
| H | $SiO_x$ Inventive Example | HMDSO | 61 | 6 | 120 | 7 | 0.024 | 0.10 | 1.3 | 1.2 |
| I | $SiO_x$ Inventive Example | HMDZ | 44 | 6 | 90 | 7 | 0.022 | 0.10 | 1.5 | 1.3 |
| J | $SiO_x$ Inventive Example | HMDZ | 61 | 6 | 90 | 7 | 0.022 | 0.10 | 1.5 | 1.2 |
| K | $SiO_x$ Inventive Example | HMDZ | 61 | 6 | 105 | 7 | 0.019 | 0.10 | 1.7 | 1.2 |

TABLE 4

$SiO_x$ COATING THICKNESS (NANOMETERS) DETECTED BY TEM

| Sample | O—Si | Thickness (nm) | Power (Watts) | HMDSO Flow Rate (sccm) | Oxygen Flow Rate (sccm) |
|---|---|---|---|---|---|
| Inventive Example A | HMDSO | 25-50 | 39 | 6 | 60 |
| Inventive Example B | HMDSO | 20-35 | 39 | 6 | 90 |

TABLE 6

EXTENT OF HOLLOW CATHODE PLASMA IGNITION

| Sample | Power | Time | Hollow Cathode Plasma Ignition | Staining Result |
|---|---|---|---|---|
| A | 25 Watts | 7 sec | No Ignition in gas inlet 310, Ignition in restricted area 292 | good |
| B | 25 Watts | 7 sec | Ignition in gas inlet 310 and restricted area 292 | poor |

TABLE 5

ATOMIC RATIOS OF THE ELEMENTS DETECTED (in parentheses, Concentrations in percent, normalized to 100% of elements detected)

| Sample | Plasma Coating | Si | O | C |
|---|---|---|---|---|
| PET Tube - Comparative Example | — | 0.08 (4.6%) | 1 (31.5%) | 2.7 (63.9%) |
| Polyethylene Terephthalate - Calculated | — | | 1 (28.6%) | 2.5 (71.4%) |
| Coated PET Tube - Inventive Example | $SiO_x$ | 1 (39.1%) | 2.4 (51.7%) | 0.57 (9.2%) |

TABLE 6-continued

EXTENT OF HOLLOW CATHODE PLASMA IGNITION

| Sample | Power | Time | Hollow Cathode Plasma Ignition | Staining Result |
|---|---|---|---|---|
| C | 8 Watts | 9 sec | No Ignition in gas inlet 310, Ignition in restricted area 292 | better |
| D | 30 Watts | 5 sec | No Ignition in gas inlet 310 or restricted area 292 | best |

TABLE 7

FLOW RATE USING GLASS TUBES

| Glass Tube | Run #1 (µg/min.) | Run #2 (µg/min.) | Average (µg/min.) |
|---|---|---|---|
| 1 | 1.391 | 1.453 | 1.422 |
| 2 | 1.437 | 1.243 | 1.34 |
| 3 | 1.468 | 1.151 | 1.3095 |
| 4 | 1.473 | 1.019 | 1.246 |
| 5 | 1.408 | 0.994 | 1.201 |
| 6 | 1.328 | 0.981 | 1.1545 |
| 7 | Broken | Broken | Broken |
| 8 | 1.347 | 0.909 | 1.128 |
| 9 | 1.171 | 0.91 | 1.0405 |
| 10 | 1.321 | 0.946 | 1.1335 |
| 11 | 1.15 | 0.947 | 1.0485 |
| 12 | 1.36 | 1.012 | 1.186 |
| 13 | 1.379 | 0.932 | 1.1555 |
| 14 | 1.311 | 0.893 | 1.102 |
| 15 | 1.264 | 0.928 | 1.096 |
| Average | 1.343 | 1.023 | 1.183 |
| Max | 1.473 | 1.453 | 1.422 |
| Min | 1.15 | 0.893 | 1.0405 |
| Max-Min | 0.323 | 0.56 | 0.3815 |
| Std Dev | 0.097781 | 0.157895 | 0.1115087 |

TABLE 8

FLOW RATE USING PET TUBES

| Uncoated PET | Run #1 (µg/min.) | Run #2 (µg/min.) | Average (µg/min.) |
|---|---|---|---|
| 1 | 10.36 | 10.72 | 10.54 |
| 2 | 11.28 | 11.1 | 11.19 |
| 3 | 11.43 | 11.22 | 11.325 |
| 4 | 11.41 | 11.13 | 11.27 |
| 5 | 11.45 | 11.17 | 11.31 |
| 6 | 11.37 | 11.26 | 11.315 |
| 7 | 11.36 | 11.33 | 11.345 |
| 8 | 11.23 | 11.24 | 11.235 |
| 9 | 11.14 | 11.23 | 11.185 |
| 10 | 11.1 | 11.14 | 11.12 |
| 11 | 11.16 | 11.25 | 11.205 |
| 12 | 11.21 | 11.31 | 11.26 |
| 13 | 11.28 | 11.22 | 11.25 |
| 14 | 10.99 | 11.19 | 11.09 |
| 15 | 11.3 | 11.24 | 11.27 |
| Average | 11.205 | 11.183 | 11.194 |
| Max | 11.45 | 11.33 | 11.345 |
| Min | 10.36 | 10.72 | 10.54 |
| Max-Min | 1.09 | 0.61 | 0.805 |
| Std Dev | 0.267578 | 0.142862 | 0.195121 |

TABLE 9

FLOW RATE FOR SiOx COATED PET TUBES

| Coated PET | Run #1 (µg/min.) | Run #2 (µg/min.) | Average (µg/min.) |
|---|---|---|---|
| 1 | 6.834 | 6.655 | 6.7445 |
| 2 | 9.682 | 9.513 | Outliers |
| 3 | 7.155 | 7.282 | 7.2185 |
| 4 | 8.846 | 8.777 | Outliers |
| 5 | 6.985 | 6.983 | 6.984 |
| 6 | 7.106 | 7.296 | 7.201 |
| 7 | 6.543 | 6.665 | 6.604 |
| 8 | 7.715 | 7.772 | 7.7435 |
| 9 | 6.848 | 6.863 | 6.8555 |
| 10 | 7.205 | 7.322 | 7.2635 |
| 11 | 7.61 | 7.608 | 7.609 |
| 12 | 7.67 | 7.527 | 7.5985 |
| 13 | 7.715 | 7.673 | 7.694 |
| 14 | 7.144 | 7.069 | 7.1065 |
| 15 | 7.33 | 7.24 | 7.285 |
| Average | 7.220 | 7.227 | 7.224 |
| Max | 7.715 | 7.772 | 7.7435 |
| Min | 6.543 | 6.655 | 6.604 |
| Max − Min | 1.172 | 1.117 | 1.1395 |
| Std Dev | 0.374267 | 0.366072 | 0.365902 |

TABLE 10

WETTING TENSION MEASUREMENT OF COATED AND UNCOATED TUBES

| Example | Tube Coating | Wetting Tension (dyne/cm) |
|---|---|---|
| Reference | uncoated glass | 72 |
| Inventive Example | PET tube coated with $SiO_X$ according to $SiO_X$ Protocol | 60 |
| Comparative Example | uncoated PET | 40 |
| Inventive Example | PET tube coated according to Hydrophobic layer Protocol | 34 |
| Comparative Example | Glass (+silicone fluid) glass syringe, Part No. | 30 |

TABLE 11

WATER MASS DRAW (GRAMS)

| | Pressurization Time (days) | | | | | | |
|---|---|---|---|---|---|---|---|
| Tube | 0 | 27 | 46 | 81 | 108 | 125 | 152 | 231 |
| BD PET (commercial control) | 3.0 | | | | 1.9 | | 1.0 | |
| Uncoated PET (internal control) | 4.0 | 3.1 | | | 2.7 | | | |
| $SiO_X$-Coated PET (inventive example) | 4.0 | 3.6 | | | 3.3 | | | |

TABLE 12

CALCULATED NORMALIZED AVERAGE VACUUM DECAY RATE AND TIME TO 10% VACUUM LOSS

| Tube | Normalized Average Decay rate (delta mL/initial mL · da) | Time to 10% Loss (months) - Accelerated |
|---|---|---|
| BD PET (commercial control) | 0.0038 | 0.9 |
| Uncoated PET (internal control) | 0.0038 | 0.9 |
| SiOx-Coated PET (inventive example) | 0.0018 | 1.9 |

TABLE 13

SYRINGE BARRELS WITH LUBRICITY LAYER, ENGLISH UNITS

| Sample | Power, (Watts) | O—Si Flow, (sccm) | O$_2$ Flow, (sccm) | time (sec) | Avg. Force, (lb.) | St. dev. |
|---|---|---|---|---|---|---|
| Glass with Silicone | No coating | No coating | No coating | No coating | 0.58 | 0.03 |
| Uncoated COC | No coating | No coating | No coating | No coating | 3.04 | 0.71 |
| A | 11 | 6 | 0 | 7 | 1.09 | 0.27 |
| B | 17 | 6 | 0 | 14 | 2.86 | 0.59 |
| C | 33 | 6 | 0 | 14 | 3.87 | 0.34 |
| D | 6 | 6 | 90 | 30 | 2.27 | 0.49 |
| Uncoated COC | — | — | — | — | 3.9 | 0.6 |
| SiO$_x$ on COC | | | | | 4.0 | 1.2 |
| E | 11 | 1.25 | 0 | 5 | 2.0 | 0.5 |
| F | 11 | 2.5 | 0 | 5 | 2.1 | 0.7 |
| G | 11 | 5 | 0 | 5 | 2.6 | 0.6 |
| H | 11 | 2.5 | 0 | 10 | 1.4 | 0.1 |
| I | 22 | 5 | 0 | 5 | 3.1 | 0.7 |
| J | 22 | 2.5 | 0 | 10 | 3.3 | 1.4 |
| K | 22 | 5 | 0 | 5 | 3.1 | 0.4 |

TABLE 13

SYRINGE BARRELS WITH LUBRICITY LAYER, METRIC UNITS

| Sample | Power, (Watts) | O—Si Flow, (sccm) | O$_2$ Flow, (sccm) | time (sec) | Avg. Force, (Kg.) | St. dev. |
|---|---|---|---|---|---|---|
| Glass syringe with sprayed silicone | No coating | No coating | No coating | No coating | 0.26 | 0.01 |
| Uncoated COC | No coating | No coating | No coating | No coating | 1.38 | 0.32 |
| A | 11 | 6 | 0 | 7 | 0.49 | 0.12 |
| B | 17 | 6 | 0 | 14 | 1.29 | 0.27 |
| C | 33 | 6 | 0 | 14 | 1.75 | 0.15 |
| D | 6 | 6 | 90 | 30 | 1.03 | 0.22 |
| Uncoated COC | — | — | — | — | 1.77 | 0.27 |
| SiO$_x$ on COC, per protocol | | | | | 1.81 | 0.54 |
| E | 11 | 1.25 | — | 5 | 0.91 | 0.23 |
| F | 11 | 2.5 | — | 5 | 0.95 | 0.32 |
| G | 11 | 5 | — | 5 | 1.18 | 0.27 |
| H | 11 | 2.5 | — | 10 | 0.63 | 0.05 |
| I | 22 | 5 | — | 5 | 1.40 | 0.32 |
| J | 22 | 2.5 | — | 10 | 1.49 | 0.63 |
| K | 22 | 5 | — | 5 | 1.40 | 0.18 |

TABLE 14

PLUNGER SLIDING FORCE MEASUREMENTS OF HMDSO- AND OMCTS-BASED PLASMA COATINGS

| Example | Description | Monomer | Coating Time (sec) | Coating Si-0 Flow Rate (sccm) | Coating Power (Watts) | Maximum Force (lb, kg.) | Normalized Maximum Force |
|---|---|---|---|---|---|---|---|
| A | uncoated Control | | | | | 3.3, 1.5 | 1.0 |
| B | HMDSO Coating | HMDSO | 7 | 6 | 8 | 4.1, 1.9 | 1.2 |
| C | OMCTS Lubricity layer | OMCTS | 7 | 6 | 8 | 1.1, 0.5 | 0.3 |
| D | uncoated Control | | | | | 3.9, 1.8 | 1.0 |
| E | OMCTS Lubricity layer | OMCTS | 7 | 6 | 11 | 2.0, 0.9 | 0.5 |
| F | Two Layer Coating | 1 COC Syringe Barrel + SiO$_x$ | 14 | 6 | 50 | | |
| | | 2 OMCTS Lubricity layer | 7 | 6 | 8 | 2.5, 1.1 | 0.6 |
| G | OMCTS Lubricity layer | OMCTS | 5 | 1.25 | 11 | 2, 0.9 | 0.5 |
| H | OMCTS Lubricity layer | OMCTS | 10 | 1.25 | 11 | 1.4, 0.6 | 0.4 |

TABLE 15

OTR AND WVTR MEASUREMENTS (Prophetic)

| Sample | OTR (cc/barrel · day) | WVTR (gram/barrel · day) |
|---|---|---|
| COC syringe-Comparative Example | 4.3 X | 3.0 Y |
| PVdC-COC laminate COC syringe-Inventive Example | X | Y |

TABLE 16

OPTICAL ABSORPTION OF SiOx COATED PET TUBES (NORMALIZED TO UNCOATED PET TUBE)

| Sample | Coating Time | Average Absorption (@ 615 nm) | Replicates | St. dev. |
|---|---|---|---|---|
| Reference (uncoated) | — | 0.002-0.014 | 4 | |
| Inventive A | 3 sec | 0.021 | 8 | 0.001 |
| Inventive B | 2 × 3 sec | 0.027 | 10 | 0.002 |
| Inventive C | 3 × 3 sec | 0.033 | 4 | 0.003 |

TABLE 17

ATOMIC CONCENTRATIONS (IN PERCENT, NORMALIZED TO 100% OF ELEMENTS DETECTED) AND TEM THICKNESS

| Sample | Plasma Coating | Si | O | C |
|---|---|---|---|---|
| HMDSO-based Coated COC syringe barrel | $Si_wO_xC_y$ | 0.76 (22.2%) | 1 (33.4%) | 3.7 (44.4%) |
| OMCTS-based Coated COC syringe barrel | $Si_wO_xC_y$ | 0.46 (23.6%) | 1 (28%) | 4.0 (48.4%) |
| HMDSO Monomer-calculated | $Si_2OC_6$ | 2 (21.8%) | 1 (24.1%) | 6 (54.1%) |
| OMCTS Monomer-calculated | $Si_4O_4C_8$ | 1 (42%) | 1 (23.2%) | 2 (34.8%) |

TABLE 18

VOLATILE COMPONENTS FROM SYRINGE OUTGASSING

| Sample | Coating Monomer | $Me_3SiOH$ (ng/test) | Higher SiOMe oligomers (ng/test) |
|---|---|---|---|
| Uncoated COC syringe-Comparative Example | Uncoated | ND | ND |
| HMDSO-based Coated COC syringe-Comparative Example | HMDSO | 58 | ND |
| OMCTS-based Coated COC syringe-Inventive Example | OMCTS | ND | 26 |

TABLE 19

PLASMA COATING DENSITY FROM XRR DETERMINATION

| Sample | Layer | Density g/cm³ |
|---|---|---|
| HMDSO-based Coated Sapphire-Comparative Example | $Si_wO_xC_yH_z$ | 1.21 |
| OMCTS-based Coated Sapphire-Inventive Example | $Si_wO_xC_yH_z$ | 1.46 |

TABLE 20

THICKNESS OF PECVD COATINGS BY TEM

| Sample ID | TEM Thickness I | TEM Thickness II | TEM Thickness III |
|---|---|---|---|
| Protocol for Forming COC Syringe Barrel; Protocol for Coating COC Syringe Barrel Interior with $SiO_x$ | 164 nm | 154 nm | 167 nm |
| Protocol for Forming COC Syringe Barrel; Protocol for Coating COC Syringe Barrel Interior with OMCTS Lubricity layer | 55 nm | 48 nm | 52 nm |
| Protocol for Forming PET Tube; Protocol for Coating Tube Interior with $SiO_x$ | 28 nm | 26 nm | 30 nm |
| Protocol for Forming PET Tube (uncoated) | — | — | — |

TABLE 21

OMCTS LUBRICITY LAYER PERFORMANCE (English Units)

| Sample | Average Plunger Force (lbs.)* | Percent Force Reduction (vs uncoated) | Power (Watts) | OMCTS Flow (sccm) |
|---|---|---|---|---|
| Comparative (no coating) | 3.99 | — | — | — |
| Sample A | 1.46 | 63% | 14 | 0.75 |
| Sample B | 1.79 | 55% | 11 | 1.25 |
| Sample C | 2.09 | 48% | 8 | 1.75 |
| Sample D | 2.13 | 47% | 14 | 1.75 |
| Sample E | 2.13 | 47% | 11 | 1.25 |
| Sample F | 2.99 | 25% | 8 | 0.75 |

*Average of 4 replicates

TABLE 21

OMCTS LUBRICITY LAYER PERFORMANCE (Metric Units)

| Sample | Average Plunger Force (lbs.)* | Percent Force Reduction (vs uncoated) | Power (Watts) | OMCTS Flow (sccm) |
|---|---|---|---|---|
| Comparative (no coating) | 1.81 | — | — | — |
| Sample A | 0.66 | 63% | 14 | 0.75 |
| Sample B | 0.81 | 55% | 11 | 1.25 |
| Sample C | 0.95 | 48% | 8 | 1.75 |
| Sample D | 0.96 | 47% | 14 | 1.75 |
| Sample E | 0.96 | 47% | 11 | 1.25 |
| Sample F | 1.35 | 25% | 8 | 0.75 |

Above force measurements are the average of 4 samples.

The invention claimed is:

1. A syringe or syringe parts comprising: a barrel and a piston, the barrel having an inner surface and the piston having a side surface engaging the barrel inner surface, wherein at least one of the inner surface and the side surface is a substrate coated with a lubricity layer configured to provide a lower piston sliding force or breakout force than the uncoated substrate the lubricity layer having one of the following atomic ratios, measured by X-ray photoelectron spectroscopy (XPS), $Si_wO_xC_y$, or $Si_wN_xC_y$, where w is 1, x in this formula is from about 0.5 to 2.4, and y is from about 0.6 to about 3;

the lubricity layer having a thickness by transmission electron microscopy (TEM) between 10 and 500 nm;

the lubricity layer deposited by plasma enhanced chemical vapor deposition (PECVD) under conditions effective to form a coating from a precursor selected from a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

2. The syringe or syringe parts of claim 1, in which the precursor comprises hexamethyldisiloxane, octamethyltrisiloxane, decamethyltetrasiloxane, hexamethylcyclotrisiloxane, octamethylcyclotetrasiloxane, decamethylcyclopentasiloxane, dodecamethylcyclohexasiloxane, a poly(methylsilsesquioxane) according to the T8 cube formula:

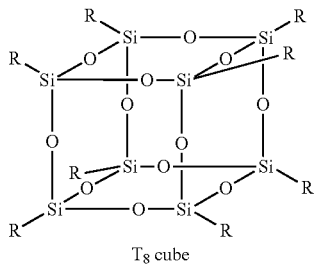

T₈ cube in which each R is methyl, a poly(Methyl-Hydridosilsesquioxane) according to the T8 cube formula in which 90% of the R groups are methyl and 10% are hydrogen atoms, methyltrimethoxysilane, or a combination of any two or more of these.

3. The syringe or syringe parts of claim 1, in which the precursor comprises octamethylcyclotetrasiloxane (OMCTS).

4. The syringe or syringe parts of claim 1, in which the precursor consists essentially of octamethylcyclotetrasiloxane (OMCTS).

5. The syringe or syringe parts of claim 1, in which the lubricity layer has a thickness of 10-200 nm.

6. The syringe or syringe parts of claim 1, in which the lubricity layer has a thickness of 20 to 100 nm.

7. The syringe or syringe parts of claim 1, in which the substrate comprises glass.

8. The syringe or syringe parts of claim 1, in which the substrate comprises a polymer.

9. The syringe or syringe parts of claim 1, in which the substrate comprises a polycarbonate polymer.

10. The syringe or syringe parts of claim 1, in which the substrate comprises an olefin polymer.

11. The syringe or syringe parts of claim 1, in which the substrate comprises a cyclic olefin copolymer.

12. The syringe or syringe parts of claim 1, in which the substrate comprises a polypropylene polymer.

13. The syringe or syringe parts of claim 1, in which the substrate comprises a polyester polymer.

14. The syringe or syringe parts of claim 1, in which the substrate comprises a polyethylene terephthalate polymer.

15. The syringe or syringe parts of claim 1, further comprising an outer wall of the syringe barrel and a barrier coating on the outer wall of the syringe barrel.

16. The syringe or syringe parts of claim 15, in which the barrier coating is an oxygen barrier coating.

17. The syringe or syringe parts of claim 16, in which the barrier coating is a water barrier coating.

18. The syringe or syringe parts of claim 16, in which the barrier coating comprises polyvinylidene chloride.

19. The syringe or syringe parts of claim 16, in which the barrier coating is applied as a water-based coating.

20. The syringe or syringe parts of claim 1, in which the lubricity layer materials and conditions are effective to reduce the syringe piston sliding force or breakout force moving through the syringe barrel at least 45 percent relative to an uncoated syringe barrel.

21. The syringe or syringe parts of claim 1, in which the lubricity layer materials and conditions are effective to reduce the syringe piston sliding force or breakout force moving through the syringe barrel at least 60 percent relative to an uncoated syringe barrel.

22. The syringe or syringe parts of claim 1, in which the lubricity layer materials and conditions are effective to reduce the syringe piston sliding force or breakout force moving through the syringe barrel more than 60 percent relative to an uncoated syringe barrel.

23. The syringe or syringe parts of claim 1, in which the lubricity layer is applied to the barrel inner surface.

24. The syringe or syringe parts of claim 1, in which the lubricity layer is applied to the piston side surface.

25. The syringe or syringe parts of claim 1, in which the lubricity layer is applied to the barrel inner surface and the piston side surface.

26. The syringe or syringe parts of claim 1, further comprising a barrier coating of $SiO_x$, in which x is from about 1.5 to about 2.9, on the interior surface of the barrel.

27. The syringe or syringe parts of claim 26, in which the lubricity layer is applied to the barrier coating of SiOx.

28. The syringe or syringe parts of claim 1, in which the lubricity layer interfaces with the side surface of the piston, the piston further comprises a back portion, and the syringe further comprises a push rod engaging the back portion and configured for advancing the piston in a syringe barrel.

29. The syringe or syringe parts of claim 1, in which the lubricity layer has a density between 1.25 and 1.65 g/cm³ as determined by X-ray reflectivity (XRR).

30. The syringe or syringe parts of claim 1, in which the lubricity layer has an outgas component as determined by gas chromatography/mass spectrometry substantially free of trimethylsilanol.

31. The syringe or syringe parts of claim 1, in which the lubricity layer has an outgas component as determined by gas chromatography/mass spectrometry having at least 10 ng/test of oligomers containing repeating -(Me)2SiO— moieties, as determined by gas chromatography/mass spectrometry using the following test conditions:

GC Column: 30 m×0.25 mm DB-5MS (J&W Scientific), 0.25 µm film thickness

Flow rate: 1.0 ml/min, constant flow mode

Detector: Mass Selective Detector (MSD)

Injection Mode: Split injection (10:1 split ratio)

Outgassing Conditions: 1W (37 mm) Chamber, purge for three hour at 85° C., flow 60 ml/min Oven temperature: 40° C. (5 min.) to 300° C. @10° C./min.; hold for 5 min, at 300° C.

32. The syringe or syringe parts of claim 1, in which the lubricity layer has atomic concentrations from 25 to 45% carbon, 25 to 65% silicon, and 10 to 35% oxygen.

33. The syringe or syringe parts of claim 1, in which the lubricity layer precursor comprises a monocyclic siloxane, a monocyclic silazane, a polycyclic siloxane, a polycyclic silazane, or any combination of two or more of these.

34. The syringe or syringe parts of claim 1, in which the lubricity layer precursor comprises a monocyclic siloxane, a monocyclic silazane, or any combination of two or more of these.

35. The syringe or syringe parts of claim 1, in which the lubricity layer precursor comprises a monocyclic siloxane or any combination of two or more of these.

36. The syringe or syringe parts of claim 1, in which the lubricity layer has an atomic concentration of carbon, normalized to 100% of carbon, oxygen, nitrogen, and silicon, as determined by XPS, greater than the atomic concentration of carbon in the atomic formula for the precursor.

37. The syringe or syringe parts of claim 36, in which the atomic concentration of carbon increases by from 1 to 80 atomic percent.

38. The syringe or syringe parts of claim 1, in which the lubricity layer has an atomic concentration of silicon, normalized to 100% of carbon, oxygen, nitrogen, and silicon, as determined by XPS, less than the atomic concentration of silicon in the atomic formula for the precursor.

39. The syringe or syringe parts of claim 38, in which the atomic concentration of silicon decreases by from 1 to 80 atomic percent.

40. The syringe or syringe parts of claim 1, in which the lubricity layer is characterized by a sum formula wherein the atomic ratio C:O is increased and/or the atomic ratio Si:O is decreased in comparison to the sum formula of the organosilicon precursor.

41. The syringe or syringe parts of claim 1, wherein the substrate is the inside wall of the syringe barrel defining a lumen, the lumen having a void volume of from 0.5 to 50 mL.

42. The syringe or syringe parts of claim 1, wherein the lubricity layer has a lower wetting tension than the uncoated surface.

43. The syringe or syringe parts of claim 1, additionally comprising at least one barrier layer of SiOx, wherein x is from 1.5 to 2.9, wherein the SiOx layer is situated between the substrate surface and the lubricity layer.

44. The syringe or syringe parts of claim 43, wherein the layer of SiOx and the lubricity layer are a graded composite of SiOx to the lubricity layer.

45. The syringe or syringe parts of claim 1, comprising at least one further barrier layer of plastic or SiOx, wherein x is from 1.5 to 2.9, formed over the lubricity layer.

46. The syringe or syringe parts of claim 1, which contains a compound or composition in a lumen of the barrel which is a biologically active compound or composition, a biological fluid, a citrate or a citrate containing composition, a medicament, blood or blood cells.

47. A syringe having a barrel and a plunger, the barrel having an inner surface and the plunger having a side surface engaging the barrel inner surface, wherein at least one of the inner surface and the side surface is a substrate treated by applying a lubricity layer having one of the following atomic ratios, measured by X-ray photoelectron spectroscopy (XPS), $Si_wO_xC_y$ or $Si_wN_xC_y$, where w is 1, x in this formula is from about 0.5 to 2.4, and y is from about 0.6 to about 3, wherein the lubricity layer is configured to provide a lower piston sliding force or breakout force than the uncoated substrate and is applied by the following process:

providing a precursor selected from a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors; and applying the precursor as a coating to a substrate and polymerizing or crosslinking the coating, or both, by plasma enhanced chemical vapor deposition (PECVD).

48. The syringe of claim 47, in which the applying step is carried out by vaporizing the precursor and providing it in the vicinity of the substrate.

49. The syringe of claim 47, in which during polymerizing or crosslinking a plasma is formed in the vicinity of the substrate.

50. The syringe of claim 47, in which during polymerizing or crosslinking a non-hollow-cathode plasma is formed in the vicinity of the substrate.

51. The syringe of claim 47, in which during polymerizing or crosslinking the precursor is provided in the substantial absence of oxygen.

52. The syringe of claim 47, in which during polymerizing or crosslinking the precursor is provided in the substantial absence of a carrier gas.

53. The syringe of claim 47, in which during polymerizing or crosslinking the precursor is provided in the substantial absence of nitrogen.

54. The syringe of claim 47, in which during polymerizing or crosslinking the precursor is provided at less than 1 Torr absolute pressure.

55. The syringe of claim 47, in which during polymerizing or crosslinking the precursor is provided to the vicinity of a plasma emission.

56. The syringe of claim 47, in which the lubricity layer has a thickness of 10 to 5000 nm.

57. The syringe of claim 47, in which the lubricity layer has a thickness of 10 to 1000 nm.

58. The syringe of claim 47, in which during polymerizing or crosslinking the precursor is contacted with a plasma made by energizing the vicinity of the precursor with electrodes powered at a frequency of 10 kHz to 2.45 GHz.

59. The syringe of claim 47, in which during polymerizing or crosslinking the precursor is contacted with a plasma made by energizing the vicinity of the precursor with electrodes supplied with electric power at from 1 to 22 Watts.

60. The syringe of claim 47, in which during polymerizing or crosslinking the precursor is contacted with a plasma made by energizing the vicinity of the precursor with electrodes supplied with electric power at less than 10 Watts per ml, of plasma volume.

61. The syringe of claim 47, in which during polymerizing or crosslinking the precursor is contacted with a plasma made by energizing the vicinity of the precursor with electrodes supplied with electric power from 0.1 to 5 Watts per ml, of plasma volume.

62. The syringe of claim 47, the lubricity layer having a thickness by transmission electron microscopy (TEM) between 10 and 500 nm.

63. The syringe of claim 47, wherein during polymerizing or crosslinking a gaseous reactant comprising the precursor and $O_2$ is present, and the $O_2$ is present in a volume-volume ratio to the gaseous reactant of from 0:1 to 0.5:1.

64. The syringe of claim 63, wherein the gaseous reactant comprises less than 1 vol % $O_2$.

65. The syringe of claim 47, wherein the substrate is the inside wall of the syringe barrel defining a lumen, the lumen having a void volume of from 0.5 to 50 mL.

66. The syringe of claim 47, wherein the polymerizing or crosslinking step is carried out by generating plasma with electrodes powered with sufficient power to form a coating on the substrate surface.

67. The syringe of claim 66, wherein the electrodes are supplied with an electric power of from 0.1 to 25 W.

68. The syringe of claim 66, wherein the ratio of the electrode power to the plasma volume is less than 10 W/ml.

69. The syringe of claim 47, wherein the plasma enhanced chemical vapor deposition (PECVD) is performed at a flow of the organosilicon precursor of not more than 6 sccm.

70. The syringe of claim 47, wherein:
the polymerizing or crosslinking step comprises plasma enhanced chemical vapor deposition (PECVD),
the substrate surface is part or all of the inner surface of the syringe barrel,
the syringe barrel has at least one opening and an inner surface, and
the gaseous reactant fills an interior lumen of the barrel and the plasma is generated in part or all of the interior lumen of the barrel.

71. The syringe of claim 47, wherein the polymerizing or crosslinking step comprises plasma enhanced chemical vapor deposition (PECVD), wherein the plasma is generated with electrodes powered at a frequency of from 10 kHz to less than 300 MHz.

72. The syringe of claim 47, wherein the polymerizing or crosslinking step comprises plasma enhanced chemical vapor deposition (PECVD), wherein the plasma is generated at less than 300 mTorr.

73. The syringe of claim 47, wherein the polymerizing or crosslinking step comprises plasma enhanced chemical vapor deposition (PECVD), wherein the PECVD deposition time is from 1 to 30 sec.

74. The syringe of claim 47, wherein the lubricity layer has a thickness of in the range of from 1 to 100 nm.

75. The syringe of claim 47, wherein the polymerizing or crosslinking step comprises plasma enhanced chemical vapor deposition (PECVD), wherein the atomic ratio of carbon to oxygen is increased in comparison to the organosilicon precursor, or wherein the atomic ratio of oxygen to silicon is decreased in comparison to the organosilicon precursor, or both.

76. The syringe of claim 47, wherein the polymerizing or crosslinking step comprises plasma enhanced chemical vapor deposition (PECVD), wherein the precursor is octamethylcyclotetrasiloxane and wherein the coating has a density higher than the density of a coating made from HMDSO under the same plasma enhanced chemical vapor deposition (PECVD) reaction conditions.

77. The syringe of claim 47, wherein the polymerizing or crosslinking step comprises plasma enhanced chemical vapor deposition (PECVD), wherein the coating has a lower frictional resistance than the uncoated surface.

* * * * *

UNITED STATES PATENT AND TRADEMARK OFFICE
CERTIFICATE OF CORRECTION

| | |
|---|---|
| PATENT NO. | : 7,985,188 B2 |
| APPLICATION NO. | : 12/779007 |
| DATED | : July 26, 2011 |
| INVENTOR(S) | : John T. Felts et al. |

It is certified that error appears in the above-identified patent and that said Letters Patent is hereby corrected as shown below:

Title page, INID Code (75), line 5: replace "Johathan" with -- Jonathan --.

Column 20, line 42, replace "FIG." with -- FIGS. --.

Column 25, line 42, replace "FIGS." with -- FIG. --.

Column 32, line 60, in the structure, replace the subscript "n" with the subscript -- a --.

Column 71, line 50, replace "COG" with -- COC --.

Column 102, line 14, in "Ru(III)," show "(III)" as a superscript.

Table 13, Column 122, lines 27-30, replace the two rows between rows D and E with the following two rows to correct spacing errors:

| | | | | | |
|---|---|---|---|---|---|
| Uncoated COC | - | - | - | 1.77 | 0.27 |
| SiOx on COC, per protocol | | | | 1.81 | 0.54 |

Col. 126, line 56, in "(Me)2SiO," show "2" as a subscript.

Col. 126, line 64, replace "1W" with -- 1½ --.

Col. 126, line 67, replace "min," with -- min --.

Col. 127, line 43, in "SiOx," show "x" as a subscript.

Col. 127, line 44, in "SiOx," show "x" as a subscript.

Col. 127, line 47, in "SiOx," show "x" as a subscript.

Col. 127, line 48, in "SiOx," show "x" as a subscript.

Col. 127, line 50, in "SiOx," show "x" as a subscript.

Col. 128, line 52, replace "ml," with -- ml --.

Col. 128, line 57, replace "ml," with -- ml --.

Signed and Sealed this
Fourth Day of October, 2011

David J. Kappos
*Director of the United States Patent and Trademark Office*

CERTIFICATE OF CORRECTION (continued)
U.S. Pat. No. 7,985,188 B2

Col. 129, line 23, replace "the gaseous" with -- a gaseous --.